US010214777B2

(12) United States Patent
O'Donnell et al.

(10) Patent No.: US 10,214,777 B2
(45) Date of Patent: *Feb. 26, 2019

(54) MOLECULAR DIAGNOSTIC TEST FOR CANCER

(71) Applicant: Almac Diagnostics Limited, Craigavon (GB)

(72) Inventors: Jude O'Donnell, Galbally (GB); Max Bylesjo, Glasgow (GB); Fionnuala Patterson, Greenisland (GB); Steve Deharo, Hillsborough (GB); Laura A. Hill, Lisburn (GB); Katherine E. Keating, Magherafelt (GB); Timothy Davison, Hillsborough (GB); Vitali Proutski, Hillsborough (GB); Denis Paul Harkin, Dromore (GB); Richard Kennedy, Belfast (GB); Nicolas Goffard, Belfast (GB)

(73) Assignee: Almac Diagnostics Limited, Craigavon (GB)

(*) Notice: Subject to any disclaimer, the term of this patent is extended or adjusted under 35 U.S.C. 154(b) by 619 days.

This patent is subject to a terminal disclaimer.

(21) Appl. No.: 14/825,480

(22) Filed: Aug. 13, 2015

(65) Prior Publication Data
US 2016/0060705 A1    Mar. 3, 2016

Related U.S. Application Data

(63) Continuation of application No. 13/821,404, filed as application No. PCT/US2011/051803 on Sep. 15, 2011, now Pat. No. 9,670,547.

(60) Provisional application No. 61/490,039, filed on May 25, 2011, provisional application No. 61/383,201, filed on Sep. 15, 2010.

(51) Int. Cl.
*C12Q 1/68* (2018.01)
*C40B 30/04* (2006.01)
*G06F 19/20* (2011.01)
*G06F 19/24* (2011.01)
*C12Q 1/6886* (2018.01)
*C12Q 1/6876* (2018.01)
*A61K 33/24* (2019.01)
*G16H 50/30* (2018.01)
*G06F 19/00* (2018.01)

(52) U.S. Cl.
CPC ............ *C12Q 1/6886* (2013.01); *A61K 33/24* (2013.01); *C12Q 1/6876* (2013.01); *G06F 19/00* (2013.01); *G06F 19/20* (2013.01); *G06F 19/24* (2013.01); *G16H 50/30* (2018.01); *C12Q 2600/106* (2013.01); *C12Q 2600/112* (2013.01); *C12Q 2600/158* (2013.01); *C40B 30/04* (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,661,028 A | 8/1997 | Foote |
| 5,800,992 A | 9/1998 | Fodor et al. |
| 6,228,575 B1 | 5/2001 | Gingeras et al. |
| 6,308,170 B1 | 10/2001 | Balaban |
| 7,695,913 B2 | 4/2010 | Cowens et al. |
| 2003/0073083 A1 | 4/2003 | Tamayo et al. |
| 2004/0146921 A1 | 7/2004 | Eveleigh et al. |
| 2006/0142231 A1 | 6/2006 | Ashworth et al. |

(Continued)

FOREIGN PATENT DOCUMENTS

| | | |
|---|---|---|
| CN | 1839205 A1 | 9/2006 |
| CN | 1922490 A | 2/2007 |

(Continued)

OTHER PUBLICATIONS

Korean Office Action for co-pending Korean Patent Application No. 10-2013-7009145, dated Nov. 29, 2017, 21 pages, English translation included.

(Continued)

*Primary Examiner* — Kaijiang Zhang
(74) *Attorney, Agent, or Firm* — Finnegan, Henderson, Farabow, Garrett & Dunner, LLP

(57) ABSTRACT

Methods and compositions are provided for the identification of a molecular diagnostic test for cancer. The test defines a novel DNA damage repair deficient molecular subtype and enables classification of a patient within this subtype. The present invention can be used to determine whether patients with cancer are clinically responsive or non-responsive to a therapeutic regimen prior to administration of any chemotherapy. This test may be used in different cancer types and with different drugs that directly or indirectly affect DNA damage or repair, such as many of the standard cytotoxic chemotherapeutic drugs currently in use. In particular, the present invention is directed to the use of certain combinations of predictive markers, wherein the expression of the predictive markers correlates with responsiveness or non-responsiveness to a therapeutic regimen.

28 Claims, 13 Drawing Sheets
Specification includes a Sequence Listing.

(56) References Cited

U.S. PATENT DOCUMENTS

| | | | |
|---|---|---|---|
| 2007/0218512 | A1 | 9/2007 | Strongin et al. |
| 2009/0023149 | A1 | 1/2009 | Knudsen |
| 2009/0062196 | A1 | 3/2009 | D'Andrea et al. |
| 2010/0304989 | A1 | 12/2010 | Von Hoff et al. |

FOREIGN PATENT DOCUMENTS

| | | |
|---|---|---|
| EP | 0373203 B2 | 6/1990 |
| EP | 0785280 B1 | 7/1997 |
| WO | WO 95/21265 | 8/1995 |
| WO | WO 96/31622 | 10/1996 |
| WO | WO 97/10365 | 3/1997 |
| WO | WO 97/27317 | 7/1997 |
| WO | WO 2004/106495 A2 | 12/2004 |
| WO | WO 2005/026735 A2 | 3/2005 |
| WO | WO 2005/054508 A2 | 6/2005 |
| WO | WO 2005/083128 A2 | 9/2005 |
| WO | WO 2005/083440 A2 | 9/2005 |
| WO | WO 2006/048291 A2 | 5/2006 |
| WO | WO 2006/093507 A2 | 9/2006 |
| WO | WO 2007/038792 A2 | 4/2007 |
| WO | WO 2007/045996 A1 | 4/2007 |
| WO | WO 2007/084992 A2 | 7/2007 |
| WO | WO 2007/112330 A2 | 10/2007 |
| WO | WO 2008/005281 A2 | 1/2008 |
| WO | WO 2008/089465 A2 | 7/2008 |
| WO | WO 2008/104543 A2 | 9/2008 |
| WO | WO 2008/132176 A2 | 11/2008 |
| WO | WO 2010/006048 A2 | 1/2010 |
| WO | WO 2010/040083 A2 | 4/2010 |
| WO | WO 2010/045463 A2 | 4/2010 |
| WO | WO 2010/060055 A1 | 5/2010 |
| WO | WO 2011/109440 A1 | 9/2011 |
| WO | WO 2011/153545 A2 | 12/2011 |

OTHER PUBLICATIONS

Lord et al., "Targeted therapy for cancer using PARP inhibitors," Curr Opin Pharmacol, 8(4):363-369, (2008).
Japanese Office Action for co-pending Japanese Patent Application No. 2016-238969, dated Nov. 7, 2017, 9 pages, English translation included.
"The Area Under an ROC Curve", http://gim.unmc.edu/dxtests/roc3.htm, 2 pages, accessed Aug. 24, 2017.
Communication pursuant to Article 94(3) EPC for corresponding EP Application No. 11825959.7-1404, dated Aug. 2, 2017.
Hsu et al., "Pharmacogenomic strategies provide a rational approach to the treatment of cisplatin-resistant patients with advanced cancer", J Clin Oncol, 25(28):4350-4357, (2007). Retracted as of Nov. 16, 2010.
Kerr et al., "Expression profiling of BRCA1 and BRCA2 deficient human tumors and cell-lines using a breast specific platform to identify a biomarker of DNA repair deficiency", European Journal of Cancer, 7(4):Supplement p. 21, Abstract No. pp. 128, (2009).
Kim et al., "Analysis of Chromosomal Changes in Serous Ovarian Carcinoma by Microarray Comparative Genomic Hybridization: Potential Predictive Markers for Chemoresistant Disease", Acta Obstetrica et Gynaecologica Japonica, 58(2):794(S-646), p. IS-41, (2006).
Miyoshi et al., "Predictive factors for response to chemotherapy in breast cancers", Japanese Journal of Clinical Medicine, 65(Suppl. 6):154-159, (2007).
Nagasaki et al., "Identification of drug-responsiveness genes towards personalized medicine for breast cancer", Proceedings of the Japanese Cancer Association, 63:486-486, p. 13, (2004).
Raitman et al., "Characterizing the role of CXCL10 in basal and luminal breast cancer subtypes", 100th annual meeting of the American association for cancer research, 50:806, (2009).
Australian First Office Action dated Mar. 21, 2014 in co-pending Australian Patent Application No. 2011302004.

Chinese Office Action and Search Report dated Jan. 14, 2014 in co-pending Chinese Patent Application No. 201180047116.5.
Chinese Second Office Action in co-pending Chinese Patent Application No. 201180047116.5, dated Oct. 14, 2014.
Chinese Notification of the Third Office Action for corresponding Chinese Patent Application No. 201180047116.5, dated Jun. 18, 2015. 23 pages. English excerpt included.
Chinese Notification of the Fourth Office Action for corresponding Chinese Patent Application No. 201180047116.5, dated Feb. 22, 2016. 21 pages. English excerpt included.
Notice of Reasons of Rejection of Japanese Patent Application No. 2013-529331, dated Sep. 15, 2015.
Decision of Rejection of Japanese Patent Application No. 2013-529331, dated Aug. 9, 2016.
Eurasian First Office Action in co-pending Eurasian Patent Application No. 201390370, dated Oct. 27, 2014.
European Supplemental Search Report dated Feb. 7, 2014 in co-pending European Patent Application No. 11825959.7.
Final Office Action in U.S. Appl. No. 14/047,949, dated Jul. 29, 2016.
International Preliminary Report on Patentability for International Application No. PCT/US2011/051803, dated Mar. 19, 2013.
International Search Report for International Application No. PCT/GB2014/052727, dated Dec. 16, 2014. (U.S. Appl. No. 14/917,925).
International Search Report for International Application No. PCT/GB2014/052728, dated Dec. 18, 2014. (U.S. Appl. No. 14/917,913).
Office Action for Israeli Application No. 225076, dated Sep. 24, 2015.
Office Action for Israeli Application No. 225076, dated Dec. 18, 2016.
Substantive Examination Report Stage I for Indonesian Application No. W-00201301459. 4 pages. English excerpt included.
Written Opinion of Singaporean Application No. 2013016175, dated Aug. 7, 2014.
Written Opinion of the International Searching Authority for International Application No. PCT/GB2014/052727, dated Dec. 16, 2014. (U.S. Appl. No. 14/917,925).
Written Opinion of the International Searching Authority for International Application No. PCT/GB2014/052728, dated Dec. 18, 2014. (U.S. Appl. No. 14/917,913).
New Zealand Office Action dated Jul. 29, 2013 in co-pending New Zealand Patent Application No. 608459.
New Zealand Second Office Action dated Feb. 10, 2014 in co-pending New Zealand Patent Application No. 608459.
New Zealand Third Office Action in co-pending New Zealand Patent Application No. 608459, dated Jan. 23, 2015.
New Zealand First Office Action dated Feb. 10, 2014 in co-pending New Zealand Patent Application No. 620799.
Co-pending U.S. Appl. No. 14/917,925.
Co-pending U.S. Appl. No. 14/917,913.
American Cancer Society: *Cancer Facts and Figures* (2010).
Benjamini and Hochberg, "Controlling the False Discovery Rate: a Practical and Powerful Approach to Multiple Testing." *J. R. Stat. Soc.*, 57:289:300 (1995).
Bonnefoi, et al, "Validation of gene signatures that predict the response of breast cancer to neoadjuvant chemotherapy: a substudy of the EORTC 10994/BIG 00-01 clinical trial." *Lancet Oncol.*, 8:1071-1078 (2007).
Burlingame, et al., "Mass Spectrometry." *Anal. Chem.*, 70:647 R-716R (1998).
Dudoit, et al., "Comparison of Discrimination Methods for the Classification of Tumors Using Gene Expression Data." *J. Am. Statist. Assoc.*, 97(457):77-87 (2002).
Hess, et al., "Pharmacogenomic Predictor of Sensitivity to Preoperative Chemotherapy with Paclitaxel and Fluorouracil, Doxorubicin, and Cyclophosphamide in Breast Cancer." *J Clin Oncol.*, 24(26):4236-4244 (2006).
Ino et al., "indoleamine 2,3-dioxygenase is a novel prognostic indicator for endometrial cancer," British Journal of Cancer, 2006, vol. 95: 1555-1561.
Iwamoto, et al., "Gene Pathways Associated with Prognosis and Chemotherapy Sensitivity in Molecular Subtypes of Breast Cancer." *J Natl Cancer Inst.*, 103:264-272 (2011).

(56) References Cited

OTHER PUBLICATIONS

Jackson and Bartek, "The DNA-damage response in human biology and disease." *Nature*, 461(22):1071-1078 (2009).
Kennedy and D'Andrea., "DNA Repair Pathways in Clinical Practice: Lessons From Pediatric Cancer Susceptibility Syndromes." *J Clin Onco*, 24(23):3799-3808 (2006).
Lee, et al., "Prospective Comparison of Clinical and Genomic Multivariate Predictors of Response to Neoadjuvant Chemotherapy in Breast Cancer." *Clin Cancer Res*,16:711-718 (2010).
Linn and Van 'T Veer, "Clinical relevance of the triple negative breast cancer concept: Genetic basis and clinical utility of the concept." *J. Eur J Cancer*, 45 (Suppl 1):11-26 (2009).
Nguyen and Rock, "Tumor classification by partial least squares using microarray gene expression data." *Bioinformatics*, 18:39-50 (2002).
O'Shaughnessy, et al., "Iniparib plus Chemotherapy in Metastatic Triple-Negative Breast Cancer." *N Engl J Med.*, 364(3):205-214 (2011).
Rodier, et al., "Persistent DNA damage signaling triggers senescence-associated inflammatory cytokine secretion." *Nat Cell Biol.*, 11(8):973-979 (2009).
Schena, et al., "Parallel human genome analysis: Microarray-based expression monitoring of 1000 genes." *Proc. Natl. Acad. Sci. USA*, 93:10614-10619 (1996).
Stahle and Wold, "Partial least squares analysis with cross-validation for the two-class problem: A Monto Carlo study." *J. Chemom.*, 1:185-196 (1987).
Tabchy, et al., "Evaluation of a 30-Gene Paclitaxel, Fluorouracil, Doxorubicin, and Cyclophosphamide Chemotherapy Response Predictor in a Multicenter Randomized Trial in Breast Cancer." *Clin Cancer Res*, 16(21):5351-5361 (2010).
Tibshirani, et al., "Estimating the numbers of clusters in a data set via the gap statistic." *J. R. Stat. Soc.*, 63(2):411-423 (2002).
Tibshirani, et al., "Diagnosis of multiple cancer types by shrunken centroids of gene expression." *Proc.Natl. Acad. Sci. USA*, 99(10):6567-6572 (2002).
Vanderwerf, et al., "TLR8-dependent TNF-α overexpression in Fanconi anemia group C cells." *Blood*, 114(26):5290-5298 (2009).
Van'T Veer, et al., "Gene expression profiling predicts clinical outcome of breast cancer." *Nature*, 415:530 (2002).
Wold, "Pattern recognition by means of disjoint principal components models." *Pattern Recogn.*, 8:127-139 (1976).
Wray, et. al., "The Genetic Interpretation of Area under the ROC Curve in Genomic Profiling." *PLoS Genetics*, 6(2):e1000864 (9 pages).
Xu, "DNA damage: a trigger of innate immunity but a requirement for adaptive immune homeostasis," *Nat Rev Immuno.*, 16:261-270 (2006).
International Search Report and Written Opinion dated Apr. 18, 2012 for PCT/US2011/051803, pp. 1-11.
Liang et al., "DNA Damage Response Pathways in Tumor Suppression and Cancer Treatment," World J. Surg. 2009, 33:661-666.
ClinicalTrials.gov, "AzD2281 and Carboplatin in Treating Patients with BRCA1/BRCA2-Associated or Hereditary Metastic or Unresectable Breast and/or Ovarian Cancer," [online] Mar. 28, 2008 (retrieved Mar. 19, 2012), available on the Internet: <URL: http://clinicaltrials.gov/archive/NCT00647062/2008_03_28>.
Final Office Action in co-pending U.S. Appl. No. 14/047,949 dated Aug. 20, 2014, 10 pages.
United States First Office Action in co-pending U.S. Appl. No. 14/047,949 dated Mar. 10, 2014 pp. 1-13.
Arun et al., "Visual inspection Versus Quantitative Flow Cytometry to Detect Aberrant C Expression in Malignant T Cells," Cytometry B Clin Cytom., May 2010, vol. 78, No. 3, pp. 169-175.
Cleator, S. et al., "Gene Expression Patterns for Doxorubicin (Adriamycin) and Cyclophosphamide (Cytoxan) (AC) Response and Resistance," Breast Cancer Research and Treatment, Feb. 1, 2006, vol. 95, No. 3, pp. 229-233.
Doolan et al., "Prevalence and Prognostic and Predictive Relevance of PRAME in Breast Cancer," Breast Cancer Res Treat, 2008, vol. 109, No. 2, pp. 359-365.
Farmer, P. et al., "A Stroma-Related Gene Signature Predicts Resistance to Epirubicin-Containing Neoadjuvant Chemotherapy in Breast Cancer," Breast Cancer Research and Treatment, Nov. 3, 2007, vol. 106, No. Suppl 1, pp. S11.
Jiang et al., "CXCL10 Expression and Prognostic Significance in Stage II and III Colorectal Cancer," Mol Biol Rep., Jul. 2010, vol. 37, No. 6, pp. 3029-3036.
Kawano, R. et al., "Oncogene Associated cDNA Microarray Analysis Shows PRAME Gene Expression is a Marker for Response to Anthracycline Containing Chemotherapy in Patients with Diffuse Large B-Cell Lymphoma," Journal of Clinical and Experimental Hematopathology, May 1, 2009, vol. 49, No. 1, pp. 1-7.
Kennedy et al., "The Fanconi Anemia/BRCA Pathway: New Faces in the Crowd," Genes Dev. 2005, vol. 19: pp. 2925-2940.
Korrat, A. et al., "Gene Signature-Based Prediction of Tumor Response to Cyclophosphamide," Cancer Genomics & Protemics, May 1, 2007, vol. 4, No. 3, pp. 187-195.
Ooyama, A. et al., "Gene Expression Analysis Using Human Cancer Xenografts to Identify Novel Predictive Marker Genes for the Efficacy of 5-Fluorouracil-Based Drugs," Cancer Science, Jun. 1, 2006, vol. 97, No. 6, pp. 510-522.
Rodriguez, A. et al., "DNA Repair Signature is Associated with Anthracycline Response in Triple Negative Breast Cancer Patients," Breast Cancer Research and Treatment, Jun. 26, 2010, vol. 123, No. 1, pp. 189-196.
Tsao, D. et al., "Gene Expression Profiles for Predicting the Efficacy of the Anticancer Drug 5-Fluorouracil in Breast Cancer," DNA and Cell Biology, Jun. 17, 2010, pp. 285-296.
Non-Final Office Action in co-pending U.S. Appl. No. 13/821,404, dated Jan. 29, 2015, 16 pages.
Non-Final Office Action in U.S. Appl. No. 14/047,949, dated Nov. 3, 2015.
Final Office Action in U.S. Appl. No. 13/821,404, dated Nov. 3, 2015.
Kerr, P. et al., "PP128-Expression profiling of BRCA1 and BRCA2 deficient human tumors and cell-lines using a breast specific platform to identify a biomarker of DNA repair deficiency," European Journal of Cancer, 2009, vol. 7, No. 4, Supplement, p. 189-196.
Ino, K et al., "Indoleamine 2,3-dioxygenase is a novel prognostic indicator for endometrial cancer," British Journal of Cancer, 2006, vol. 95: p. 1555-1561.
Langer et al., "Prediction of response to neoadjuvant chemotherapy of Barrett's carcinomas by quantitative gene expression analysis," Pathology—Research and Practice, Elsevier, Amsterdam, NL, 200(4):295-296, XP004958276, ISSN:0344-0338, DOI:10.1016/S0344-0338(04)80555-7, (2004).
Theisen et al., "Gene Expression as Predictor of Response in Neoadjuvant Treated Patients with Esophageal Adenocarcinoma," American Association for Cancer Research, Proceedings of the Annual Meeting; [Cancer Research; Apr. 2004, vol. 64, Issue 7, Supplement], American Association for Cancer Research, US, 41:641, AB4072, XP001118944, ISSN:0197-016X, (2000).
Vilmar et al., "Customising chemotherapy in advanced nonsmall cell lung cancer: daily practice and perspectives," Eur Respir Rev, 20(119):45-52, (2011).
Wang et al., "Negative feedback regulation of IFN-gamma pathway by IFN regulatory factor 2 in esophageal cancers," Cancer Res, 68(4):1136-1143, (2008).
Oberthuer et al., "The tumor-associated antigen PRAME is universally expressed in high-stage neuroblastoma and associated with poor outcome," Clin Cancer Res, 10(13):4307-4313, (2004).
Summons to attend oral proceedings pursuant to Rule 115(1) EPC for Application No. 11825959.7-1118 / 2619574, dated Aug. 9, 2018.

MOLECULAR DIAGNOSTIC TEST FOR CANCER

CROSS-REFERENCE TO RELATED APPLICATIONS

This application is a continuation of U.S. patent application Ser. No. 13/821,404, filed on May 20, 2013, which is a 35 U.S.C. § 371 national stage application of International Patent Application No. PCT/US2011/051803, filed on Sep. 15, 2011, which claims the benefit of priority to U.S. Provisional Patent Application No. 61/383,201, filed on Sep. 15, 2010, and U.S. Provisional Patent Application No. 61/490,039, filed on May 25, 2011, all of which are incorporated herein by reference in their entirety.

FIELD OF THE INVENTION

The present invention relates to a molecular diagnostic test useful for diagnosing cancers from different anatomical sites that includes the use of a common DNA damage repair deficiency subtype. The invention includes the use of a 44-gene classification model that is used to identify this DNA damage repair deficiency molecular subtype. One application is the stratification of response to, and selection of patients for breast cancer therapeutic drug classes, including DNA damage causing agents and DNA repair targeted therapies. Another application is the stratification of ovarian cancer patients into those that respond and those that do not respond to DNA damage causing agents. The present invention provides a test that can guide conventional therapy selection as well as selecting patient groups for enrichment strategies during clinical trial evaluation of novel therapeutics. DNA repair deficient subtypes can be identified from fresh/frozen (FF) or formalin fixed paraffin embedded (FFPE) patient samples.

BACKGROUND

The pharmaceutical industry continuously pursues new drug treatment options that are more effective, more specific or have fewer adverse side effects than currently administered drugs. Drug therapy alternatives are constantly being developed because genetic variability within the human population results in substantial differences in the effectiveness of many drugs. Therefore, although a wide variety of drug therapy options are currently available, more therapies are always needed in the event that a patient fails to respond.

Traditionally, the treatment paradigm used by physicians has been to prescribe a first-line drug therapy that results in the highest success rate possible for treating a disease. Alternative drug therapies are then prescribed if the first is ineffective. This paradigm is clearly not the best treatment method for certain diseases. For example, in diseases such as cancer, the first treatment is often the most important and offers the best opportunity for successful therapy, so there exists a heightened need to chose an initial drug that will be the most effective against that particular patient's disease.

It is anticipated that there will be 207,090 new female breast cancer diagnoses in the US this year and 39,840 female breast cancer related deaths (American Cancer Society: Cancer Facts and FIGS. 2010). Standard chemotherapy typically includes direct DNA damaging agents such as anthracyclines and alkylating agents as well as antimetabolites and antimicrotubule agents.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these differed histologies arise from different aetiologies. The current standard treatment for ovarian cancer is debulking surgery and standard platinum taxane based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens.

Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

Molecular markers have been used to select appropriate treatments, for example, in breast cancer. Breast tumors that do not express the estrogen and progesterone hormone receptors as well as the HER2 growth factor receptor, called "triple negative", appear to be responsive to PARP-1 inhibitor therapy (Linn, S. C., and Van't Veer, L., J. Eur J Cancer 45 Suppl 1, 11-26 (2009); O'Shaughnessy, J., et al. N Engl J Med 364, 205-214 (2011). Recent studies indicate that the triple negative status of a breast tumor may indicate responsiveness to combination therapy including PARP-1 inhibitors, but may not be sufficient to indicate responsiveness to individual PARP-1 inhibitors. (O'Shaughnessy et al., 2011).

Furthermore, there have been other studies that have attempted to identify gene classifiers associated with molecular subtypes to indicate responsiveness of chemotherapeutic agents (Farmer et al. Nat Med 15, 68-74 (2009); Konstantinopoulos, P. A., et al., J Clin Oncol 28, 3555-3561 (2010)). However, to date there does not exist a diagnostic test that works across cancer diseases to accurately define a molecular subtype that demonstrates a deficiency in DNA damage repair, that can also predict sensitivity to any drug that directly or indirectly targets DNA damage repair across diseases.

What is therefore needed is a test that identifies DNA repair deficient tumors with sufficient accuracy to allow the stratification of patients into those who are likely to respond to chemotherapeutic agents that damage DNA, and those who should receive alternative therapies.

What is also needed is a molecular subtype classifier that is predictive of therapeutic responsiveness across different cancer types with sufficient accuracy.

SUMMARY OF THE INVENTION

The invention is directed to methods of using a collection of gene product markers expressed in cancer such that when some or all of the transcripts are over or under-expressed, they identify a subtype of cancer that has a deficiency in DNA damage repair. Designation of this subtype can be considered a diagnostic test as it is not related to any specific drug but rather describes the biology of the cancer in a manner that has utility in screening and selecting appropriate cancer therapies. The invention also provides methods for indicating responsiveness or resistance to DNA-damage therapeutic agents. In different aspects, this gene or gene product list may form the basis of a single parameter or a multiparametric predictive test that could be delivered using methods known in the art such as microarray, Q-PCR, immunohistochemistry, ELISA or other technologies that can quantify mRNA or protein expression.

In addition, the biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment of the invention, these genes or gene products are useful for evaluating both breast and ovarian cancer tumors.

The invention described herein is not limited to any one drug; it can be used to identify responders and non responders to any of a range of drugs that directly or indirectly affect DNA damage and/or DNA damage repair e.g. neoadjuvant 5-fluorouracil, anthracycline and cyclophosphamide based regimens such as FEC (5-fluorouracil/epirubicin/cyclophosphamide) and FAC (5-fluorouracil/Adriamycin/cyclophosphamide). In specific aspects this invention, it is useful for evaluating paclitaxel, fluorouracil, doxorubicin (Adriamycin), and cyclophosphamide (T/FAC) neoadjuvant treatment in breast cancer. In other aspects this invention, it is useful for evaluating platinum or platinum plus taxol treatment in ovarian cancer.

The present invention relates to prediction of response to drugs using different classifications of response, such as overall survival, progression free survival, radiological response, as defined by RECIST, complete response, partial response, stable disease and serological markers such as, but not limited to, PSA, CEA, CA125, CA15-3 and CA19-9. In specific embodiments this invention can be used to evaluate pathological complete response in breast cancer treated with FEC or FAC either alone or in the context of standard treatment, or RECIST and serum CA125 levels in ovarian cancer.

In another aspect, the present invention relates to the identification of a DNA damage response deficiency (DDRD) molecular subtype in breast and ovarian cancer. This molecular subtype can be detected by the use of two different gene classifiers—one being 40 genes in length and one being 44 genes in length. The DDRD classifier was first defined by a classifier consisting of 53 probesets on the Almac Breast Disease Specific Array (DSA™). So as to validate the functional relevance of this classifier in the context of its ability to predict response to DNA-damaging containing chemotherapy regimens, the classifier needed to be re-defined at a gene level. This would facilitate evaluation of the DDRD classifier using microarray data from independent datasets that were profiled on microarray platforms other than the Almac Breast DSA™. In order to facilitate defining the classifier at a gene level, the genes to which the Almac Breast DSA™ probesets map to needed to be defined. This involved the utilization of publicly available genome browser databases such as Ensembl and NCBI Reference Sequence. Results are provided only for the 44-gene DDRD classifier model, as this model supersedes that of the 40-gene DDRD classifier model. These results demonstrate that the classifier model is an effective and significant predictor of response to chemotherapy regimens that contain DNA damaging therapeutics.

The identification of the subtype by both the 40-gene classifier model and the 44-gene classifier model can be used to predict response to, and select patients for, standard breast and ovarian cancer therapeutic drug classes, including DNA damage causing agents and DNA repair targeted therapies.

In another aspect, the present invention relates to kits for conventional diagnostic uses listed above such as qPCR, microarray, and immunoassays such as immunohistochemistry, ELISA, Western blot and the like. Such kits include appropriate reagents and directions to assay the expression of the genes or gene products and quantify mRNA or protein expression.

The invention also provides methods for identifying DNA damage response-deficient (DDRD) human tumors. It is likely that this invention can be used to identify patients that are sensitive to and respond, or are resistant to and do not respond, to drugs that damage DNA directly, damage DNA indirectly or inhibit normal DNA damage signaling and/or repair processes.

The invention also relates to guiding conventional treatment of patients. The invention also relates to selecting patients for clinical trials where novel drugs of the classes that directly or indirectly affect DNA damage and/or DNA damage repair.

The present invention and methods accommodate the use of archived formalin fixed paraffin-embedded (FFPE) biopsy material, as well as fresh/frozen (FF) tissue, for assay of all transcripts in the invention, and are therefore compatible with the most widely available type of biopsy material. The expression level may be determined using RNA obtained from FFPE tissue, fresh frozen tissue or fresh tissue that has been stored in solutions such as RNAlater®.

BRIEF DESCRIPTION OF DRAWINGS

(FIG. 1D) Sensitivity plus specificity plot of the cross validation predictions used to select threshold. The maximum sensitivity plus specificity is 1.682 with a corresponding signature score of ~0.37.

(FIG. 8A) Western blot analysis confirming increased expression of BRCA1 in the HCC1937-BR cells compared with the HCC1937-EV cells. (FIG. 8B) Mean 44-gene model (DDRD) classifier score (±SEM) within the control vector-only transfected HCC1937 (HCC1937-EV) and HCC1937 with returned exogenous expression of BRCA1 (HCC1937-BR) cell-lines. Histogram representation of cell-viability of HCC1937 parental and HCC1937-BR cells under constant exposure to a range of concentrations of PARP inhibitor KU0058948 (FIG. 8C) and cisplatin (FIG. 8D).

DETAILED DESCRIPTION OF THE INVENTION

Figure 1A:
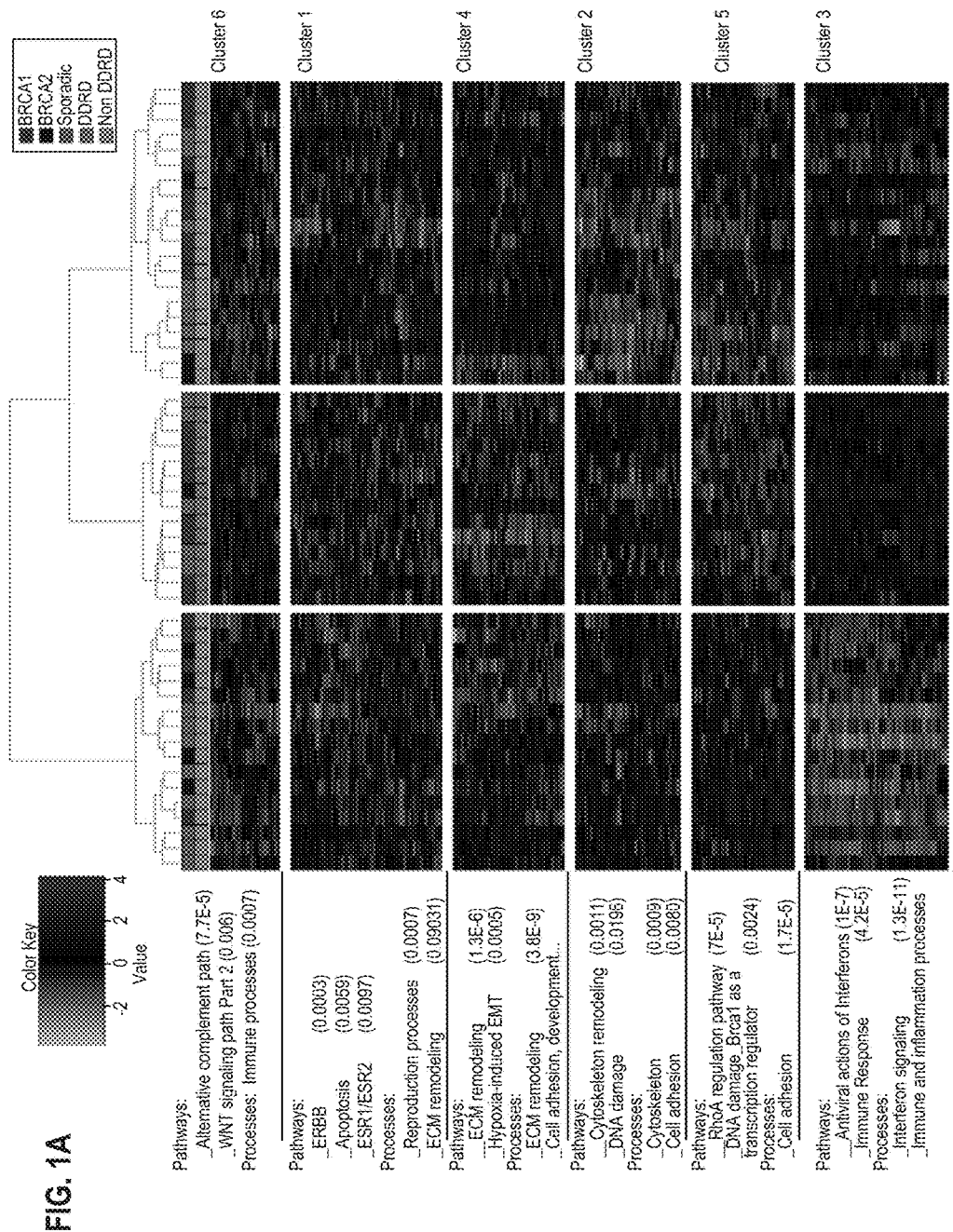
FIG. 1A and FIG. 1B provide a diagram representing the hierarchical analysis of ER-negative (FIG. 1A) and ER-positive (FIG. 1B) BRCA1/2 mutant and sporadic wildtype control breast samples. Probeset cluster groups are annotated on the right-hand side and pathway analysis of each probeset cluster group is annotated on the left-hand side of each image. The legend for each image indicates a sample's mutational status as well as the signature group each sample was assigned to for classifier generation.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

The articles "a" and "an" are used herein to refer to one or to more than one (i.e., to at least one) of the grammatical object of the article. By way of example, "an element" means one element or more than one element, unless explicitly indicated to the contrary.

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individual's response to a foreign compound or drug. Agents or modulators which have a stimulatory or inhibitory effect on expression of a marker of the invention can be administered to individuals to treat (prophylactically or therapeutically) cancer in a patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a marker of the invention in an individual can be determined to thereby select appropriate agent(s) for therapeutic or prophylactic treatment of the individual.

The invention is directed to a unique collection of gene or gene product markers (hereinafter referred to as "biomarkers") expressed in a cancer tissue. In different aspects, this biomarker list may form the basis of a single parameter or multiparametric predictive test that could be delivered using methods known in the art such as microarray, Q-PCR, immunohistochemistry, ELISA or other technologies that can quantify mRNA or protein expression.

The present invention also relates to kits and methods that are useful for prognosis following cytotoxic chemotherapy or selection of specific treatments for cancer. Methods are provided such that when some or all of the transcripts are over or under-expressed, the expression profile indicates responsiveness or resistance to DNA-damage therapeutic agents. These kits and methods employ gene or gene product markers that are differentially expressed in tumors of patients with cancer. In one embodiment of the invention, the expression profiles of these biomarkers are correlated with clinical outcome (response or survival) in archival tissue samples under a statistical method or a correlation model to create a database or model correlating expression profile with responsiveness to one or more DNA-damage therapeutic agents. The predictive model may then be used to predict the responsiveness in a patient whose responsiveness to the DNA-damage therapeutic agent(s) is unknown. In many other embodiments, a patient population can be divided into at least two classes based on patients' clinical outcome, prognosis, or responsiveness to DNA-damage therapeutic agents, and the biomarkers are substantially correlated with a class distinction between these classes of patients. The biological pathways described herein are common to cancer as a disease, similar to grade and stage, and as such, the classifiers and methods are not limited to a single cancer disease type.

Predictive Marker Panels/Expression Classifiers

A unique collection of biomarkers as a genetic classifier expressed in a cancer tissue is provided that is useful in determining responsiveness or resistance to therapeutic agents, such as DNA-damage therapeutic agents, used to treat cancer. Such a collection may be termed a "marker panel", "expression classifier", or "classifier".

The biomarkers useful in the present methods are identified in Table 1. These biomarkers are identified as having predictive value to determine a patient response to a therapeutic agent, or lack thereof. Their expression correlates with the response to an agent, and more specifically, a DNA-damage therapeutic agent. By examining the expression of a collection of the identified biomarkers in a tumor, it is possible to determine which therapeutic agent or combination of agents will be most likely to reduce the growth rate of a cancer, and in some embodiments, breast or ovarian cancer cells. By examining a collection of identified transcript gene or gene product markers, it is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

TABLE 1A

Sense genes (166)

| Gene Symbol | EntrezGene ID | Antisense of known genes (24) | | SEQ ID NO: |
|---|---|---|---|---|
| | | Almac Gene ID | Almac Gene symbol | |
| ABCA12 | 26154 | | N/A | |
| ALDH3B2 | 222 | | N/A | |
| APOBEC3G | 60489 | | N/A | |
| APOC1 | 341 | | N/A | |
| APOL6 | 80830 | | N/A | |
| ARHGAP9 | 64333 | | N/A | |
| BAMBI | 25805 | | N/A | |
| BIK | 638 | | N/A | |
| BIRC3 | 330 | AS1_BIRC3 | Hs127799.0C7n9_at | 1 |
| BTN3A3 | 10384 | | N/A | |
| C12orf48 | 55010 | | N/A | |
| C17orf28 | 283987 | | N/A | |
| C1orf162 | 128346 | | N/A | |
| C1orf64 | 149563 | | N/A | |
| C1QA | 712 | | N/A | |
| C21orf70 | 85395 | | N/A | |
| C22orf32 | 91689 | | N/A | |
| C6orf211 | 79624 | | N/A | |
| CACNG4 | 27092 | | N/A | |
| CCDC69 | 26112 | | N/A | |
| CCL5 | 6352 | | N/A | |
| CCNB2 | 9133 | | N/A | |
| CCND1 | 595 | | N/A | |
| CCR7 | 1236 | | N/A | |
| CD163 | 9332 | | N/A | |
| CD2 | 914 | | N/A | |
| CD22 | 933 | | N/A | |
| CD24 | 100133941 | | N/A | |
| CD274 | 29126 | | N/A | |
| CD3D | 915 | | N/A | |
| CD3E | 916 | | N/A | |
| CD52 | 1043 | | N/A | |
| CD53 | 963 | | N/A | |
| CD79A | 973 | | N/A | |
| CDH1 | 999 | | N/A | |
| CDKN3 | 1033 | | N/A | |
| CECR1 | 51816 | | N/A | |
| CHEK1 | 1111 | | N/A | |
| CKMT1B | 1159 | | N/A | |
| CMPK2 | 129607 | | N/A | |
| CNTNAP2 | 26047 | | N/A | |
| COX16 | 51241 | | N/A | |
| CRIP1 | 1396 | | N/A | |
| CXCL10 | 3627 | | N/A | |
| CXCL9 | 4283 | | N/A | |
| CYBB | 1536 | | N/A | |
| CYP2B6 | 1555 | | N/A | |
| DDX58 | 23586 | | N/A | |
| DDX60L | 91351 | | N/A | |
| ERBB2 | 2064 | | N/A | |
| ETV7 | 51513 | | N/A | |
| FADS2 | 9415 | | N/A | |
| FAM26F | 441168 | | N/A | |
| FAM46C | 54855 | | N/A | |
| FASN | 2194 | | N/A | |
| FBP1 | 2203 | | N/A | |
| FBXO2 | 26232 | | N/A | |
| FKBP4 | 2288 | | N/A | |
| FLJ40330 | 645784 | | N/A | |

TABLE 1A-continued

Sense genes (166)

| Gene Symbol | EntrezGene ID | Almac Gene ID | Antisense of known genes (24) Almac Gene symbol | SEQ ID NO: |
|---|---|---|---|---|
| FYB | 2533 | | N/A | |
| GBP1 | 2633 | | N/A | |
| GBP4 | 115361 | | N/A | |
| GBP5 | 115362 | AS1_GBP5 | BRMX.5143C1n2_at | 2 |
| GIMAP4 | 55303 | | N/A | |
| GLRX | 2745 | | N/A | |
| GLUL | 2752 | | N/A | |
| GVIN1 | 387751 | | N/A | |
| H2AFJ | 55766 | | N/A | |
| HGD | 3081 | | N/A | |
| HIST1H2BK | 85236 | | N/A | |
| HIST3H2A | 92815 | | N/A | |
| HLA-DOA | 3111 | | N/A | |
| HLA-DPB1 | 3115 | | N/A | |
| HMGB2 | 3148 | | N/A | |
| HMGB3 | 3149 | | N/A | |
| HSP90AA1 | 3320 | | N/A | |
| IDO1 | 3620 | | N/A | |
| IFI27 | 3429 | | N/A | |
| IFI44 | 10561 | | N/A | |
| IFI44L | 10964 | AS1_IFI44L | BRSA.1606C1n4_at | 3 |
| IFI6 | 2537 | | N/A | |
| IFIH1 | 64135 | | N/A | |
| IGJ | 3512 | AS1_IGJ | BRIH.1231C2n2_at | 4 |
| IKZF1 | 10320 | | N/A | |
| IL10RA | 3587 | | N/A | |
| IL2RG | 3561 | | N/A | |
| IL7R | 3575 | | N/A | |
| IMPAD1 | 54928 | | N/A | |
| IQGAP3 | 128239 | AS1_IQGAP3 | BRAD.30779_s_at | 5 |
| IRF1 | 3659 | | N/A | |
| ISG15 | 9636 | | N/A | |
| ITGAL | 3683 | | N/A | |
| KIAA1467 | 57613 | | N/A | |
| KIF20A | 10112 | | N/A | |
| KITLG | 4254 | | N/A | |
| KLRK1 | 22914 | | N/A | |
| KRT19 | 3880 | | N/A | |
| LAIR1 | 3903 | | N/A | |
| LCP1 | 3936 | | N/A | |
| LOC100289702 | 100289702 | | N/A | |
| LOC100294459 | 100294459 | AS1_LOC100294459 | BRSA.396C1n2_at | 6 |
| LOC150519 | 150519 | | N/A | |
| LOC439949 | 439949 | | N/A | |
| LYZ | 4069 | | N/A | |
| MAL2 | 114569 | | N/A | |
| MGC29506 | 51237 | | N/A | |
| MIAT | 440823 | | N/A | |
| MS4A1 | 931 | | N/A | |
| MX1 | 4599 | AS1_MX1 | BRMX.2948C3n7_at | 7 |
| NAPSB | 256236 | | N/A | |
| NCKAP1L | 3071 | | N/A | |
| NEK2 | 4751 | | N/A | |
| NLRC3 | 197358 | | N/A | |
| NLRC5 | 84166 | | N/A | |
| NPNT | 255743 | | N/A | |
| NQO1 | 1728 | | N/A | |
| OAS2 | 4939 | | N/A | |
| OAS3 | 4940 | | N/A | |
| PAQR4 | 124222 | | N/A | |
| PARP14 | 54625 | | N/A | |
| PARP9 | 83666 | | N/A | |
| PIK3CG | 5294 | | N/A | |
| PIM2 | 11040 | | N/A | |
| PLEK | 5341 | | N/A | |
| POU2AF1 | 5450 | | N/A | |
| PP14571 | 100130449 | | N/A | |
| PPP2R2C | 5522 | | N/A | |
| PSMB9 | 5698 | | N/A | |
| PTPRC | 5788 | | N/A | |
| RAC2 | 5880 | | N/A | |
| RAMP1 | 10267 | | N/A | |
| RARA | 5914 | | N/A | |
| RASSF7 | 8045 | | N/A | |

TABLE 1A-continued

Sense genes (166)

| Gene Symbol | EntrezGene ID | Almac Gene ID | Almac Gene symbol | SEQ ID NO: |
|---|---|---|---|---|
| RSAD2 | 91543 | | N/A | |
| RTP4 | 64108 | | N/A | |
| SAMD9 | 54809 | | N/A | |
| SAMD9L | 219285 | | N/A | |
| SASH3 | 54440 | | N/A | |
| SCD | 6319 | | N/A | |
| SELL | 6402 | | N/A | |
| SIX1 | 6495 | AS1_SIX1 | Hs539969.0C4n3_at | 8 |
| SLAMF7 | 57823 | | N/A | |
| SLC12A2 | 6558 | | N/A | |
| SLC9A3R1 | 9368 | AS1_SLC9A3R1 | Hs396783.3C1n4_at | 9 |
| SPOCK2 | 9806 | | N/A | |
| SQLE | 6713 | | N/A | |
| ST20 | 400410 | | N/A | |
| ST6GALNAC2 | 10610 | | N/A | |
| STAT1 | 6772 | AS1_STAT1 | BRMX.13670C1n2_at | 10 |
| STRA13 | 201254 | | N/A | |
| SUSD4 | 55061 | | N/A | |
| SYT12 | 91683 | | N/A | |
| TAP1 | 6890 | | N/A | |
| TBC1D10C | 374403 | | N/A | |
| TNFRSF13B | 23495 | | N/A | |
| TNFSF10 | 8743 | | N/A | |
| TOB1 | 10140 | AS1_TOB1 | BRAD.30243_at | 11 |
| TOM1L1 | 10040 | | N/A | |
| TRIM22 | 10346 | | N/A | |
| UBD | 10537 | AS1_UBD | BRMX.941C2n2_at | 12 |
| UBE2T | 29089 | | N/A | |
| UCK2 | 7371 | | N/A | |
| USP18 | 11274 | | N/A | |
| VNN2 | 8875 | | N/A | |
| XAF1 | 54739 | | N/A | |
| ZWINT | 11130 | | N/A | |

Antisense of known genes (24)

| Almac Gene ID | Almac Gene symbol | SEQ ID NO: |
|---|---|---|
| AS1_C1QC | BRMX.4154C1n3_s_at | 13 |
| AS1_C2orf14 | BRAD.39498_at | 14 |
| AS1_EPSTI1 | BRAD.34868_s_at | 15 |
| AS1_GALNT6 | 5505575.0C1n42_at | 16 |
| AS1_HIST1H4H | BREM.1442_at | 17 |
| AS1_HIST2H4B | BRHP.827_s_at | 18 |
| AS2_HIST2H4B | BRRS.18322_s_at | 19 |
| AS3_HIST2H4B | BRRS.18792_s_at | 20 |
| AS1_KIAA1244 | Hs632609.0C1n37_at | 21 |
| AS1_LOC100287927 | Hs449575.0C1n22_at | 22 |
| AS1_LOC100291682 | BRAD.18827_s_at | 23 |
| AS1_LOC100293679 | BREM.2466_s_at | 24 |

TABLE 1B

Novel genes

| Gene symbol | SEQ ID NO: |
|---|---|
| BRAD.2605_at | 25 |
| BRAD.33618_at | 26 |
| BRAD.36579_s_at | 27 |
| BRAD1_5440961_s_at | 28 |
| BRAD1_66786229_s_at | 29 |
| BREM.2104_at | 30 |
| BRAG_AK097020.1_at | 31 |
| BRAD.20415_at | 32 |
| BRAD.29668_at | 33 |
| BRAD.30228_at | 34 |
| BRAD.34830_at | 35 |
| BRAD.37011_s_at | 36 |
| BRAD.37762_at | 37 |
| BRAD.40217_at | 38 |
| BRAD1_4307876_at | 39 |
| BREM.2505_at | 40 |
| Hs149363.0CB4n5_s_at | 41 |
| Hs172587.9C1n9_at | 42 |
| Hs271955.16C1n9_at | 43 |
| Hs368433.18C1n6_at | 44 |
| Hs435736.0C1n27_s_at | 45 |
| Hs493096.15C1n6_at | 46 |
| Hs493096.2C1n15_s_at | 47 |
| Hs592929.0CB2n8_at | 48 |
| Hs79953.0C1n23_at | 49 |
| BRMX.2377C1n3_at | 50 |

All or a portion of the biomarkers recited in Table 1 may be used in a predictive biomarker panel. For example, biomarker panels selected from the biomarkers in Table 1 can be generated using the methods provided herein and can comprise between one, and all of the biomarkers set forth in Table 1 and each and every combination in between (e.g., four selected biomarkers, 16 selected biomarkers, 74 selected biomarkers, etc.). In some embodiments, the predictive biomarker set comprises at least 5, 10, 20, 40, 60, 100, 150, 200, or 300 or more biomarkers. In other embodiments, the predictive biomarker set comprises no more than 5, 10, 20, 40, 60, 100, 150, 200, 300, 400, 500, 600 or 700 biomarkers. In some embodiments, the predictive biomarker set includes a plurality of biomarkers listed in Table 1. In some embodiments the predictive biomarker set includes at least about 1%, about 5%, about 10%, about 20%, about 30%, about 40%, about 50%, about 60%, about 70%, about 80%, about 90%, about 95%, about 96%, about 97%, about 98%, or about 99% of the biomarkers listed in Table 1. Selected predictive biomarker sets can be assembled from the predictive biomarkers provided using methods described herein and analogous methods known in the art. In one embodiment, the biomarker panel contains all 203 biomarkers in Table 1. In another embodiment, the biomarker panel contains 40 or 44 biomarkers in Table 1 or 2.

Predictive biomarker sets may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug or drug class. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("decisive function") is compared with a pre-determined reference point or value. The comparison with the reference point or value may be used to diagnose, or predict a clinical condition or outcome.

As described above, one of ordinary skill in the art will appreciate that the biomarkers included in the classifier provided in Table 1 will carry unequal weights in a classifier for responsiveness or resistance to a therapeutic agent. Therefore, while as few as one sequence may be used to diagnose or predict an outcome such as responsiveness to therapeutic agent, the specificity and sensitivity or diagnosis or prediction accuracy may increase using more sequences.

As used herein, the term "weight" refers to the relative importance of an item in a statistical calculation. The weight of each biomarker in a gene expression classifier may be determined on a data set of patient samples using analytical methods known in the art.

In one embodiment the biomarker panel is directed to the 40 biomarkers detailed in Table 2A with corresponding ranks and weights detailed in the table or alternative rankings and weightings, depending, for example, on the disease setting. In another embodiment, the biomarker panel is directed to the 44 biomarkers detailed in Table 2B with corresponding ranks and weights detailed in the table or alternative rankings and weightings, depending, for example, on the disease setting. Tables 2A and 2B rank the biomarkers in order of decreasing weight in the classifier, defined as the rank of the average weight in the compound decision score function measured under cross-validation. Table 2C present the probe sets that represent the genes in Table 2A and 2B with reference to their sequence ID numbers. Table 2D presents the antisense probe sequences that were present on the array for the genes in the signatures.

TABLE 2A

Gene IDs and EntrezGene IDs for 40-gene DDRD classifier model with associated ranking and weightings
DDRD classifier 40 genes model

| Rank | Genes Symbol | EntrezGene ID | Weights |
| --- | --- | --- | --- |
| 1 | GBP5 | 115362 | 0.022389581 |
| 2 | CXCL10 | 3627 | 0.021941734 |
| 3 | IDO1 | 3620 | 0.020991115 |
| 4 | MX1 | 4599 | 0.020098675 |
| 5 | IFI44L | 10964 | 0.018204957 |
| 6 | CD2 | 914 | 0.018080661 |
| 7 | PRAME | 23532 | 0.016850837 |
| 8 | ITGAL | 3683 | 0.016783359 |
| 9 | LRP4 | 4038 | -0.015129969 |
| 10 | SP140L | 93349 | 0.014646025 |
| 11 | APOL3 | 80833 | 0.014407174 |
| 12 | FOSB | 2354 | -0.014310521 |
| 13 | CDR1 | 1038 | -0.014209848 |
| 14 | RSAD2 | 91543 | 0.014177132 |
| 15 | TSPAN7 | 7102 | -0.014111562 |
| 16 | RAC2 | 5880 | 0.014093627 |
| 17 | FYB | 2533 | 0.01400475 |
| 18 | KLHDC7B | 113730 | 0.013298413 |
| 19 | GRB14 | 2888 | 0.013031204 |
| 20 | KIF26A | 26153 | -0.012942351 |
| 21 | CD274 | 29126 | 0.012651964 |
| 22 | CD109 | 135228 | -0.012239425 |
| 23 | ETV7 | 51513 | 0.011787297 |
| 24 | MFAP5 | 8076 | -0.011480443 |
| 25 | OLFM4 | 10562 | -0.011130113 |
| 26 | PI15 | 51050 | -0.010904326 |
| 27 | FAM19A5 | 25817 | -0.010500936 |
| 28 | NLRC5 | 84166 | 0.009593449 |
| 29 | EGR1 | 1958 | -0.008947963 |
| 30 | ANXA1 | 301 | -0.008373991 |
| 31 | CLDN10 | 9071 | -0.008165127 |
| 32 | ADAMTS4 | 9507 | -0.008109892 |
| 33 | ESR1 | 2099 | 0.007524594 |
| 34 | PTPRC | 5788 | 0.007258669 |
| 35 | EGFR | 1956 | -0.007176203 |
| 36 | NAT1 | 9 | 0.006165534 |
| 37 | LATS2 | 26524 | -0.005951091 |
| 38 | CYP2B6 | 1555 | 0.005838391 |
| 39 | PPP1R1A | 5502 | -0.003898835 |
| 40 | TERF1P1 | 348567 | 0.002706847 |

TABLE 2B

Gene IDs and EntrezGene IDs for 44-gene DDRD classifier model with associated ranking and weightings
DDRD Classifier - 44 Gene Model (NA: genomic sequence)

| Rank | Gene symbol | EntrezGene ID | Weight |
| --- | --- | --- | --- |
| 1 | CXCL10 | 3627 | 0.023 |
| 2 | MX1 | 4599 | 0.0226 |
| 3 | IDO1 | 3620 | 0.0221 |
| 4 | IFI44L | 10964 | 0.0191 |
| 5 | CD2 | 914 | 0.019 |
| 6 | GBP5 | 115362 | 0.0181 |
| 7 | PRAME | 23532 | 0.0177 |
| 8 | ITGAL | 3683 | 0.0176 |
| 9 | LRP4 | 4038 | -0.0159 |
| 10 | APOL3 | 80833 | 0.0151 |
| 11 | CDR1 | 1038 | -0.0149 |
| 12 | FYB | 2533 | -0.0149 |
| 13 | TSPAN7 | 7102 | 0.0148 |
| 14 | RAC2 | 5880 | -0.0148 |
| 15 | KLHDC7B | 113730 | 0.014 |
| 16 | GRB14 | 2888 | 0.0137 |
| 17 | AC138128.1 | N/A | -0.0136 |

TABLE 2B-continued

Gene IDs and EntrezGene IDs for 44-gene DDRD classifier model with associated ranking and weightings
DDRD Classifier - 44 Gene Model (NA: genomic sequence)

| Rank | Gene symbol | EntrezGene ID | Weight |
|---|---|---|---|
| 18 | KIF26A | 26153 | −0.0136 |
| 19 | CD274 | 29126 | 0.0133 |
| 20 | CD109 | 135228 | −0.0129 |
| 21 | ETV7 | 51513 | 0.0124 |
| 22 | MFAP5 | 8076 | −0.0121 |
| 23 | OLFM4 | 10562 | −0.0117 |
| 24 | PI15 | 51050 | −0.0115 |
| 25 | FOSB | 2354 | −0.0111 |
| 26 | FAM19A5 | 25817 | 0.0101 |
| 27 | NLRC5 | 84166 | −0.011 |
| 28 | PRICKLE1 | 144165 | −0.0089 |
| 29 | EGR1 | 1958 | −0.0086 |
| 30 | CLDN10 | 9071 | −0.0086 |
| 31 | ADAMTS4 | 9507 | −0.0085 |
| 32 | SP140L | 93349 | 0.0084 |
| 33 | ANXA1 | 301 | −0.0082 |
| 34 | RSAD2 | 91543 | 0.0081 |
| 35 | ESR1 | 2099 | 0.0079 |
| 36 | IKZF3 | 22806 | 0.0073 |
| 37 | OR2I1P | 442197 | 0.007 |
| 38 | EGFR | 1956 | −0.0066 |
| 39 | NAT1 | 9 | 0.0065 |
| 40 | LATS2 | 26524 | −0.0063 |
| 41 | CYP2B6 | 1555 | 0.0061 |
| 42 | PTPRC | 5788 | 0.0051 |
| 43 | PPP1R1A | 5502 | −0.0041 |
| 44 | AL137218.1 | N/A | −0.0017 |

TABLE 2C

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| FYB | BRAD.10849_at | 83 |
| CLDN10 | BRAD.10890_at | 84 |
| PPP1R1A | BRAD.11026_at | 85 |
| PI15 | BRAD.12809_at | 86 |
| MFAP5 | BRAD.14326_s_at | 87 |
| ESR1 | BRAD.15436_s_at | 88 |
| FYB | BRAD.15833_s_at | 89 |
| ESR1 | BRAD.19080_s_at | 90 |
| TERF1P1 | BRAD.2707_at | 91 |
| PRICKLE1 | BRAD.27716_s_at | 92 |
| LATS2 | BRAD.28628_s_at | 93 |
| IKZF3 | BRAD.28643_at | 94 |
| MX1 | BRAD.28663_s_at | 95 |
| CD274 | BRAD.29038_at | 96 |
| FAM19A5 | BRAD.30917_at | 97 |
| LATS2 | BRAD.31470_at | 98 |
| EGFR | BRAD.32716_at | 99 |
| EGFR | BRAD.33042_at | 100 |
| EGFR | BRAD.33341_at | 101 |
| ANXA1 | BRAD.33405_at | 102 |
| EGFR | BRAD.33431_at | 103 |
| KLHDC7B | BRAD.35695_at | 104 |
| IKZF3 | BRAD.35710_at | 105 |
| PTPRC | BRAD.37907_at | 106 |
| TERF1P1 | BRAD.40353_at | 107 |
| EGFR | BRAD.40654_s_at | 108 |
| FYB | BRAD.4701_at | 109 |
| PTPRC | BRAD.5967_at | 110 |
| EGFR | BRAD.7701_at | 111 |
| ESR1 | BREM.1048_at | 112 |
| EGFR | BREM.1129_at | 113 |
| NAT1 | BREM.1226_at | 114 |
| FOSB | BREM.1262_at | 115 |
| OR2I1P | BREM.130_at | 116 |
| ADAMTS4 | BREM.1689_s_at | 117 |
| CYP2B6 | BREM.2334_at | 118 |
| EGFR | BREM.2382_at | 119 |
| ETV7 | BREM.532_at | 120 |
| ANXA1 | BRHP.106_s_at | 121 |
| ESR1 | BRIH.10647C1n2_at | 122 |
| EGFR | BRIH.1453C1n2_at | 123 |
| EGR1 | BRIH.1518C1n4_at | 124 |
| ANXA1 | BRIH.2770C3n31_at | 125 |
| NAT1 | BRIH.365C1n2_at | 126 |
| IFI44L | BRIH.5410C1n7_at | 127 |
| MX1 | BRIH.5478C1n2_s_at | 128 |
| ESR1 | BRIH.5650C1n2_at | 129 |
| CD109 | BRIH.5952C1n2_s_at | 130 |
| CXCL10 | BRIH.7359C1n3_s_at | 131 |
| FYB | BRIHRC.10930C1n2_s_at | 132 |
| AC138128.1 | BRMX.13731C1n18_at | 133 |
| TERF1P1 | BRMX.25436C1n2_at | 134 |
| GBP5 | BRMX.25712C1n2_at | 135 |
| EGR1 | BRMX.3079C1n3_at | 136 |
| EGR1 | BRMX.3079C2n3_at | 137 |
| ESR1 | BRPD.10690C1n5_at | 138 |
| FYB | BRPD.4019C1n3_s_at | 139 |
| GBP5 | BRPD.5301C1n2_at | 140 |
| NLRC5 | BRRS.12588_at | 141 |
| GBP5 | BRRS.13369_s_at | 142 |
| RSAD2 | BRRS.13576_at | 143 |
| PTPRC | BRRS.13647_at | 144 |
| PTPRC | BRRS.13648_s_at | 145 |
| CD109 | BRRS.13767_at | 146 |
| SP140L | BRRS.13859_at | 147 |
| KLHDC7B | BRRS.13881_at | 148 |
| APOL3 | BRRS.14465_s_at | 149 |
| PRICKLE1 | BRRS.15053_at | 150 |
| CLDN10 | BRRS.16228_s_at | 151 |
| EGFR | BRRS.16746_s_at | 152 |
| EGFR | BRRS.16747_at | 153 |
| PRAME | BRRS.16948_s_at | 154 |
| TERF1P1 | BRRS.17863_s_at | 155 |
| TERF1P1 | BRRS.17909_s_at | 156 |
| AL137218.1 | BRRS.18137_at | 157 |
| KIF26A | BRRS.18652_s_at | 158 |
| FYB | BRRS.2573_s_at | 159 |
| CXCL10 | BRRS.2644_s_at | 160 |
| CD2 | BRRS.2783_s_at | 161 |
| EGR1 | BRRS.2935_at | 162 |
| IDO1 | BRRS.3099_at | 163 |
| ITGAL | BRRS.3131_at | 164 |
| LRP4 | BRRS.3220_at | 165 |
| MX1 | BRRS.3319_at | 166 |
| MX1 | BRRS.3319_s_at | 167 |
| RAC2 | BRRS.3645_s_at | 168 |
| MFAP5 | BRRS.4126_s_at | 169 |
| NAT1 | BRRS.455_at | 170 |
| CDR1 | BRRS.4562_at | 171 |
| ANXA1 | BRRS.487_s_at | 172 |
| GRB14 | BRRS.4891_s_at | 173 |
| TSPAN7 | BRRS.4996_at | 174 |
| CYP2B6 | BRRS.524_s_at | 175 |
| ADAMTS4 | BRRS.5356_at | 176 |
| EGFR | BRRS.5451_at | 177 |
| OLFM4 | BRRS.6371_at | 178 |
| FOSB | BRRS.6611_at | 179 |
| PPP1R1A | BRRS.6619_at | 180 |
| PPP1R1A | BRRS.6619-22_at | 181 |
| IFI44L | BRRS.6684_at | 182 |
| CD274 | BRRS.7616_at | 183 |
| LATS2 | BRRS.7901_at | 184 |
| ESR1 | BRRS.81_at | 185 |
| ESR1 | BRRS.81-22_at | 186 |

TABLE 2C-continued

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| FAM19A5 | BRRS.8480_s_at | 187 |
| PI15 | BRRS.8711_at | 188 |
| ETV7 | BRRS.8900_s_at | 189 |
| EGR1 | BRSA.1686C1n5_at | 190 |
| RAC2 | BRSA.8072C1n2_s_at | 191 |
| SP140L | Hs369056.20C1n2_at | 192 |
| EGFR | Hs488293.0CB1n69_at | 193 |
| ANXA1 | Hs494173.0CB4n15_at | 194 |
| GBP5 | Hs513726.0C2n39_s_at | 195 |
| TERF1P1 | Hs514006.0C1n8_at | 196 |
| TERF1P1 | Hs522202.0C1n6_at | 197 |
| PRICKLE1 | Hs524348.0CB1n97_at | 198 |
| PRICKLE1 | Hs524348.2C1n5_s_at | 199 |
| NLRC5 | Hs528836.0C1n3_s_at | 200 |
| TERF1P1 | Hs591893.1C1n4_s_at | 201 |
| RSAD2 | Hs7155.0CB1n102_at | 202 |

TABLE 2D

Almac IDs and Almac Gene symbol and SEQ ID numbers for antisense probe sets in 40-gene signature
(D) Almac IDs and Almac Gene symbol and SEQ ID numbers for antisense probe sets in 40 gene signature

| Gene Symbol | EntrezGene ID (40) | Almac Gene ID (32) | Almac Gene symbol | SEQ ID NO: |
|---|---|---|---|---|
| ADAMTS4 | 9507 | | | |
| ANXA1 | 301 | | | |
| ANXA1 | 301 | AS1_ANXA1 | BRAD.33405_at | 51 |
| APOL3 | 80833 | | | |
| CD109 | 135228 | | | |
| CD2 | 914 | | | |
| CD274 | 29126 | | | |
| CD274 | 29126 | AS1_CD274 | Hs584242.2C1n64_at | 52 |
| CDR1 | 1038 | | | |
| CDR1 | 1038 | AS1_CDR1 | BRRS1RC_NM_004065_at | 53 |
| CLDN10 | 9071 | | | |
| CLDN10 | 9071 | AS1_CLDN10 | BRRS.8182_at | 54 |
| CXCL10 | 3627 | | | |
| CXCL10 | 3627 | AS1_CXCL10 | BRMX.13815C1n5_at | 55 |
| CYP2B6 | 1555 | | | |
| EGFR | 1956 | | | |
| EGFR | 1956 | AS1_EGFR | BRMX.2637C1n26_at | 56 |
| EGFR | 1956 | AS2_EGFR | BRAD.36737_at | 57 |
| EGFR | 1956 | AS3_EGFR | BRAD.3853_at | 58 |
| EGFR | 1956 | AS4_EGFR | BRAD1_19760734_at | 59 |
| EGR1 | 1958 | | | |
| EGR1 | 1958 | AS1_EGR1 | BRMX.2797C4n2_at | 60 |
| ESR1 | 2099 | | | |
| ESR1 | 2099 | AS1_ESR1 | BRMX.10399C1n5_at | 61 |
| ESR1 | 2099 | AS2_ESR1 | BRMX.8912C1n3_at | 62 |
| ETV7 | 51513 | | | |
| FAM19A5 | 25817 | | | |
| FOSB | 2354 | | | |
| FOSB | 2354 | AS1_FOSB | BRMX.13731C1n18_at | 63 |
| FYB | 2533 | | | |
| FYB | 2533 | AS1_FYB | BRAD.25947_at | 64 |
| GBP5 | 115362 | | | |
| GBP5 | 115362 | AS1_GBP5 | BRMX.5143C1n2(2)_at | 65 |
| GRB14 | 2888 | | | |
| IDO1 | 3620 | | | |
| IFI44L | 10964 | | | |
| IFI44L | 10964 | AS1_IFI44L | Hs633116.0C1n30_at | 66 |
| IFI44L | 10964 | AS2_IFI44L | BRSA.1606C1n4(2)_at | 67 |
| ITGAL | 3683 | | | |
| ITGAL | 3683 | AS1_ITGAL | BRAD.41047_at | 68 |
| ITGAL | 3683 | AS2_ITGAL | BRAD.4420_at | 69 |
| KIF26A | 26153 | | | |
| KLHDC7B | 113730 | | | |
| KLHDC7B | 113730 | AS1_KLHDC7B | Hs137007.0C1n9_at | 70 |
| LATS2 | 26524 | | | |
| LATS2 | 26524 | AS1_LATS2 | BRSA.18050C1n3_at | 71 |
| LRP4 | 4038 | | | |
| MFAP5 | 8076 | | | |
| MX1 | 4599 | | | |
| MX1 | 4599 | AS1_MX1 | BRMX.2948C3n7(2)_at | 72 |

TABLE 2D-continued

Almac IDs and Almac Gene symbol and SEQ ID numbers
for antisense probe sets in 40-gene signature
(D) Almac IDs and Almac Gene symbol and SEQ ID numbers for
antisense probe sets in 40 gene signature

| Gene Symbol | EntrezGene ID (40) | Almac Gene ID (32) | Almac Gene symbol | SEQ ID NO: |
|---|---|---|---|---|
| MX1 | 4599 | AS2_MX1 | Hs43047.0C4n40_at | 73 |
| MX1 | 4599 | AS2_MX1 | Hs926.1C10n7_at | 74 |
| NAT1 | 9 | | | |
| NLRC5 | 84166 | | | |
| NLRC5 | 84166 | AS1_NLRC5 | Hs528836.0CB6n98_s_at | 75 |
| OLFM4 | 10562 | | | |
| OLFM4 | 10562 | AS1_OLFM4 | BRMX.7284C1n6_at | 76 |
| PI15 | 51050 | | | |
| PI15 | 51050 | AS1_PI15 | BRAD1_19751014_at | 77 |
| PPP1R1A | 5502 | | | |
| PRAME | 23532 | | | |
| PTPRC | 5788 | | | |
| RAC2 | 5880 | | | |
| RAC2 | 5880 | AS1_RAC2 | BRMX.13502C1n6_at | 78 |
| RSAD2 | 91543 | | | |
| SP140L | 93349 | | | |
| SP140L | 93349 | AS1_SP140L | BRMX.1111C4n3_at | 79 |
| SP140L | 93349 | AS2_SP140L | Hs369056.9C26n3_at | 80 |
| TERF1P1 | 348567 | | | |
| TERF1P1 | 348567 | AS1_TERF1P1 | BRMX.24432C1n2_at | 81 |
| TERF1P1 | 348567 | AS2_TERF1P1 | BRRS.17773_at | 82 |
| TSPAN7 | 7102 | | | |

In different embodiments, subsets of the biomarkers listed in Table 2A and Table 2B may be used in the methods described herein. These subsets include but are not limited to biomarkers ranked 1-2, 1-3, 1-4, 1-5, 1-10, 1-20, 1-30, 1-40, 1-44, 6-10, 11-15, 16-20, 21-25, 26-30, 31-35, 36-40, 36-44, 11-20, 21-30, 31-40, and 31-44 in Table 2A or Table 2B. In one aspect, therapeutic responsiveness is predicted in an individual by conducting an assay on a biological sample from the individual and detecting biomarker values that each correspond to at least one of the biomarkers GBP5, CXCL10, IDO1 and MX1 and at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. In some embodiments, when referring to a biomarker of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, the biomarker comprises an mRNA of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, respectively. In further or other embodiments, when referring to a biomarker of MX1, GBP5, IFI44L, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, the biomarker comprises an antisense transcript of MX1, IFI44L, GBP5, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, respectively.

In a further aspect, therapeutic responsiveness is predicted, or a cancer diagnosis is indicated, in an individual by conducting an assay on a biological sample from the individual and detecting biomarker values that each correspond to the biomarkers GBP5, CXCL10, IDO1 and MX1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. In a further aspect, therapeutic responsiveness is predicted, or a cancer diagnosis is indicated, in an individual by conducting an assay on a biological sample from the individual and detecting biomarker values that each correspond to the biomarker GBP5 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker MX-1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39.

In a further aspect, therapeutic responsiveness is predicted, or a cancer diagnosis is indicated, in an individual by conducting an assay on a biological sample from the individual and detecting biomarker values that each correspond to at least two of the biomarkers CXCL10, MX1, IDO1 and IFI44L and at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarkers CXCL10, MX1, IDO1 and IFI44L and one of at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker MX1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IFI44L and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43.

In other embodiments, the probes listed in Table 2C (SEQ ID NOs:83-202), or subsets thereof, may be used in the methods described herein. These subsets include but are not limited to a subset of SEQ ID NOs corresponding to one or more of GBP5, CXCL10, IDO1, MX1, IF144I, CD2, PRAME, ITGAL, LRP4, and APOL3. In other embodiments, the probes correspond to all of the biomarkers CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. It should be understood that each subset can include multiple probes directed to the same biomarker. For example, the probes represented by SEQ ID NOs: 135, 140, 142 and 195 are all directed to GBP5. Accordingly, a subset containing probes directed or corresponding to GBP5 includes one or more of SEQ ID NOs: 135, 140, 142 and 195. A subset containing probes directed to or corresponding to CXCL10 includes one or more of SEQ ID NOs: 131 and 160.

Measuring Gene Expression Using Classifier Models

A variety of methods have been utilized in an attempt to identify biomarkers and diagnose disease. For protein-based markers, these include two-dimensional electrophoresis, mass spectrometry, and immunoassay methods. For nucleic acid markers, these include mRNA expression profiles, microRNA profiles, FISH, serial analysis of gene expression (SAGE), methylation profiles, and large-scale gene expression arrays.

When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is one that is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression. Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Creating a Biomarker Expression Classifier

In one embodiment, the relative expression levels of biomarkers in a cancer tissue are measured to form a gene expression profile. The gene expression profile of a set of biomarkers from a patient tissue sample is summarized in the form of a compound decision score and compared to a score threshold that is mathematically derived from a training set of patient data. The score threshold separates a patient group based on different characteristics such as, but not limited to, responsiveness/non-responsiveness to treatment. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. The threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc. Using a linear classifier on the normalized data to make a diagnostic or prognostic call (e.g. responsiveness or resistance to therapeutic agent) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is above the score threshold (decision function positive) or below (decision function negative).

Effectively, this means that the data space, i.e. the set of all possible combinations of biomarker expression values, is split into two mutually exclusive halves corresponding to different clinical classifications or predictions, e.g. one corresponding to responsiveness to a therapeutic agent and the other to resistance. In the context of the overall classifier, relative over-expression of a certain biomarker can either increase the decision score (positive weight) or reduce it (negative weight) and thus contribute to an overall decision of, for example, responsiveness or resistance to a therapeutic agent.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In a preferred embodiment of the present method, Partial Least Squares Discriminant Analysis (PLS-DA) is used for determining the weights. (L. Ståle, S. Wold, J. Chemom. 1 (1987) 185-196; D. V. Nguyen, D. M. Rocke, Bioinformatics 18 (2002) 39-50). Other methods for performing the classification, known to those skilled in the art, may also be with the methods described herein when applied to the transcripts of a cancer classifier.

Different methods can be used to convert quantitative data measured on these biomarkers into a prognosis or other predictive use. These methods include, but not limited to methods from the fields of pattern recognition (Duda et al. Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998).

In a training step, a set of patient samples for both responsiveness/resistance cases are measured and the prediction method is optimised using the inherent information from this training data to optimally predict the training set or a future sample set. In this training step, the used method is trained or parameterised to predict from a specific intensity pattern to a specific predictive call. Suitable transformation or pre-processing steps might be performed with the measured data before it is subjected to the prognostic method or algorithm.

In a preferred embodiment of the invention, a weighted sum of the pre-processed intensity values for each transcript is formed and compared with a threshold value optimised on the training set (Duda et al. Pattern Classification, $2^{nd}$ ed., John Wiley, New York 2001). The weights can be derived by a multitude of linear classification methods, including but not limited to Partial Least Squares (PLS, (Nguyen et al., 2002, Bioinformatics 18 (2002) 39-50)) or Support Vector Machines (SVM, (Schölkopf et al. Learning with Kernels, MIT Press, Cambridge 2002)).

In another embodiment of the invention, the data is transformed non-linearly before applying a weighted sum as described above. This non-linear transformation might include increasing the dimensionality of the data. The non-linear transformation and weighted summation might also be performed implicitly, e.g. through the use of a kernel function. (Schölkopf et al. Learning with Kernels, MIT Press, Cambridge 2002).

In another embodiment of the invention, a new data sample is compared with two or more class prototypes, being either real measured training samples or artificially created prototypes. This comparison is performed using suitable similarity measures, for example, but not limited to Euclidean distance (Duda et al. Pattern Classification, $2^{nd}$ ed., John Wiley, New York 2001), correlation coefficient (Van't Veer, et al. 2002, Nature 415:530) etc. A new sample is then assigned to the prognostic group with the closest prototype or the highest number of prototypes in the vicinity.

In another embodiment of the invention, decision trees (Hastie et al., The Elements of Statistical Learning, Springer, New York 2001) or random forests (Breiman, Random Forests, Machine Learning 45:5 2001) are used to make a prognostic call from the measured intensity data for the transcript set or their products.

In another embodiment of the invention neural networks (Bishop, Neural Networks for Pattern Recognition, Clarendon Press, Oxford 1995) are used to make a prognostic call from the measured intensity data for the transcript set or their products.

In another embodiment of the invention, discriminant analysis (Duda et al., Pattern Classification, $2^{nd}$ ed., John Wiley, New York 2001), comprising but not limited to linear, diagonal linear, quadratic and logistic discriminant analysis, is used to make a prognostic call from the measured intensity data for the transcript set or their products.

In another embodiment of the invention, Prediction Analysis for Microarrays (PAM, (Tibshirani et al., 2002, Proc. Natl. Acad. Sci. USA 99:6567-6572)) is used to make a prognostic call from the measured intensity data for the transcript set or their products.

In another embodiment of the invention, Soft Independent Modelling of Class Analogy (SIMCA, (Wold, 1976, Pattern Recogn. 8:127-139)) is used to make a predictive call from the measured intensity data for the transcript set or their products.

Therapeutic Agents

As described above, the methods described herein permit the classification of a patient as responsive or non-responsive to a therapeutic agent that targets tumors with abnormal DNA repair (hereinafter referred to as a "DNA-damage therapeutic agent"). As used herein "DNA-damage therapeutic agent" includes agents known to damage DNA directly, agents that prevent DNA damage repair, agents that inhibit DNA damage signaling, agents that inhibit DNA damage induced cell cycle arrest, and agents that inhibit processes indirectly leading to DNA damage. Some current such therapeutics used to treat cancer include, but are not limited to, the following DNA-damage therapeutic agents.

1) DNA Damaging Agents:
  a. Alkylating agents (platinum containing agents such as cisplatin, carboplatin, and oxaliplatin; cyclophosphamide; busulphan).
  b. Topoisomerase I inhibitors (irinotecan; topotecan)
  c. Topoisomerase II inhibitors (etoposide; anthracyclines such as doxorubicin and epirubicin)
  d. Ionising radiation
2) DNA Repair Targeted Therapies
  a. Inhibitors of Non-homologous end-joining (DNA-PK inhibitors, Nu7441, NU7026)
  b. Inhibitors of homologous recombination
  c. Inhibitors of nucleotide excision repair
  d. Inhibitors of base excision repair (PARP inhibitors, AG014699, AZD2281, ABT-888, MK4827, BSI-201, INO-1001, TRC-102, APEX 1 inhibitors, APEX 2 inhibitors, Ligase III inhibitors
  e. Inhibitors of the Fanconi anemia pathway
3) Inhibitors of DNA Damage Signalling
  a. ATM inhibitors (CP466722, KU-55933)
  b. CHK 1 inhibitors (XL-844, UCN-01, AZD7762, PF00477736)
  c. CHK 2 inhibitors (XL-844, AZD7762, PF00477736)
4) Inhibitors of DNA Damage Induced Cell Cycle Arrest
  a. Wee1 kinase inhibitors
  b. CDC25a, b or c inhibitors
5) Inhibition of Processes Indirectly Leading to DNA Damage
  a. Histone deacetylase inhibitors
  b. Heat shock protein inhibitors (geldanamycin, AUY922), Diseases and Tissue Sources The predictive classifiers described herein are useful for determining responsiveness or resistance to a therapeutic agent for treating cancer. The biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment, this collection of genes or gene products is useful for evaluating both breast and ovarian cancer tumors.

As used herein, cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, and the like.

In one embodiment, the methods described herein refer to cancers that are treated with chemotherapeutic agents of the classes DNA damaging agents, DNA repair target therapies, inhibitors of DNA damage signalling, inhibitors of DNA damage induced cell cycle arrest and inhibition of processes indirectly leading to DNA damage, but not limited to these classes. Each of these chemotherapeutic agents is considered a "DNA-damage therapeutic agent" as the term is used herein.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

In such cases, the target cells may be tumor cells, for example colon cancer cells or stomach cancer cells. The target cells are derived from any tissue source, including human and animal tissue, such as, but not limited to, a newly obtained sample, a frozen sample, a biopsy sample, a sample of bodily fluid, a blood sample, preserved tissue such as a paraffin-embedded fixed tissue sample (i.e., a tissue block), or cell culture.

Methods and Kits

Kits for Gene Expression Analysis

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a biomarker expression analysis, such as reagents for performing RT-PCR, qPCR, northern blot, proteomic analysis, or immunohistochemistry to determine expression levels of biomarkers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below.

The kits featured herein can also include an instruction sheet describing how to perform the assays for measuring biomarker expression. The instruction sheet can also include instructions for how to determine a reference cohort, including how to determine expression levels of biomarkers in the reference cohort and how to assemble the expression data to establish a reference for comparison to a test patient. The instruction sheet can also include instructions for assaying biomarker expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The kits featured herein can also contain software necessary to infer a patient's likelihood of having a positive response to a specific therapeutic agent from the biomarker expression.

a) Gene Expression Profiling Methods

Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for predicting responsiveness of a cancer therapeutic agent, where the methods comprise detecting, in a biological sample from an individual, at least N biomarker values that each correspond to a biomarker selected from the group consisting of the biomarkers provided in Tables 1 or 2, wherein a classification, as described in detail below, using the biomarker values indicates whether the individual will be responsive to a therapeutic agent. While certain of the described predictive biomarkers are useful alone for predicting responsiveness to a therapeutic agent, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays"). Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes' to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Clinical Uses

In some embodiments, methods are provided for identifying and/or selecting a cancer patient who is responsive to a therapeutic regimen. In particular, the methods are directed to identifying or selecting a cancer patient who is responsive to a therapeutic regimen that includes administering an agent that directly or indirectly damages DNA. Methods are also provided for identifying a patient who is non-responsive to a therapeutic regimen. These methods typically include determining the level of expression of a collection of predictive markers in a patient's tumor (primary, metastatic or other derivatives from the tumor such as, but not limited to, blood, or components in blood, urine, saliva and other bodily fluids)(e.g., a patient's cancer cells), comparing the level of expression to a reference expression level, and identifying whether expression in the sample includes a pattern or profile of expression of a selected predictive biomarker or biomarker set which corresponds to response or non-response to therapeutic agent.

In some embodiments a method of predicting responsiveness of an individual to a DNA-damage therapeutic agent comprises the following steps: obtaining a test sample from the individual; measuring expression levels of one or more biomarkers in the test sample, wherein the one or more biomarkers are selected from the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and responsiveness; and comparing the test score to the threshold score; wherein responsiveness is predicted when the test score exceeds the threshold score. One of ordinary skill in the art can determine an appropriate threshold score, and appropriate biomarker weightings, using the teachings provided herein including the teachings of Example 1.

In other embodiments, the method of predicting responsiveness of an individual to a DNA-damage therapeutic agent comprises measuring the expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a likelihood that the individual will be responsive to a DNA-damage therapeutic agent.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways, for instance, the size of a tumor or the expression of tumor markers appropriate for that tumor type may be measured.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc.

An application of this test will predict end points including, but not limited to, overall survival, progression free survival, radiological response, as defined by RECIST, complete response, partial response, stable disease and serological markers such as, but not limited to, PSA, CEA, CA125, CA15-3 and CA19-9.

Alternatively, non-array based methods for detection, quantification and qualification of RNA, DNA or protein within a sample of one or more nucleic acids or their biological derivatives such as encoded proteins may be employed, including quantitative PCR (QPCR), enzyme-linked immunosorbent assay (ELISA) or immunohistochemistry (IHC) and the like.

After obtaining an expression profile from a sample being assayed, the expression profile is compared with a reference or control profile to make a diagnosis regarding the therapy responsive phenotype of the cell or tissue, and therefore host, from which the sample was obtained. The terms "reference" and "control" as used herein in relation to an expression profile mean a standardized pattern of gene or gene product expression or levels of expression of certain biomarkers to be used to interpret the expression classifier of a given patient and assign a prognostic or predictive class. The reference or control expression profile may be a profile that is obtained from a sample known to have the desired phenotype, e.g., responsive phenotype, and therefore may be a positive reference or control profile. In addition, the reference profile may be from a sample known to not have the desired phenotype, and therefore be a negative reference profile.

If quantitative PCR is employed as the method of quantitating the levels of one or more nucleic acids, this method quantifies the PCR product accumulation through measurement of fluorescence released by a dual-labeled fluorogenic probe (i.e. TaqMan® probe).

In certain embodiments, the obtained expression profile is compared to a single reference profile to obtain information regarding the phenotype of the sample being assayed. In yet other embodiments, the obtained expression profile is compared to two or more different reference profiles to obtain more in depth information regarding the phenotype of the assayed sample. For example, the obtained expression profile may be compared to a positive and negative reference profile to obtain confirmed information regarding whether the sample has the phenotype of interest.

The comparison of the obtained expression profile and the one or more reference profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228, 575, the disclosures of which are herein incorporated by reference. Methods of comparing expression profiles are also described above.

The comparison step results in information regarding how similar or dissimilar the obtained expression profile is to the one or more reference profiles, which similarity information is employed to determine the phenotype of the sample being assayed. For example, similarity with a positive control indicates that the assayed sample has a responsive phenotype similar to the responsive reference sample. Likewise, similarity with a negative control indicates that the assayed sample has a non-responsive phenotype to the non-responsive reference sample.

The level of expression of a biomarker can be further compared to different reference expression levels. For example, a reference expression level can be a predetermined standard reference level of expression in order to evaluate if expression of a biomarker or biomarker set is informative and make an assessment for determining whether the patient is responsive or non-responsive. Additionally, determining the level of expression of a biomarker can be compared to an internal reference marker level of expression which is measured at the same time as the biomarker in order to make an assessment for determining whether the patient is responsive or non-responsive. For example, expression of a distinct marker panel which is not comprised of biomarkers of the invention, but which is known to demonstrate a constant expression level can be assessed as an internal reference marker level, and the level of the biomarker expression is determined as compared to the reference. In an alternative example, expression of the selected biomarkers in a tissue sample which is a non-tumor sample can be assessed as an internal reference marker level. The level of expression of a biomarker may be determined as having increased expression in certain aspects. The level of expression of a biomarker may be determined as having decreased expression in other aspects. The level of expression may be determined as no informative change in expression as compared to a reference level. In still other aspects, the level of expression is determined against a pre-determined standard expression level as determined by the methods provided herein.

The invention is also related to guiding conventional treatment of patients. Patients in which the diagnostics test reveals that they are responders to the drugs, of the classes that directly or indirectly affect DNA damage and/or DNA damage repair, can be administered with that therapy and both patient and oncologist can be confident that the patient will benefit. Patients that are designated non-responders by the diagnostic test can be identified for alternative therapies which are more likely to offer benefit to them.

The invention further relates to selecting patients for clinical trials where novel drugs of the classes that directly or indirectly affect DNA damage and/or DNA damage repair. Enrichment of trial populations with potential responders will facilitate a more thorough evaluation of that drug under relevant criteria.

The invention still further relates to methods of diagnosing patients as having or being susceptible to developing a cancer associated with a DNA damage response deficiency (DDRD). DDRD is defined herein as any condition wherein a cell or cells of the patient have a reduced ability to repair DNA damage, which reduced ability is a causative factor in the development or growth of a tumor. The DDRD diagnosis may be associated with a mutation in the Fanconi anemia/BRCA pathway. The DDRD diagnosis may also be associated with breast cancer or ovarian cancer. These methods of diagnosis comprise the steps of obtaining a test sample from the individual; measuring expression levels of one or more biomarkers in the test sample, wherein the one or more biomarkers are selected from the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and a diagnosis of the cancer; and comparing the test score to the threshold score; wherein the individual is determined to have the cancer or is susceptible to developing the cancer when the test score exceeds the threshold score. One of ordinary skill in the art can determine an appropriate threshold score, and appropriate biomarker weightings, using the teachings provided herein including the teachings of Example 1.

In other embodiments, the methods of diagnosing patients as having or being susceptible to developing a cancer associated with DDRD comprise measuring expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a diagnosis of cancer or of being susceptible to developing a cancer.

The following examples are offered by way of illustration and not by way of limitation.

EXAMPLES

Example 1

Tissue Processing, Hierarchical Clustering, Subtype Identification and Classifier Development Tumor Material The genes determined to be useful in the present methods (Table 2) were identified from gene expression analysis of a cohort of 107 macrodissected breast tumor FFPE tissue samples sourced from the Mayo Clinic Rochester. Ethical approval for this study was obtained from the Institutional Review Board and the Office of Research Ethics Northern Ireland.

This cohort of samples can be further described as follows:
- 47 samples were wild-type for BRCA1 and BRCA2 i.e. expressed biologically functional BRCA1 and BRCA2 proteins. These samples shall henceforth be referred to as sporadic controls.
- 31 samples were BRCA1 mutant i.e. did not express biologically functional BRCA1 protein.
- 29 samples were BRCA2 mutant i.e. did not express biologically functional BRCA2 protein.

Gene Expression Profiling

Total RNA was extracted from the macrodissected FFPE tumor samples using the Roche High Pure RNA Paraffin Kit (Roche Diagnostics GmbH, Mannheim, Germany). Total RNA was amplified using the NuGEN WT-Ovation™ FFPE System (NuGEN Technologies Inc., San Carlos, Calif., USA). The amplified single-stranded cDNA was then fragmented and biotin labeled using the FL-Ovation™ cDNA Biotin Module V2 (NuGEN Technologies Inc.). It was then hybridized to the Almac Breast Cancer DSA™. The Almac's Breast Cancer DSA™ research tool has been optimised for analysis of FFPE tissue samples, enabling the use of valuable archived tissue banks. The Almac Breast Cancer DSA™ research tool is an innovative microarray platform that represents the transcriptome in both normal and cancerous breast tissues. Consequently, the Breast Cancer DSA™ provides a comprehensive representation of the transcriptome within the breast disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MAS5 pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end of a polynucleotide. Therefore standard Affymetrix RNA quality measures were adapted—for housekeeping genes intensities of 3' end probesets along with ratios of 3' end probeset intensity to the average background intensity were used in addition to usual 3'/5' ratios. Hybridization controls were checked to ensure that their intensities and present calls conform to the requirements specified by Affymetrix.

Tumor samples from the BRCA1/2 mutant and sporadic control training set were split into 2 datasets based on the transcript levels of ESR1 (Estrogen receptor 1). mRNA expression level $E_{.avg}$ for each sample was determined by the average expression of all ESR1 probe sets (BRAD.15436_s_at, BRAD.19080_s_at, BREM.1048_at, BRIH.10647C1n2_at, BRIH.5650C1n2_at, BRPD.10690C1n5_at, BRRS.81_at and BRRS.81-22_at). The mRNA median expression ($E_{.med.all}$) was calculated for all samples. Samples were considered ER positive when $E_{.avg} - E_{.med.all} > 0.5$ and ER negative when $E_{.avg} - E_{.med.all} < 0.5$.

Pre-processing was performed in expression console v1.1 with Robust Multi-array Analysis (RMA) (Irizarry et al., 2003) resulting in 2 data matrices of ER positive and ER negative samples composed of 56 and 51 samples respectively. An additional transformation was performed to remove the variance associated with array quality as described by Alter (Alter et al., 2000).

Feature Selection

A combined background & variance filter was applied to each data matrix to identify the most variable probesets. The background filter is based on the selection of probe sets with expression E and expression variance $var_E$ above the thresholds defined by background standard deviation σBg (from the Expression Console software) and quantile of the standard normal distribution $z_a$ at a specified significance a probesets were kept if:

$$E > \log_2(\Box z_a \sigma_{Bg} \Box); \Box \log_2(\Box var_E) > 2\ [\log_2(\sigma_{Bg}) - E - \log_2(\log(2))]$$

where the significance threshold was $a = 6.3 \cdot 10^{-5}$, see Table 1 for the list of selected probesets and their gene annotations.

Hierarchical Clustering Analysis

Figure 1B:
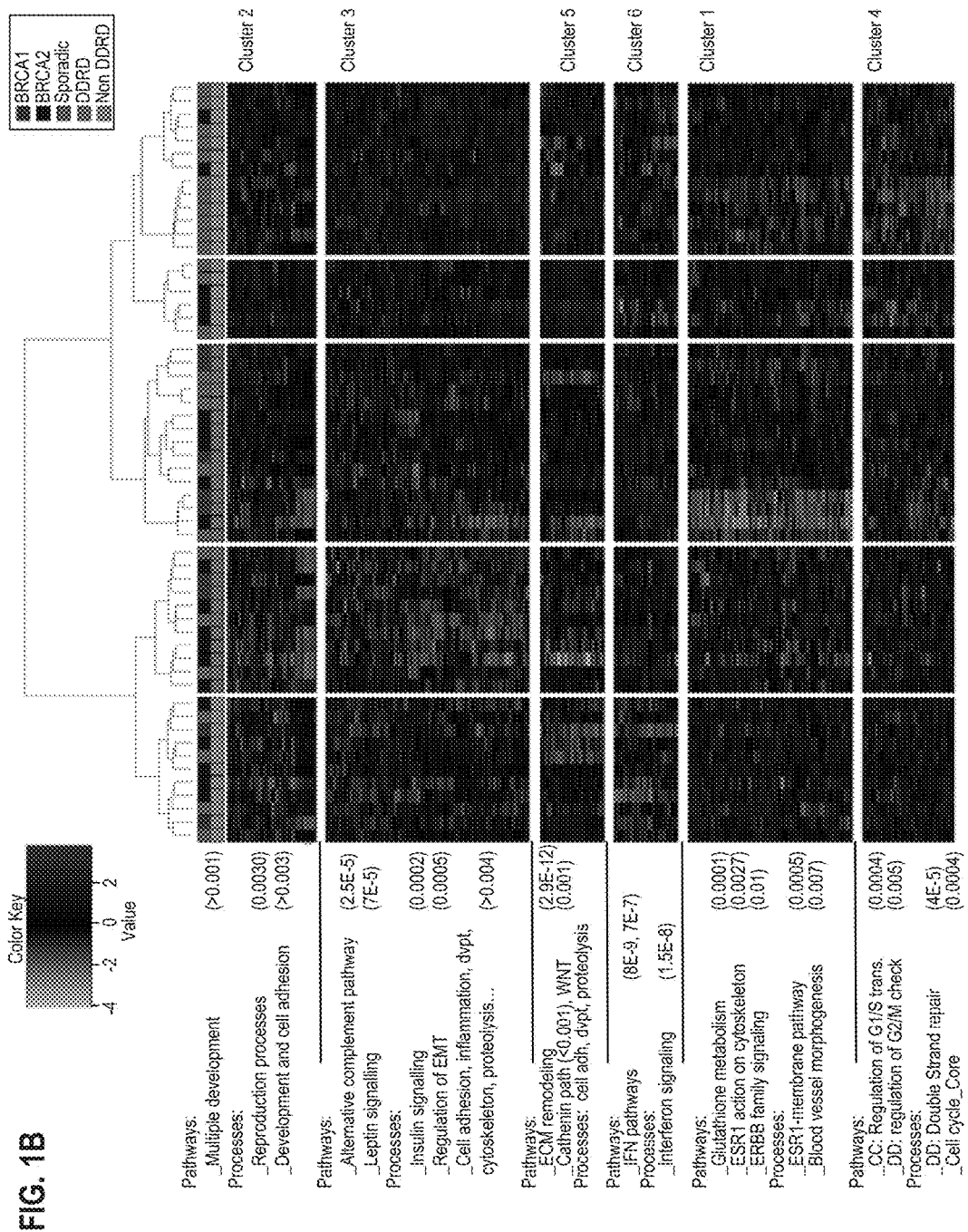
Figure 2A:
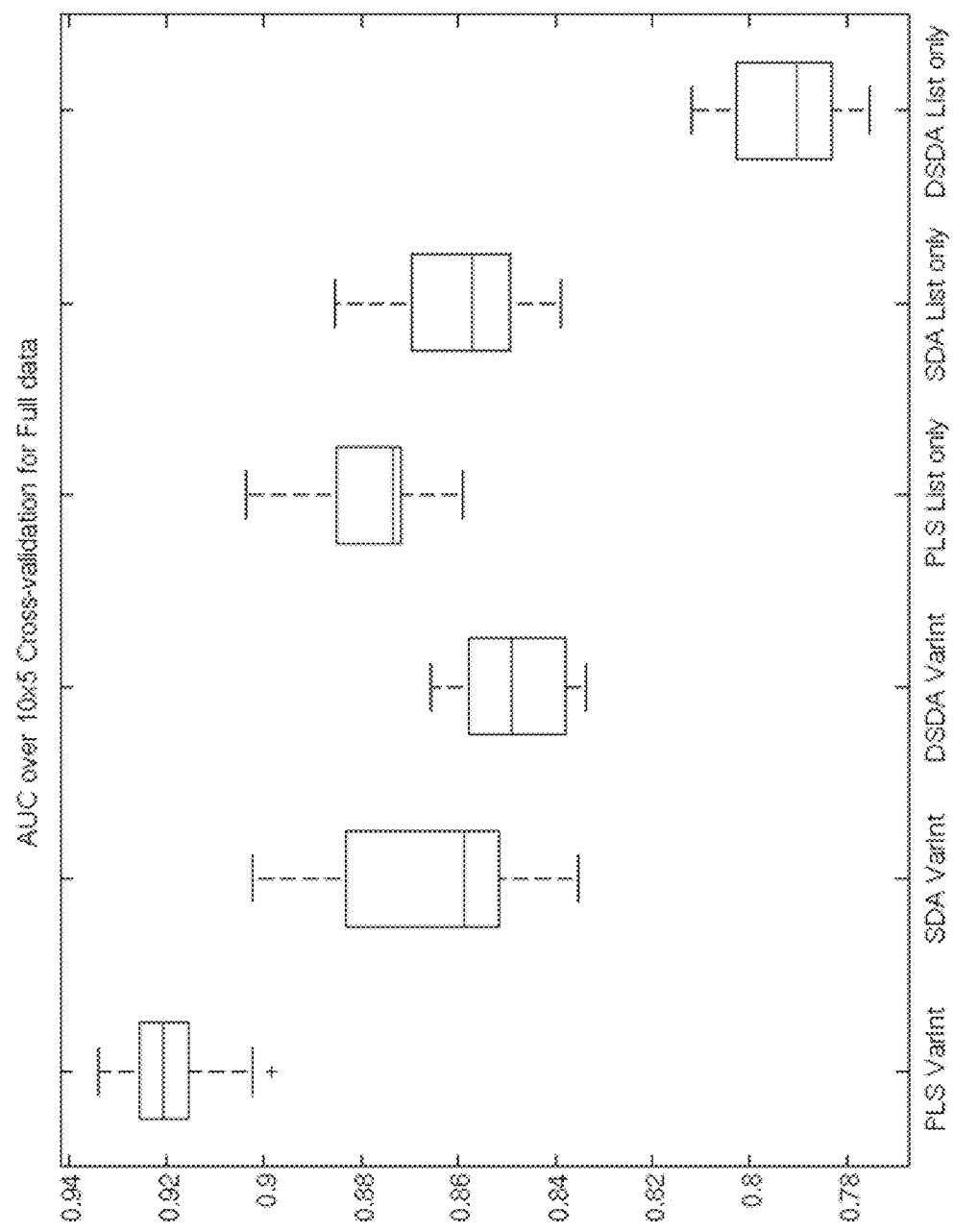
FIG. 2A, FIG. 2B, FIG. 2C, and FIG. 2D provide a diagramofbox plots comparing the AUC performance of each classification model under a 10 repeats of 5-fold cross validation for (FIG. 1A) the combined sample set, (FIG. 1B) the ER-negative sample set and (FIG. 1C) the ER-positive sample set.
Figure 2B:
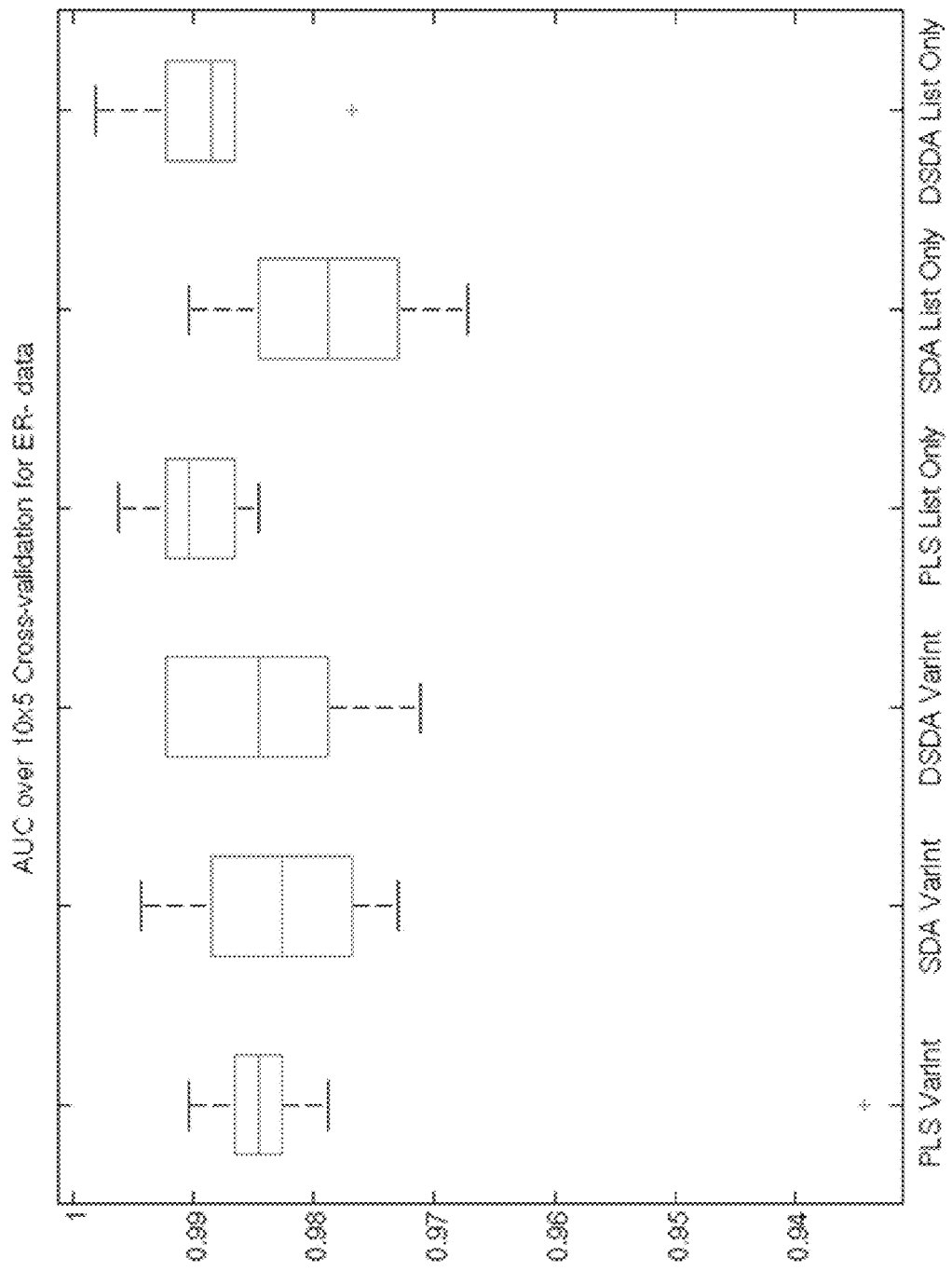
Figure 2C:
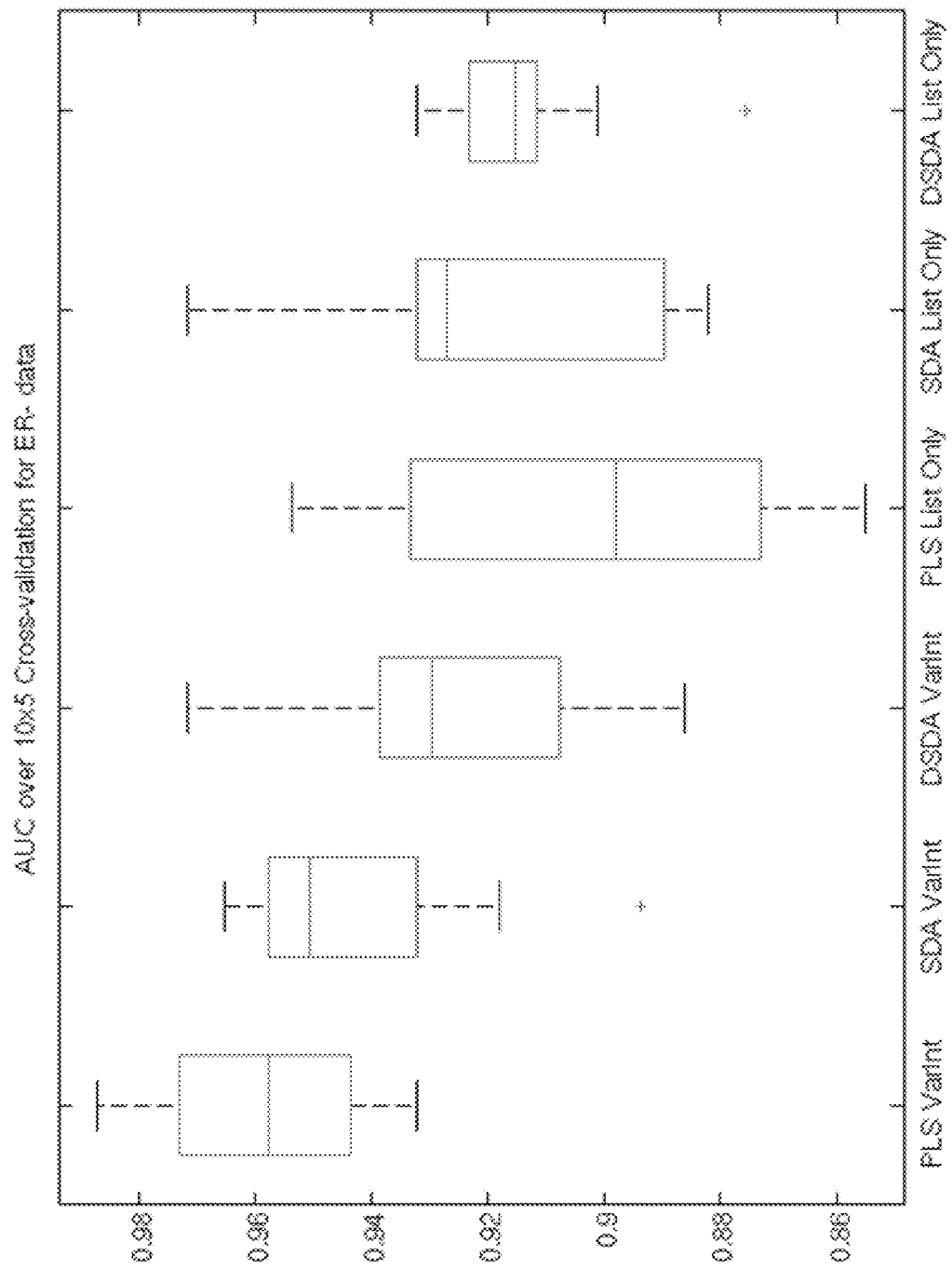
Figure 2D:
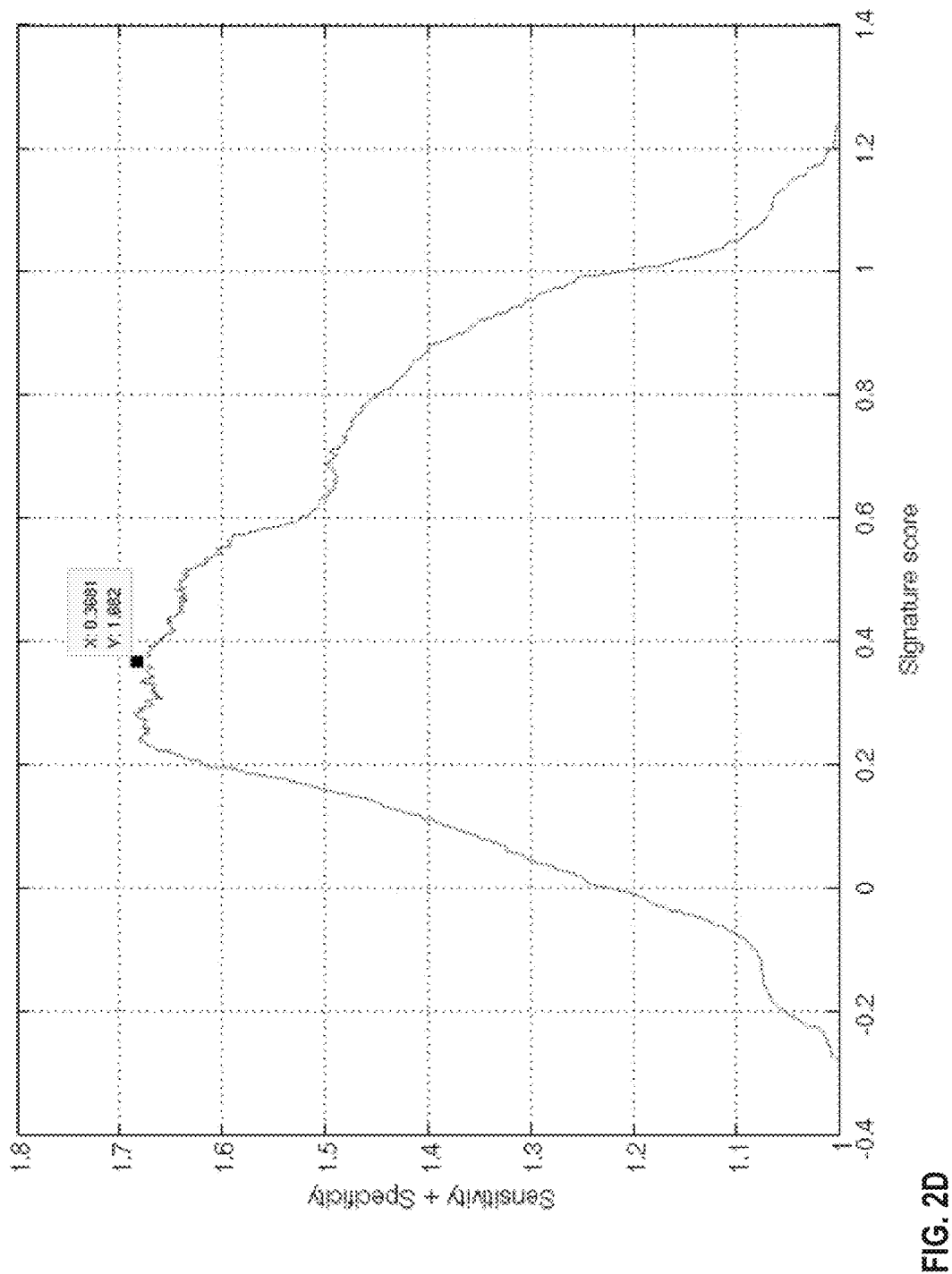

Hierarchical clustering techniques were applied to microarray data from 199 epithelial serous ovarian tumors analysed using the Ovarian Cancer DSA™ (disease specific array) platform (FIG. 1). Raw expression data was preprocessed using the standard Robust Multichip Algorithm (RMA) procedure. Non-biological systematic variance in the data set was identified and removed. Those probesets whose expression levels varied significantly from tumor to tumor were identified. These probesets formed the intrinsic list.

2-D cluster analysis (tumor, probeset) was performed to establish tumor relationships based on the intrinsic list. Hierarchical agglomerative clustering was applied (Pearson correlation distance and Ward's linkage). Optimal partition number was selected using the GAP index (Tibshirani et al., 2002, J. R. Stat. Soc., 63:411-423). All probesets available in the subclusters were mapped to genes names.

Functional Analysis of Gene Clusters

To establish the functional significance of the probeset clusters, probesets were mapped to genes (Entrez gene ID) and an enrichment analysis, based on the hypergeometric function (False Discovery Rate applied (Benjamini and Hochberg, 1995, J. R. Stat. Soc. 57:289:300)), was performed. Over-representation of biological processes and pathways were analysed for each gene group generated by the hierarchical clustering for both ER-positive and ER-negative samples using Metacore™ single experiment analysis workflow from GeneGo®. Antisense probesets were excluded from the analysis. Hypergeometric p-values were assessed for each enriched functional entity class. Functional entity classes with the highest p-values were selected as representative of the group and a general functional category representing these functional entities was assigned to the gene clusters based on significance of representation (i.e. p-value).

Genes in clusters enriched for the IFN/DD general functional terms were grouped into a DNA-damage response-deficiency (DDRD) sample group and used for the classifier generation. The sample clusters from ER-positive and ER-negative datasets represented by the IFN/DD general functional terms were selected for classification and labelled as DDRD. Those not represented by these functional terms were labelled as non-DDRD.

Classifier Development at a Probeset Level

Following the identification of a class of tumors that form the DDRD subgroup, computational classification of these tumors vs. all the others in the tumor cohort (non-DDRD) was performed, with reference to the functional DDRD gene list (Table 1), to identify a refined gene classification model that classifies the DDRD subgroup. This was evaluated using all combinations of the following options (a total of 18):

Three Sample Sets
  Combined sample set of ER-negative and ER-positive samples (combined sample set)
  ER-negative samples alone
  ER-positive samples alone Two Feature Sets
  Full feature list with 75% variance/intensity filtering and forced inclusion of the DDRD list. Here 75% of the probesets with the lowest combined variance and intensity were removed, based on the average rank of both. When used, the term "VarInt" refers to this option.
  DDRD list only. When used, the term "List only" refers to this option.

Three Classification Algorithms
  PLS (Partial Least Squares) (de Jong, 1993)
  SDA (Shrinkage Discriminate Analysis)(Ahdesmaki and Strimmer, 2010)
  DSDA (Diagonal SDA)(Ahdesmaki and Strimmer, 2010)

The AUC was used to assess the performance of the different models. Iterative Feature Elimination (IFE) was implemented throughout the development of each model, where the maximum AUC was the main criteria in selecting an optimal number of features over cross validation. In cases where there was no visible AUC difference across features, the minimum feature length was selected.

Classifier Development at a Gene Level

To facilitate validation of the classifier across multiple array platforms, the selected probeset classifier was regenerated at the gene level. A redevelopment of the probeset classifier at a gene level required two separate steps:

1. The expression intensities of the unique genes in the probeset classifier were estimated from the median of the probesets mapping to each gene, excluding antisense probesets.
2. The classifier parameters used for classification were re-estimated A threshold was chosen based on the maximum sensitivity and specificity over all cross validation predictions.

Similarly the gene level defined expression intensities for the 10 top genes (or any number of features present in current 44 gene signature) could be used to re-develop the classifier based on only these 10 genes (or any number of features present in current 44 gene signature) by re-estimating classification parameters in cross-validation in the training data set as well as to re-establish the threshold by assessing and maximising the sensitivity and specificity obtained from all cross-validation predictions. The methodology would be similar to the method used when working from a larger feature set (described above) except there will be no feature selection involved: the features will remain the same but will be assigned new weights.

Calculating Classifier Scores for Validation Data Sets

Public Datasets

The datasets used for this analysis are namely: FAC1 [GEO accession number GSE20271, (Tabchy et al., 2010), FAC2 [GEO accession number GSE22093, (Iwamoto et al., 2011)], FEC [GEO accession number GSE6861, (Bonnefoi et al., 2007)], T/FAC1 (Hess et al., 2006)], T/FAC2 [GEO accession number GSE16716, (Lee et al., 2010)] and T/FAC3 [GEO accession number GSE20271, (Tabchy et al., 2010)]. It must be noted that there is an overlap in 31 samples between the FAC1 and FAC2 datasets. These samples were removed from the FAC2 dataset and as such were only included once in the combined analysis of the FAC1, FAC2 and FEC datasets. In addition, sample GSM508092 was removed from FAC1 as it is a metastatic lymph node sample.

All datasets were pre-processed using RMA (Irizarry et al., 2003). For each validation set, the probesets that map to the classifier genes were determined, excluding antisense probesets (if applicable). Annotation for Affymetrix X3P and U133A arrays are available from the Affymetrix website. The median intensity over all probesets mapping to each gene in the classifier was calculated, resulting in a gene intensity matrix. The classifier was then applied to this data matrix to produce a classifier score/prediction for each sample.

Calculating Performance Metrics

To calculate NPV and PPV, the prevalence of each end point (BRCA status/Response) was estimated using the proportions of each class in the corresponding data set.

Univariate and Multivariate Analysis

Univariate and multivariate analysis was carried out to assess respectively the association between the DDRD classifier and response, and to determine if the association, if any, was independent to known clinical predictors. The p-values presented Table 4, for univariate analysis were calculated using logistic regression in MATLAB. For the multivariate analysis we used step-wise logistic regression (Dupont, 2009), where the p-values represent the log-likelihood of the variable. The log-likelihood is a measure of the importance of the variable's fit to the model, thus highlighting it's independence as a predictor relative to the other predictors. In both univariate and multivariate analysis, a p-value <0.05 was used as the criterion for significance. Furthermore, samples with unknown clinical factors were excluded in this assessment.

Results

Selection of Samples for Classifier Generation

The objective of this study was to characterize at a transcriptomic level a set of genes that would be capable of determining responsiveness or resistance of a pathogenic cell to DNA-damage therapeutic agents. With this in mind, those samples within the Almac breast cancer dataset that best represented this biology were to be selected and compared to the remaining samples for classifier generation (see next section). It was decided that the samples from sample cluster two within the ER−ve sample set were the most relevant samples for this selection as these showed the greatest proportion of BRCA mutant samples (64%) and they exhibited the most dominant biology (IFN/immune response). From within the ER+ve sample set, the samples from sample cluster two and three were selected as these sample clusters had 73% and 67% BRCA mutant tumors respectively. In addition, the most dominant biology within these clusters was related to cell cycle, DNA damage response and IFN/immune response Immune signaling and cell-cycle pathways have been reported to be modulated in response to DNA-damage (Jackson, S. P., and Bartek, J., Nature 461, 1071-1078 (2009); Rodier, F., et al., Nat Cell Biol 11, 973-979 (2009); Xu, Y., Nat Rev Immunol 6, 261-270 (2006), and these subgroups were combined to form a putative DDRD subgroup. Those samples within cluster two of the ER−ve sample set (described below) and clusters two and three of the ER+ve sample set (described below) were class labelled DDRD (DNA damage response deficient) (see FIG. 1A) whilst the samples within sample clusters one and three of the ER−ve sample set and sample clusters one, four, five and six of the ER+ve sample set were class labeled non-DDRD (see FIG. 1B).

ER−ve sample set: Within the ER−ve sample set, the hierarchical cluster analysis defined three sample clusters and six probeset cluster groups. Probeset cluster three was identified as the most significant biology within the ER−ve sample set and was enriched for interferon and immune response signaling.

ER+ve sample set: Within the ER+ve sample set, the hierarchical analysis defined six sample groups and six probeset cluster groups. Probeset cluster five was identified as the most significant biology within the ER+ve sample set and was enriched for extracellular matrix remodeling. The next most significant probeset cluster within the ER+ve sample set is probeset cluster six and again was enriched for interferon and immune response signaling.

Development and Validation of the DDRD Classifier Model

Following the identification of a class of tumors, that form the DDRD subgroup, computational classification of these tumors vs. all others in the tumor cohort with reference to the functional DDRD (IFN/DNA damage) gene list was performed to identify a refined gene classification model, which classifies the DDRD subgroup.

The classification pipeline was used to derive a model using the set of combined ER−ve and ER+ve breast cancer samples. The classification pipeline has been developed in accordance with commonly accepted good practice [MAQC Consortium, Nat Biotechnol 2010]. The process will, in parallel: 1) derive gene classification models from empirical data; and 2) assess the classification performance of the models, both under cross-validation. The performance and success of the classifier generation depends on a number of parameters that can be varied, for instance the choice of classification method or probe set filtering. Taking this into account, two feature sets were evaluated (i) the full feature list with 75% variance/intensity filtering (with forced inclusion of the DDRD (IFN/DNA damage) list, Table 1) and (ii) the DDRD (IFN/DNA damage) list only; and three classification algorithms were evaluated, namely PLS (Partial Least Squares); SDA (Shrinkage Discriminate Analysis) and DSDA (Diagonal SDA). Iterative Feature Elimination (IFE) was used throughout model development, which is an iterative procedure removing a fraction of the worst-ranked features at each iteration; stopping when only a minimum number of features remain. The Area under the Receiver Operating Characteristics Curve (AUC-ROC), denoted AUC, was used to assess the classification performance, as this measure is independent of cut-off between groups and prevalence rates in the data. It is also one of the recognized measurements of choice for classification performance. As such, the best number of features for each model was chosen based on the average AUC under cross-validation.

A cross comparison of the models was made, by first selecting the best number of features for each model based on the highest average AUC, and then using box-plots to visualize the performance for each model. This is demonstrated in FIG. 2. From left to right, the first three plots represent the PLS, SDA and DSDA classifiers respectively that were developed using an initial filtering of probe sets to remove 75% with the lowest average variance and intensity (forcing the inclusion of the gene list). The next three plots respectively represent the PLS, SDA and DSDA classifiers developed using the DDRD (IFN/DNA damage) list only.

From FIG. 2, it is clear that the 'PLS VarInt' classification model, comprising 53 probe sets, is the highest performing model, with a significantly higher AUC than the majority of the other 5 models. This model was then taken forward to the next phase for validation on independent external data sets, to assess the ability of the DDRD classification scores to stratify patients with respect to response and prognosis.

A non-orthodox approach to validating the classification model was taken, due to the fact that the validation data sets where either public or internal data with different array platforms. Commonly used approaches are not designed to be applicable to alternative array platforms, and as such a phased approach for classification model development and independent validation was followed:

1. Phase I—Model generation at the probe set level, selecting the best model under cross validation for classifying the DDRD subgroup (described previously)
2. Phase II—Transformation of the probe set level classification model to a gene level classification model
3. Phase III—Validation of re-developed gene classification model using external data sets Having selected a candidate model to progress to the validation stage, this model needed to be re-built at the gene level (Phase II). This involved mapping the probe sets in the classification model to the gene level and recalculating the weights for each gene. The 53 probe sets in the selected model mapped to 40 genes listed in Table 2A and subsequently mapped to 44 genes listed in Table 2B when the accuracy of the annotation pipeline was improved through further analysis.

In the re-development of the gene classification model, to ensure that all information relating to the gene is used, the median intensity of all probe sets associated with each gene (Table 2C) is used as the gene expression value. This was calculated for all samples, resulting in a gene expression data matrix, as opposed to a probe set expression data matrix that was used in Phase I for model development and selection. To stabilize the intensities across different batches, the median of all probe sets for each sample was subtracted from the corresponding intensity of each gene for that sample.

New weights were calculated for each gene using PLS regression, resulting in the final gene classifier models (40-gene and 44-gene classifier models) that may be used for validation on external data sets from different array platforms (Phase III).

In Phase III, the validation of the classifier using data sets that may be from other array platforms, the following steps were taken:
1. The probe sets that map to the genes in the classifier are determined, excluding antisense probe sets (if applicable)
2. The median intensity over all probe sets relating to each gene in the classifier is calculated resulting in a reduced gene intensity matrix
    a. If no probe sets exist for the gene on the particular array platform, the observed average from the training data will be used as a replacement
3. The median value of all probe sets for each sample is calculated and subtracted from the reduced gene intensity matrix
4. The value for each gene is multiplied by the "weight" of that gene in the signature.
5. The values obtained in point 4 for each of the genes in the signature are added together to produce a signature score for that sample.
6. The classifier produces a score for each sample, which can then be used to stratify patients from say, more likely to respond to less likely to respond.

Example 2

In Silico Validation of the 44-gene DDRD Classifier Model

The performance of the 44-gene DDRD classifier model was validated by the Area Under the ROC (Receiver Operator Characteristic) Curve (AUC) within the original Almac breast dataset and three independent datasets. The AUC is a statistic calculated on the observed disease scale and is a measure of the efficacy of prediction of a phenotype using a classifier model (Wray et. al., PLoS Genetics Vol 6, 1-9). An AUC of 0.5 is typical of a random classifier, and an AUC of 1.0 would represent perfect separation of classes. Therefore, in order to determine if the 44-gene DDRD classifier model is capable of predicting response to, and selecting patients for, standard breast and ovarian cancer therapeutic drug classes, including DNA damage causing agents and DNA repair targeted therapies, the hypothesis is that the AUCs following application within these datasets should be above 0.5 with the lowest confidence interval also above 0.5.

Assessment of 44-gene Classifier Model's Ability to Separate BRCA Mutant from Sporadic Tumors The classifier scores for predicting DDRD status were utilized to assess the ability of the model to separate BRCA mutant samples from sporadic samples. This analysis was performed to assess the relationships between the classifier model and BRCA mutation status. BRCA mutant tumors display a high degree of genomic instability due to a deficiency in DNA damage response by virtue of the loss of functional BRCA1/2. As such, the hypothesis is that the DDRD classifier models should be able to separate BRCA mutant samples from BRCA wildtype sporadic samples.

Figure 3:
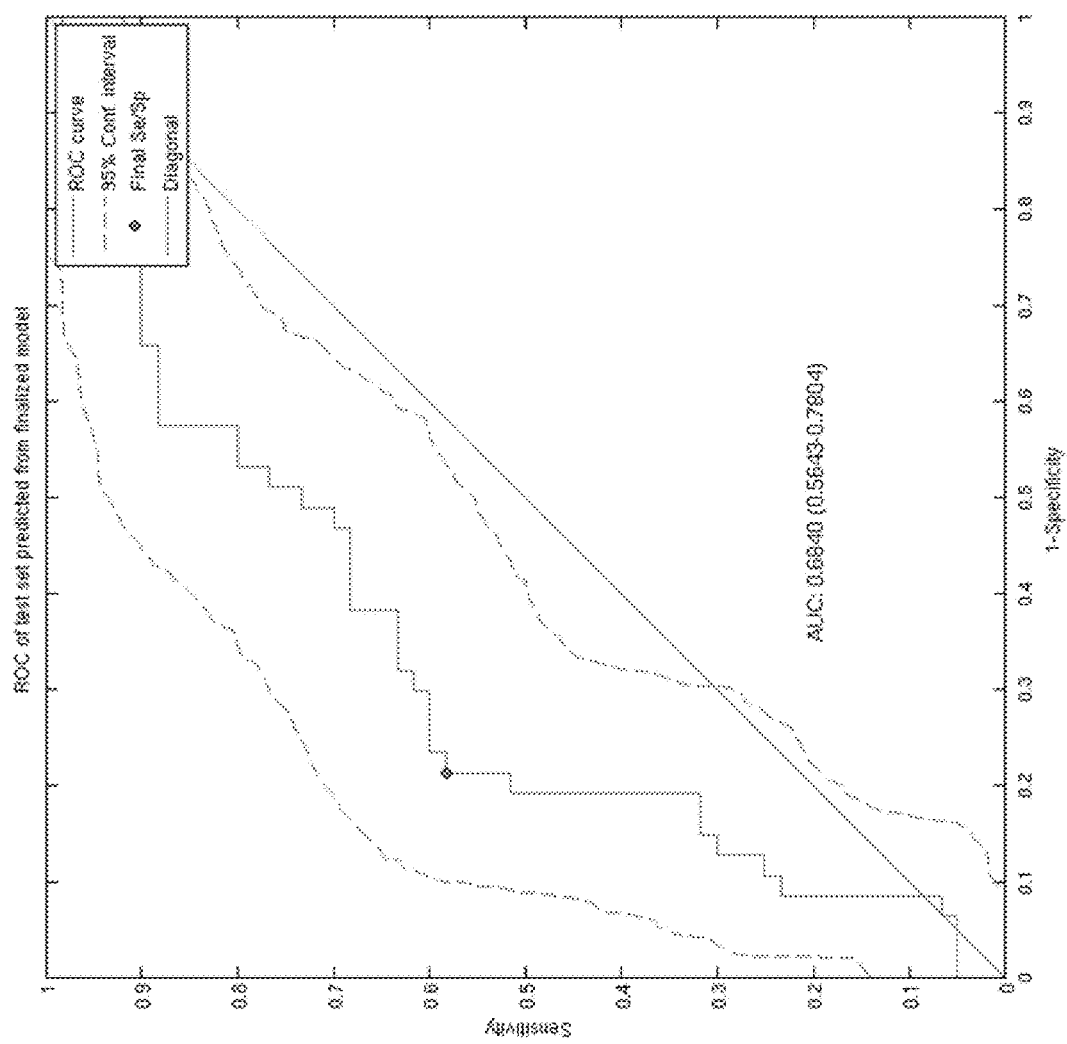
FIG. 3 provides a diagram of a ROC curve of the classification performance for predicting BRCA status using the 44-gene classifier model, estimated by cross validation. The AUC is ~0.68 following application the classifier model. The 95% confidence limits have been estimated from bootstrap with 1000 iterations.

FIG. 3 shows that the 44-gene classifier models separate the BRCA mutants from the sporadic samples with an AUC of ~0.68, where the lower confidence interval is ~0.56 for both models (Table 3A); showing that the performance is significantly better than a random classifier. As such, this analysis confirms that the 44-gene DDRD classifier model is capable of identifying samples with high genomic instability due to an inability to repair DNA damage.

Application of Classifier Model to Independent Microarray Clinical Datasets

Independent Breast Microarray Clinical Datasets
(1) Assessment of the 44-gene DDRD Classifier Model's Predictive Power to DNA-damaging Chemotherapy To assess the ability of the 44-gene DDRD classifier model to predict response to DNA-damaging chemotherapeutics, it was applied to data combined from three publicly available datasets. In each study, breast cancer patients were treated with neoadjuvant 5-fluorouracil, anthracycline, and cyclophosphamide-based regimens, drugs that directly damage DNA. The first (Tabchy et al., 2010) and second (Iwamoto et al., 2011) datasets had response data for 87 and 50 ER-positive and ER-negative primary breast tumor samples respectively following neoadjuvant treatment with fluorouracil, doxorubicin and cyclophosphamide (FAC). The third dataset (Bonnefoi et al., Lancet Oncol 8, 1071-1078(2007)) had response data for 66 ER-negative primary breast tumor samples following neoadjuvant 5-fluorouracil, epirubicin and cyclophosphamide (FEC) treatment. Each study used pathological complete response (pCR) or residual disease (RD) as endpoints. As each dataset was relatively small, the data was combined to increase the power of the analysis.

Figure 4:
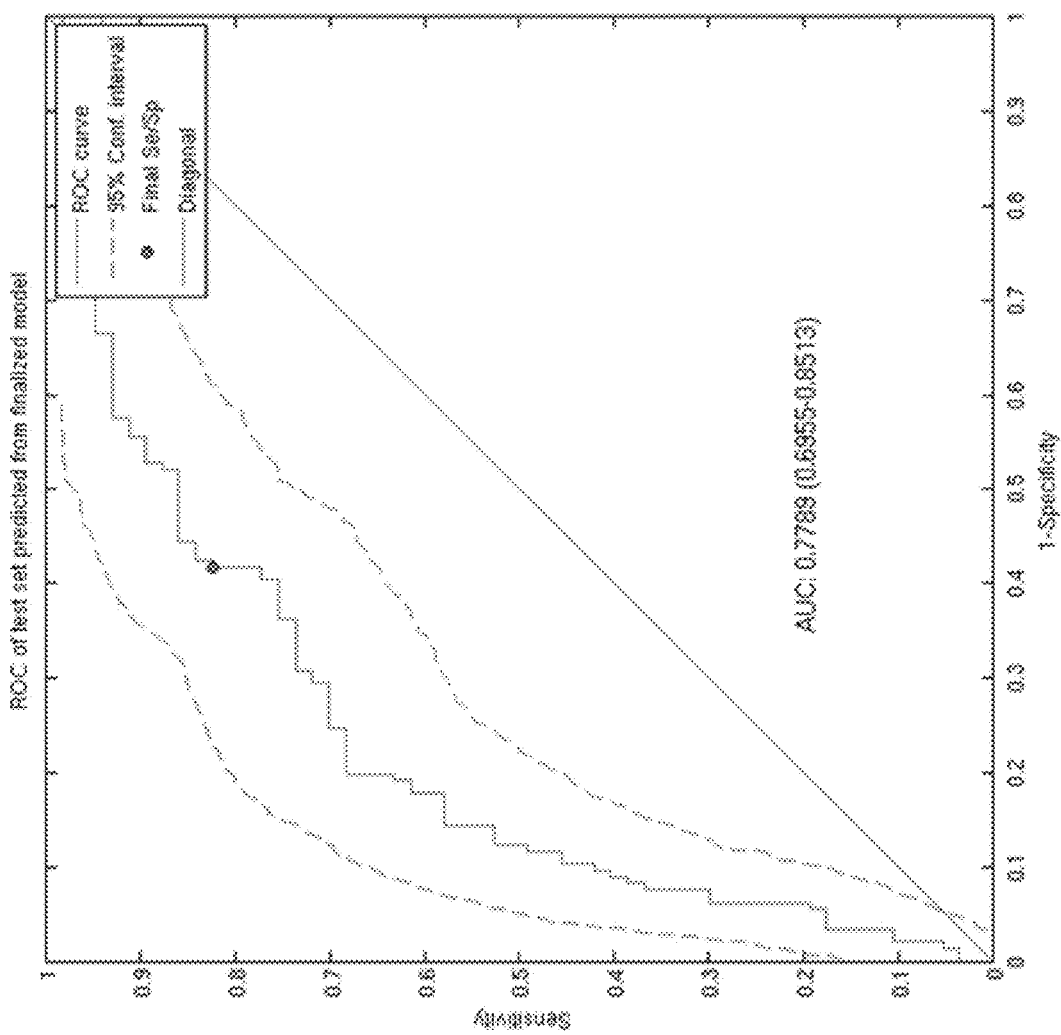
FIG. 4 provides a diagram of a ROC curve of the classification performance of the 44-gene classifier model in a combined analysis of three independent datasets: FEC, FAC1 and FAC2 (Bonnefoi et al., 2007; Iwamoto et al., J Natl Cancer Inst 103, 264-272 (2011); Lee, J. K., et al. Clin Cancer Res 16, 711-718 (2010) for predicting response to anthracycline-based chemotherapy. The AUC is ~0.78 following application of the classifier model. The 95% confidence limits have been estimated from bootstrap with 1000 iterations.

The analysis revealed that that the 44-gene DDRD classifier model was significantly associated with response to anthracycline-based chemotherapy (relative risk (RR)=4.13, CI=1.94-9.87; AUC=0.78, CI=0.70-0.85, P=0.001; Table 3B, FIG. 4). The negative predictive value (NPV) of the classifier was considerably higher than the positive predictive value (PPV) (0.90 versus 0.44, Table 3B), indicating that DDRD-negative tumors were unlikely to respond to DNA-damaging chemotherapy.

Stepwise logistic regression was used to determine the ability of the 44-gene DDRD classifier model to predict response in the combined datasets when adjusting for clinical variables (Table 4). The 44-gene DDRD classifier model was determined to be the most significant clinical variable in univariate analysis. Multivariate analysis confirmed that the 44-gene DDRD classifier model's predictive value was independent of stage, grade and notably ER status.

Negativity for estrogen, progesterone and HER2 receptors has been suggested as a biomarker of abnormal DDR and thus response to DNA-damaging and DNA repair targeted therapies (Foulkes et al., 2010). However, this approach excludes the 20% of BRCA1 and the 40% of BRCA2 mutant tumors that are reported to be ER-positive (Foulkes et al., 2004; Tung et al., 2010). In contrast, by virtue of the analysis approach we adopted, the 44-gene DDRD classifier detects the DDRD subgroup in both ER-positive and ER-negative tumors, as validated by the multivariate analysis of the 44-gene DDRD classifier's predictive value within the combined analysis of FEC and FAC datasets, demonstrating its independence from ER status. Clinically, this is an important aspect of the translational application of the DDRD classifier as it suggests it can be applied to all breast cancer patients, irrespective of ER status, to determine their predicted responsiveness to DNA-damaging therapeutics.

Figure 5:
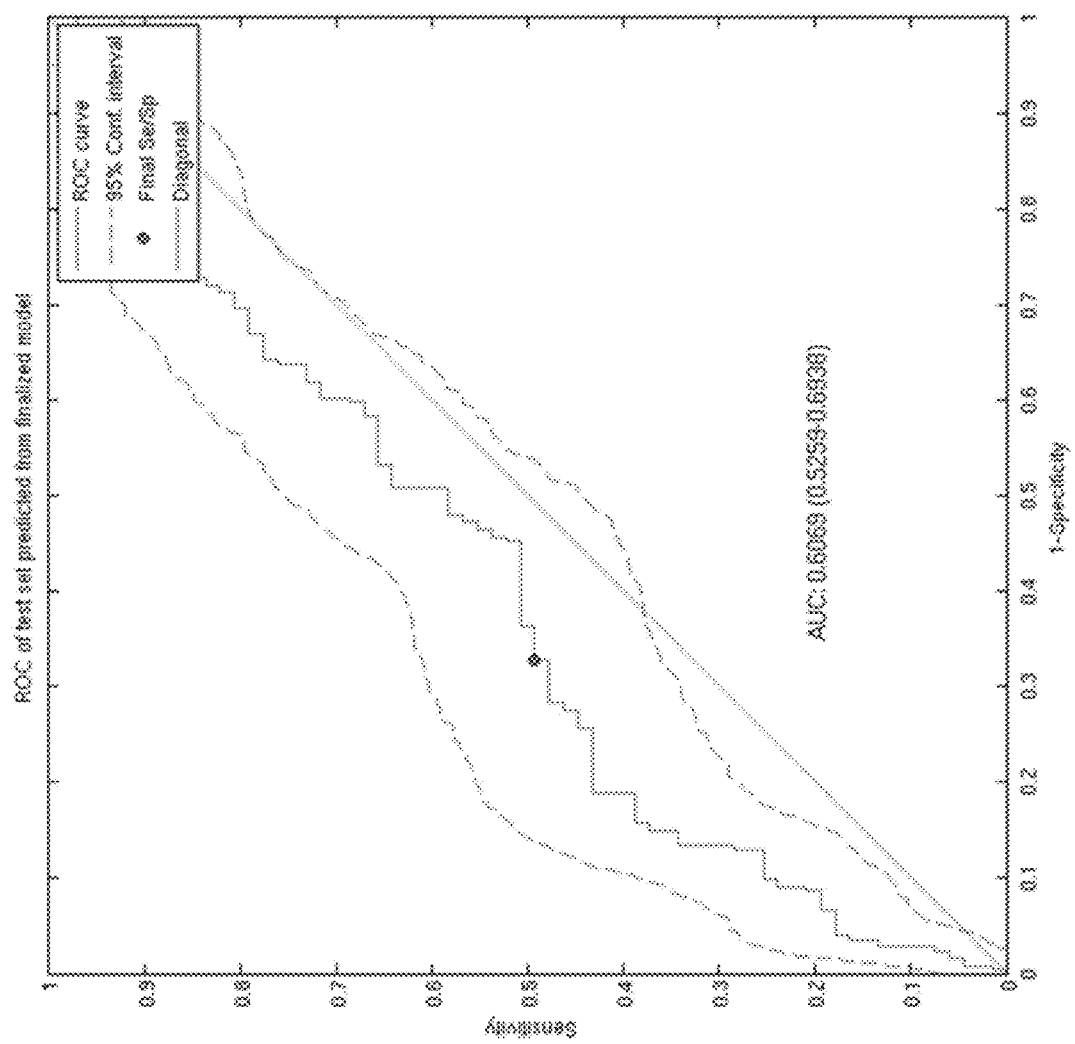
FIG. 5 provides a diagram of a ROC curve of the classification performance of the 44-gene classifier model in a combined analysis of three independent datasets in response in T/FAC treated samples (Hess et al., J Clin Oncol 24, 4236-4244 (2006); Lee et al., 2010; Tabchy, A., et al. Clin Cancer Res 16, 5351-5361 (2010). The AUC is ~0.61 following application of the classifier model respectively. The 95% confidence limits were determined using 1000 bootstrap iterations.

(2) Assessment of 44-gene DDRD classifier model's predictive power to taxane-containing chemotherapy regimens The ability of the 44-gene DDRD classifier model to predict response to chemotherapy regimens that contained non-DNA-damaging agents such as taxanes was assessed. Data was combined from 3 datasets with response data following neoadjuvant treatment with paclitaxel and FAC (T/FAC) for 321 primary breast cancer patients, where response was defined as pCR (Hess et al., 2006; Lee et al., 2010; Tabchy et al., 2010). Whilst the 44-gene DDRD classifier model was both associated with response (AUC=0.61, CI=~0.52-0.69, Table 3B, FIG. 5), this performance was significantly reduced compared to that within the FAC/FEC only treated samples. In addition, multivariate analysis indicated the DDRD classifier was not independent from other clinical parameters (P=0.21) in its ability to predict response to T/FAC (Table 4). This suggests that the subgroup detected by the DDRD classifier is more sensitive to DNA-damaging only regimens rather than regimens also containing anti-microtubule agents.

Independent Ovarian Microarray Clinical Datasets

Figure 6:
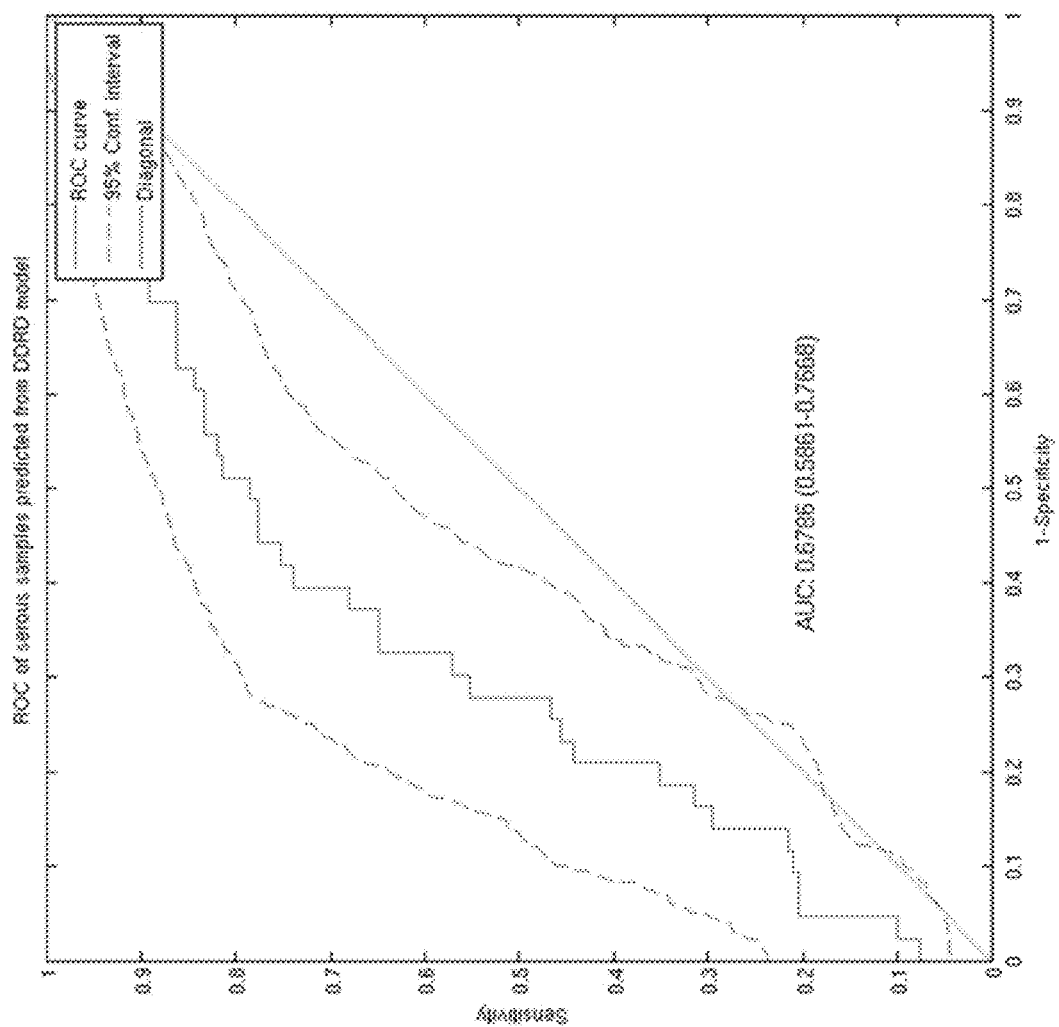
FIG. 6 provides a diagram of a ROC curve of the classification performance of the 44-gene classifier model within 259 serous ovarian cancer samples in response in platinum and taxol treated samples from the in-house Almac Diagnostics ovarian dataset. The AUC is ~0.68 following application of the classifier model. The 95% confidence limits were determined using 1000 bootstrap iterations.

It was decided to explore the performance of the 44-gene DDRD classifier model in another disease area. As such, the performance of the classifier models was assessed within a set of 259 FFPE primary ovarian cancer samples with serous histology. These samples were from patients that received either adjuvant platinum treatment or adjuvant platinum and taxane treatment and were profiled on the Ovarian cancer DSA™. Response data was determined by RESIST and/or the serum marker CA125 levels. Applying the 44-gene DDRD classifier model to these samples proved to separate the responders from the non-responders significantly, with an AUC of ~0.68 and a lower confidence limit of approx 0.59 (FIG. 6). The 44-gene DDRD classifier model detects dysfunction of the Fanconi Anemia/BRCA pathway.

Figure 7:
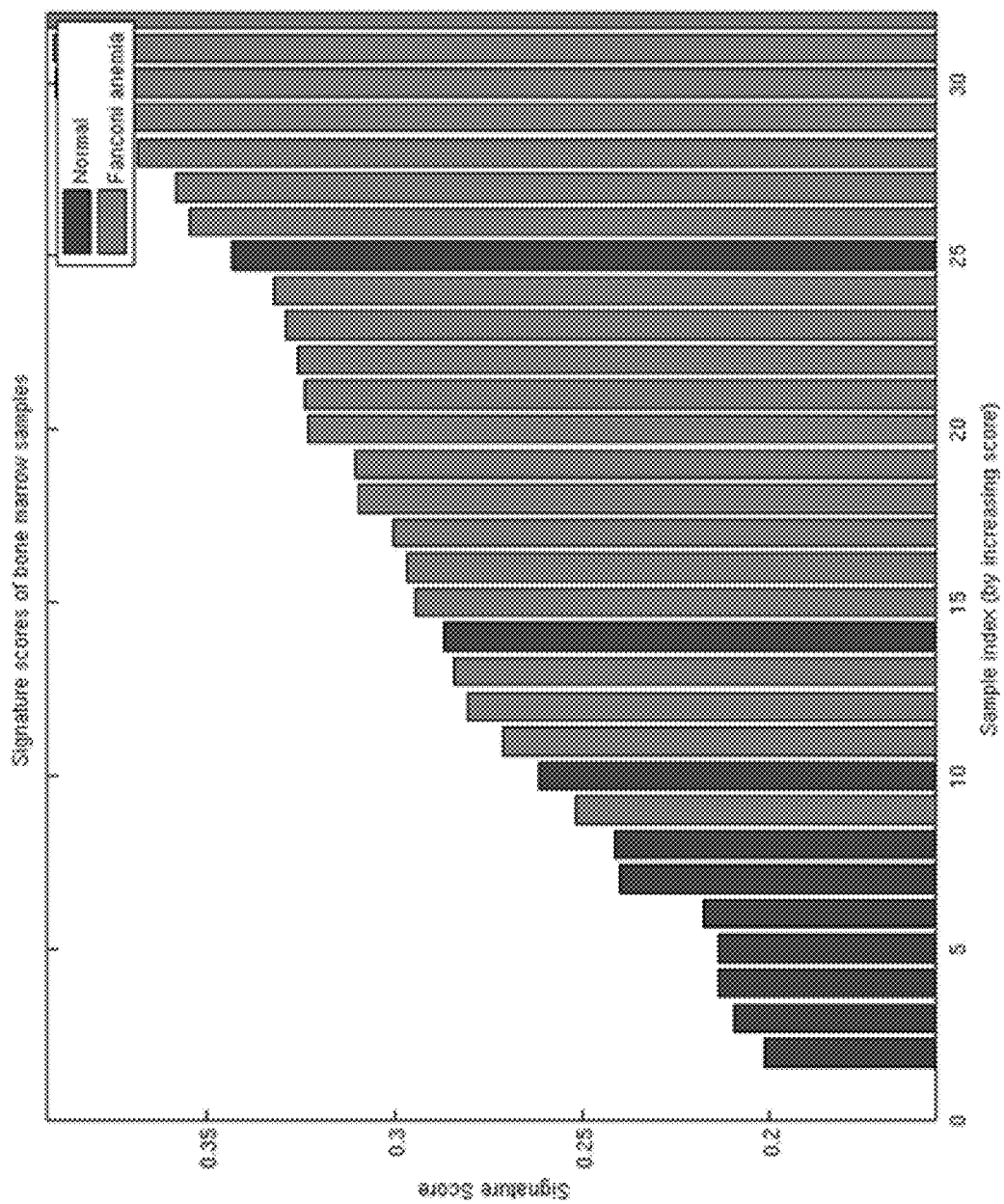
FIG. 7 provides a histogram representation of the 44-gene DDRD classifier scores in bone marrow samples taken from healthy donors and patients with Fanconi Anaemia mutations. The AUC is 0.90 following application of the classifier model. The 95% confidence limits were determined using 1000 bootstrap iterations.
Figure 8A:
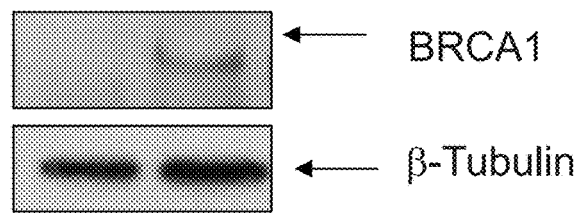
FIG. 8A, FIG. 8B, FIG. 8C, and FIG. 8D provide a figure correlating the 44-gene classifier model with therapeutic response in BRCA1 mutant and wildtype cell-lines.
Figure 8B:
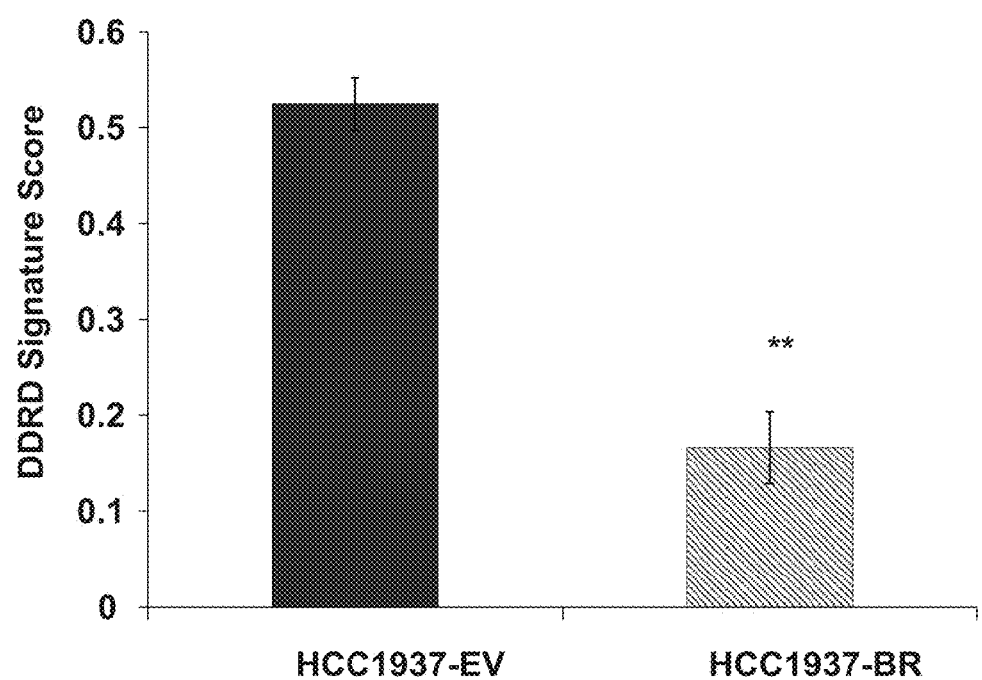
Figure 8C:
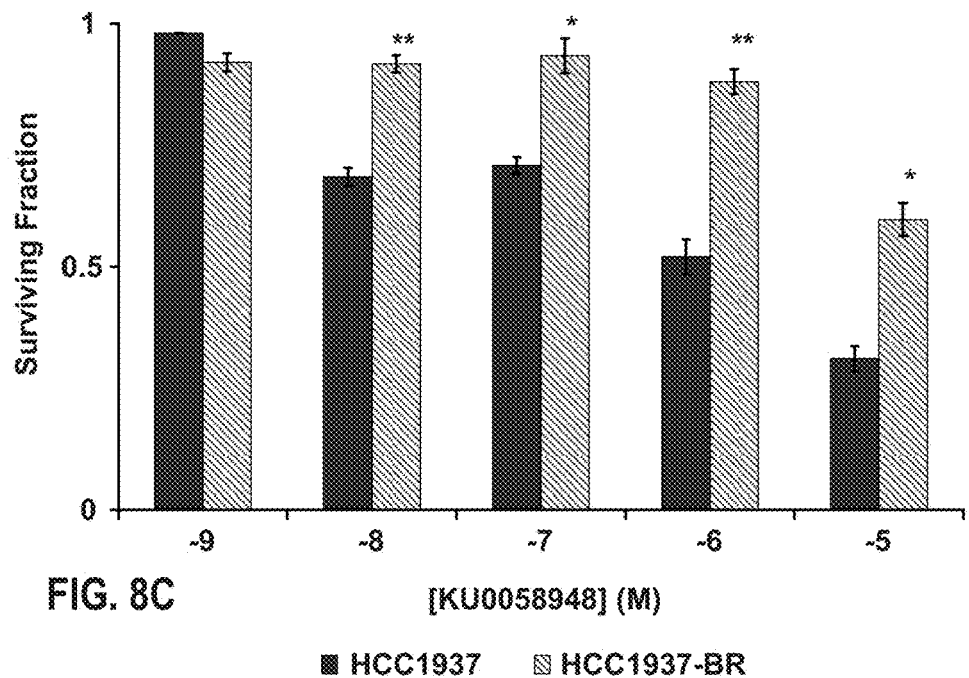
Figure 8D:
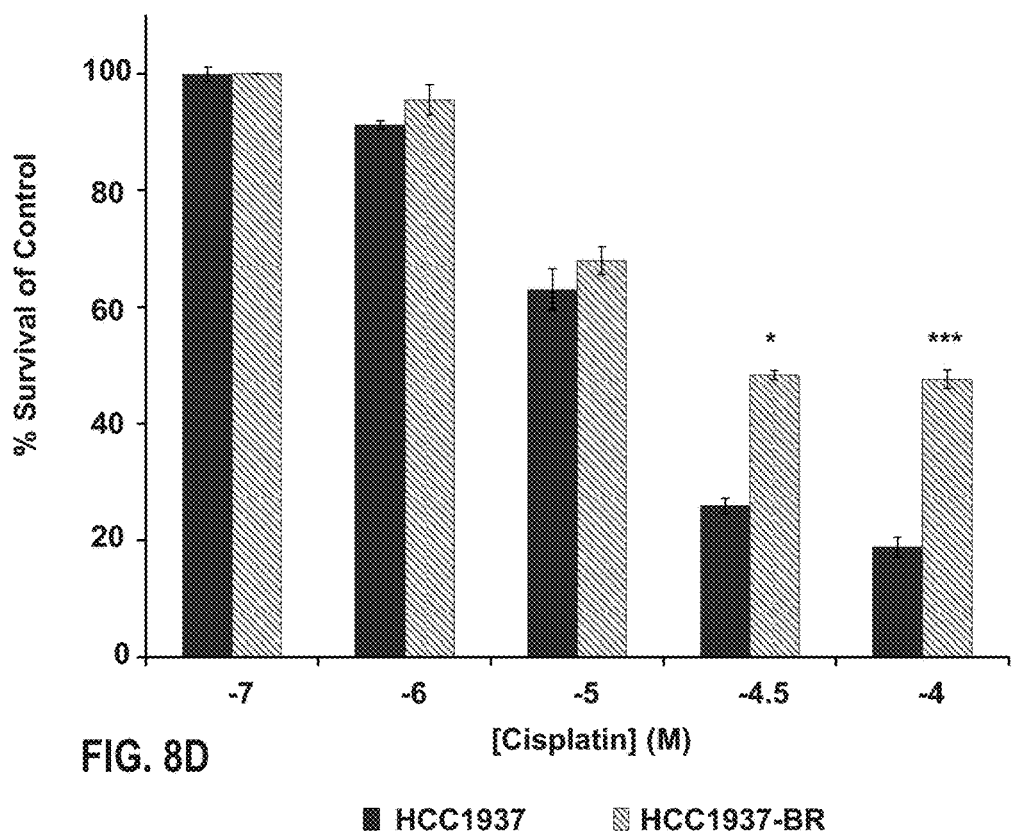

The Fanconi anemia/BRCA (FA/BRCA) pathway, which includes BRCA1 and BRCA2, plays an integral role in DNA repair and can be lost in breast cancer either due to mutation or epigenetic silencing (Kennedy and D'Andrea, 2006). It was therefore determined if the 44-gene DDRD classifier model could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf, S. M., et al., Blood 114, 5290-5298 (2009). The 44-gene DDRD classifier model significantly distinguished between the FA/BRCA mutant and normal samples with an AUC of 0.90 (CI=0.76-1.00, P<0.001, FIG. 7), demonstrating a strong correlation between the DDRD classifier and dysfunction of the FA/BRCA pathway through multiple mechanisms.

Summary of In Silico Validation of 44-Gene DDRD Classifier Model

The in silico validation of the 44-gene DDRD classifier model has shown the following:

(a) The 44-gene DDRD classifier model is able to significantly separate BRCA mutant breast tumor samples from wildtype BRCA (sporadic) breast tumor samples. This implies that the DDRD classifier model is capable of detecting biology related to tumors with a high level of genomic instability, such as BRCA mutant tumors. These tumors typically respond better to DNA damaging chemotherapeutic regimens.

(b) The 44-gene DDRD classifier model is able to significantly separate defined responders (those that demonstrated pCR) from the non-responders (those that did not demonstrate pCR) in a combination of three independent breast datasets following neoadjuvant treatment with FAC and FEC (Bonnefoi et al., 2007; Iwamoto et al., 2011; Tabchy et al., 2010) and T/FAC (Hess et al., 2006; Lee et al., 2010; Tabchy et al., 2010). The 44-gene DDRD classifier model was found to be independent of other clinical factors and the most significant independent predictor of response in the FAC/FEC combined analysis. These studies were carried out using fresh frozen (FF) samples and using two different microarray platforms, namely the Affymetrix X3P microarray and the Affymetrix U133A microarray. These results validate the performance of the 44-gene DDRD classifier model within independent breast datasets utilizing a different sample material (FF instead of FFPE) and utilizing microarray data from two different microarray platforms.

(c) The 44-gene DDRD classifier model is able to significantly separate responders from non-responders within an independent Almac ovarian dataset following adjuvant treatment with platinum or platinum/taxane based therapy. This data was generated using FFPE samples profiled upon the Almac Ovarian DSA™.

(d) The 44-gene DDRD classifier model is able to significantly distinguish between FA/BRCA mutant and normal samples using bone marrow tissue samples, demonstrating a strong correlation between the DDRD classifier and dysfunction of the FA/BRCA pathway through multiple mechanisms.

In summary, the DDRD classifier model has been independently validated and demonstrated robustness in performance across three different disease areas (breast, ovarian and FA), demonstrated ability to separate responders from non-responders to four different chemotherapeutic regimens (FAC, FEC, T/FAC and platinum/taxane) in two different sample types (FFPE and FF) utilizing data from four different microarray platforms (Almac Breast DSA™ and Almac Ovarian DSA™, Affymetrix X3P microarray and Affymetrix U133A microarray). It has been demonstrated that the DDRD is an independent predictor of response to DNA-damage therapeutic agents and can predict mutations in the FA/BRCA pathways. This plasticity and repeatability of performance implies that the biology identified within the DDRD subgroup identified via the 44-gene classifier model is significantly and robustly related to predicting response to DNA damage causing agents and as such supports the claim of this invention which is to identify a subtype that can be used to predict response to, and select patients for, standard breast and ovarian cancer therapeutic drug classes, including drugs that damage DNA directly, damage DNA indirectly or inhibit normal DNA damage signaling and/or repair processes.

Methods

Maintenance of Cell-Lines

The HCC1937 parental, HCC1937-EV and HCC1937-BR cell-lines were kindly donated by Professor Paul Harkin from Queen's University College Belfast (QUB). The cell-lines were routinely maintained in RPMI-1640 medium

TABLE 3

Performance metrics and independence assessment of the 44-gene DDRD classifier model in breast datasets

| Data set | No. | Treatment | Clinical Outcome | AUC (CI) | ACC (CI) | SENS (CI) | SPEC (CI) | PPV (CI) | NPV (CI) | RR (CI) |
|---|---|---|---|---|---|---|---|---|---|---|
| (A) Prediction of BRCA mutation status using the 44-gene DDRD classifier model | | | | | | | | | | |
| Training | 107 | N/A | BRCA mutant V wildtype | 0.68 (0.56-0.78) | 0.70 (0.57-0.76) | 0.58 (0.48-0.65) | 0.79 (0.64-0.86) | 0.78 (0.63-0.85) | 0.60 (0.49-0.65) | 1.93 (1.23-2.55) |
| (B) Prediction of pCR using 44-gene DDRD classifier model | | | | | | | | | | |
| FAC1 FAC2 and FEC | 203 | FEC and FAC | pCR V RD | 0.78 (0.70-0.85) | 0.76 (0.64-0.83) | 0.82 (0.69-0.92) | 0.58 (0.52-0.62) | 0.44 (0.36-0.48) | 0.90 (0.81-0.95) | 4.13 (1.94-9.87) |
| T/FAC | 321 | T/FAC | pCR V RD | 0.61 (0.53-0.69) | 0.53 (0.43-0.62) | 0.49 (0.38-0.60) | 0.67 (0.64-0.70) | 0.29 (0.22-0.35) | 0.83 (0.80-0.87) | 1.72 (1.05-2.65) |

Numbers in brackets denote the 95% confidence limits from +/−2SD from cross-validation (A) or bootstrapping with 1000 repeats (B). AUC = Area Under the Receiver Operating Characteristics Curve; ACC = Accuracy; SENS = Sensitivity; SPEC = Specificity; PPV = Positive Predictive value; NPV = Negative Predictive Value; RR = Relative Risk, pCR = pathological complete response, RD = residual disease.

TABLE 4

Univariate and Multivariate Analysis of the 44-gene DDRD classifier model
Comparison of the 44-gene DDRD classifier model to standard pathological parameters in independent validation sets.
The predictive value of the DDRD classifier model as well as significant clinical parameters were evaluated in a univariate and multivariate analysis using logistic regression models with p-values coming from a log-likelihood test.
Univariate and Multivariate Analysis of the 44-gene DDRD classifier model

| Variable | Univariate P value | Multivariate P value |
|---|---|---|
| FAC1, FAC2 and FEC | | |
| DDRD classifier | 0.0000 | 0.0014 |
| ER | 0.0004 | 0.0249 |
| Stage | 0.0459 | 0.0492 |
| Grade | 0.0100 | 0.0468 |
| T/FAC | | |
| DDRD classifier | 0.0129 | 0.2100 |
| ER | 0.0000 | 0.0000 |
| Stage | 0.3626 | 0.0359 |
| Grade | 0.0000 | 0.0115 |

Example 3

In Vitro Validation of the 44-gene DDRD Classifier Model

In order to assess the biology underlying the genes contained within the 44-gene classifier model, a number of studies were carried out in vitro using a panel of breast cell-lines.

supplemented with 50 U penicillin/ml, 50 μg streptomycin/ml, 2 mM glutamine, 1 mM Sodium Pyruvate and 20% (v/v) fetal bovine serum (FBS). The HCC1937-EV and HCC937-BR cell-lines also required 0.2 ml/mg geneticin. Cell-lines were cultured at 37° C. with a humidified atmosphere of 5% $CO_2$.

Clonogenic Assays—Determination of PARP-1 Inhibitor Sensitivity

For measurement of sensitivity to PARP-1 inhibitor (KU0058948), exponentially growing cells were seeded into 6-well plates. Twenty-four hours following seeding the cells were exposed to medium containing increasing doses of drug. Cell medium was replenished every 4-5 days. After 12-14 days the cells were fixed in methanol, stained with crystal violet and counted. The percentage survival of control for a given dose was calculated as the plating efficiencies for that dose divided by the plating efficiencies of vehicle-treated cells. Survival curves and half maximal inhibitory concentration ($IC_{50}$) values were calculated using GraphPad Prism.

Cell Viability Assay—Determination of Cisplatin Sensitivity

For measurement of sensitivity to cisplatin, exponentially growing cells were seeded into 96-well plates. 24 hours following seeding the cells were exposed to medium containing increasing doses of cisplatin. Cells were incubated in the presence of drug for 96 hours following which time the viability of the cells was assessed using the Promega CellTitre-Glo luminescent cell viability assay. The sensitivity of the cells was calculated as the percentage of vehicle (DMSO) control. Survival curves and half maximal inhibitory concentration ($IC_{50}$) values were calculated using GraphPad Prism.

Results

The DDRD Subgroup can be Identified within Breast Cancer Cell-line Models

A preclinical model system was used to confirm that the 44-gene DDRD classifier was a measure of abnormal DDR. The HCC1937 breast cancer cell-line is DDRD due to a BRCA1 mutation (Tomlinson et al., 1998). The 44-gene classifier was applied to HCC1937 empty vector control cells (HCC1937-EV) and HCC1937 cells in which BRCA1 functionality was corrected (HCC1937-BR) (FIG. 7A). The DDRD 44-gene classifier score was found to be higher within HCC1937-EV relative to HCC1937-BR cells, with average scores of 0.5111 and 0.1516 respectively (FIG. 7B). Consistent with the DDRD 44-gene classifier scores, the HCC1937 BRCA1 mutant cell-line was more sensitive to the PARP-1 inhibitor KU0058948 (FIG. 7C) and cisplatin (FIG. 7D) relative to the BRCA1 corrected cell-line. These preclinical data suggest that the DDRD 44-gene classifier measures immune signalling in DDRD-positive tumor cells and correlates with response to both a DNA-damaging agent (cisplatin) and a DNA repair targeted agent (PARP-1 inhibitor).

The DDRD 44-gene Classifier Detects Dysfunction of the Fanconi Anemia/BRCA Pathway The Fanconi anemia/BRCA (FA/BRCA) pathway, which includes BRCA1 and BRCA2, plays an integral role in DNA repair and can be lost in breast cancer either due to mutation or epigenetic silencing (Kennedy, R. D., and D'Andrea, A. D., J Clin Oncol 24, 3799-3808 (2006)). It was determined if the DDRD 44-gene classifier could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf et al., 2009). The DDRD 44-gene classifier significantly distinguished between the FA/BRCA mutant and normal samples with an AUC of 0.90 (CI=0.76-1.00, P<0.001), demonstrating a strong correlation between the DDRD classifier and dysfunction of the FA/BRCA pathway through multiple mechanisms.

CONCLUSION

The DDRD 44-gene classifier score was significantly higher in the BRCA1 mutant, and thus DDRD, HCC1937 breast cancer cell-line relative to an isogenic BRCA1 corrected cell-line. As the 44-gene classifier score correlates with DDR dysfunction within these cells, it demonstrates that the immune signalling detected by the DDRD classifier is intrinsic to the cell and not a function of lymphocytic infiltrate. BRCA1 and BRCA2 represent part of the FA/BRCA DDR network, which contains a number of other proteins that have been reported to be mutant or under-expressed in approximately 33% of breast cancer (Kennedy, R. D., and D'Andrea, A. D., J Clin Oncol 24, 3799-3808 (2006). As described previously, the DDRD 44-gene classifier significantly separated bone marrow samples from patients with FA mutations from normal controls. This suggests that the DDRD classifier is capable of detecting any abnormality within the pathway rather than specifically BRCA1 or BRCA2 dysfunction. It is possible that the DDRD 44-gene classifier may identify tumors with DDR-deficiency due to other mechanisms such as PTEN loss, cell-cycle checkpoint dysfunction or increased reactive oxygen species due to metabolic disturbance. Due to constitutive DNA-damage, these tumors are likely to respond to DNA repair targeted therapies such as PARP-1 or CHK1/2 inhibitors.

```
SEQUENCE LISTING
Hs127799.0C7n9_at
                                                      (SEQ ID NO: 1)
GGGACCAAGGTGGAGATCAAACGTAAGTGCACTTTCCTAATGCTTTTTCTTATAAGG

TTTTAAATTTGGAGCCTTTTTGTGTTTGAGATATTAGCTCAGGTCAATTCCAAAGAG

TACCAGATTCTTTCAAAAAGTCAGATGAGTAAGGGATAGAAAAGTAGTTCATCTTA

AGGAACAGCCAAGCGCTAGCCAGTTAAGTGAGGCATCTCAATTGCAAGATTTTCTC

TGCATCGGTCAGGTTAGTGATATTAACAGCGAAAAGAGATTTTTGTTTAGGGGAAA

GTAATTAAGTTAACACTGTGGATCACCTTCGGCCAAGGGACACGACTGGAGATTAA

ACGTAAGTAATTTTTCACTATTGTCTTCTGAAATTTGGGTCTGATGGCCAGTATTGA

CTTTTAGAGGCTTAAATAGGAGTTTGGTAAAGATTGGTAAATGAGGGCATTTAAGA

TTTGCCATGGGTTGCAAAAGTTAAACTCAGCTTCAAAAATGGATTTGGAGAAAAAA

AGATTAAATTGCTCTAAACTGAATGACACAAAGT

BRMX.5143C1n2_at
                                                      (SEQ ID NO: 2)
TTTATTGGTCTTCAGATGTGGCTGCAAACACTTGAGACTGAACTAAGCTTAAAACAC

GGTACTTAGCAATCGGGTTGCCAGCAAAGCACTGGATGCAAGCCTTGCCTTCCAGA

AGCTTACCAGTCGGGTTGCCAGCAAAGCAGTGGATGCAAGACTTGCCCTCCAGGAG

CTTACCATCACAACGAAGAAGACAAATAAATGCATAATATATAGACGACATAAATC

CATACTGTACACATTTAAGAATAAACAGTCCAGTAGTAAGAGGCAGTACATATTCA

ATCTGCTGAGAAATGTAGACAATAACTACTATAAGAATCCTAATGCTACAGAAGTC

ACTGGCTGCTGGGAAACCGGGGAAAACTTGGCTATGGACGTGGGGGCTTGTGTCGG

ACTCTGAATAAAGAGCAGAATGATTGGCGTCCTACTGAGATACATAGTAAAGGGGG
```

-continued

CGAGGGCAGGGAGGAAGTGGCAAGAATAACATTTGTGAAGATGTCCAGGTGAGAA

ATAGAGGTTTTAATGCTCAAGATGTTTCCTTTTCCCTTTTAAATCTGACCTGTGATTT

CCAGCATTGCTATTTCGAATATCACTGATTGTTTTTAA

BRSA.1606C1n4_at (SEQ ID NO: 3)
TGTGGCACATATACACCATGGAATACTATGCAGCCATAAAAAAGAATGGGATCATG

TCCTGTGCAGCAACGTGGATGGAGCTGGAAGCCATTATCCTAAATGAACTCACTCA

GAAACAGAAAACCAAATACCACATGTTCTCACTTATAAGTAGAAGCTAAACATTGA

GTACACATGGATACAAAGAAGGGAACCGCAGACACTGGGGCCTACCTGAGGTCGG

AGCATGGAAGGAGGGTGAGGATCAAAAAACTACCTATCTGGTACTATGCTTTTTAT

CTGGATGATGAAATAATCTGTACAACAAACCCTGGTGACATGCAATTTACCTATATA

GCAAGCCTACACATGTGCCCCTGAACCTAAAAAAAAAGTTAAAAGAAAAACGTTTG

GATTATTTTCCCTCTTTCGAACAAAGACATTGGTTTGCCCAAGGACTACAAATAAAC

CAACGGGAAAAAGAAAGGTTCCAGTTTTGTCTGAAAATTCTGATTAAGCCTCTGG

GCCCTACAGCCTGGAGAACCTGGAGAATCCTACACCCACAGAACCCGGCTTTGTCC

CCAAAGAATAAAAACACCTCTCTAAAAAAAAAAAAAAAA

BRIH.1231C2n2_at (SEQ ID NO: 4)
TCCTTATGGGGCCCGGTATGTGGGCTCCATGGTGGCTGATGTTCATCGCACTCTGGT

CTACGGAGGGATATTTCTGTACCCCGCTAACAAGAAGAGCCCCAATGGAAAGCTGA

GACTGCTGTACGAATGCAACCCCATGGCCTACGTCATGGAGAAGGCTGGGGGAATG

GCCACCACTGGGAAGGAGGCCGTGTTAGACGTCATTCCCACAGACATTCACCAGAG

GGCGCCGGTGATCTTGGGATCCCCCGACGACGTGCTCGAGTTCCTGAAGGTGTATG

AGAAGCACTCTGCCCAGTGAGCACCTGCCCTGCCTGCATCCGGAGAATTGCCTCTAC

CTGGACCTTTTGTCTCACACAGCAGTACCCTGACCTGCTGTGCACCTTACATTCCTA

GAGAGCAGAAATAAAAAGCATGACTATTTCCACCATCAAATGCTGTAGAATGCTTG

GCACTCCCTAACCAAATGCTGTCTCCATAATGCCACTGGTGTTAAGATATATTTTGA

GTGGATGGAGGAGAAATAAACTTATTCCTCCTTAAAAAAAAAAAAAAAAAAAAA

AAAAAAAAAAAAAAAAAAAAAAAAAAAAAAAA

BRAD.30779_s_at (SEQ ID NO: 5)
CGGGCGTGGTAGCGGGCGCCTGTAGTCCCAGCTACTCGGGAGGCTGAGGCAGGAGA

ATGGCGTGAACCCGGGAGGCGGAGCTTGCAGTGAGCCGAGATCGCGCCACTGCACT

CCAGCCTGGGCGACAGAGCGAGACTCCGTCTCAAAAAAAAAAAAAAAAAAAAAAA

TACAAAAATTAGCCGGGCGTGGTGGCCCACGCCTGTAATCCCAGCTACTCGGGAGG

CTAAGGCAGGAAAATTGTTTGAACCCAGGAGGTGGAGGCTGCAGTGAGCTGAGATT

GTGCCACTTCACTCCAGCCTGGGTGACAAAGTGAGACTCCGTCACAACAACAACAA

CAAAAAGCTTCCCCAACTAAAGCCTAGAAGAGCTTCTGAGGCGCTGCTTTGTCAAA

AGGAAGTCTCTAGGTTCTGAGCTCTGGCTTTGCCTTGGCTTTGCCAGGGCTCTGTGA

CCAGGAAGGAAGTCAGCATGCCTCTAGAGGCAAGGAGGGGAGGAACACTGCACTC

TTAAGCTTCCGCCGTCTCAACCCCTCACAGGAGCTTACTGGCAAACATGAAAAATC

GGCTTACCATTAAAGTTCTCAATGCAACCATAAAAAAAAA

BRSA.396C1n2_at (SEQ ID NO: 6)

TACAGATACTCAGAAGCCAATAACATGACAGGAGCTGGGACTGGTTTGAACACAGG

GTGTGCAGATGGGGAGGGGGTACTGGCCTTGGGCCTCCTATGATGCAGACATGGTG

AATTTAATTCAAGGAGGAGGAGAATGTTTTAGGCAGGTGGTTATATGTGGGAAGAT

AATTTTATTCATGGATCCAAATGTTTGTTGAGTCCTTTCTTTGTGCTAAGGTTCTTGC

GGTGAACCAGAATTATAACAGTGAGCTCATCTGACTGTTTTAGGATGTACAGCCTA

GTGTTAACATTCTTGGTATCTTTTTGTGCCTTATCTAAAACATTTCTCGATCACTGGT

TTCAGATGTTCATTTATTATATTCTTTTCAAAGATTCAGAGATTGGCTTTTGTCATCC

ACTATTGTATGTTTTGTTTCATTGACCTCTAGTGATACCTTGATCTTTCCCACTTTCTG

TTTTCGGATTGGAGAAGATGTACCTTTTTTGTCAACTCTTACTTTTATCAGATGATCA

ACTCACGTATTTGGATCTTTATTTGTTTTCTCAAATAAATATTTAAGGTTATACATTT

AAAAAAAAAAAAAAAAAAAAAAAAAAA

BRMX.2948C3n7_at (SEQ ID NO: 7)

TGAGAAGTAGTTACTGTGCACATGTGTAGATTTGCAGTTCTGTGGCTCCTGATGGAT

CTGAGAAGATGGACGTGGAGGATGAAAATCTGTCTGATTATTTTGAACTGATGTTTG

TTGCTATGGAGATGCTGCCTATATGTTGATGTTGCAGACGTTAAGTCACTAGCCCAC

AGCCTTGTATTCCATACTCAGAGACCCTGCTACTTACTTGACATCTCAACTTGAAAG

TCCAATTAATATGCACTTCAAACTTTAATAGGCTTCAAACAGAATTTCTTTCATTATC

TCTGCAAAACAGCTTCTCTCATCATCTTGAAATTAGTGAATGGCATTTTACTGTTTTA

GTTGGAGTCATTTCTGTGGTTTTCTTTCACATCCTACATAACAATCCATCAGTAAGTT

CTATGAGCTCTTCTTTGAAAACAAACAGAATCCAACTGTTTCATTCCCACTTCTGCT

CTGGTCAAGCCACTGCCAACACTCACCTTTATTATTGTAGCACCCTCATTGCCTAGT

TCTGTCCCACAGATTTCCAATAAAAGGTGAATAAAATCAGGTCACTCTTCTGCTAAA

AAAAAAAAAAAAAAAAAAAAAAAAA

Hs539969.0C4n3_at (SEQ ID NO: 8)

NNNNNTTTGCTACAGCCAGGGTTAGCTCAGCAGGTGAAAACCCCGAGGGTGGGTGA

AACCCCTCTGGGGCTCAGACATGCAAACCTTGGGCATCTCTCTGTCCCAGCTGGCCC

CGCCAGCCGGTAGGAAGTTTCCCCTGAGTTCTCAGTTTTTTCTTCTGAAAAATGAGG

GGTTGTATGCAAGGTTCTCCTCCTGGCCTGTGGTCCCCAGAGAAGGGCAGGAAGGA

ACCTTAGATAATTCTCATATGCATTTAACAGACGAGGAAACTGAGACCCAGAGCCG

TCACATCAATACCTCATTTGATCTTCATAAGAGCACCTGGAGGAGGGGGTGGGGT

GTTTGTGTTTGTTTAAANNNNNNNNGTGAAAAAAATGAAGATAGGCATTTTGTAG

ACAATCTGGAAGTTCTGGACCGGAATCCATGATGTAGTCAGGGAAGAAATGACCCG

TGTCCAGTAACCCCAGGCCTCGAGTGTGTGGTGTATTTTTCTACATAATTGTAATCA

TTCTATACATACAAATTCATGTCTTGACCATCATATTAATATTTGGTAAGTTTCTCTC

TCTTTAGAGACTCCACAATAAAGTTTTCAACATGG

Hs396783.3C1n4_at (SEQ ID NO: 9)

TNTTNTNTTTTTTTTTTTTTTTTTTTTNCATAGTTGTTATCTTAAGGTGATTTCCA

ATTTTTTTTCCATTTACATTTTTCCACAAGCATTGTCCACTTTATTCTGTAACCTTTT

CAACTACCATTTTGAAATTTGCTTTTATCCATGTGGTTGTTTGTGATGAACTACAGGT

-continued
```
TGCTGACTTTCTTCCCCTTCTGTNNNNNNNNNNNNNNNNNNNNNNNGTNNTNNNNC

TCAAGAGGATCTCATCAGTGGAATCATTAGATCAAAGGATATGACTGTTGCTCAGC

TCTCTGTGTGTATGTAAATTAATAGGCTGTTTATTTGAGCAGTTGTAGGCTTACAAA

AATATTGAGTCAAAAGTATAGAATTCCCATATATTCTCCTCTTCTCCC
```

BRMX.13670C1n2_at
(SEQ ID NO: 10)
```
ATCTTCCCACCTCGATGGGGGGTTGCTGATAAGACCTTCAGGCCTCCTTATTACCAT

AGGAACTGCATGAGTGAGTTCATGGGACTCATCCGAGGTCACTATGAGGCAAAGCA

AGGTGGGTTCCTGCCAGGGGGAGGGAGTCTACACAGCACAATGACCCCCCATGGAC

CTGATGCTGACTGCTTTGAGAAGGCCAGCAAGGTCAAGCTGGCACCTGAGAGGATT

GCCGATGGCACCATGGCATTTATGTTTGAATCATCTTTAAGTCTGGCGGTCACAAAG

TGGGGACTCAAGGCCTCCAGGTGTTTGGATGAGAACTACCACAAGTGCTGGGAGCC

ACTCAAGAGCCACTTCACTCCCAACTCCAGGAACCCAGCAGAACCTAATTGAGACT

GGAACATTGCTACCATAATTAAGAGTAGATTTGTGAAGATTCTTCTTCAGAATCTCA

TGCTTTCTGGTAGTATTGGAGGAGGGGGTTGGTTAAAATGAAAATTCACTTTTCATA

GTCAAGTAACTCAGAACTTTTATGGAAACGCATTTGCAAAGTTCTATGGCTGTCACC

TTAATTACTCAATAAACTTGCTGGTGTTCTGTGGA
```

BRAD.30243_at
(SEQ ID NO: 11)
```
GGGAGCTAAGTATCCAGCCTCTCCCAAACCTCTTTGAACAAAGCTTCTGTCCCTCCC

ACACCTCTCACCTCACAGGCACATCAGGCTGCAGAATGCGCTTTAGAAAGCATTGTT

TTAGTCCAGGCACAGTGGCTCACGCCTGTAATCCCAGCACTTTGGGAGGCCGAGGT

GGGTGGATCACAAGGTTGGGAGATTGAGACCATCCTGGCTAACACAGTGAAACCCT

GTCTCTACTAAAAAAATACAAAAAATTAGCTTGGCGTGGTGGTGGGCGCCTGTAGT

CCCAGCAGCTTGGGAGGCTGAGGCTGGAGAATGGTGTGAACCCAGGAGGCGGAGC

TTGCAGTGAGCCAAGATCGCGCCACTGCACTCCAGCCCGGGTGACAGAGCAAGACT

CCGTCTCAAAAAAAAGAAAAGAAAAAAGAAAGCATTGTTTTAATTGAGAGGGGCA

GGGCTGGAGAAGGAGCAAGTTGTGGGGAGCCAGGCTTCCCTCACGCAGCCTGTGGT

GGATGTGGGAAGGAGATCAACTTCTCCTCACTCTGGGACAGACGATGTATGGAAAC

TAAAAAGAACATGCGGCACCTTAAAAAAAAAAAAAAAAAA
```

BRMX.941C2n2_at
(SEQ ID NO: 12)
```
TTTATTGGTCTTCAGATGTGGCTGCAAACACTTGAGACTGAACTAAGCTTAAAACAC

GGTACTTAGCAATCGGGTTGCCAGCAAAGCACTGGATGCAAGCCTTGCCTTCCAGA

AGCTTACCAGTCGGGTTGCCAGCAAAGCAGTGGATGCAAGACTTGCCCTCCAGGAG

CTTACCATCACAACGAAGAAGACAAATAAATGCATAATATATAGACGACATAAATC

CATACTGTACACATTTAAGAATAAACAGTCCAGTAGTAAGAGGCAGTACATATTCA

ATCTGCTGAGAAATGTAGACAATAACTACTATAAGAATCCTAATGCTACAGAAGTC

ACTGGCTGCTGGGAAACCGGGGAAAACTTGGCTATGGACGTGGGGGCTTGTGTCGG

ACTCTGAATAAAGAGCAGAATGATTGGCGTCCTACTGAGATACATAGTAAAGGGGG

CGAGGGCAGGGAGGAAGTGGCAAGAATAACATTTGTGAAGATGTCCAGGTGAGAA

ATAGAGGTTTTAATGCTCAAGATGTTTCCTTTTCCCTTTTAAATCTGACCTGTGATTT

CCAGCATTGCTATTTCGAATATCACTGATTGTTTTTAA
```

-continued

BRMX.4154C1n3_s_at (SEQ ID NO: 13)
ATCCCAAAGGCCCTTTTTAGGGCCGACCACTTGCTCATCTGAGGAGTTGGACACTTG

ACTGCGTAAAGTGCAACAGTAACGATGTTGGAAGGCTTATGATTTTACTGTGTATGT

ATTTGGGAGAAGAAATTCTGTCAGCTCCCAAAGGATAAACCAGCAGTTGCTTTATT

GGTCTTCAGATGTGGCTGCAAACACTTGAGACTGAACTAAGCTTAAAACACGGTAC

TTAGCAATCGGGTTGCCAGCAAAGCACTGGATGCAAGCCTTGCCTTCCAGAAGCTT

ACCAGTCGGGTTGCCAGCAAAGCAGTGGATGCAAGACTTGCCCTCCAGGAGCTTAC

CATCACAACGAAGAAGACAAATAAATGCATAATATATAGACGACATAAATCCATAC

TGTACACATTTAAGAATAAACAGTCCAGTAGTAAGAGGCAGTACATATTCAATCTG

CTGAGAAATGTAGACAATAACTACTATAAGAATCCTAATGCTACAGAAGTCACTGG

CTGCTGGGAAACCGGGGAAAACTTGGCTATGGACGTGGGGGCTTGTGTCGGACTCT

GAATAAAGAGCAGAATGATTGGCAAAAAAAAAAAAAA

BRAD.39498_at (SEQ ID NO: 14)
CGTCTTCTAAATTTCCCCATCTTCTAAACCCAATCCAAATGGCGTCTGGAAGTCCAA

TGTGGCAAGGAAAAACAGGTCTTCATCGAATCTACTAATTCCACACCTTTTATTGAC

ACAGAAAATGTTGAGAATCCCAAATTTGATTGATTTGAAGAACATGTGAGAGGTTT

GACTAGATGATGGATGCCAATATTAAATCTGCTGGAGTTTCATGTACAAGATGAAG

GAGAGGCAACATCCAAAATAGTTAAGACATGATTTCCTTGAATGTGGCTTGAGAAA

TATGGACACTTAATACTACCTTGAAAATAAGAATAGAAATAAAGGATGGGATTGTG

GAATGGAGATTCAGTTTTCATTTGGTTCATTAATTCTATAAGCCATAAAACAGGTAA

TATAAAAAGCTTCCATGATTCTATTTATATGTACATGAGAAGGAACTTCCAGGTGTT

ACTGTAATTCCTCAACGTATTGTTTCGACAGCACTAATTTAATGCCGATATACTCTA

GATGAAGTTTTACATTGTTGAGCTATTGCTGTTCTCTTGGGAACTGAACTCACTTTCC

TCCTGAGGCTTTGGATTTGACATTGCATTTGAC

BRAD.34868_s_at (SEQ ID NO: 15)
ACTCAAATGCTCAGACCAGCTCTTCCGAAAACCAGGCCTTATCTCCAAGACCAGAG

ATAGTGGGGAGACTTCTTGGCTTGGTGAGGAAAAGCGGACATCAGCTGGTCAAACA

AACTCTCTGAACCCCTCCCTCCATCGTTTTCTTCACTGTCCTCCAAGCCAGCGGGAA

TGGCAGCTGCCACGCCGCCCTAAAAGCACACTCATCCCCTCACTTGCCGCGTCGCCC

TCCCAGGCTCTCAACAGGGGAGAGTGTGGTGTTTCCTGCAGGCCAGGCCAGCTGCC

TCCGCGTGATCAAAGCCACACTCTGGGCTCCAGAGTGGGGATGACATGCACTCAGC

TCTTGGCTCCACTGGGATGGGAGGAGAGGACAAGGGAAATGTCAGGGGCGGGGAG

GGTGACAGTGGCCGCCCAAGGCCCACGAGCTTGTTCTTTGTTCTTTGTCACAGGGAC

TGAAAACCTCTCCTCATGTTCTGCTTTCGATTCGTTAAGAGAGCAACATTTTACCCA

CACACAGATAAAGTTTTCCCTTGAGGAAACAACAGCTTTAAAAGAAAAAGAAAAA

AAAAGTCTTTGGTAAATGGCAAAAAAAAAAAAAAAAAA

Hs505575.0C1n42_at (SEQ ID NO: 16)
GGGATTTGTTAAAATGGAGGTCTTTGGTGACCTTAACAGAAAGGGTTTTTGAGGAG

TAGTGGAGTGGGGAGGGGCAGCAGGAAGGGGAGATTGTACACACCCCAGGAGACA

AGTCTTCTAGCAGTTCTGCCAGAATGGGCAGGAGAGAAGTGCCATAGAGCTGGAAG

-continued

```
GCTACATTGAATAGAGAAATTTCTTTAACTTGTTTTTTAAGAAGGGTGATAAAAAGG

CATGTTCTGATGGTGATAGGGATGTTTCCATAACTGGAAAGAAATTGATGTGCAAG

AGAAAGAATATAATTGCAGGAGGACTTGAAGAAGTTGGAGAGAAAAAGCCTTTAG

GGACCCTGAACCAATGAATCTGAAATTCCCCAACTGCCAGATGTATCTTCATTTTTC

ATTTTCCGGGAGATGTAATATGTCCTAAAAATCACAGTCGCTAGATTGAAATCAACC

TTAAAAATCATCTAGTCCAATGTCTACTCCCAGTCCACTACTTGAATCCCCTGTGTC

CCCTCCCAGTAGTCGTCTTGACAACCTCCACTGAAAGGCAATTTCTACACTCCATCC

ACCCCACCACCAACCCATGGTTCATGATCTCTTCGGA
```

BREM.1442_at (SEQ ID NO: 17)
```
TTACTATATCAACAACTGATAGGAGAAACAATAAACTCATTTTCAAAGTGAATTTGT

TAGAAATGGATGATAAAATATTGGTTGACTTCCGGCTTTCTAAGGGTGATGGATTGG

AGTTCAAGAGACACTTCCTGAAGATTAAAGGGAAGCTGATTGATATTGTGAGCAGC

CAGAAGGTTTGGCTTCCTGCCACATGATCGGACCATCGGCTCTGGGGAATCCTGATG

GAGTTTCACTCTTGTCTCCCAGGCTGGAGTACAATGGCATGATCTCAGCTTACTGCA

ACCTCCGTCTCCTGGGTTCAAGCGATTCTCCTGCCTCAGCCTTCCAAGTAGCTGGGA

TTACAGGTGCCCACCACCACACCTGGCTAGGTTTTGTATTTTTAGTAGAGATGGGGT

TTTTTTCATGTTGGCCAGGCTGATCTGGAACTCCTGACCTCAAGTGATCCACCTGCC

TTGGCCTCCCAAAGTGCTGGGATTTTAGGTGTGAGCCACCTCGCCTGGCAAGGGATT

CTGTTCTTAGTCCTTGAAAAAATAAAGTTCTGAATCTTCAAAAAAAAAAAAAAAAA

AAAAAAAAAAAAAAAAAAAAAAAAAAAAA
```

BRHP.827_s_at (SEQ ID NO: 18)
```
GTGTATCATGAGCCAACCCTCAAAGGACCCGTATTACAGTGCCACGTTGGAAAACG

CTACAGGAAGCATGACCTATCCACATCTTTCCAAGATAGACACTAACATGTCATGTC

CCAAACATTAGCACGTGGGGGTTGAGCTCTGTGCAGTAATCGAGATTGGGAGAATT

TGGGCAGCGCGTGAGAAGTGCTAAGCTACTTGTTTTCTCACTTGAGCCCGGGTAGGC

TGTGTTGGCCCTCACTTGGGATTCTCAGCAGTTACATGAAAGTTGTGCTGATAATCT

CTTCTCTTGTACCAATTTTAGTCAGGCAGAAAATGGTAAACATGAGGGTGCTCTTGT

GACTTAATTTTTGTTCAAGGGACTAAATTGCTTATGTTTATTCCCTGTCAGCGGAGT

GGAGAATGTCATTCATCAATAAACCAAAGCCAATAGCTGGAGAATTGAGATCTGGT

TGAAAGTGGTTTATGGTTTACATGCTGTACTATCCTGAGGAATTGCGAGATATTGCT

GAGGGGAAAAAAAAATGACCTTTTCTTGAAATGTAACTTGAAAACAAAATAAAATG

TGGAACATAAAAAAAAAAAAAAAAAAAAAAAAAA
```

BRRS.18322_s_at (SEQ ID NO: 19)
```
CCAGAGGCAGAAGGATTGGGACTAGGCCAACATAGAGATTGGCGATGGTTGTGAG

ATTCTAAGAGTGTGTGTGCATCTTGACAATATTAGAGGAGGCTGAGCCCAAGCAGG

CACATTCTCTTCGACCCCTCCCTCATTCAGTCTGCTTTGGAGTCTACTGAACATCAAG

CTTGCTATGAGCAGGATCTTAGAGCTGAGGAATTGGCCTCCCAATCCGAACAGGTG

TTATAATCCTTTCTTAATAGGTTGTGCTGTGGACCCAATGTGAGGGCTGTGCTGGTG

TAAATGGTGACATATTGAGCTGGGGGGATGCTTTCGGGGTGGGGGGACTGGTTCCA

TTCCATCAAAGGCCCTCTTGAGAGTCTATCCAGGGACCCATTGTTTTACTTTAACAG

ACCAGAAAAGATGTTTGTTTTCCATGTCATTACCCCCAGGGGATACCGAATGTGTGG
```

```
GTAGAAATTTCTCTGTAGATTAAAAATCAGATTTTTACATGGATTCAACAAAGGAGC

GTCACTTGGATTTTTGTTTTCATCCATGAATGTAGCTGCTTCTGTGTAAAATGCCATT

TTGCTATTAAAAATCAATTCACGCTGGAAAAAA

BRRS.18792_s_at
                                                          (SEQ ID NO: 20)
GCACGTCTACGGGGCTGGACAGAGTGTGGTTAACCGGGGAACTGGGCAAGCCGGC

GCCGAGCCTGCGTCAGCCGTGCAAGCCGCTCCTTCAGGAACTTCCGCTTGTCGCTGG

TGTCGCTCCGCTCCTTCAGGAGCCAGCTGTAGGTGTCCTTGTCCTGCAGGAGCTGCA

GCATGGCCTTCTGAAGCTGCTGGCCGTACGTCTGGAGCATGAAGAACTGGATGATC

AAAGGGATGTGGCTGGAGATGCGCTTGCTGGCCTCCTGGTGATAGGCCATCAGGTG

CTGAAAGATCTCCTCCATGGAAGAGTCTGTTGCCGAGCTGGACTGGAAAGCCCCAA

AATCCCAGGATTTCTTCTTCTTTTCTTCTTCCAGCTCCTTCTCTCTGACCTTCTGCAAT

GCACCCCTGTATACCTGGTCCTGGCAGTAGACAATCTGTTCCATCTGGAAGTGGAGG

CGGATCAGCTTCTCACCTTCTCTCTCTTGTTCTGCTCTAATGTCTTCAATTTTGGACTT

GGCGGTTCTGTGGAGGTTAAAAAACTCTTCAAAATTTTTTATCGCCAACTTTTTTGT

ACAAAGTTGGCCTTATAAAGAAAGCATTGCT

Hs632609.0C1n37_at
                                                          (SEQ ID NO: 21)
NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNN

NCCAAATGAGTGATGCATTGACCGTTCGTAATTCTTGGATGCAAAAGTAGAACTCA

AGCTACTTAATAACAATCATGGTGGCATGGGCACCAGCAAGTCAGGGTGGACAACA

GCCATAGTTCTGGAGCATGGTCCTCAAGACTACCTTTTGTATGCAGAGTATTAACAC

TTTAACTCTTAGATCCTTGGAACATAAGGAAGAGAGGCTGGAACAAAAAGGGGTTG

GCATTTGGAGGTGGAGAGGTAGTGTAAGGCACAACTGTTTATCAACTGGTATCTAA

GTATTTCAGGCCAGACACGTGGCTCACACCTCTAATCCCAGCACTTTGGGAGCTGAG

CCAGGAGGATTGCTTGAGTCTAGGAGTTCAAGACCGGTCTGGGCAACATGGTGAAA

CCCTGTCTCTACAAAAAAATACAAAAATTAGCCAGGTGTGGTGGGGCACGCCTATG

GTCCCAGCTACTGGGGAGGCTGAGATGGGAGGATCCACCTGAGC

Hs449575.0C1n22_at
                                                          (SEQ ID NO: 22)
TTTTTTTTAATTAACTTGACTTTATTGATAGTTACAGCACAATTTATTAATTAACTTG

ACTTTATTGATAGTTACAGCACAATCTGTCCAAAACCACCAGAATATACATTCTTTT

CAAGAGCTCAAATGGAACATTTACCACAAAAGACCATATTCTGGGCTTCAAAATAA

GCCTAAATAAATACAAAAGCATTTAGGACCTATGAATCAGAAGACTGAATATGCAC

ATATACAAAATGAGAATCATTCTCTCACATACAAAACTTATATAGGTAGTAAAGAT

ACAGTTGATTAGGTAGATTTGAATGTTGAATCACTGACATTTCCTGAAGGTAGAGCT

ACAAATTACTTTTTTAAAACCACTAACCCACCCCCACCCTTACCTCACTTACTCTTTTT

GGCCTTACCACCTACTTTAGTCATACCCTATACATGTTACTCAGACCAAATGGCTCT

CATAAACAATCTCAGTATATGT

BRAD.18827_s_at
                                                          (SEQ ID NO: 23)
TTAAGAAGGTATGGAAAGAGTCTGGGAGTGACTAAACTATCCAATGTCATTGAAAT

AAAGCAATGAAGAATAAGAGTAATTTTGTTGCTTTATTAAATTTTTTCTCACAGAA
```

-continued

```
TTCTTTATAAAAACACCATGTCCCTAAAATGTCATTCAACATATATGCACACCTTCG

ATGTATAGGACACTGATCAAAAAAGACAGAGAAATGTGTCCCTGGTGTTTTGTTTTT

GNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNGGGACTACAGGCACATAC

CACCACACCTGGCTTCATGTTCCCGGTATTAGTACAATGCCAAAATATTTAAAATTC

TTAAAGGTTAACTCAAATATCTTAAGTTTTACTTCACTTACAATTTCAATAATGCTG

AAATTTTGATTGAATATTGTGTTTGTAGTGCTACCTCTTTTTCGTTCATAAGAACAAA

AGCCTATCATTCTCTTAGTTTCTAAAAAATATATGTTCATATGGTTTAGATACATATA

TAAATATNTACACAAAACAATGTTTTTTGAGTTGTA
```

BREM.2466_s_at (SEQ ID NO: 24)
```
GCCCGTGCCGCCCCAGCCGCTGCCGCCTGCACCGGACCCGGAGCCGCCATGCCCAA

GTGTCCCAAGTGCAACAAGGAGGTGTACTTCGCCGAGAGGGTGACCTCTCTGGGCA

AGGACTGGCATCGGCCCTGCCTGAAGTGCGAGAAATGTGGGAAGACGCTGACCTCT

GGGGGCCACGCTGAGCACGAAGGCAAACCCTACTGCAACCACCCCTGCTACGCAGC

CATGTTTGGGCCTAAAGGCTTTGGGCGGGGCGGAGCCGAGAGCCACACTTTCAAGT

AAACCAGGTGGTGGAGACCCCATCCTTGGCTGCTTGCAGGGCCACTGTCCAGGCAA

ATGCCAGGCCTTGTCCCCAGATGCCCAGGGCTCCCTTGTTGCCCCTAATGCTCTCAG

TAAACCTGAACACTTGGAAAAAAAAAAAAAAAAAA
```

BRAD.2605_at (SEQ ID NO: 25)
```
CAACCAGGAAGAACCGTACCAGAACCACTCCGGCCGATTCGTCTGCACTGTACCCG

GCTACTACTACTTCACCTTCCAGGTGCTGTCCCAGTGGGAAATCTGCCTGTCCATCG

TCTCCTCCTCAAGGGGCCAGGTCCGACGCTCCCTGGGCTTCTGTGACACCACCAACA

AGGGGCTCTTCCAGGTGGTGTCAGGGGGCATGGTGCTTCAGCTGCAGCAGGGTGAC

CAGGTCTGGGTTGAAAAAGACCCCAAAAAGGGTCACATTTACCAGGGCTCTGAGGC

CGACAGCGTCTTCAGCGGCTTCCTCATCTTCCCATCTGCCTGAGCCAGGGAAGGACC

CCCTCCCCCACCCACCTCTCTGGCTTCCATGCTCCGCCTGTAAAATGGGGCGCTAT

TGCTTCAGCTGCTGAAGGGAGGGGCTGGCTCTGAGAGCCCCAGGACTGGCTGCCC

CGTGACACATGCTCTAAGAAGCTCGTTTCTTAGACCTCTTCCTGGAATAAACATCTG

TGTCTGTGTCTGCTGAACATGAGCTTCAGTTGCTACTCGGAGCATTGAGAGGGAGGC

CTAAGAATAATAACAATCCAGTGCTTAAGAGTCA
```

BRAD.33618_at (SEQ ID NO: 26)
```
GGGTCGACCCTTGCCACTACACTTCTTAAGGCGAGCATCAAAAGCCGGGGAGGTTG

ATGTTGAACAGCACACTTTAGCCAAGTATTTGATGGAGCTGACTCTCATCGACTATG

ATATGGTGCATTATCATCCTTCTAAGGTAGCAGCAGCTGCTTCCTGCTTGTCTCAGA

AGGTTCTAGGACAAGGAAAATGGAACTTAAAGCAGCAGTATTACACAGGATACAC

AGAGAATGAAGTATTGGAAGTCATGCAGCACATGGCCAAGAATGTGGTGAAAGTA

AATGAAAACTTAACTAAAATTCATCGCCATCAAGAATAAGTATGCAAGCAGCAAACT

CCTGAAGATCAGCATGATCCCTCAGCTGAACTCAAAAGCCGTCAAAGACCTTGCCT
```

-continued

CCCCACTGATAGGAAGGTCCTAGGCTGCCGTGGGCCCTGGGGATGTGTGCTTCATTG

TGCCCTTTTTCTTATTGGTTTAGAACTCTTGATTTTGTACATAGTCCTCTGGTCTATCT

CATGAAACCTCTTCTCAGACCAGTTTTCTAAACATATATTGAGGAAAAATAAAGCG

ATTGGTTTTTCTTAAGGTAAAAAAAAAAAAAAAAAA

BRAD.36579_s_at
(SEQ ID NO: 27)
CAGAAAGGCCCGCCCCTCCCCAGACCTCGAGTTCAGCCAAAACCTCCCCATGGGGC

AGCAGAAAACTCATTGTCCCCTTCCTCTAATTAAAAAGATAGAAACTGTCTTTTTC

AATAAAAAGCACTGTGGATTTCTGCCCTCCTGATGTGCATATCCGTACTTCCATGAG

GTGTTTTCTGTGTGCAGAACATTGTCACCTCCTGAGGCTGTGGGCCACAGCCACCTC

TGCATCTTCGAACTCAGCCATGTGGTCAACATCTGGAGTTTTTGGTCTCCTCAGAGA

GCTCCATCACACCAGTAAGGAGAAGCAATATAAGTGTGATTGCAAGAATGGTAGAG

GACCGAGCACAGAAATCTTAGAGATTTCTTGTCCCCTCTCAGGTCATGTGTAGATGC

GATAAATCAAGTGATTGGTGTGCCTGGGTCTCACTACAAGCAGCCTATCTGCTTAAG

AGACTCTGGAGTTTCTTATGTGCCCTGGTGGACACTTGCCCACCATCCTGTGAGTAA

AAGTGAAATAAAAGCTTTGACTAGAAAAAAAAAAAAAAAAAAAAAAAAAAAA

AAAAAAAAAAAAAAAAAAAAAAAAAAAAAAAAA

BRAD1_5440961_s_at
(SEQ ID NO: 28)
TCAGCACTGAGTGTTCAAAGACAGTAGGACGTCGGTTGCTGACCTGCCTCTTAGAA

GCTAGTTTAACTCAGCGGGTAAGGATCTAGGACTTCTACATTAGTTACCACTGTAAT

GATAACACCACCAGAAAAGTCTGTAGTTTAATATTTCCCACCTTATGCCTGTTTCTT

CATTCACGCAAAGAAAATAAAAATATAATACCTAAGCCTCTTTGTATTACATAAAG

CAAAATGCAAAGCACTGTATCTTCCAAATACTTCCTCTTGATATGGTGGAATTATAG

AGTAGTATCATTTGTAACNTGAAATGTCTTCTAGGGTTGCTATGCGAAAGCAAGACT

GTGGTTTCATTCCAATTTCCTGTATATCGGAATCATCACCATCTGTGTATGTGTGATT

GAGGTGTTGGGGATGTCCTTTGCACTGACCCTGAACTGCCAGATTGACAAAACCAG

CCAGACCATAGGGCTATGATCTGCAGTAGTCCTGTGGTGAAGAGACTTGTTTCATCT

CCGGGAAATGCAAAACCATTTATAGGCATGAAGCCCTACATGATCACTTGCAGGGT

GANCCTCCTCCCATCCTTTTCCCTTTTAGGGTC

BRAD1_66786229_s_at
(SEQ ID NO: 29)
GCCTGGGACGCTGCTGCTGTTCAGGAAACGATGGCAGAACGAGAAGCTCGGGTTGG

ATGCCGGGGATGAATATGAAGATGAAAACCTTTATGAAGGCCTGAACCTGGACGAC

TGCTCCATGTATGAGGACATCTCCCGGGGCCTCCAGGGCACCTACCAGGATGTGGG

CAGCCTCAACATAGGAGATGTCCAGCTGGAGAAGCCGTGACACCCCTACTCCTGCC

AGGCTGCCCCCGCCTGCTGTGCACCCAGCTCCAGTGTCTCAGCTCACTTCCCTGGGA

CATTCTCCTTTCAGCCCTTCTGGGGGCTTCCTTAGTCATATTCCCCAGTGGGGGGTG

GGAGGGTAACCTCACTCTTCTCCAGGCCAGGCCTCCTTGGACTCCCCTGGGGGTGTC

CCACTCTTCTTCCCTCTAAACTGCCCCACCTCCTAACCTAATCCCCCGCCCCGCTGC

CTTTCCCAGGCTCCCCTCACCCCAGCGGGTAATGAGCCCTTAATCGCTGCCTCTAGG

GGAGCTGATTGTAGCAGCCTCGTTAGTGTCACCCCCTCCTCCCTGATCTGTCAGGGC

CACTTAGTGATAATAAATTCTTCCCAACTGCA

-continued

BREM.2104_at (SEQ ID NO: 30)

GGATTCAGCCAGTGCGGATTTTCCATATAATCCAGGACAAGGCCAAGCTATAAGAA

ATGGAGTCAACAGAAACTCGGCTATCATTGGAGGCGTCATTGCTGTGGTGATTTTCA

CCATCCTGTGCACCCTGGTCTTCCTGATCCGGTACATGTTCCGCCACAAGGGCACCT

ACCATACCAACGAAGCAAAGGGGGCGGAGTCGGCAGAGAGCGCGGACGCCGCCAT

CATGAACAACGACCCCAACTTCACAGAGACCATTGATGAAAGCAAAAAGGAATGG

CTCATTTGAGGGGTGGCTACTTGGCTATGGGATAGGGAGGAGGGAATTACTAGGGA

GGAGAGAAAGGGACAAAAGCACCCTGCTTCATACTCTTGAGCACATCCTTAAAATA

TCAGCACAAGTTGGGGAGGCAGGCAATGGAATATAATGGAATATTCTTGAGACTG

ATCACAAAAAAAAAAAACCTTTTTAATATTTCTTTATAGCTGAGTTTTCCCTTCTGTA

TCAAAACAAATAATACAAAAAATGCTTTTAGAGTTTAAGCAATGGTTGAAATTTG

TAGGTAATATCTGTCTTATTTTGTGTGTGTTTAGAGGT

BRAG_AK097020.1_at (SEQ ID NO: 31)

ATGTCCAAAAAGATACAGAAGAACTAAAGAGCTGTGGTATACAAGACATATTTGTT

TTCTGCACCAGAGGGGAACTGTCAAAATATAGAGTCCCAAACCTTCTGGATCTCTAC

CAGCAATGTGGAATTATCACCCATCATCATCCAATCGCAGATGGAGGGACTCCTGA

CATAGCCAGCTGCTGTGAAATAATGGAAGAGCTTACAACCTGCCTTAAAAATTACC

GAAAAACCTTAATACACTGCTATGGAGGACTTGGGAGATCTTGTCTTGTAGCTGCTT

GTCTCCTACTATACCTGTCTGACACAATATCACCAGAGCAAGCCATAGACAGCCTGC

GAGACCTAAGAGGATCCGGGGCAATACAGACCATCAAGCAATACAATTATCTTCAT

GAGTTTCGGGACAAATTAGCTGCACATCTATCATCAAGAGATTCACAATCAAGATC

TGTATCAAGATAAAGGAATTCAAATAGCATATATATGACCATGTCTGAAATGTCAG

TTCTCTAGCATAATTTGTATTGAAATGAAACCACCAGTGTTATCAACTTGAATGTAA

ATGTACATGTGCAGATATTCCTAAAGTTTTATTGAC

BRAD.20415_at (SEQ ID NO: 32)

GGTTTCCTTCCCAGGACAGCTGCAGGGTAGAGATCATTTTAAGTGCTTGTGGAGTTG

ACATCCCTATTGACTCTTTCCCAGCTGATATCAGAGACTTAGACCCAGCACTCCTTG

GATTAGCTCTGCAGAGTGTCTTGGTTGAGAGAATAACCTCATAGTACCAACATGAC

ATGTGACTTGGAAAGAGACTAGAGGCCACACTTGATAAATCATGGGGCACAGATAT

GTTCCCACCCAACAAATGTGATAAGTGATTGTGCAGCCAGAGCCAGCCTTCCTTCAA

TCAAGGTTTCCAGGCAGAGCAAATACCCTAGAGATTCTCTGTGATATAGGAAATTT

GGATCAAGGAAGCTAAAAGAATTACAGGGATGTTTTTAATCCCACTATGGACTCAG

TCTCCTGGAAATAGGTCTGTCCACTCCTGGTCATTGGTGGATGTTAAACCCATATTC

CTTTCAACTGCTGCCTGCTAGGGAAAACTGCTCCTCATTATCATCACTATTATTGCTC

ACCACTGTATCCCCTCTACTTGGCAAGTGGTTGTCAAGTTCTAGTTGTTCAATAAAT

GTGTTAATAATGCTTAAAAAAAAAAAAAAAAAA

BRAD.29668_at (SEQ ID NO: 33)

ATTCCAGGAAGCATGGGATTTTATTTTGCTTGATTTTGGGCACATGAAATAATAGCT

CTAGGAAAATGCGCATCTTAATGACTCTTTGTAAAGAGAGGCATTTCTTACAACTGT

GATGTTTGCTTACATAAAAGTTACCTCATAAGTTAATTCTAACTTTTATTCTTGAATT

TTATTTCATTTCAATAGCTTGTTTCATTTGCACGCCTTTGTATTTTGATTGACCTGTA

```
GAATGGATGTTAGGAAACTCAAAATTGAACACAGTGAAACAAATGGTATTTGAAGA

AATGTAATATCTTTTATATTCTATTTATGATATCCATAATCAAATGAGATTATTTTAC

CACATAAATGTTTTAAATATCAGATTTTTAGTTTGCAGTTTTAGGAAAATGCTTTAG

ATAGAAAAGGTTCTTATGCATTGAATTTGGAGTACTACCAACAATGAATGAATTTAT

TTTTTATATTCTTACACATTTTATTGGTCATTGTCACAGATAGTAAATACTAAAAATT

TCAGGTCAGTTTGTTTTGAAACTGAAATTGGAAATAAATCTGGAAATGTTTTGTTGC

ACTAAAATAATAAAATGAATTGTACTG

BRAD.30228_at
                                                 (SEQ ID NO: 34)
TAGGCCAGCCCTGTCACCACCTCCACTGCCATGACCAGGCCGAAGGCAGGGAACGC

CCTCCCCAGTCCCGCTGTCCAGCAAGGCCCCGAGACTTTTCTTCTGTGATTTCCAAA

AGCAAGGCAGCCGTGCTGTTCTAGTTCCTCTCCATCCGCCACCTCCCCTCCCGCTGC

CCCAGAAGTTTCTATCATTCCATGGAGAAAGCTGTGTTCCAATGAATCCTACCTCTT

GCCCAGTCCCAGGCAGAGTAAGCAGGGCCCACCTAGGGACCAAGAAAGAGTAGGA

AGAAGGGGACGAGCCGGGAGCAAAACCACCTCAGACACCCGGGCCTTCTCAGCCTT

CTCCCCGCGGCCAGCTGGGTCTCCGGGGACCCTGGGCCCTGGGCCGCCCATTCCTGG

CCCTCCCGCTGCATCTCAGACCTGACACCCAACGGGGGGATGTGGTGGCCTGTGCC

CACCTTCTCTCCCTCCTCCCGACCCGCCCCCTCGCCCCCACCCCTGTGTGTTTCGCCA

GTTAAGCACCTGTGACTCCAGTACCTACTACTGGTTTTGGGTTGGTTGTTCTGTCTTT

TTTTTAATTAAATAAAAACATTTTTAAAATGTT

BRAD.34830_at
                                                 (SEQ ID NO: 35)
TGCTCAGACCAGCTCTTCCGAAAACCAGGCCTTATCTCCAAGACCAGAGATAGTGG

GGAGACTTCTTGGCTTGGTGAGGAAAAGCGGACATCAGCTGGTCAAACAAACTCTC

TGAACCCCTCCCTCCATCGTTTTCTTCACTGTCCTCCAAGCCAGCGGGAATGGCAGC

TGCCACGCCGCCCTAAAAGCACACTCATCCCCTCACTTGCCGCGTCGCCCTCCCAGG

CTCTCAACAGGGGAGAGTGTGGTGTTTCCTGCAGGCCAGGCCAGCTGCCTCCGCGT

GATCAAAGCCACACTCTGGGCTCCAGAGTGGGGATGACATGCACTCAGCTCTTGGC

TCCACTGGGATGGGAGGAGAGGACAAGGGAAATGTCAGGGGCGGGGAGGGTGACA

GTGGCCGCCCAAGGCCCACGAGCTTGTTCTTTGTTCTTTGTCACAGGGACTGAAAAC

CTCTCCTCATGTTCTGCTTTCGATTCGTTAAGAGAGCAACATTTTACCCACACACAG

ATAAAGTTTTCCCTTGAGGAAACAACAGCTTTAAAAGAAAAAGAAAAAAAAAGTCT

TTGGTAAATGGCAAAAAAAAAAAAAAAAAAAAAAAA

BRAD.37011_s_at
                                                 (SEQ ID NO: 36)
TCCCCAGACACCGCCACATGGCTTCCTCCTGCGTGCATGTGCGCACACACACACACA

CACGCACACACACACACACACTCACTGCGGAGAACCTTGTGCCTGGCTCAGAGC

CAGTCTTTTTGGTGAGGGTAACCCCAAACCTCCAAAACTCCTGCCCCTGTTCTCTTC

CACTCTCCTTGCTACCCAGAAATCATCTAAATACCTGCCCTGACATGCACACCTCCC

CTGCCCCACCAGCCCACTGGCCATCTCCACCCGGAGCTGCTGTGTCCTCTGGATCTG

CTCGTCATTTTCCTTCCCTTCTCCATCTCTCTGGCCCTCTACCCCTGATCTGACATCCC

CACTCACGAATATTATGCCCAGTTTCTGCCTCTGAGGGAAAGCCCAGAAAAGGACA

GAAACGAAGTAGAAAGGGGCCCAGTCCTGGCCTGGCTTCTCCTTTGGAAGTGAGGC
```

ATTGCACGGGGAGACGTACGTATCAGCGGCCCCTTGACTCTGGGGACTCCGGGTTT

GAGATGGACACACTGGTGTGGATTAACCTGCCAGGGAGACAGAGCTCACAATAAA

AATGGCTCAGATGCCACTTCAAAGAAAAAAAAAA

BRAD.37762_at
(SEQ ID NO: 37)
GGGCGGTTCTCCAAGCACCCAGCATCCTGCTAGACGCGCCGCGCACCGACGGAGGG

GACATGGGCAGAGCAATGGTGGCCAGGCTCGGGCTGGGGCTGCTGCTGCTGGCACT

GCTCCTACCCACGCAGATTTATTCCAGTGAAACAACAACTGGAACTTCAAGTAACTC

CTCCCAGAGTACTTCCAACTCTGGGTTGGCCCCAAATCCAACTAATGCCACCACCAA

GGTGGCTGGTGGTGCCCTGCAGTCAACAGCCAGTCTCTTCGTGGTCTCACTCTCTCT

TCTGCATCTCTACTCTTAAGAGACTCAGGCCAAGAAACGTCTTCTAAATTTCCCCAT

CTTCTAAACCCAATCCAAATGGCGTCTGGAAGTCCAATGTGGCAAGGAAAAACAGG

TCTTCATCGAATCTACTAATTCCA

BRAD.40217_at
(SEQ ID NO: 38)
ACCCTGTGCCAGAAAAGCCTCATTCGTTGTGCTTGAACCCTTGAATGCCACCAGCTG

TCATCACTACACAGCCCTCCTAAGAGGCTTCCTGGAGGTTTCGAGATTCAGATGCCC

TGGGAGATCCCAGAGTTTCCTTTCCCTCTTGGCCATATTCTGGTGTCAATGACAAGG

AGTACCTTGGCTTTGNCACATGTCAAGGCTGAAGAAACAGTGTCTCCAACAGAGCT

CCTTGTGTTATCTGTTTGTACATGTGCATTTGTACAGTAATTGGTGTGACAGTGTTCT

TTGTGTGAATTACAGGCAAGAATTGTGGCTGAGCAAGGCACATAGTCTACTCAGTC

TATTCCTAAGTCCTAACTCCTCCTTGTGGTGTTGGATTTGTAAGGCACTTTATCCCTT

TTGTCTCATGTTTCATCGTAAATGGCATAGGCAGAGATGATACCTAATTCTGCATTT

GATTGTCACTTTTTGTACCTGCATTAATTTAATAAAATATTCTTATTTATTTTGTTAN

NTNGTANANNANNATGTCCATTTTCTTGTTTATTTTGTGTTTAATAAAATGTTCAGTT

TAACATCCCANNNGAGAAAGTTAAAAAA

BRAD1_4307876_at
(SEQ ID NO: 39)
CTCCTGGTTCAAAAGCAGCTAAACCAAAAGAAGCCTCCAGACAGCCCTGAGATCAC

CTAAAAAGCTGCTACCAAGACAGCCACGAAGATCCTACCAAAATGAAGCGCTTCCT

CTTCCTCCTACTCACCATCAGCCTCCTGGTTATGGTACAGATACAAACTGGACTCTC

AGGACAAAACGACACCAGCCAAACCAGCAGCCCCTCAGCATCCAGCAACATAAGC

GGAGGCATTTTCCTTTTCTTCGTGGCCAATGCCATAATCCACCTCTTCTGCTTCAGTT

GAGGTGACACGTCTCAGCCTTAGCCCTGTGCCCCCTGAAACAGCTGCCACCATCACT

CGCAAGAGAATCCCCTCCATCTTTGGGAGGGGTTGATGCCAGACATCACCAGGTTG

TAGAAGTTGACAGGCAGTGCCATGGGGGCAACAGCCAAAATAGGGGGGTAATGAT

GTAGGGGCCAAGCAGTGCCCAGCTGGGGGTCAATAAAGTTACCCTTGTACTTGCAA

AAAAAAAAAAAAAAAA

BREM.2505_at
(SEQ ID NO: 40)
GCCATCAAGAATTTACTGAAAGCAGTTAGCAAGGAAAGGTCTAAAAGATCTCCTTA

AAACCAGAGGGGAGCAAAATCGATGCAGTGCTTCCAAGGATGGACCACACAGAGG

CTGCCTCTCCCATCACTTCCCTACATGGAGTATATGTCAAGCCATAATTGTTCTTAGT

TTGCAGTTACACTAAAAGGTGACCAATCATGGTCACCAAATCAGCTGCTACTACTCC

TGTAGGAAGGTTAATGTTCATCATCCTAAGCTATTCAGTAATAACTCTACCCTGGCA

CTATAATGTAAGCTCTACTGAGGTGCTATGTTCTTAGTGGATGTTCTGACCCTGCTTC

AAATATTTCCCTCACCTTTCCCATCTTCCAAGGGTATAAGGAATCTTTCTGCTTTGGG

GTTTATCAGAATTCTCAGAATCTCAAATAACTAAAAGGTATGCAATCAAATCTGCTT

TTTAAAGAATGCTCTTTACTTCATGGACTTCCACTGCCATCCTCCCAAGGGGCCCAA

ATTCTTTCAGTGGCTACCTACATACAATTCCAAACACATACAGGAAGGTAGAAATA

TCTGAAAATGTATGTGTAAGTATTCTTATTT

Hs149363.0CB4n5_s_at (SEQ ID NO: 41)

GGGAAATCAGTGAATGAAGCCTCCTATGATGGCAAATACAGCTCCTATTGATAGGA

CATAGTGGAAGTGGGCTACAACGTAGTACGTGTCGTGTAGTACGATGTCTAGTGAT

GAGTTTGCTAATACAATGCCAGTCAGGCCACCTACGGTGAAAAGAAAGATGAATCC

TAGGGCTCAGAGCACTGCAGCAGATCATTTCATATTGCTTCCGTGGAGTGTGGCGA

GTCAGCTAAATGGCAGGGGCAGCAAGATGGTGTTGCAGACCCAGGTCTTCATTTCT

CTGTTGCTCTGGATCTCTGGTGCCTACGGGACATCGTGATGACCCAGTCTCCAGAC

TCCCTGGCTGTGTCTCTGGGCGAGAGGGCCACCATCAAGTGCAAGTCCAGCCAGAG

TATTTTATATAGGTCCAACAACAAGAACTACTTAGCTTGGTACCAGCAGAAAGCAG

GACAGCCTCCTAAATTGTTCATTTACTGGGCATCTACCCGGGAATCCGGGGTCCCTG

ACCGATT

Hs172587.9C1n9_at (SEQ ID NO: 42)

AACGAAAGTCTAGCCTTTCGTACCCGTATATATAAAGACACCCCTGTTCTGATTGGA

CAAGGCAGCCTTTCCCCTGCAGCTCGATTGGTGGAGACGCCCACTCCCTGACAGAA

CATCTCCTGCATGTAGACCAAATATTAAAACTTTCCTCCGTCCATCTTTAACTGCTG

GTGTTTTCAACCCTTTCCCCTCTGTGCCATGTTTCTAGCTTTTATTTAAAACGTACTTT

GGTTTTCCTTGGCAAAATTGTGTCTAGCTACTAGGATGACGTGTCTTAATTTTTTTTT

AAATGTTGGCGCTGAAACTGGCTTTGATCAACGTTTTAAAAAGACGCGCGCTAGTT

GTGATTGGCCAAGTGATTTCTTCTTACCCTCTTAAGTTTAGAAAGGTTAATTTCATAT

CTTGATTTGTCTATTTAAACTTGGAGATATTTTCAATAATTTGTTCCAAATGCACCAT

GACTATTAACTCATAAGTAACAATATGAAACCTGATGTTAAGCTACATGAACACAT

TTAATTTCACCACAATATGACATCCTCATATGAAAGCACTCTCTTATCTTTTACAAGT

TCAACTGGTATTTGTGTAATCTGCTGT

Hs271955.16C1n9_at (SEQ ID NO: 43)

TGCTACCATGCCTGACTAGTTTTTGTATTTTTAGTAGAGACAGGGTTTGACCATATT

GGCCAGGTTGGTCTTGGACTCCTGACAAGTGATCCGCCCTCCTCNNNCNCNCGAAG

TGCTAGGGTTACNAGGTGTGAACCACCATGCCTAACTATCGTTGCTACTTTCTATTG

GAAGAGAAGGCAGCCCTGATTTAGTCTGTTTACAGTCTGCATTATGTGGAGAATAG

AGAGCCATCATAGTCCCTAAAACTTTCCTTGCCAGTTAACCCAGCAGGACAACCTGT

CTTTGTCTCTTGACAACTGTTAACTGAGAACAGGGCCCTTGCTCCTCTAGGTGTGCA

CATTAAGGACTTTGCACAGTGTGGATGTAGCTCATGCTGCTCTGCCNTNNAGTACAT

GCTGCTTGAATTTTCATCATNANCCTCCACNCCTTNCACCTNCNNGNNAAAAAAAA

AGCGTGCAGGAAGTAGCATTTCAGATCCTTCTCCACCACCTCTGCTTCCCTTCTCCCT

TCTTTTCCTCCTTGCAGCATTCCCTTTAGTACNAGGGAGGGATGGTGGTTGAAAATG

GGGGGAATGATGTTGCTCAGAAAAAAAAAAA

Hs368433.18C1n6_at (SEQ ID NO: 44)

ATAATGCTGGAAACAGAAGCACCAAACTGATTGTGCAATTACTCCTTTTGTAGAAG

AGGCCAAAATCCTCCTCCTCCTTCCTTTCTCCTATATTCACTCCTCCAGGATCATAAA

GCCTCCCTCTTGTTTATCTGTGTCTGTCTGTCTGATTGGTTAGATTTGGCTNCCCTTC

CAAGCTAATGGTGTCAGGTGGAGAACAGAGCAACCTTCCCTCGGAAGGAGACAATT

CGAGGTGCTGGTACATTTCCCTTGTTTTCTATGTTCTTCTTTCTAGTGGGTCTCATGT

AGAGATAGAGATATTTTTTTGTTTTAGAGATTCCAAAGTATATATTTTTAGTGTAAG

AAATGTACCCTCTCCACACTCCATGATGTAAATAGAACCAGGAATAAATGTGTCATT

GTGATAATCCCATAGCAATTTATGGTAAGAACAAGACCCCTTTCCCTCACCACCGAG

TCTCGTGGTCTGTGTCTGTGAACCAGGGCAGGTAATTGTGACACTGCATCTCATAGA

ACTCTGCCTGCCCAGATTTTTGTGTGCTCACCTCAATGGGTGAAAAATAAAGTCTGT

GTAAACTGTTAAAAAAAAAAAAAAAAAAA

Hs435736.0C1n27_s_at (SEQ ID NO: 45)

TCCTCAGACCCAGTAATTCCACCCCTAGGAATCCAGCTTACACACACAAGAAAGAA

AAGATAAATGTACAAGGTTAGTCACTGCACAGTGAGACAGCAAAAGATTAGAAAG

AACCCAAGTGATTATTGATCTGGGTTTTATTCCTTTATAGCCCAACCATATGATGGA

ATACTATAATGTTGTAAAAATGGGTTAAGAGTTCTTTATGAATTGGTGTGGAAACAT

CGCCAAGATATGAAAGCCAAATGCAGAAAAATATATGTGGTATGCTATTATCTATG

TGAAAAAGACATTACTATTCTCTGGAAGGATAAACACAAATTTGAGAATGGTGGAT

ATCTGGGGTGAGAGGTATCCTTTTCACTGTTCTTTAAAAGTTTTGNNATTTTGGTGTT

TGCCTATTCAAAAAAATGGTTAAAATCAGTTGCCACCAATTAAAAATTAGGAGAAT

GCATATAAAGAANNNAANTTCCTGTTAAAAAAAAAAAAAAAAAAAA

Hs493096.15C1n6_at (SEQ ID NO: 46)

GCCCATAGTCCCATCTTTTTACAGGCATTTTTTACACCTGGAGCAGCCAGAGGACGC

ATGCATGGCTCTTCGGAAGGTAATTTAGGGATCACCCATGTAAGTTTCCTAAGGATT

TCTTTAACATGGTTCTTCTGATTCAGTCCGGCCAATTAAATCTAAATCCACCCCTGA

AAGCCATCTGGTGTGGATAACAAGCCCACAAATGAGCAGTCAGCTTTTTGTGCCCTT

TAGGGCCTGGGACAACCACGGGATCTAAAAGGGGCTGGAACTAGAGGTCTTGAGCT

CCTGTTCCTAAAATCATCTTCATCCTATATCTGCAGCCTTCTCCTGCCACGGCATGCA

CCCACACATGCGAGCCTCCCGGGTACTGTCATCCTGAATTCTGAGACCATCCAGCAC

TTCCTTTAGTTTTGCCCTGGTGCTGTTGACTTTTGTTTACTGAAGAGTGTGCTGGAGG

CAGGACAAGGGACATGGAAGGCTGCAATTTAAGAGTCTAAAAGGTTTTAGAATCCT

GAAGGAGGTTTAACAAGCTGAATTGAAGAATAATACCTTTCTCAACTGGAGAGAAT

TTACATGATTGCATTATTGTTAAAATTAACA

Hs493096.2C1n15_s_at (SEQ ID NO: 47)

ATCATTTAGTTGAATCATTATAAGTCTAGGACTGTCTGTAGATGTAAATTTGTTAAG

AATTAGGACTCAAGAGTAGAATTCCTTTAATCCACATAGACTTACAATGGTGCTGTG

CACATGGAGCCCCTAAATCATTGCTGACTGAGTAGATTTCCCAGGGTAAGCCCAAG

```
AAGTTACTCCTAGAAGGGGCTGGTAGGGGAAAGAGCCAACATCCCACATGCCTGCC

CACTTTGGGTCTGGTCCCAAGAAACAAACTCCAGTGGCCTCGAAAATTTAATATTGC

TGTCAGAAGGGCCTCCCCTTCAAAGGAACAGGTCCTGATAGCTCTTGTTATATGCAA

AGTGGAAAGGTAACGTGACTGTTCTCTGCATTTCCTGCCTTTCAATTGAGTGAAGAC

AGACAGATGATTTATTGGGCATTTCCTAGCCTCCCCTTCACCATAGGAAACCAGACT

GAAAAAAGGTGCAAATTTTAAAAAGATGTGTGAGTATCTTGAGGGGGCTGGGGG

AGAATTCCTGTGTACCACTAAAGCAAAAAAAGAAAACTCTCTAACAGCAGGACCTC

TGATCTGGAGGCATATTGACCATAAATTTACGCCA

Hs592929.0CB2n8_at
                                                        (SEQ ID NO: 48)
TTTTTCTGAGCAACATCATTCCCCCCATTTTCAACCACCATCCCTCCCTGGTACTAAA

GGGAATGCTGCAAGGAGGAAAAGAAGGGAGAAGGGAAGCAGAGGTGGTGGAGAA

GGATCTGAAATGCTACTTCCTGCACGCTTTTTTTCTTCTTGGAGGTGGAAGGAGTGG

AGGATGATGATGAAAATTCAAGCAGCATGTACTAGACGGCAGAGCAGCATGAGCT

ACATCCACACTGTGCAAAGTCCTTAATGTGCACACCTAGAGGAGCAAGGGCCCTGT

TCTCAGTTAACAGTTGTCAAGAGACAAAGACAGGTTGTCCTGCTGGGTTAACTGGC

AAGGAAAGTTTTAGGGACTATGATGGCTCTCTATTCTCCACATAATGCAGACTGTAA

ACAGACTAAATCAGGGCTGCCTTCTCTTCCAATAGAAAGTAGCAACGATAGTTAGG

CATGGTGGTTCACACCTTGTAACCCTAGCACTTCGTGGGCAG

Hs79953.0C1n23_at
                                                        (SEQ ID NO: 49)
ATCAGAACAATTTCATGTTATACAAATAACATCAGAAAAATATCTTAAATTATATGG

CATATTCTATTGATTCATCCACAAATTTATAAGTCCTTACCACCTTTCATTATATTGG

TACTAGGCATTATAGTAGTGCTAGGCACTATAGTAATGCTGGGGTATAAACAAGAA

TAAAACAAAATAAGTTCCTTATTTCAGGTAACTTACAGTATAGGTCAGTGGTTCTTA

GCTTGCTTTTTAATTATGAATTCCTTTGAAAGTCTAGTAAAATAATCCAACACCATT

ATTCCCCATTGCACATACCCCCAGATGTTTTAGACATATTTTCAATTGCTCCATGGA

CCTTAAGAAAACTTGGTTGGTGTGCAGTTTGGTGTATTATGGGTAAGACTGGACCTG

GTGTTAGAAAATCTGCATTTGAGGCTTTGTTCTGACAGTGTCTAGTGTAAACATGGG

CAGACCACTTAAACCTCTCTTTAGTCTTCTCTGTAGAATGATGATAATACCATCTAA

TTAGCAGGATTGTTGTTTTATTCAGTGAGACAGCATATGTAAATAACTTAGTAAAAT

AAAAAGCAACGTGTTTATAATGGTAAAAAA

BRMX.2377C1n3_at
                                                        (SEQ ID NO: 50)
TGGGAATCATGAACTCCTTCGTCAACGACATCTTCGAACGCATCGCGGGTGAGGCTT

CCCGCCTGGCGCATTACAACAAGCGCTCGACCATCACCTCCAGGGAGATCCAGACG

GCCGTGCGCCTGCTGCTGCCCGGGGAGTTGGCCAAGCACGCCGTGTCCGAGGGCAC

CAAGGCCGTCACCAAGTACACCAGCGCTAAGTAAACTTGCCAAGGAGGGACTTTCT

CTGGAATTTCCTGATATGACCAAGAAAGCTTCTTATCAAAAGAAGCACAATTGCCTT

CGGTTACCTCATTATCTACTGCAGAAAAGAAGACGAGAATGCAACCATACCTAGAT

GGACTTTTCCACAAGCTAAAGCTGGCCTCTTGATCTCATTCAGATTCCAAAGAGAAT
```

```
CATTTACAAGTTAATTTCTGTCTCCTTGGTCCATTCCTTCTCTCTAATAATCATTTACT

GTTCCTCAAAGAATTGTCTACATTACCCATCTCCTCTTTTGCCTCTGAGAAAGAGTA

TATAAGCTTCTGTACCCCACTGGGGGGTTGGGGTAATATTCTGTGGTCCTCAGCCCT

GTACCTTAATAAATTTGTATGCCTTTTCTCTT
```

BRAD.33405_at (SEQ ID NO: 51)
```
GAAAGTGATAATACAGAAAGGTGGGGCTGGTGTAGGGNTNAAGNCAGGATGCTTT

GGNANAGCATGNAAGGTCNCCGANTCCAGTGNTNAGGAACTAATGANGGGTTTNT

NAAGANCGTNATGAGATCAATGCNGATGAGNCACTTAGAAGNAGCAATTAGTTAG

GCAAAGGGAAGTGAATGTGNAGGAGGAACAAGCATTCCAGGCAAGAAGAACACCC

TATCGAAAAGCCTGGAAGCAAAACATTAGTGAGGCTACCTTTCATAAATTGCTTTCT

GTAAGTCATGCCATTGTGTAGTCTTAATTGCTTTCTCTCACCAGGGAAGGTGTGGGA

AGGACTTGTGAAATACATATTCGAGGAAAAACTATGCACAAGGCCGTGCATTTAAA

AATAAACTCCCTAAGGCTGGGGTGAAACCTGCTACGGTCTGCGCAAGTTGACTGTT

AATGAATTTGATTCTCAGGTGTGAGTGATTAAAAGAACACTGATCATGTCATTTTCT

TTTTGGTCACTAATTCCCTCCCTCCCTTCTCTTTCTTTTCTTTTTTCTTTTCTTTTCTTT

TTCTTTCTTTCTTCCCGACAGAGAAAGACTCCATCTC
```

Hs584242.2C1n64_at (SEQ ID NO: 52)
```
TAAGATGTTTAAGTATATCCAACCGTCCCAGACCACATTGGCCTATTTCCTCCTCTT

GGCAACACTGCTCGGGTTTTCCCCTCGCATCATCCTTATGCTATGACACTGGACTAA

ATTGTAATAATACATTTTCTTGTTAATCTCCTCATTATACTATGAGCTCCTTGAGGAC

AGGTACTTTGTCTTGCTCACATCTGTAGATTCAATGCCTGGCACAGCGATTGATATT

GCAAGGGCACTTAATAAATGGTTTTTGAATAAAAGAATTGCTTAAAGTAAAATATA

GCTGTAAATTGTATTATAAAAGGACAGTGGGTGGCAGTCTGAGGTCTGCTATTTACT

GGTTTGGGCAAGTTACTTAATCTGTTTGCTTCCTCAGCTGTACGATGGGTAAAATAA

TAGTGGTTATCACAACAGGGTGGTTACAGCGATGAAATGAGATTATGTGTGTAGGC

TACCACATAATTGTAAAGCTGATATTTAAATGGAACAGATACTGCACAGACACTTG

AGGTCTGAGAATAAGATTAGGTCAACCAGAGTATTAATGGGTTAAATAAAGGTGAC

ATCCTATGCAACCAACGGTTTGATCTTTATGCT
```

BRRS1RC_NM_004065_at (SEQ ID NO: 53)
```
GTCTTCCAGTCAGTCAGTGTCTTCCAGAAAAATCTACGTCTTCCACCAAATCCAGGT

CTTCCAGTCAATCCACATCTTCCGGAAAAAATCCAGGTCTTCCAGCCAATATATGTC

TTCCTGAAGATCCACGTCTTCCAGAAAATCCATGTCTTCCAGAAAATCCATGTCTTC

CAGTAACCTCCCAGTCTTCCAGAAAATCCACGTCTTCCCAACAATCCAAGTCTTCCG

GATAATTTGGGTCTTCCTGAAAATCTACGTCTTCCAAAAAAGCCATGTCTTCCAGAA

AATCCACATCTTCCAATGGCCTCCAGGTCTTCCAGACTATCCATGTCTTCCAGAAAA

TCCTTGTCTTCCCTTAAATCTATAGCTTCCAAAAAATCCGGGTCTTCCAGGAAATCC

GTGTCTTCCAGCAAGTCCACGTCTTCCAACAAAGCCATGTCTTCCAGACTATCCATG

TCTTCCAGAAAATCCTTGTCTTCCCTCAAATCCATAGCTTCCGAAAAATCCAGGTCT

TCCAGGAAATCCGTGTCTTCCAGCAAATCCACGTCTTCCAACAAAGCCATGTCTTCC

ATCAAATTAATGTCTTCCAGCCTACTTGTG
```

-continued

BRRS.8182_at (SEQ ID NO: 54)
AGCATCGTTTATGAAAACAACTAAATATTCACTAATGGTGCCAGTGGAATAAATCA

GAGAACATCCCCTGCTACGTAACTCTCTGCATACATCAAAGAGAATGGTGTGGCTTT

GCTTTTTCAACAATCTACTGAGTGGCCATGGGCATGTGGATATGGCCATGAATGAGC

AAGATCCTCTCTGATCCTGTAGAAGTTAAGTTCTACCAGATAACTTGCTGCTTCAAC

AAAAAGATTTACCTTTTTAAATAAATGTTGTAGAATACTTAAAAAAAACAAACTAG

AATTTGCCTGTGTGCAGCCAGTAACATGTCTATTTAACCTGGACACCTTTTGAGGAA

TATTCTCAGATTGCCCCCATGCTGTTTATAAGACATTGTTCCTTATACACCTGTTTAT

GAATGAAAGAAACATAAGGAGTGGGTACAAAGACTTCTATCTATGAATGATTAAA

AAGGCTAGAGTACGAATACTTCTTGAACCTTTGGTACTAAATGCTTTTCATGTTCTA

TATAAATGTAGAAAACATTTTACAAATCCTGTAAATAAACTGTTTATTTTTTATAGA

AAGCCAAAAAAAAAAAAAAAAAAAAAAAAAA

BRMX.13815C1n5_at (SEQ ID NO: 55)
TCTTTCAACATTTAGATAGTCTTTCTTAATATTTCCAGGAGAGTACCTCATTTTTATT

TTGAAAACCATTCAGCACATTTATCTTATGTAACATGCAGAGCATATATCTATCTGT

ATTTTTAAAATTTTCCTGTTACTCATTGATACATAGTACTTAATTACATGTTATTCCA

TGTACACTGAAAACAATATAGGAAATATATACATCTAAGACTTCTACTTTGTACAGT

CTTTCATTAAATAAGAATACTTACACATACATTTTCAGATATTTCTACCTTCCTGTAT

GTGTTTGGAATTGTATGTAGGTAGCCACTGAAAGAATTTGGGCCCCTTGGGAGGAT

GGCAGTGGAAGTCCATGAAGTAAAGAGCATTCTTTAAAAAGCAGATTTGATTGCAT

ACCTTTTAGTTATTTGAGATTCTGAGAATTCTGATAAACCCCAAAGCAGAAAGATTC

CTTAGTACCCTTGGAAGATGGGAAAGGTGAGGGAAATATTTGAAGCAGGGTCAGAA

CATCCACTAAGAACATAGCACCTCAGTAGAGCTTACATTATAGTGCCAGGGTAGAG

TTATTACTGAACCAACTTTTTTGTACAAAGT

BRMX.2637C1n26_at (SEQ ID NO: 56)
TCCATCAGGGCACGGTAGAAGTTGGAGTCTGTAGGACTTGGCAAATGCATTCTTTCA

TCCCCCTGAATGACAAGGTAGCGCTGGGGGTCTCGGGCCATTTTGGAGAATTCGAT

GATCAACTCACGGAACTTTGGGCGACTATCTGCGTCTATCATCCAGCACTTGACCAT

GATCATGTAGACATCGATGGTACATATGGGTGGCTGAGGGAGGCGTTCTCCTTTCTC

CAGGATGGAGGAGATCTCGCTGGCAGGGATTCCGTCATATGGCTTGGATCCAAAGG

TCATCAACTCCCAAACGGTCACCCCGTAGCTCCAGACATCACTCTGGTGGGTATAGA

TTCTGTGTAAAATTGATTCCAATGCCATCCACTTGATAGGCACTTTGCCTCCTTCTGC

ATGGTATTCTTTCTCTTCCGCACCCAGCAGTTTGGCCAGCCCAAAATCTGTGATCTT

GACATGCTGCGGTGTTTTCACCAGTACGTTCCTGGCTGCCAGGTCGCGGTGCACCAA

GCGACGGTCCTCCAAGTAGTTCATGCCCTTTGCGATCTGCACACACCAGTTGAGCAG

GTACTGGGAGCCAATATTGTCTTTGTGCCAA

BRAD.36737_at (SEQ ID NO: 57)
CTGTCCAGAATGTAGAGGACAGACCCATGGGAACTTCAAAATTCCCCTCTCAATNC

CCATTTTATGTTAGAAAATCAAGTACCGAGAATGTTAANGTTAAATTATGTGACCAA

AACAAGGAAAGAGGCTGGTAAAACTGCATTTTGCACAAAAGTGTTGATTCAACATG

AAGTCAAATAATATGTTCTAATGAAACCACACCTCTCACACACATATCCTTTCTCTC

```
AAACCTCGGTGTTACTCTGGCCAAAAGTCTTAGGTTTCTTGAAGTGTTTGTGGAAGA

GTAGATGGAGTTTTATTTAACATTATCAAGAAATCCAAGCTGCAGACCCCACACAT

A

BRAD.3853_at
                                                    (SEQ ID NO: 58)
AGACTTTTTAGTAGCTTCCAACTACAAAAAAAGAGAAATAATCAATTATGTACTAA

TCAGACACTTTTAAAAATTACAACAGTTTATTCAGAGAAACAAGCTTTGTGTGACAT

TCTAAGCGGATTTTATTCTGCAGGTCCTTTTAACATAATGAGTAATATTTGTGTTGG

GAATGACTGAGAAGAAATTTCATAATGATGTGAAGATCTACCTGTAAATAGTTCCT

CTGTCGTATGCTGGTATTTATATTCTAGCATCTCAACAGTGCTGATGGTCACTCATCT

TGGAGTTCCCTGAATTTTTTTTTTTTTTCAAAACTCCTGTAATGTTACATTACCCAT

ACTTTTGTTGTTGCTGCTGTTGTTGTTGTTTTGAGACGGAGTGTCGCTCTGTCGCCCA

GGCTGGAGTGCANGTNGNNCCGCGCCCGGCACATGACTGCATACTTTCAAGGAGAG

GACTCAGAGCTTTTATTTATTTAAAGAAACTTGAAAGGAGGAAAGTGGATTAAGAA

AAAAAAAA

BRAD1_19760734_at
                                                    (SEQ ID NO: 59)
TTTTTTTTTTTTTTACATAAAGGCATGAATATACAAGGTAATGTCAGCAGCTGTACTC

CACTCTTTATTCGTTGCAAATCTACCTATTTGTTTCCAAAGGATGTCTGCAAATAAAT

AGGTAACATTGTACAGCTTTCAACAGTGGATCAGAACATAGATGTCTCTTCTAATTC

ACAAGTACCAATGGCTCAATTAATTTAAGGGACATTTTCTGAGTTGTGTGATTTCAC

ATGTATTTATCGTGTCTAGAAGTGTGCAAACTTTTGTTTCATTTCTCTCTTAGATTTC

TGTAGGAAGAGTTAAAGGATGTGAAGTAGTCATTTTACTTATTCATAACACATTTTA

GGGAAAATTGTGCTGTTGCTGTTGGGGAGAAAGTTAAAGCTATCAACTATAACCTG

GACTCCAGTCCAATTTTTCACATCTGGTTGCTACTTTTAAAAAGGATCATTTTAATTT

TTAAATGCAGAATGTGTTGCACTTTACCTTTGACATTCCAGGTTTCCTCATGGTCATT

TAGAAAAATAAAGCAGGAAATTCTAATGCCTTAGCATCTACTTTAATAAGATGTTTG

CATTTATAAAAATAACAAGAAACTGA

BRMX.2797C4n2_at
                                                    (SEQ ID NO: 60)
TTTAATTTTTTGGAAGGATATACACCACATATCCCATGGGCAATAAAGCGCATTCAA

TGTGTTTATAAGCCAAACAGTCACTTTGTTTAAGCAAACACAAGTACAAAGTAAAA

TAGAACCACAAAATAATGAACTGCATGTTCATAACATACAAAAATCGCCGCCTACT

CAGTAGGTAACTACAACATTCCAACTCCTGAATATATTTATAAATTTACATTTTCAG

TTAAAAAAATAGACTTTTGAGAGTTCAGATTTTGTTTTAGATTTTGTTTTCTTACATT

CTGGAGAACCCGAAGCTNCAGCTCAGCCCCTCTTCCCTTATTTTGCTCCCCAAAGCC

TTCCCCCCAAATCATCACTCNCCTGCCCCCCTTAAGGGCTAGAGGGTGAGGCATGTC

CCTCACAATTGGCACATGGTNCAAGGCCATCAGGCAAGGGNGCATTCACACAAAAG

GGCACCAGG

BRMX.10399C1n5_at
                                                    (SEQ ID NO: 61)
GAAACAACTGGTAAACACAGTAAGCCCATTTCTGGGCTTTTAGAAAAACATTGCTC

TCTTTTCTTTCCCCACCCAGTGTATTCCCAAGGACTTAATGCTGCACTCTGACCTAGC

CCTCAATGATGGTTAAAACTGATTCTGAACCAAAGGTAAACAGGGTTCCTCCCCAT
```

-continued

```
GCCTTGGAGAGCTCCAGTCTGCAGAAAGCTAATGAAGCCCTTGAAGCAGTATCTTG

TCTTCCATCCACACTTTATTGAAATGCTTTTGAATCTTATTGTGTTGTAATTACATAC

TATAGAAAACTCCGCCAACCTCTATTTCAAGGTTTGGGCCCATGACTCTCGCTAAAA

CATTTCAGTTCCATTTTCCAGAACATACCATTTCTAAATGCATCTGTGAGGGCCCTC

CACAAGTATTTTCAGTCCACATTTCAGAAAACTTGAAAGTGACGCAGGTTCCTGACT

TAGTTGATGGTGGGTAAAGGGAATGCCATTATGAGTGGTGGAGGTTGTTTTCTTTTT

TCTTGCCATATTCTCAGCATAATATTTGAAACCTACAAAAGAAGTTTGATAATATAA

CTGTATATTTTATGCCTGCACTAGTGGAGGA
```

BRMX.8912C1n3_at
(SEQ ID NO: 62)
```
GAGGTAGGAACTGATATTCCCATTGTACAGATGAGAAGACAGATGCTCAGAGAGCT

TATTTGTCTGTTGAAGCCAAAACCTGTGCCCTTGACCACAATGGACACTATATCTTC

TGAGCTCCACTTAATTAGAGAATTTGGATCAAGTGACTAAATAAATCACACACCAC

ACACATTAAGATACGCCAGAGTGACAGGGACATTAAATAAATCAAGTATCCATGAA

GTTTGCTGCCTTCCAAATCAGCCCCCTATTCTTTTGCCCTAAGATATCCCATCATAGT

CTGTTTCCTTCCCTTCTCTCTTTGCCCTCAACCTTTCCTTCCCTCTTATCCATGGGAAT

GACTCTAGGAATCCTGTTGAGTGTATGTGTGTGCGTGTTCTTTTCTTTTTCTCTCATG

AATATTACACTTTTATTAGCCAGCTATACTTGTGTTGATGAAAAAGACAAAATGGAA

TTTTGTTTTCCTTTAACAATCAAGTATGAATGGTCTGCTTACAGGATGTCCCTTCTTG

GGGTCCTTGGAGGTAACAAAAGCTCATCATTAAACAGGTAGCTATCATTTCTACATG

CTTAGTATCACTTCCGATTATCTTATTC
```

BRMX.13731C1n18_at
(SEQ ID NO: 63)
```
GGGCTGAGGGTCCTGAGGAGAGAGAGAGAGGCCACGTGGATGGAGGACTGTCACC

CCCTTCTCGGTTCTGTCACCCCCTTGAGTCTAACTCACTGTTGAGGGGAGGAAGAAG

GGGGATGGACGGAAGGGAGACCGAGGAAAGGCTTTCGGGAGTGGGGACATTATCC

CCCCAGAGGTGTGCTGCCCCACCCAGCTGCACCCCACAATCTGGCCAACTCATTTCA

CAGTATAAATCACTCCAGCAGGACGGCATCACAGCAGCCCCTGCTGCCTGAAATCA

GAGCGGCCCAACGAGGAAGGCCAGGAGGGTCGGCTGGCAGGGGGCAGGGTCTTGG

GATAACACTGTCATCAGAAACAAGGCTGGGGGCTGATTTCGGGGTGGGGAGCCTTA

GGAGGCCAGAAATTCCAATCAGAGCCAGTTTTTCTGGGAGGGAGTGGCTAGACAGT

CAAGGAAGGACGTTCACATTTCAAAAGAAGTCGGGTGGGGGGATGAGATTATTCTA

GGGGGGCATCGAATTCCCTTTAAGGGGGGGGCTCACTTCTGCCCAGAGTAAAGAGG

ATCTCACACCATGGAAATGTGCCAACTTTTTTGTACAAAGT
```

BRAD.25947_at
(SEQ ID N: 64)
```
CTTCCATTCCTCATGATTTTAGGGTTATCCTCATTCAGATCTACTCTAGTTATAATAG

TACTTTAAACAGAGCACAGAATTAAACCATTAGTATGTGAATCTGCAAAAAGAGAA

CTTGTTTTAGACTCTTCTACAGTTTAGACTTCAATGTGCATACTAAATGCATAACATT

CGTATCAAATAATTAACATTTATATACAATTAACAAATAAGGACAAATTTTATACAA

AACTTCTACTACTGCTATAATTTTTGAAAACATTTAACCCACTAGCAAGAGGTAAGA

CAGCACTGCCTTTTTAAAAGACAGGTCACTTGAATAGAGAATATAAGATATAACCA

TAAGTAGGAGTATAAACAATAATTTTTCTTCTTGTGGAATGTTTTTAAATTTCCTTTC

TTATATTATTATTCTTCCTTAGGTTTTTTTAGACAGGTCATTTCTTCCTGAATGATTTT
```

-continued

CCTTTTTCTTTTATTTTTATTTTTTGAAGGAGGATTATTTACTGGTGGTCTAAAAGAA

GTACCTTCAACTTCTTCATAATTGTAGCCAAAGCGGAAATGGAATATTTAATAATTC

TTACATCTCACTAATGTAGTCTTCTG

BRMX.5143C1n2(2)_at
(SEQ ID NO: 65)
AATAATTATAAAGTTTATTTAAATGTTGATTGTCCCAAGGTCTACAGTTTCTTTTCTG

TTGTGTCATCAGTGACAAAGAGTAAAAAAAAGGAAACTCCCATATTTAGCACTTTA

GAGTAAAACACATGGATCATCGTTATTAACAGTCCTCTGGGCGTGCTGGAGCTCACT

GAGAAGGCTTCTATTTTGAGCTTGGAATGTTGTGCTGAGCTGTGCAGCCTGTTCCTG

CATCTGTTGTTCCTGCATTTTCTGTTGCTCTGCCAGCCAATTTTGTTTGGCTATCTCC

ATTTAACTCACTTGTTCCTGATGGAGTCTCTCCCTCTCCTGCATCATTTGCTCGTTCT

GCCTTTGAATCGCCGCCAACCTTTGCGCTTCAGCCTTTTCAGCTTCTGCTTTCACTTG

TGCCTCTGAGGAGAAAAAGATAATC

Hs633116.0C1n30_at
(SEQ ID NO: 66)
GTGTCAACATTTATGCTCCTAAAGGATGTTGGGTCAAATGAAATGTTCCTCATTGTT

TCTCTCTCTTGATCTCTCCTTCACTCCTTCTCTTCCTTGCAGGATCTCCAACTCCTTCA

TAAGGGCACTCTGTGTTACCCCTTTAAACAAAATAAAGAAGTCCTACATTCTGCCCA

GATTTTTTTCAGGCTCCACCAAAGGGTTGGGTGAATTATGGCCCAAAAGTTGGTGAG

GATGATGGTGAACCTTCAATCACCTTCAGTCTCCCAACCAACAATGGTCATGGCTTG

TTTTCTCCCTGGATTACATGGAGAAAATCATGCCCTACTTTTTGGACCTGTTGCTTCT

ACATTTGTATGGTAACTGTGAAACCATCCTAATGAACAGCAAACATTAACCACTAC

ATAAAATGTAGACTTTGAATAAAAACACAGCTAAGTACTAACCAGCTTGCCCTTTA

AGCCAATTCCCTGTAGCTACTTACAGCACGACTGTTAGCTCCTTTCCTTATAGTTTCT

TACTGCCTTAAAGTCACATAGATGTGGTCACAAGGCACTAACTTCCCTTAGTTATTT

CTATAAGATAATATATGTAACGTTGGCA

BRSA.1606C1n4(2)_at
(SEQ ID NO: 67)
AGTGCAGAGAGGATGAGAATATCCTTCATGGGGTCCAGTTCCAAATCTGAAGCATA

ATTTCCAACCATCAAAATATTGGAAATAGGAATGCCTAGCATTTTATGGACATTCAT

GACCCGGCTTTGAGAAGTCATAGATCTACTCATGTTTAAAAAGTTGTCTTGAAGAAC

CTCACTGCAATCATCCACTTTAGTAAGCAAGGCCACATATGCTATACCACAGTTTAA

TACTTCTTTGTGAACTTGCTTCACTTTTGCCAACATTTTAGAGTAGAGATTGTCAATA

GAGTTGATGTCTAAGACATAAGCCACACAGTGAATCCTGTCCTTCAGAGATGGAGA

GGTGATAAAAGTAGAATGCTCAGGTGTAATTGGTTTACGGGAATTAAACTGTTATA

AAAACATAAGGTAACATTCAGAAATCAGAGAGCCTCTGTTTAACCCTTAAAGACAC

AATTAATGCTTCTAATACTGTAACTACTGATCTCCCTCTTTCTCCTCAGCTACTCTTT

CCCCAAACAGTAGCACCTCCTCTTTACTTCCTTTCTCACTGGGGGGCATAATGCCAC

CAACTTTTTTGTACAAAGTTCCCTTTTTAATG

BRAD.41047_at
(SEQ ID NO: 68)
TTATCTTATACTAAATTCCAACATGTATCTGAGTTTGCTTCTAGATTTTCTGTTCTGT

CCCAGTGGTTGGATATTTCTTCATACACGTCTATCATACTGTTTTGACTATAGAGGCT

TTTCAGTGTCATTTAATATCTGTGATGGCAATCCCTACTCAAAGCTCTTTGTTTTCAG

-continued

TGTTCCTGTATTGCTCTTTTGTTAATCCCTTAATATAAAAGTAAATAATAACCCAGTT

GGCATATTATTTTGATGACATTAAATTGGGGAGAATAGATACTGTGATTTTTGAAGC

TTCCTACAAATATGATATGCTTTTCATTTGTGCAAGTACTTTAGTATAATGTTAACTG

GTGGTGGTAATGGAGGAAATTCTGTCATGTTCCTTACTTTTAGTTTCCTCTAGCGCTT

TCTATTTTTTATTTTTTTTCAGATGGAGTCTTGCTCTGTCTTCTATCCAGGCTGAGGC

AGGAGGATCACTTGAACCCAGTAGTTCAAGGCTGCAGTGAGCTATGGTTACACCAC

TGCACTCCAGCCTGGGTGACAGAGCAAGATGCCATCTCTTAAAAAAAAAAAAAAAA

A

BRAD.4420_at (SEQ ID NO: 69)
GTTAATATCTTTTTCGTTTATTGTCTGTCTCTGAAGGTAGGGACTTTGCCTCATTTAC

TGCTTTTCAGTTCTTGGAACAATGCTCGGCACATAGGCAATCAACGAATGTTTGTTG

AATAAATGATTTTTTTCTCTGGAAATTGTCAAAATCTGCATGAGGTGTATCAGGCCA

GCCATTGTCAGCCTCAGTTTAGAGGCAAGGAAATAGGTTCAGAAAGGTTCAAGGAC

GTGCTGAAGTCACAGGGCGAGGCAGCAGCAGAGAGCCTGCTTGTTGAGAGCCAAGT

CTTATGGGACTTGCCTCCTTCTCTCCCACTGAGGCTGGGGACACCAGGTGGCCCAGA

GGCATGTGGATACCTCCAGTGGGAGGTTAGGAGAGTGCTACACAGAAACTCTGAGT

TCTAACACTCTTGGGACCATAAAAAATGGAACAAGTCTGGGCATGGTAACTCACGC

CTGTAATCACAGTATTTTGAGAGGCTGAGGTGGGAGGATCACTTGTGGCCAGGAGT

TCGAGGCTGCAGTGAGCTATGATCCTGCCACTGTACTCCAGCCTGGGCAACACAGA

GAGACCTCACTTCTTTAAAAAAAAAAAAAAAAAAA

Hs137007.0C1n9_at (SEQ ID NO: 70)
AGGAGAAAGGGAAGTCAAATGTCTCGTCCAAGTCTACACAGCTAAAAGGGGCAG

AACTAGGGTGACGCTCAGGCCTCATTTAGAGATCGGGGGTTGGCGAGAAGTGGGGT

GGGCTTCTGGAGGGGCTGGGAGAGCCCCACAAGGCTGCAGAGGGTGGTGAGCCCG

GAGTGGGCCTGGCCTGGTGTGGGCTGGGGGTATGGGCAGGAGCTGCAGACAGCAG

GGCTGCACCAGCGGACCAGTTTCAGAGGCAAGGGTTCTAGGCCCTTGAGAATCCAC

AGTGCCAAACAGACCCAGATAGCTACGGGGTTGGTACCTGGGGAGGCCTTAGGACA

GGCAGAAAGTCCCAGAGGCGAGGGCGTTGCCTGGGGACGTTTTTGCTCCCTGTCCT

GCTGACAGAGCATAGGAAGTGTGAATGTTTTCTACCCCCTCCTCTCTCGGCTCAGCA

GAGCTCCAGCGAGCCAAGTCCTTGTCTGTGGAGACGCATCAGTCCCTGGCTCTAGG

GAATAGGGAGTCCCACAGACAGGGGGGTGTCAGCAAGCTGAGAGGGTCTGTAAGT

AGGTACGGAATTGAGTCAGGAAACAGTCTGGGTGTGGAGTGAG

BRSA.18050C1n3_at (SEQ ID NO: 71)
TGCAAAAAGCCAAAAAAAGCAGCTTTTAACATTATATCATTATATCACAATTTTGAA

ACATGGGNNNNNNNNNNNNNNNNNNNNCCATTGTGTGGATAAAATGGTCTCCGTGA

CATTGAGCAGAGTGTTATCNNNNNNNNNNNNNNACATTATTGCACAGAGATTTCTCA

TCAATGTTCTTCAGTTTTTATGTCTTTTCCTAAATGTGAATAAGTGCTATGGATAAAA

TACAAATGTAGAAAATAACAGCAGCATGATTTGTCAAAGTTAATCCCTATAATTTA

GTAAGAAAAAATGGATATAAACAAAATAAGTGCTCTTTCTAAACTGTACTAAATTT

TCAAAAATATTGTTTTAATGCAGTGAAGGTCCTGAAAAGCCTATTGAAAGCGATGC

TGAGTCCTGTTTTCAAAAGTGTCCTGTTTGGGTTTTCTTGGTGAAGAGCAGAATTTC

-continued

AAGTGAAGTAATCGACGGACTAATTTAAAACAAAACAGCCCTCGGCTTCCCTATTG

GCCTGTGAGGGCACCGGCTCCGGGACCCTGACCTGGGAGGCAGCGAGTGGTGGGG

GTGCCTGGCCCCCATCTACACGTACACAGGCTGGCCAA

BRMX.2948C3n7(2)_at (SEQ ID NO: 72)
GCACGTCTACGGGGCTGGACAGAGTGTGGTTAACCGGGGAACTGGGCAAGCCGGC

GCCGAGCCTGCGTCAGCCGTGCAAGCCGCTCCTTCAGGAACTTCCGCTTGTCGCTGG

TGTCGCTCCGCTCCTTCAGGAGCCAGCTGTAGGTGTCCTTGTCCTGCAGGAGCTGCA

GCATGGCCTTCTGAAGCTGCTGGCCGTACGTCTGGAGCATGAAGAACTGGATGATC

AAAGGGATGTGGCTGGAGATGCGCTTGCTGGCCTCCTGGTGATAGGCCATCAGGTG

CTGAAAGATCTCCTCCATGGAAGAGTCTGTTGCCGAGCTGGACTGGAAAGCCCCAA

AATCCCAGGATTTCTTCTTCTTTTCTTCTTCCAGCTCCTTCTCTCTGACCTTCTGCAAT

GCACCCCTGTATACCTGGTCCTGGCAGTAGACAATCTGTTCCATCTGGAAGTGGAGG

CGGATCAGCTTCTCACCTTCTCTCTCTTGTTCTGCTCTAATGTCTTCAATTTTGGACTT

GGCGGTTCTGTGGAGGTTAAAAAACTCTTCAAAATTTTTTATCGCCAACTTTTTTGT

ACAAAGTTGGCCTTATAAAGAAAGCATTGCT

Hs43047.0C4n40_at (SEQ ID NO: 73)
NNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNCTAA

AAAAATATGTACTGCTTATTTTGTTAGCATACTTTTAATTATATTCTTATTCTTTCTA

CCCCTCTCAAAATGTATTTTTCCAGCTTGCCATTTAATTGGTAAACAGCTGTAAAGT

TCAAACGTGAAATTCTTAAAGCTCCCTAGAGACATACACAATAACTTCTGTGGCATG

GACTTTTCTCGGCATTAAAAAAATCTAGTACCTCTCTTGGCCAGAACCCCTAATTTT

ACACTTTATGGTGTTGCGTCGTTTTTCNNNNNNNNNNNNNNNNNNNNNNNNNNNT

TACTGGCAAGTTTTTCCTCCAAACAGTTTTCTAATCAAGTCTAATAAGTT

Hs926.1C10n7_at (SEQ ID NO: 74)
NNNNNNNNNNNNNNNNNNNNNNNNNNNNNNNNNNNNNNNNNGATGAGCCAG

GCATGGTGGTATGTGCCTTTAGTCCCAGCTATCTGGGAATNNNNNNNNNNNNNNNNN

NNNNNNNNNNNNTGACGGCAAGAGCCTGTCTCTGNNNNNNNNNNNNNNNNNNNN

NNNNNNNNNTCTGATCAGTTAAATGAATATGGAAACTTAATCTTGTACCCCTTACCTC

CCAAGCATACAGCCACAGTTTACCGTTGGAGGGATCTTTCCACGGAGGTAAACAGT

GCTGTTTTCTCCAAGTGCCAGAACAAAAACACAACAGCACACACACAATGAGATGG

TTTGGCTCTGTGTCCCCAACCAAATCTCATCTCAAATTGTGTTTGGCTCTGTGTCCCC

AACCAAATCTCATCTCAAATTGTGTTTGGCTCTGTGTCCCCATCCAAATCTCATCTCA

AATTGTAATCCCCATGTGTCAAGAGAGCAACCTGGTGGGAGGTGACTAGGTCATGG

GGGTGGTTTTTCTCATGCTGCTCTCATGATGGTAAGTGAGTTCTCACAGGATCTGAT

AGTTTAAAAGTGTTTAGGGGCTGGGAGCAGTGGCTCAT

Hs528836.0CB6n98_s_at (SEQ ID NO: 75)

GGGTGAGGACCCACAGCTCTGATGTGGGCGCTTCAGGCCATGGTGGAGCTGAGATT

CAGGTTGGCTTTTCCCCTCAGCTCCCAGCTGGCTGGTGAACCCATCATCATAGCCAA

AAGTACTCAGCAGCAGCACCTCCAGGTCCAGAGGCACCTCCAGCTGCATGCACACA

CAATGAATGAAAGACTGCCAGGTGTCCGAACCCTGGACATGCAGCTTGTTGAGTTG

CAGGATGACTCTCTGTTCAGGGTCCAAGGTCTCGTTCCTGGAATCCAGGTCCGTGTT

GGGGAGGAAGAACTTCATCTTGGCGTTCAGCCATTCTGGGTCTTTGGTGAGCAGCCT

CACAAGACAGCTCCACAGGTTCTTGTTGCCGAGCTGGAGGCCAACGGGGTCCATGA

GGAGCCAGCCTTGGTCTCCTCGTTCATGATAGGTGCTCTAGGGTCCCCACGGAGAG

GGTCTCATGGGTGTCTGGGCTATGTGTGCCTTGAGCTGGATTGACAGGTTGTTTCCA

TAGTGCAGACTCCCTCAGCGCTCGCGGCTCCTCCGCGCTCTGCACGAAACTGAAAGT

AGAAGCCGCCGCCTAGAGCTGCTCCGCCAGTGCAT

BRMX.7284C1n6_at (SEQ ID NO: 76)

TGGCAAGGACATTGTTTTTGTCTAGTGTCTCAAGCTTCTCTACCAAGAGAGTCATAT

TTCTTATCTCCACCTCCAGCTGGTCAACAATTTCTGAGCTTCCACCAAAACTCTCCTT

CAGCTGTATGACCAGTTTTTCCATCTCCTTCACTTCTACCTTGATCAGCTCGAAGTCC

AGTTCAGTGTAAGAAATGGTATCCTTCTCCATGATGTCAATTCGGACAGTTAGGTTT

AACAGTTTCTTTTCATACACACTAATTAATTGGACATATTCCCTCACTTTAGAAAGTT

CTTTCTCAAACTTCTGAGAAAGAACATGAGCTGTGAATTCCAAGCGTTCCACTCTGT

CCACGGGAAAGGTGGTGTCTGGCAGGGAAACAGAGCACTGGCAGGTCCCACGGTC

ATCCACGGAGCCGGTGAAATTGGAAAACAACTGGGACACAGAACCTCCGCTGCCTA

AGCTGCGGCTGGAGCTGGAGCCCGACCTGGAGCTGGAGCTGAAGCTGGAGCTGGA

GTCAACACCTGGGAAAGAGCTGAAGCCGGGCTGGGAATTGGAGGTCCCACATCCC

CCAAATCCCCTGCAGCTTGGCCAAGGAAGCCAA

BRAD1_19751014_at (SEQ ID NO: 77)

TCTTTTATTGAAAGAAAAAACAATACAATGGACTTTAAAAAGCTACATTTGTTATGG

TTCATAAGGACAGAGGTTTACACAGGTTTTATATATGTACACACTGACAATACTATA

TCACAACATCAGAGGCACCATTTTTGCCACAGAATTAGGTAATGAATAAAACTTCTC

CAAATTAATCTGTTTAAAAAATATCTAAAATGGTACAGTATATTTGAGGATTATATA

AATATGTGAGACATATTTAGATATTTTTTAAAAATAGTGTTTATATATATGCATCAC

AATCTTCTCTAATTCTCAAAATATTATGGCACCAAAATTCTGTTTGTCAAATAAAAC

ACAAGATGCTGTAATATGTATCCAAGCACCAGCTTAGCACAGTATTTAATTCTCCCC

CAAACTGAAAGACTGCTAACAGGTACAAACTGAACTGAATATTTCACACAACCATT

GAAATAATTTAGGCCCTCAAATTTTTTTTTATTAGCTGATTGTTTTTAGAGAAAAA

AGAGGGAGCTAAACCATTTACATTAATGTTGCTCTGTGTGATAGAATCAATCCTAGG

GCTCAGAGAAGATATTCCTAGGCACTGGAGA

BRMX.13502C1n6_at (SEQ ID NO: 78)

TCAAACTTGAATCNTTTAAATTTATTTTCTGCTTAAGCAGGTTTGAGTTGGGTTTTCT

ATTTGCAATAGCAAAAGTCCTGACTGGCAAGGTTTAAAAGTTTGAAGACTCTCACA

GGTAAGTGCAGCTCAGGATCCTGTGAGTGCAGCAGAAAGTCTTAAGAAATGGCAGG

-continued

GGCTGGTTGAACCCAGATTTTCCATTGGCTGAGCAGATATCCCCAGAGGCGTAGAA

AATTAAATTTGTTTTATGTTGTTCCAAAAGAGGAGAACTGAGGCCAGAGGAGCACA

CTTCTGAGACACTCATTTTTGCTGGGTAGAGGAACTCTCTGGGCAAGCAGGACCATC

GATATTAGAGCAGCTGGCCTCAGGAGGGGAGTAAGAGCCCCATCCCTGAAGGTACA

CAAGTTGTGGCAGCAACCATCTGGCCTGCAGTTTCCAGAGGGGAGTCAGGCGTGGG

GTGGGACTGGAGTGAACGGGTACC

BRMX.1111C4n3_at (SEQ ID NO: 79)
TTTTTTCTTCTTTTCCTCTTGGGTTTTCCCAAAGTAGAGTTGTTTGCAATATCCACAG

TATCCATTTTGCCACATGCTTGGTCACTTTCCTTCCTTGCTTCCGGGCTTTCTGGCAC

TTCTCCTTGTTTAAGACTTAGTTTGATGTCAGGCCTCTCTTCCCTTTCTTTTCGATCAC

TTTCTTGGAAAGACAATTTGTCTTGGATTGCATTTTTGAAGCTTTTATAAATGTGAAT

TAAATCGGGTATTCCTGCATGTTGACCTCGCTGAACAGTGCTTCCAAAACTGACAG

GTTAAATGTCTTCTCCAGTTCACTGAGAACATTGTACACCACTCTTTGTACAGGGAC

CAGGTTTCTACAAGAATCTTCAGAATCTTCAAACATTTTATTTGTGATGAGTTCCCG

ATCGCGGAGGCCCTCAAGGAATGGAAATGTCTTTTTTATTGCATTTGATATCTCCAG

CTTATGTCTTTTGAAGTGCTTGAATACAGTGTCATAGACAAGTCCCTCATCTACATC

CTGGTCTTCCGTGAACAGCCTGGCTCGGAAGGTCCTACGCCCACGGACTCTCACTGA

TTGCTAGCACAGCAGTCTGAGCCAA

Hs369056.9C26n3_at (SEQ ID NO: 80)
CCTTCCCCATTTCTCACTTTCCACAGGTGGGATGTGGCAGTCCTCATGGAAGACTCT

TGAACAAGTGTCGCAACAGAACAGCTCCCCTCCGTCCCGGCACACCTCACACTCAT

CCAAGTTTCTCATCTAGAAGGTAAAACAGTGTCCACGTCACTGGGAATCACAAGAT

TCAGGAAGGCCACCCCTCTGGGCATCTAGAACACACTGCTTATGTGTGAGCCTGTAT

AGACAGGCATATGCTTCTCCCTGGGATATGAAGGAAAAATATGGCATGGAGATTTC

AGAACAAATCCTGGTCTGCAGTGAAGTTCAGGAGGAAGGGGTATATGTCAGAATAA

AAACGTTTTCCTTATAAAACCAGAGATTATGACACAGAAAGCCTAGCAACAAAGCA

AGAGGATGATCTTATAGGAATCTGAATAATTGTATTATGCTGCAGATAAAACCAGG

TTTTGAAGTAAAAGTGTTAAATCCATTTGTCTATACTACAAATCAACTCATGAAAGG

GAGACCCAGAGAATTACATATGATGGAATAACCTTCTAAGATATCATCACATCCCA

TATTCTTGGCCATAAGTTCCCCATGAGTTGAAGACAG

BRMX.24432C1n2_at (SEQ ID NO: 81)
GTGGCTGTTGCTGGCCCCACCTCCGCTTATGTCCTTAACATGCCTCAGGTGGTTCAT

CCCTTTTGGCACTCATGGTGCCCCCTGTGGGCTGATACAGGAGTGAGTCTACTGTGA

AGGCACTCAGTATAGTGGAAAAAACAAATATCAACCTCCTGCTTTTTTTCAGTGTAA

AAACTATAAGCTCTATGGGAGTTTCTGCAGATGGTACCATAATGGCCTGAGGGAGG

AGTATCACAGTCACAGAGTATTGGTTCTCTCACTGCATAAGCCATGGTTTTACCCAC

CTTCACAGGCTAAAGGTGCTTCATAACCTTGTTCATGTATTGAGGTTCTGTTGGCTCT

TGTAATGGTAATTTCACATGTGGGCAGTTGTTCATATTGATGTTTCTATAGGGGTAT

GATAGCTGGAGAGGTCTGCGCCACTGTCTTGCTCTGCCTTGATCANNNNNNNNNNN

NAACAAGAATTTGTCTCCTCCTAGTTTTTCTTTTTCTCTTAACCGACCTAGGTTTAGC

-continued

CTTTTAATCCTTCTCCCTCCTCTGCTTCTAATGTCATTGTTTCTTTGTATGCCTATCAT

ATCTACATGCTACATGACCTTCAGCTGG

BRRS.17773_at (SEQ ID NO: 82)

AGTTTTAAGGAAAAATTGTATGATTTAAAAGATTATAAAACTTTATTACTGGGCTAT

TTACACATTTTAATTGTTTCTCATAAAATATATAACATTACAATATTTATGGAAGTA

GGATATTTTGTATCATATGTACGATGATAATTTATAGGGTATTTTAAATGATGTTTT

TTAGCCTCCTTAAGTTTTAAGTGGATCTTGCAAATGAAAACAAGTATTATTGAGTTT

GACATACTCAAATTGCCCAAATATCAGCTGTTTAAACAACCAAGTCATCATTGATAC

TTTAGTAAAGGTTAGTAAATGTCATCAAAGGCTTATTTGCAGTTTACAGTTTTTATT

ACTTAGGAGACTTAAGGAGTACCTGCCAGGTTTGTCCATGCTAATGCTACGATTTTG

TTTTTGTAGTTCAACCATATTTTGTATGGAGATACTTTGAGGCTCTGTAAATTTCTGG

TTACTCCTCAGAACCCACTAGATTTAGCATTTCATGGATGACTTGTGTTTGAACAAT

TATTACTATAATGGTTGCCAGATGATTATTTTCTTATTCTCTTCTTTGTTCTACATGG

AGAAATAAAACCAATAAATAAGGGAGA

BRAD.10849_at (SEQ ID NO: 83)

GTGCCAATGTGAAGTCTGGATTTTAATTGGCATGTTATTGGGTATCAAGAAAATTAA

TGCACAAAACCACTTATTATCATTTGTTATGAAATCCCAATTATCTTTACAAAGTGT

TTAAAGTTTGAACATAGAAAATAATCTCTCTGCTTAATTGTTATCTCAGAAGACTAC

ATTAGTGAGATGTAAGAATTATTAAATATTCCATTTCCGCTTTGGCTACAATTATGA

AGAAGTTGAAGGTACTTCTTTTAGACCACCAGTAAATAATCCTCCTTC

BRAD.10890_at (SEQ ID NO: 84)

AATGCTTATGTCTAAAAGAGCTCGCTGGCAAGCTGCCTCTTGAGTTTGTTATAAAAG

CGAACTGTTCACAAAATGATCCCATCAAGGCCCTCCCATAATTAACACTCAAAACT

ATTTTTAAAATATGCATTTGAAGCATCTGTTGATTGTATGGATGTAAGTGTTCTTAC

ATAGTTAGTTATAT

BRAD.11026_at (SEQ ID NO: 85)

CTGGGCACCTCTGGGACAGCAAAAAAAACTGCAGAATGCATCCCTAAAACTCACGA

GAGAGGCAGTAAGGAACCCAGCACAAAAGAACCCTCAACCCATATACCACCACTG

GATTCCAAGGGAGCCAACTCGGTCTGAGAGAGGAGGAGGTATCTTGGGATCAAGAC

TGCAGTTTGGGAATGCATGGACACCGGATTTGTTTCTTA

BRAD.12809_at (SEQ ID NO: 86)

ACCATGTTCATCTTGTCCTCCAAGTTATGGGGGATCTTGTACTGACAATCTGTGTTTT

CCAGGAGTTACGTCAAACTACCTGTACTGGTTTAAATAAGTTTACCTTTTCCTCCAG

GAAATATAATGATTTCTGGGAACATGGGCATGTATATATATATATGGAGAGAGAAT

TTTGCACATATTATACATATTTTGTGCTAATCTTGTTTTCCTCTTAGTATTCCTTTGTA

TAAATTAGTGTTTGTCTAGCATGTTTGTTTAATCCTTT

BRAD.14326_s_at (SEQ ID NO: 87)

GATGGCTGGTCTGCCCCCTAGGAGACTCCGTCGCTCCAATTACTTCCGACTTCCTCC

CTGTGAAAATGTGGATTTGCAGAGACCCAATGGTCTGTGATCATTGAAAAAGAGGA

AAGAAGAAAAAATGTATGGGTGAGAGGAAGGAGGATCTCCTTCTTCTCCAACCATT

```
                                      -continued
GACAGCTAACCCTTAGACAGTATTTCTTAAACCAATCCTTTTGCAATGTCCAGCTTT

TACCCCTA

BRAD.15436_s_at
                                                          (SEQ ID NO: 88)
GGCATGGAGCATCTGTACAGCATGAAGTGCAAGAACGTGGTGCCCCTCTATGACCT

GCTGCTGGAGATGCTGGACGCCCACCGCCTACATGCGCCCACTAGCCGTGGAGGGG

CATCCGTGGAGGAGACGGACCAAAGCCACTTGGCCACTGCGGGCTCTACTTCATCG

CATTCCTTGCAAAAGTATTACATCACGGGGGAGGCAGAGGGTTTCCCTGCCACAGT

CTGAGAG

BRAD.15833_s_at
                                                          (SEQ ID NO: 89)
GAAATTAGAGTCCTATATTCAACTAAAGTTACAACTTCCATAACTTCTAAAAAGTGG

GGAACCAGAGATCTACAGGTAAAACCTGGTGAATCTCTAGAAGTTATACAAACCAC

AGATGACACAAAAGTTCTCTGCAGAAATGAAGAAGGGAAATATGGTTATGTCCTTC

GGAGTTACCTAGCGGACAATGATGGAGAGATCTATGATGATATTGCTGATGGCTGC

ATCTATGACAATGACT

BRAD.19080_s_at
                                                          (SEQ ID NO: 90)
TTAGATTTCCAGCTTGTCACCTTCAAGGTTACCTTGTGAATAGGACTTTTTTGAGCTA

TTTCTATCCAGTTGACTATGGATTTTGCCTGTTGCTTTGTTTCCACCAACTCTCCCTG

AAGATGAGGCGCACAGACAGACAACTCACAGGCAAGAACAGCCTGGTCCATCTTG

AAAGATTCTCAAGACTATTCTCCACAAG

BRAD.2707_at
                                                          (SEQ ID NO: 91)
TGTTTAAAAATGTTGTGGGTACATAGTATGTGTTGTGGGTACATCGTATGTGTTGTG

GGTACATAGTATNGTGGGGTCCATGAGATGTTTTGATACAGGCATGCAATGTGAAA

TAAGCACATCATGGGGAATGGGGTATCCCTCCCCTCAAGCGTTTATCCTTCAAGTTA

TAAAAAATTCAATTACAGTCTTAGTTATGTCAAAATGTAC

BRAD.27716_s_at
                                                          (SEQ ID NO: 92)
ACCAGAATTTATGGATGAACTGATTGCTTATATTTTAGTCAGGGTTTATAAATGTAG

ATGGTCAAATTTACATTGCCTAGTGATGGAAAATTCAACTTTTTTTGATTTTTTTTC

CAATATTAAAAAAGGCTCTGTATGCATGGTGGG

BRAD.28628_s_at
                                                          (SEQ ID NO: 93)
AAGATTCCTGTGTACTGGTTTACATTTGTGTGAGTGGCATACTCAAGTCTGCTGTGC

CTGTCGTCGTGACTGTCAGTATTCTCGCTATTTTATAGTCGTGCCATGTTGTTACTCA

CAGCGCTCTGACATACTTTCATGTGGTAGGTTCTTTCTCAGGAACTCAGTTTAACTA

TTATTTATTGATATATCATTACCTTTGAAAAGCTTCTACTGGCACAATTTATTAT

BRAD.28643_at
                                                          (SEQ ID NO: 94)
TCTCCTCTCATCTGCATTTCTCAGAAATGCCCTCCCTGCCCAGTGGTGACTTTCCCTC

GTCACTCCTATGGAGTTCTACCTGGAGCCCAGCCATGTGTGGAACTGTGAAGTTTAC

TCCTCTGTAAAGATGGTTTAAAGAAAGTCAGCTTCTGAAATGTAACAATGCTAACCC

TTGCTGGAACCCTGTAAGAAATAGCCCTGCTGATAGTTTTCTAGGTTTATCATGTTT

GATTTTTACACTGAAA
```

-continued

BRAD.28663_s_at
(SEQ ID NO: 95)
GAATTTTTCTCTATTTCCAGCACGCTGATTTGATTTAAAAATGTAATAAGACCAAGA

GTTGGAGTAAAGGGATATTCATTCCATGTTAAAAGTGGCTTCATAGCTACTGACAA

ATGTCTGAACTATTGTCGTGCCCTTCAAAACTGGAGTTTTCTAAAATAATCTTATTTT

TATACTTGTATGTTCCAGCAATTTAAGATATATACCATTGAAAGGGAAAT

BRAD.29038_at
(SEQ ID NO: 96)
GGCTGAGCAAGGCACATAGTCTACTCAGTCTATTCCTAAGTCCTAACTCCTCCTTGT

GGTGTTGGATTTGTAAGGCACTTTATCCCTTTTGTCTCATGTTTCATCGTAAATGGCA

TAGGCAGAGATGATACCTAATTCTGCATTTGATTGTCACTTTTTGTACCTGCATTAAT

TTA

BRAD.30917_at
(SEQ ID NO: 97)
AACGCAGGCCGCTTTATTCCTCTGTACTTAGATCAACTTGACCGTACTAAAATCCCT

TTCTGTTTTAACCAGTTAAACATGCCTCTTCTACAGCTCCATTTTTGATAGTTGGATA

ATCCAGTATCTGCCAAGAGCATGTTGGGTCTCCCGTGACTGCTGCCTCATCGATACC

CCATTTAGCTCCAGAAAGCAAAGAAAACTCGAGTAACACTTGTTTGA

BRAD.31470_at
(SEQ ID NO: 98)
TCATCTCCGTATTCTTCAGCTTCATCCAAAACTGACTTAGAAGCCTCCCTTGACCCTC

ACCTGACTATTCACAGGTTATAGCACTTTATGTTTTTCAGTTCTGTTATTTTAATTGG

TGCCTCTGTTTGTGATCTTTAAGAACATAAAATTCTGGCAAGTAACTATTTGCTA

BRAD.32716_at
(SEQ ID NO: 99)
CACTTTGCAGCCTTGAGAGGTGCAGAAGAGACACCGAGGGGTTCACCACCAGAGCC

ACCATTGTCAGAGAGGCGTCCAGCTGTGTCCACCTGGGACTCTGCCTTCAGGGCTTC

TTGCCTGGCTGGGAGCTGCACAGGCAGACTCCTGGGACGGTGTGCCGACAGCTCTG

GGCACCCCCTTCTAGGATCTGATTCCTGAGGAATCACAATGTGGATTTCACAATCAC

TTCCAGTGTCTTTTGCCAACCTCTGTGAACAGATGT

BRAD.33042_at
(SEQ ID NO: 100)
AAGTTTGCACAGTTCTAGACACGATAAATACATGTGAAATCACACAACTCAGAAAA

TGTCCCTTAAATTAATTGAGCCATTGGTACTTGTGAATTAGAAGAGACATCTATGTT

CTGATCCACTGTTGAAAGCTGTACAATGTTACCTATTTATTTGCAGACATCCTTTGG

AAACAAATAGGTAGATTTGCAACAAATAAAGAGTGGAGTACAGCTGCTGACATTAC

CTTGTATATTCATGCCTTTATG

BRAD.33341_at
(SEQ ID NO: 101)
GACTGCACAGCAGCAAGACAGATTGCCATGGAGCATGTTGTGCCCAACTAGGGACA

GCGCAGATAGATTCTGTAATTTGCCTAACAATGTCTATAGGATGATCCCATTTGTCA

AAAAAAAANNGAACTGGGCTTTATTGATGTCACCTAAATGCACCTAAACTTCTTTT

TTGCCCCATGCTCTTCTGTACTCTTGATCTTTCCCCAAATTTTTAAAAACATGACACT

CATTCCCTTATTTTTCCTACTTAG

BRAD.33405_at
(SEQ ID NO: 102)
TTAATTGCTTTCTCTCACCAGGGAAGGTGTGGGAAGGACTTGTGAAATACATATTCG

AGGAAAAACTATGCACAAGGCCGTGCATTTAAAAATAAACTCCCTAAGGCTGGGGT

-continued

GAAACCTGCTACGGTCTGCGCAAGTTGACTGTTAATGAATTTGATTCTCAGGTGTGA

GTGATTAAAAGAACACTGATCATGTCATTTTCTTTTTGGTCACTAATTCCCTCC

BRAD.33431_at
(SEQ ID NO: 103)
GTCATCCAGAGTTATAATGGCCCATTATCTAATGGTCAGAGTTTACTTAGGCTTTCA

CTACTTCCACTGCCCACTTGAAACAGGGAAAAATATTTTCCCCCCGCGCTGTGAGTG

TGCTATTTAGAGCTGACCACAAGCGGGGGGAAGAGAGGATGGCTCGGATGCTGCAT

TTCCACTGAGAACACAAGGCTGGCAAAGCTTGTCTGCTGCCCAGCAAGCACTTCAG

GCTCACACCATTTTAGGTTCACTTTAAGTAGTTTCTCAAT

BRAD.35695_at
(SEQ ID NO: 104)
TGGACAGTGGACGTCTGTCACCCAAGAGAGTTGTGGGAGACAAGATCACAGCTATG

AGCACCTCGCACGGTGTCCAGGATGCACAGCACAATCCATGATGCGTTTTCTCCCCT

TACGCACTTTGAAACCCATGCTAGAAAAGTGAATACATCTGACTGTGCTCCACTCCA

ACCTCCAGCCTGGATGTCCCTGTCTGGGCCCTTTTTCTGTTTTTTATTCTATGTTCAG

CACCACTGGCACCAAATACATTT

BRAD.35710_at
(SEQ ID NO: 105)
TCCATGGCAACAGTCCCAACATGTTTGAGACTTCAGCTAAAGGAATGGATGTATNN

NGGNGTGTAGTCTTCAGTATATCACTGTATTTCCGTAATACTAGACTCNAAGNTATG

CNAGATNGNTTATTCCCTTNGTGAANNNGGAGTTGCTCATTACGTTCTTGAAATATC

GCACATCCTGTTGGTTCTTCAAAGGAAGCCTTTCCACCAGATTAGTGTTCAAGTCTT

TGCAGAGGAGACCAACTTTT

BRAD.37907_at
(SEQ ID NO: 106)
AAGGCTATGCTTTCAATCTCCTACACAAATTTTACATCTGGAATGATCTGAAGGTTC

TTCAAAGACATTCAAAATTAGGCTTTTTTATGTCCTGTTTTAAGTGAAAATATTTATT

CTTCTAAGGGTCCATTTTATTTGTATTCATTCTTTTGTAAACCTCTTTACATTTCTCTT

TACATTTTATTCTTTGCCCAAATCAAAAGTGATTCCT

BRAD.40353_at
(SEQ ID NO: 107)
CTTAGCATTAGAACACTCAGTAATCATATGAATTGTGCATTTGTTTGTTTTGCTTAAC

TCTTTCTGTTTGTTTATGTTTGGGGTTTTATTGTTGTTGTTTCACTTTTCTCCCATCTCT

TCCTGACTTGGTCAAATCCAAAGGAATNTTCCAAATTGTGGGGAGCAAGGCATCTG

AAATGGCTAAAAC

BRAD.40654_s_at
(SEQ ID NO: 108)
ATGCTATATGCTGTATCCCACCTTTCTCTGAATGTTACATTTTCTCCCCTATCCCAGG

CTGCATCTAAGAAAACTCAAAGGGAATATGCTATCTATCTTTTCCGAGCAATGAAA

GCTCTNGGGTTTTTTCCTTGCTTTTCAGGGCACNATACTTCTCTTTCTTCCTGGTTAG

ACAGGATAAGTTCTGAGTCCCNTGGTATCATCAGCTTACTTCTTCTCTGTTAAATATT

CACA

BRAD.4701_at
(SEQ ID NO: 109)
GTGGTCTTCCTCTGAATATTAGCAGAAGTTTCTTATTCAAAGGCCTCCTCCCAGAAG

AAGTCAGTGGGAAGAGATGGCCAGGGGAGGAAGTGGGTTTATTTTCTGTTGCTATT

-continued

```
GATAGTCATTGTATTACTAGAAATGAACTGTTGATGAATAGAATATATTCAGGACA

ATTTGGTCAATTCCAATGCAAGTACGGAAACTGAGTTGTCCCAAATTGATGTGACA

GTCAGGCTGTTTCATCTTTTTTG

BRAD.5967_at
                                                 (SEQ ID NO: 110)
TATCCTATTACTGTACTTAGTTGGCTATGCTGGCATGTCATTATGGGTAAAAGTTTG

ATGGATTTATTTGTGAGTTATTTGGTTATGAAAATCTAGAGATTGAAGTTTTTCATTA

GAAAATAACACACATAACAAGTCTATGATCATTTTGCATTTCTGTAATCACAGAATA

GTTCTGCAATATTTCATGTATATTGGAATTGAAGTTCAATTGAATTTTATCTGTATTT

AGTAAAAATTAACTTTAGCTTTGATACTAATGAATAAAGCTGGGTTT

BRAD.7701_at
                                                 (SEQ ID NO: 111)
GGGATTTTGAGCTATCATCTCTGCACATGCTTAGTGAGAAGACTACACAACATTTCT

AAGAATCTGAGATTTTATATTGTCAGTTAACCACTTTCATTATTCATTCACCTCAGG

ACATGCAGAAATATTTCAGTCAGAACTGGGAAACAGAAGGACCTACATTCTGCTGT

CACTTATGTGTCAAGAAGCAGATGATCGATGAGGCAGGTCAGTTGTAAGTGAGTCA

CATTGTAGCATTAAATTCT

BREM.1048_at
                                                 (SEQ ID NO: 112)
TTGAATAGATCATCAGTGGCCACTGATGTAATTAATCATGTCTATGTAATGAAGCTG

CCATAAAAAACCCAGGAGGACAGTGTTGAGAGAGCTTCTAGGTTGGTGAACACTTG

GGGGTGTCTGGAAGACAGCCCACCTGGAGAGGACACGGAGGCTCTTCGCACCTTCC

CCCATACCTGGCTCTCTCCATCTCTTCATTTGTCCATCTGTATCTTTTTCATTATATTA

TCCTTGATAATAAACTGGTAAATATAAGTGTTTCCCTAAGTTCTATGAGCCACCAT

BREM.1129_at
                                                 (SEQ ID NO: 113)
AGGCCTCTGATTGCACTTGTGTAGGATGAAGCTGGTGGGTGATGGGAACTCAGCAC

CTCCCCTCAGGCAGAAAAGAATCATCTGTGGAGCTTCAAAAGAAGGGGCCTGGAGT

CTCTGCAGACCAATTCAACCCAAATCTCGGGGGCTCTTTCATGATTCTAATGGGCAA

CCAGGGTTGAAACCCTTATTTCTAGGGTCTTCAGTTGTACAAGACTGTGGGTCTGTA

CCAGAGCCCCCGTCAGAGTAGAATAAAAGGCTGGGTAGGGTAGAGATTCCCATGTG

CAGTGGAG

BREM.1226_at
                                                 (SEQ ID NO: 114)
ATACGTTTTTCACTTTCTGACCAGGACCATGCCTGTGGAGTAGATGTTGACAAGAAA

CACTGACCAGATCAAAATGTGTCTCAAGGAGAATGGCACAATTTTGTGCAAATGAA

TCAAGGAAGTCTTATTGCACAAGAGTATCCTGGAACCCAGTGCAATTGATTTTTTAG

AAAAATATATCACATAGGGGAAAAAAACTGGAATATGTTGAAGGAGACGTATATA

ATATTTAGCATCCAGATTGATGACTTCTGCCCTAACTATGCAATG

BREM.1262_at
                                                 (SEQ ID NO: 115)
CGCTTGAACCTGGAAAGTGGACATTGCAGTGAGCTGAGATTGTGCCACTGCACTCC

AGCCTGGGCAACACAGCGAGACTCTGTCTCAAAAAAAAAAAAAAAAGAAAGAAAA

AAAAGAGAAAACTCAGAGATTCGTGGAGACTGGAACCACGGGTGTGGAGAGAGGG

GTTAGTAGAGACCAGATTCTGCAGGTACTATAATGACATTCCCAGGCTAAGGAGTT

TAGATCTT
```

-continued

BREM.130_at
(SEQ ID NO: 116)
ATCTACACCCTCAGGAATAAGAAAGTGAAGGGGGCAGCGAGGAGGCTGCTGCGGA

GTCTGGGGAGAGGCCAGGCTGGGCAGTGAGTAGTTGGGGAGGGGAGAAAGTATTA

AGCCAGAACCCAAGGATGGAAATACCCCTTAGTGAGTCAGTTTAGACTTCAGGCTG

TTCATTTTTGTATGATAATCTGCAAGATTTGTCCTAAGGAGTCCAATGGGGATATG

TTTTCCTCCCGTGAGGAAATGTTTAGTTCTTGAGGGAAAAATCCCTAAATCCTCTAT

ATA

BREM.1689_s_at
(SEQ ID NO: 117)
GGGTAGCAAGTTCACCACAGTGTTAATGGGGGTCCCAAGGTATTCTTCCCCCAGGC

CTAGGTATAGGGCTATTACTCCTCTCTGCTCCAGGTGTAGACATACATTTACATT

BREM.2334_at
(SEQ ID NO: 118)
TGGAGGGTGAAATTCTGATAGACTTGAGGCTTTGAGATGTGGTCCTGGGGTGGAGC

AAGACAAGAAAAGTACTGGAGATTGGGGTTTGAGGAGTCTATGCAATTATTTTTAT

TTTTAAAAATCTTTGTGGCTACATAGCAGGTGTATATATTTATGTGGTAAGTGAGAT

ATTTCGATACAGACATACAATGTATAATCACAGGCATACAATGTAGACAGGCATAA

AGTGTATAGTCAC

BREM.2382_at
(SEQ ID NO: 119)
AATGTGAAACTGCTCCATGAACCCCAAAGAATTATGCACATAGATGCGATCATTAA

GATGCGAAGCCATCGAGTTACCACCTGGCATGCTTAAACTGTAAAGAGTGGGTCAA

AGTAAACTGAATTGGAAAATCCAAAGTTATGCAGAAAAACAATAAAGGAGATAGT

AAAAAGGGTTAACGAGCCAGTCCAGGGGAAGCGAAGAAGACAAAAAGAGTCCTTT

TCTGGGCCAAGTTTGATAAATTAGGCCTCCCGACCCTTTGCTCTGTTGCTTTATCAAC

TCTACTCGGCAATAACAAT

BREM.532_at
(SEQ ID NO: 120)
GATTAAGAACAGTTTTTTCAACAAATAGTGTTGGGACAATGGGTGTCCACATGCAA

AAGAATAAAGTTGTCCCCTTACCTTACACCATCTCCAAAAATTAACTCAAAATATGT

CAAAGACATAAACGTAAGAGCTAAAACTGTAAAACTCCTAGAATAAAACATAGGA

GTAAATCTTCATGACCTTGGATTAGGCCATTGTGTCTTAAATATAACACCAAAAGAA

TAAGTAATAAAAAAATAGATAAATTGAACTCCATCAAAATTAAAAGCCTTTGTGCT

TCATAGGACACCA

BRHP.106_s_at
(SEQ ID NO: 121)
TCTCAAGCTATGATCAGAAGACTTTAATTATATATTTTCATCCTATAAGCTTAAATA

GGAAAGTTTCTTCAACAGGATTACAGTGTAGCTACCTACATGCTGAAAAATATAGC

CTTTAAATCATTTTTATATTATAACTCTGTATAATAGAGATAAGTCCATTTTTTAAAA

ATGTTTTCCCCAAACCATAAAACCCTATACAAGTTGTTCTAGTAACAATACATGAGA

AAGATGTCTATGTAGCTGAAAATAAAATGACGTCACAAGAC

BRIH.10647C1n2_at
(SEQ ID NO: 122)
TCTTTCTTTTCCAGACAACTTTGAATGGAGAGGAGCAAATTAGTCTTTTGGTTTAATT

CTGTCTCAGTTTGCTTATCTAAAGAAAGGAAAACAGAGTGGCTACACTTGTTTAGAA

CCATATGCATACTCCAGAGAAAGATGCTCTATTAATCCAAAAAAATACAGCCACTT

GAAACCAGCCAAAGCGAAAGTGTAAGGGACTTCATGGAAAGGAGGCAGTTCACCA

AAGTATTGAGGGGTTTTATATTTTAAACTCCGCCAGTGAATTGACGTGTTATGTCAC

TTAC

BRIH.1453C1n2_at
(SEQ ID NO: 123)
GAATTTATTGGAGCATGACCACGGAGGATAGTATGAGCCCTAAAAATCCAGACTCT

TTCGATACCCAGGACCAAGCCACAGCAGGTCCTCCATCCCAACAGCCATGCCCGCA

TTAGCTCTTAGACCCACAGACTGGTTTTGCAACGTTTACACCGACTAGCCAGGAAGT

ACTTCCACCTCGGGCACATTTTGGGAAGTTGCATTCCTTTGTCTTCAAACTGTGAAG

CATTTACAGAAACGCATCCAGCAAGAATATTGTCCCTTTGAGCAGAAAT

BRIH.1518C1n4_at
(SEQ ID NO: 124)
TCCCCGGTTACTACCTCTTATCCATCCCCGGCCACCACCTCATACCCATCCCCTGTGC

CCACCTCCTTCTCCTCTCCCGGCTCCTCGACCTACCCATCCCCTGTGCACAGTGGCTT

CCCCTCCCCGTCGGTGGCCACCACGTACTCCTCTGTTCCCCCTGCTTTCCCGGCCCAG

GTCAGCAGCTTCCCTTCCTCAGCTGTCACCAACTCCTTCAGCGCCTCCACAGGGCTT

TCGGACATGACAGCAACCTTTTCTCCCAGGACAATTGAAATTTGC

BRIH.2770C3n31_at
(SEQ ID NO: 125)
ATGAAGACTTGGCTGATTCAGATGCCAGGGCCTTGTATGAAGCAGGAGAAAGGAGA

AAGGGGACAGACGTAAACGTGTTCAATACCATCCTTACCACCAGAAGCTATCCACA

ACTTCGCAGAGTGTTTCAGAAATACACCAAGTACAGTAAGCATGACATGAACAAAG

TTCTGGACCTGGAGTTGAAAGGTGACATTGAGAAATGCCTCACAGCTATCGTGAAG

TGCGCCACAAGCAAACCAGCTTTCTTTGCAGAGAAGCTTCATCAAGCCATGAAAGT

ATGTACCATTCT

BRIH.365C1n2_at
(SEQ ID NO: 126)
TGCCTTGTGTCTTCCGTTTGACGGAAGAGAATGGATTCTGGTATCTAGACCAAATCA

GAAGGGAACAGTACATTCCAAATGAAGAATTTCTTCATTCTGATCTCCTAGAAGAC

AGCAAATACCGAAAAATCTACTCCTTTACTCTTAAGCCTCGAACAATTGAAGATTTT

GAGTCTATGAATACATACCTGCAGACATCTCCATCATCTGTGTTTACTAGTAATCAT

TTTGTTCCTT

BRIH.5410C1n7_at
(SEQ ID NO: 127)
GGTATAGCATATGTGGCCTTGCTTACTAAAGTGGATGATTGCAGTGAGGTTCTTCAA

GACAACTTTTTAAACATGAGTAGATCTATGACTTCTCAAAGCCGGGTCATGAATGTC

CATAAAATGCTAGGCATTCCTATTTCCAATATTTTGATGGTTGGAAATTATGCTTCA

GATTTGGAACTGGACCCCATGAAGGATATTCTCATCCTCTCTGCACTGAGGCAGATG

CTGCGGGCTGCAGATGATTTTTTAGAAGATTTGCCTCTTGAGGAAACTGGTGCATTT

BRIH.5478C1n2_s_at
(SEQ ID NO: 128)
TGCTTATCCGTTAGCCGTGGTGATTTAGCAGGAAGCTGTGAGAGCAGTTTGGTTTCT

AGCATGAAGACAGAGCCCCACCCTCAGATGCACATGAGCTGGCGGGATTGAAAGAT

GCTGTCTTCGTACTGGGAAAGGGATTTTCAGCCCTCAGAATCGCTCCACCTTGCAGC

TCTCCCCTTCTCTGTATTCCTAGAAACTGACACATGCTGAACATCACAGCTTATTTCC

TCATT

BRIH.5650C1n2_at (SEQ ID NO: 129)

TAGGCACCACATGGGATCCTTGTTCTTCCTCCTTGTAAGCAGTAATTGAAATCAGTT

TGGCAGCCTGGTTTACAGTGACCATGGTGGCTTGTCTCCCGTGCTCTTACCTCACTCT

GTTGATGTTGTAAAACCTCCAGCTAACTTCATGGGGTGGCTGACCCACGTTGCTCAT

TTATTCATTCAACACATATTCATTGACCATCTACTCTATGCCAGGTATTGTTATCAGC

ACTGGGAATAGATCAGTGAACTATTGATCTATTTGTCTAA

BRIH.5952C1n2_s_at (SEQ ID NO: 130)

CTCAGTTCTGGTCCTTCAAGCCTGTATGGTTTGGATTTTCAGTAGGGGACAGTTGAT

GTGGAGTCAATCTCTTTGGTAC

BRIH.7359C1n3_s_at (SEQ ID NO: 131)

CTGAGGTGCTATGTTCTTAGTGGATGTTCTGACCCTGCTTCAAATATTTCCCTCACCT

TTCCCATCTTCCAAGGGTATAAGGAATCTTTCTGCTTTGGGGTTTATCAGAATTCTCA

GAATCTCAAATAACTAAAAGGTATGCAATCAAATCTGCTTTTTAAAGAATGCTCTTT

ACTTCATGGACTTCCACTGCCATCCTCCCAAGGGGCCCAAATTCTTTCAGTGGCTAC

CTACATACAATTCCAAACACATACAG

BRIHRC.10930C1n2_s_at (SEQ ID NO: 132)

TAACAAATCATCAACTTCCACTGGTCAATATATAGATTTTGGGTGTCTGAGGCCCCA

AGATTAGATGCCACTAATCTCCAAAGATTCCCTCCAA

BRMX.13731C1n18_at (SEQ ID NO: 133)

GCAGGGTCTTGGGATAACACTGTCATCAGAAACAAGGCTGGGGGCTGATTTCGGGG

TGGGGAGCCTTAGGAGGCCAGAAATTCCAATCAGAGCCAGTTTTTCTGGGAGGGAG

TGGCTAGACAGTCAAGGAAGGACGTTCACATTTCAAAAGAAGTCGGGTGGGGGAT

GAGATTATTCTAGGGGGGCATCGAATTCCCTTTAAGGGGGGGGCTCACTTCTGCCCA

GAGTAAAGAGGATCTCACACCATGGAAAT

BRMX.25436C1n2_at (SEQ ID NO: 134)

TAGTTATACTTACACACTCCTCTCATGTTGTCTATGGAGTGGTGGATGCTGCAGGGA

GGGTGACATCCTAGTTAGTCCTAAGAGCCAGACTGCCTGAAGCTCACTATAACAAG

TCCTGCCTTGGGGAAGAAGGAAGTGTGTCTCTGTGAACCTCCCACCTGGGCCGAAA

GGGAGGCCACTCTCTCTGCTGCCTCTCCCCAACCTTGGCCTTCTGTGCTCCTAGTGA

ACCTCTCACCCCCTGCCTACAGCCTCGAATCTCAGACCATGATGACCTCTGGTCACC

CTGAATCAGAGCTTT

BRMX.25712C1n2_at (SEQ ID NO: 135)

GTAAAATTCCTATGTCAGCACCCTAATGAGACAAATGACATCCTAATTCTTCCCCTT

GGCTTGCCAGTTTGTAGGTACTAGTTTTTCAGAAGTTACTCTAAAATATTTCTGATTG

CAGCTCCTTCCTAAAGAGCAGTATGAGCAGCATGTGGTTATTTATGTATTCACTCTT

TTCTCCTACTTCTGTGGTGACCTGGAACAAATTCTCTTATGTATGTAAAGATTGGAC

AGCCCACCTGATTCCGATGTCACTTAGATACACTGTTTTTGTATCAGCCTCTTCTCTT

AGAAA

-continued

BRMX.3079C1n3_at
(SEQ ID NO: 136)
GATTGTTGGCCAATAGACCTTCCACTCCAGTAGAGAGGGAGGACTTGGCTCTGAGA

ACCTCCATCTGACCTAAGAGGAAACCTCCTCTCCTATGGCCATCTCCTCCTCCTGTC

CTTTAAGTCCTCTGTGGTTACTATATCTCCTTTTCCCTTTCTTACCCTTTCGCTTAGCA

ATTTCAAT

BRMX.3079C2n3_at
(SEQ ID NO: 137)
AAGTTCTTTGGGATAGAGGGTGAAGAACTTGGGACATGGGCTGTTTCAGGGCAGCT

GAAGTTCAAAGGGGAATAGGTAATTGGGGGGAAGGGGGGAAGTTGGGGCAGAAAG

GGATTGTTGGGCCAATAGGACCTTTCCACT

BRPD.10690C1n5_at
(SEQ ID NO: 138)
AGGATTATACTTCAGTCCCTGCTTTACATTTATTTCTTAAAGAAGCTTCTGGTAAATT

AGAGCAATAGCATCGGCTTAGTTTAGTGTTGTTCTGTTGGACTAAGGATATCAGTTC

TATCCGTATGGTCGGGCCTAAAGCCTGGGAAATATTTAATGAAGGNNNNNNNNNNN

NNNNNNNNNNNNNNNNNNNNNNNNNNNNNNNATAACAAATAACAAAACAAAAACCA

AGCCATTTCCCTTTATAGTAAGA

BRPD.4019C1n3_s_at
(SEQ ID NO: 139)
ACAGAAGCCATTGCCTCCCTTGTTTACCTTGGGTCCACCTCCACCAAAACCCAACAG

ACCACCAAATGTTGACCTGACGAAATTCCACAAAACCTCTTCTGGAAACAGTACTA

GCAAAGGCCAGACGTCTTACTCAACAACTTCCCTGCCACCACCTCCACCATCCCATC

CGGCCAGCCAACCACCATTGCCAGCATCTCACCCATCACAACCACCAGTCCCAAGC

CTACCTCCCAGAAACATTAAACCTCCGTTTGAC

BRPD.5301C1n2_s_at
(SEQ ID NO: 140)
GCACAGCTCAGCACAACATTCCAAGCTCAAAATAGAAGCCTTCTCAGTGAGCTCCA

GCACGCCCAGAGGACTGTTAATAACGATGATCCATGTGTTTTACTCTAAAGTGCTAA

ATATGGGAGTTTCCTTTTTTTTACTCTTTGTCACTGATGACACAACAGAAAAGAAAC

TGTAGACCTTGGGACAATCAACATTTAAA

BRRS.12588_at
(SEQ ID NO: 141)
CCTGCCCTGGAAGTAATCTTGCTGTCCTGGAATCTCCTCGGGGATGAGGCAGCTGCC

GAGCTGGCCCAGGTGCTGCCGAAGATGGGCCGGCTGAAGAGAGTGGACCTGGAGA

AGAATCAGATCACAGCTTTGGGGGCCTGGCTCCTGGCTGAAGGACTGGCCCAGGGG

TCTAGCATCCAAGTCATCCGCCTCTGGAATAACCCCATTCCCTGCGACATGGCCCAG

CACCTGAAGAGCCAGGAGCCCAGGCTGGACTTTGCCTTCTTTGACAACCAGCCC

BRRS.13369_s_at
(SEQ ID NO: 142)
GCACAGCTCAGCACAACATTCCAAGCTCAAAATAGAAGCCTTCTCAGTGAGCTCCA

GCACGCCCAGAGGACTGTTAATAACGATGATCCATGTGTTTTACTCTAAAGTGCTAA

ATATGGGAGTTTCCTTTTTTTACTCTTTGTCACTGATGACACAACAGAAAAGAAACT

GTAGACCTTGGGACAATCAACATTTAAA

BRRS.13576_at
(SEQ ID NO: 143)
GAGAGTTCAACTAAGAAAGGTCACATATGTGAAAGCCCAAGGACACTGTTTGATAT

ACAGCAGGTATTCAATCAGTGTTATTTGAAACCAAATCTGAATTTGAAGTTTGAATC

-continued

TTCTGAGTTGGAATGAATTTTTTTCTAGCTGAGGGAAACTGTATTTTTCTTTCCCCAA

AGAGGAATGTAA

BRRS.13647_at
(SEQ ID NO: 144)
CTCGATTATTCCCTGTACAATATTTAAAATTTATTGCTTGATACTTTTGACAACAAAT

TAGGTTTTGTACAATTGAACTTAAATAAATGTCATTAAAATAAATAAATGCAATATG

TATTAATATTCATTGTATAAAAATAGAAGAATACAAACATATTTGTTAAATATTTAC

ATATGAAATTTAATATAGCTATTTTTATGGAATTTTTCATTGATATGAAAAATATGA

TATTGCATATGCATAGTTCCCATGTTAAATCCCATTCATAACTTTCATTAAAGCATTT

ACTTTGA

BRRS.13648_s_at
(SEQ ID NO: 145)
GCAAATAAATTCATACATAGTACATACAAAATAAGAGAAAAAATTAAATTGCAGAT

GGTTAAATATCACATCACTTAACTGATGTTACTGAAAATGTATTTTCCTGCATAATC

ATATGGTTGACAGTATGCATTAAGAAGGTAAGTAAAACAATGAAGACAATTTTGAT

TTAATATGGTAATGCACAATTCCAACTAACGTACATTCAACAGATCATGAAATTGG

GTTATT

BRRS.13767_at
(SEQ ID NO: 146)
TTGCCTTCTAAATATACTGAAATGATTTAGATATGTGTCAACAATTAATGATCTTTT

ATTCAATCTAAGAAATGGTTTAGTTTTTCTCTTTAGCTCTATGGCATTTCACTCAAGT

GGACAGGGGAAAAAGTAATTGCCATGGGCTCCAAAGAATTTGCTTTATGTTTTTAG

CTAT

BRRS.13859_at
(SEQ ID NO: 147)
CCTGGCCACTCGCAAGACCTTTTATCTGAAAACCAGCCAAGCTTTATTCACGACACA

CTTCTTCCCTTCACTCTCCCACTTCTGTGGTCAACTCCCTGCAGAACTCCCAAACTGC

CGTTCTTTTCGATAGCTCACGATGGTGTATGAGTGTCAATCATCTGACCCTTCTTGG

AGTCTCATATTTCGTGGAAC

BRRS.13881_at
(SEQ ID NO: 148)
CTGAGGACCGGCTGCAGACCTCACTCTGAGTGGCAGGCAGAGAACCAAAGCTGCTT

CGCTGCTCTCCAGGGAGACCCTCCTGGGATGGGCCTGAGAGGCCGGGGCTCAGGGA

AGGGGCTGGGATCGGAACTTCCTGCTCTTGTTTCTGGACAACTTTCCCCTTCTGCTTT

AAAGGTTGTCGATTATT

BRRS.14465_s_at
(SEQ ID NO: 149)
AGTGTGATGGATCCCCTTTAGGTTATTTAGGGGTATATGTCCCCTGCTTGAACCCTG

AAGGCCAGGTAATGAGCCATGGCCATTGTCCCCAGCTGAGGACCAGGTGTCTCTAA

AAACCCAAACATCCTGGAGAGTATGCGAGAACCTACCAAGAAAAACAGTCTCATTA

CTCATATACAGCAGGCAAAGAGACAGAAAATTAACTGAAAAGCAGTTTAGAGACT

GGGGGAGGCCGGATCTCTAGAGCCATCCTG

BRRS.15053_at
(SEQ ID NO: 150)
GCGTTACAGATGGACGTAGCTGCCTTGGTTTTCCAGTCCTCAAGGGAATACTGAAG

ATGCTGACTGAAGGGGATTGGATGTTGATTTTAGAAGATGGAGAACTCCAGCCACC

TTTGTAAAGCACTAGTGTTTGTCATTTATGTAAGTCAGGTCGGCTCAGGTCTTGATA

GTCCGTCTTGGTGTGAGGCATGC

-continued

BRRS.16228_s_at (SEQ ID NO: 151)

CACAGTAATGTCGAAACTAGGCCTTTGAACCAAGGCAGTCTAGGGTAAAATATAGT

TTCAAAGTATGAATAAGAATTGGTATTTGTGTTATCTTTGAGTAAGAAACTGTCCGA

TATGAATCACAACGTGGGTGAATGTAGTATTTTCCTGAAGTGTG

BRRS.16746_s_at (SEQ ID NO: 152)

GGCCATGAACATCACCTGCACAGGACGGGGACCAGACAACTGTATCCAGTGTGCCC

ACTACATTGACGGCCCCCACTGCGTCAAGACCTGCCCGGCAGGAGTCATGGGAGAA

AACAACACCCTGGTCTGGAAGTACGCAGACGCCGGCCATGTGTGCCACCTGTGCCA

TCCAAACTGCACCTACGGG

BRRS.16747_at (SEQ ID NO: 153)

ATCACAGGTTTGAGCTGAATTATCACATGAATATAAATGGGAAATCAGTGTTTTAG

AGAGAGAACTTTTCGACATATTTCCTGTTCCCTTGGAATAAAAACA

BRRS.16948_s_at (SEQ ID NO: 154)

AGTTTCAGACAAATGTTCAGTGTGAGTGAGGAAAACATGTTCAGTGAGGAAAAAAC

ATTCAGACAAATGTTCAGTGAGGAAAAAAAGGGGAAGTTGGGGATAGGCAGATGT

TGACTTGAGGAGTTAATGTGATCTTTGGGGAGATACATCTTATAGAGTTAGAAATA

GAATCTGAATTTCTAAAGGGAGATTCTGGCTTGGGA

BRRS.17863_s_at (SEQ ID NO: 155)

AACTTAAGCTGAATGTGTAATGGATTTGTCTATAGTTTTACATATTTGGAAGCATTT

TAAAATAGGTTTTAATCTTACATAAAATTACTTTTATACTTGTGTTAACATTTTCTTC

TGTGCCTTTTGGGTAATTTAATTTCTGTTATGAATTTCTGGTGCCTATGAGCTAGCTA

TCACCTACCTGAAAGGTGCTTAGAGGTGAAGGTACTGTTTCTAAAAACACATCACT

GTGACACCTTTCTATCCTCACATTTTCAAGCTTGCCTCTTTTCT

BRRS.17909_s_at (SEQ ID NO: 156)

GTGACTGCTTATGAAGGGTTATTGCTCAGCTAAGTATTTCTGAATGAGTCTTAGGTC

TGTTGGCCTTCAATCTCTACCGAAACCCTGAGAACTTGATGATGCTTTTGTTTTCTGA

GAATCGTTTCAGTGTGCTGG

BRRS.18137_at (SEQ ID NO: 157)

CATTTGCTGCAACTCTCAGTGGTAAGAATGATTAAGTGCAGCTATAGGAGAATACTT

CCATTGGCATGCCACCTGCGTAAAACACACAATTTTGTTAAGATATACAATAAAATT

ATTATGCTAATAGCAAATATTTTATGTAGCTCACTATGTTCCATGTAGTCTTCTAAGT

GCTTCATGTTAGTCCCCAGTTAAACACCTGGTTTTGGAAGGCTGAG

BRRS.18652_s_at (SEQ ID NO: 158)

GTGAGCCTGCCAGCGTTTGCGACGTCCCCGCACGACAGGCTCATACTTTCTGAGGAT

CGTGCATAGCATAGGACGTCTGAACCTTTGTACAAATGTGTAGATGACATCTTGCTA

CAGCTTTTATTTGTGAAT

BRRS.2573_s_at (SEQ ID NO: 159)

GTAAATTCAATACAATGTCAGTTTTTAAAAGTCAAAGTTAGATCAAGAGAATATTTC

AGAGTTTTGGTTTACACATCAAGAAACAGACACACATACCTAGGAAAGATTTACAC

AATAGATAATCATCTT

BRRS.2644_at (SEQ ID NO: 160)

ACTGTACAAAGTATAAGTCTTAGATGTATATATTTCCTATATTGTTTTCAGTGTACAT

GGAATAACATGTAATTAAGTACTATGTATCAATGAGTAACAGGAAAATTTTAAAAA

TACAGATAGATATATGCTCTGCATGTTACATAAGATAAATGTGCTGAATGGTTTTCA

AATAAAAATGAGGTACTCTCCTGGAAATATTAAGAAAGACTATCTAAATGTTGAAA

GA

BRRS.2783_s_at (SEQ ID NO: 161)

GAGGACCGAGCACAGAAATCTTAGAGATTTCTTGTCCCCTCTCAGGTCATGTGTAGA

TGCGATAAATCAAGTGATTGGTGTGCCTGGGTCTCACTACAAGCAGCCTATCTGCTT

AAGAGACTCTGGAGTTTCTTATGTGCCCTGGTGGACACTTGCCCACCATCCTGTGAG

TAAAAGTGAA

BRRS.2935_at (SEQ ID NO: 162)

TCTGAACTCTCAAAAGTCTATTTTTTTAACTGAAAATGTAAATTTATAAATATATTC

AGGAGTTGGAATGTTGTAGTTACCTACTGAGTAGGCGGCGATTTTTGTATGTTATGA

ACATGCAGTTCATTATTTTGTGGTTCTATTTTACTTTGTACTTGTGTTTGCTTAAACA

AAGTGACTGTTTGGCTTATAAACACATTGAATGCGCTTTATTGCCCATGGGATATGT

GGTGTATATCCTTCCAAAAAATTAAAACGAAAATAAAGTAGCTGCGATTGG

BRRS.3099_at (SEQ ID NO: 163)

ATTCCTGTCATTACCCATTGTAACAGAGCCACAAACTAATACTATGCAATGTTTTAC

CAATAATGCAATACAAAAGACCTCAAAATACCTGTGCATTTCTTGTAGGAAAACAA

CAAAAGGTAATTATGTGTAATTATACTAGAAGTTTTGTAATCTGTATCTTATC

BRRS.3131_at (SEQ ID NO: 164)

CAGGACCCATCACGCCTGTGCAGTGGCCCCCACAGAAAGACTGAGCTCAAGGTGGG

AACCACGTCTGCTAACTTGGAGCCCCAGTGCCAAGCACAGTGCCTGCATGTATTTAT

CCAATAAATGTGAAATTCTGTCC

BRRS.3220_at (SEQ ID NO: 165)

AAAGTGGCATTTTCTTGATTGGAAAGGGGGAAGGATCTTATTGCACTTGGGCTGTTC

AGAATGTAGAAAGGACATATTTGAGGAAGTATCTATTTGAGCACTGATTTACTCTGT

AAAAAGCAAATCTCTCTGTCCTAAACTAATGGAAGCGATTCTCCCATGCTCATGTG

TAATGGTTTTAACGTTACTCACTGGAGAGATTGGACTTTCTGGAGTTATTTAACCAC

TATGTTCAG

BRRS.3319_at (SEQ ID NO: 166)

TTTATAATGTCCCTTCACAAACCCAGTGTTTTAGGAGCATGAGTGCCGTGTGTGTGC

GTCCTGTCGGAGCCCTGTCTCCTCTCTCT

BRRS.3319_s_at (SEQ ID NO: 167)

CACCCTCAGATGCACATGAGCTGGCGGGATTGAAGGATGCTGTCTTCGTACTGGGA

AAGGGATTTTCAGCCCTCAGAATCGCTCCACCTTGCAGCTCTCCCCTTCTCTGTATTC

CTAGAAACTGACACATGCTGAACATCACAGCTTATTTCCTCATTT

BRRS.3645_s_at (SEQ ID NO: 168)

AAATTTAATTTTCTACGCCTCTGGGGATATCTGCTCAGCCAATGGAAAATCTGGGTT

CAACCAGCCCCTGCCATTTCTTAAGACTTTCTGCTGCACTCACAGGATCCTGAGCTG

```
CACTTACCTGTGAGAGTCTTCAAACTTTTAAACCTTGCCAGTCAGGACTTTTGCTATT

GCA

BRRS.4126_s_at
                                                 (SEQ ID NO: 169)
CTACTCCTTACAGTCTCTAGAATTAAATGTACTCATTTAGACAACATATTAAATGCA

TATTTTAGCCACTTTAGAGAAACCTCATAGGCACAGAGTTTCCAAGATTAATTTTAA

GAATATCTTCACGAACTTGACCCTCCTACTCCACATTGCAACATTTCCATCAGACAG

CATTTCAATTCCAGTATTAT

BRRS.455_at
                                                 (SEQ ID NO: 170)
GTCATCATATATAATTAAACAGCTTTTTAAAGAAACATAACCACAAACCTTTTCAAA

TAATAATAATAATAATAATAAAAAATGTATTTTAAAGATGGCCTGTGGTTATCTTGG

AAATTGGTGATTTATGCTAGAAAGCTTTTAATGTTGGTTTATTGTTGAATTCCTAGA

A

BRRS.4562_at
                                                 (SEQ ID NO: 171)
CATGGATTAGCTGGAAGATCTGTATTTGATGGAAGACCTTGAAATTATTGGAAGAC

ATGGATTTCCTGGAAGACGTGGATTTTCCTGGAAGATCTGGATTTGGTGGAAGACC

AGTAATTGCTGGAAGACTGGATTTGCTGGAAGACTTGATTTACTGGAAGACTTGGA

GCTTCTTGGAAGACATGGATTGTCCGGAAGACATGGATTGTCTGGAAGATGTGGAT

TTTCTGGAAGCTCAG

BRRS.487_s_at
                                                 (SEQ ID NO: 172)
GTGGAGGAAACTAAACATTCCCTTGATGGTCTCAAGCTATGATCAGAAGACTTTAA

TTATATATTTTCATCCTATAAGCTTAAATAGGAAAGTTTCTTCAACAGGATTACAGT

GTAGCTACCTACATGCTGAAAAATATAGCCTTTAAATCATTTTTATATTATAACTCT

GTATAATAGAGATAAGTCCATTTTTTAAAAATGTTTTCCCCAAACCATAAAACCCTA

TACAAGTTGTTCTAGTAACAATACATGA

BRRS.4891_s_at
                                                 (SEQ ID NO: 173)
TCAATAAGGGCGTTCTTCCTTGCAAGTTGAAACATTATTGTGCTAGGATTGCTCTCT

AGACAAGCCAGAAGTGACTTATTAAACTATTGAAGGAAAAGGACTCAAGAAAAAT

AATAAAAGACCATAAATAAGGGCGAAAACATTACCATGTGAAAAGAATGTATTTCA

CCTGCAAGTTACAAAAAAATAGTTTGTGCATTGCAAATAAGCAAAGACTTGGATTG

ACTTTACATTCATC

BRRS.4996_at
                                                 (SEQ ID NO: 174)
AAGCTGTGTTGTTGCTTCTTGTGAAGGCCATGATATTTTGTTTTTCCCCAATTAATTG

CTATTGTGTTATTTTACTACTTCTCTCTGTATTTTTTCTTGCATTGACATTATAGACAT

TGAGGACCTCATCCAAACAATTTAAAAATGAGTGTGAAGGGGGAACAAGTCAAAAT

ATTTTTAAAAGATCTTCAAAAATAATGCCTCTGTCTAGCATGCCAACAAGAATGCAT

BRRS.524_s_at
                                                 (SEQ ID NO: 175)
TGCCTGTTGTAGACCACAGTCACACACTGCTGTAGTCTTCCCCAGTCCTCATTCCCA

GCTGCCTCTTCCTACTGCTTCCGTCTATCAAAAAGCCCCCTTGGCCCAGGTTCCCTG

AGCTGTGGGATTCTGCACTGGTGCTTTGGATTCCCTGATATGTTCCTTCAAA
```

-continued

BRRS.5356_at
(SEQ ID NO: 176)
GTCAGACAGATGTGGTTGCATCCTAACTCCATGTCTCTGAGCATTAGATTTCTCATT

TGCCAATAATAATACCTCCCTTAGAAGTTTGTTGTGAGGATTAAATAATGTAAATAA

AGAACTAGCATAACACTCAAAAA

BRRS.5451_at
(SEQ ID NO: 177)
TCTGTGTGTGCCCTGTAACCTGACTGGTTAACAGCAGTCCTTTGTAAACAGTGTTTT

AAACTCTCCTAGTCAATATCCACCCCATCCAATTTATCAAGGAAGAAATGGTTCAGA

AAATATTTTCAGCCTACAGTTATGTTCAGTCACACACACATACAAAATGTTCCTTTT

GCTTTTAAAGTAATTTTTGACTCCCAGATCAGTCAGAGCCCCTACAGCATTGTTAA

BRRS.6371_at
(SEQ ID NO: 178)
GTTTAAGCCTGGAACTTGTAAGAAAATGAAAATTTAATTTTTTTTCTAGGACGAGC

TATAGAAAAGCTATTGAGAGTATCTAGTTAATCAGTGCAGTAGTTGGAAACCTTGCT

GGTGTATGTGATGTGCTTCTGTGCTTTTGAATGACTTTATCATCTAGTCTTTGTCTAT

TTTTCCTTTGATGTTCAAGTCCTAGTCTATAGGATTGGCAGTTTAA

BRRS.6611_at
(SEQ ID NO: 179)
GACTGAGGGATCGTAGATTTTTACAATCTGTATCTTTGACAATTCTGGGTGCGAGTG

TGAGAGTGTGAGCAGGGCTTGCTCCTGCCAACCACAATTCAATGAATCCCCGACCC

CCCTACCCCATGCTGTACTTGTGGTTCTCTTTTTGTATTTTGCATCTGACCCCGGGGG

GCTGGGACAGATTGGCAATGGGCCGTCCCCTCTCCCCTTGGTTCTGCACTGTTGCCA

ATAAAAAGCTCTTAA

BRRS.6619_at
(SEQ ID NO: 180)
GGAGGGAAGGCAAGATTCTTTCCCCCTCCCTGCTGAAGCATGTGGTACAGAGGCAA

GAGCAGAGCCTGAGAAGCGTCAGGTCCCACTTCTGCCATGCAGCTACTATGAGCCC

TCGGGGCCTCCTCCTGGGCCTCAGCTTGCCCAGATACATACCTAAATATATATATAT

ATATATGAGGGAGAACGCCTCACCCAGATTTTATCATGCTGGAAAGAGTGTATGTA

TGTGAAGATGCTTGGTCAACTTGTACCCAGTGAACACACAAA

BRRS.6619-22_at
(SEQ ID NO: 181)
GGAGGGAAGGCAAGATTCTTTCCCCCTCCCTGCTGAAGCATGTGGTACAGAGGCAA

GAGCAGAGCCTGAGAAGCGTCAGGTCCCACTTCTGCCATGCAGCTACTATGAGCCC

TCGGGGCCTCCTCCTGGGCCTCAGCTTGCCCAGATACATACCTAAATATATATATAT

ATATATGAGGGAGAACGCCTCACCCAGATTTTATCATGCTGGAAAGAGTGTATGTA

TGTGAAGATGCTTGGTCAACTTGTACCCAGTGAACACACAAA

BRRS.6684_at
(SEQ ID NO: 182)
TATTCTTCTATAACACTCTATATAGAGCTATGTGAGTACTAATCACATTGAATAATA

GTTATAAAATTATTGTATAGACATCTGCTTCTTAAACAGATTGTGAGTTCTTTGAGA

AACAGCGTGGATTTTACTTATCTGTGTATTCACAGAGCTTAGCACAGTGCCTGGTAA

TGAGCAAGCATACTTGCCATTACTTTTCCTTCCCA

BRRS.7616_at
(SEQ ID NO: 183)
CCTAATTTGAGGGTCAGTTCCTGCAGAAGTGCCCTTTGCCTCCACTCAATGCCTCAA

TTTGTTTTCTGCATGACTGAGAGTCTCAGTGTTGGAACGGGACAGTATTTATGTATG

```
                                                        -continued
AGTTTTTCCTATTTATTTTGAGTCTGTGAGGTCTTCTTGTCATGTGAGTGTGGTTGTG

AATGATTTCTTTTGAAGATATATTGTAGTAGATGTTACAATTTTGTCGCCAAACTAA

ACTTGCTGCTTAATGATTTGCTCACATCTAGTAAA

BRRS.7901_at
                                                           (SEQ ID NO: 184)
GGACACTTTTGAAAACAGGACTCAGCATCGCTTTCAATAGGCTTTTCAGGACCTTCA

CTGCATTAAAACAATATTTTTAAAAATTTAGTACAGTTTAGAAAGAGCACTTATTTT

GTTTATATCCATTTTTTCTTACTAAATTATAGGGATTAACTTTGACAAATCATGCTGC

TGTTATTTTCTACATTTGTATTTTATCCATAGCACTTATTCACATTTAGGAAAA

BRRS.81_at
                                                           (SEQ ID NO: 185)
CAGTTTCTGTTCTCTCACAGGTGATAAACAATGCTTTTTGTGCACTACATACTCTTCA

GTGTAGAGCTCTTGTTTTATGGGAAAAGGCTCAAATGCCAAATTGTGTTTGATGGAT

TAATATGCCCTTTTGCCGATGCATACTATTACTGATGTGACTCGGTTTTGTCGCAGCT

TTGCTTTGTTTAATGAAACACACTTGTAAACCTCTTTTGCACTTTGAAAAAGAATCC

AGCGGGATGCTCGAGCACCTGTAAACAATTTTCTCAACCTATTTG

BRRS.81-22_at
                                                           (SEQ ID NO: 186)
CAGTTTCTGTTCTCTCACAGGTGATAAACAATGCTTTTTGTGCACTACATACTCTTCA

GTGTAGAGCTCTTGTTTTATGGGAAAAGGCTCAAATGCCAAATTGTGTTTGATGGAT

TAATATGCCCTTTTGCCGATGCATACTATTACTGATGTGACTCGGTTTTGTCGCAGCT

TTGCTTTGTTTAATGAAACACACTTGTAAACCTCTTTTGCACTTTGAAAAAGAATCC

AGCGGGATGCTCGAGCACCTGTAAACAATTTTCTCAACCTATTTG

BRRS.8480_s_at
                                                           (SEQ ID NO: 187)
AGCAAGTGTAGACACCTTCGAGGGCAGAGATCGGGAGATTTAAGATGTTACAGCAT

ATTTTTTTTTCTTGTTTTACAGTATTCAATTTTGTGTTGATTCAGCTAAATTATGAAA

BRRS.8711_at
                                                           (SEQ ID NO: 188)
GTCTCACATATTTATATAATCCTCAAATATACTGTACCATTTTAGATATTTTTTAAAC

AGATTAATTTGGAGAAGTTTTATTCATTACCTAATTCTGTGGCAAAAATGGTGCCTC

TGATGTTGTGATATAGTATTGTCAGTGTGTACATATATAAAACCTGTGTAAACCTCT

GTCCTTATGAACCATAACAAATGTAGCTTTTTA

BRRS.8900_s_at
                                                           (SEQ ID NO: 189)
CAGCCCCACCCCTGTAAATGGAATTTACCAGATGAAGGGAATGAAGTCCCTCACTG

AGCCTCAGATTTCCTCACCTGTGAAATGGGCTGAGGCAGGAAATGGGAAAAAGTGT

TAGTGCTTCCAGGCGGCACTGACAGCCTCAGTAACAATAAAAACAA

BRSA.1686C1n5_at
                                                           (SEQ ID NO: 190)
TCAGCTGCCCTGAAACAGCCCATGTCCCAAGTTCTTCACCTCTATCCAAAGAACTTG

ATTTGCATGGATTTTGGATAAATCATTTCAGTATCATCTCCATCATATGCCTGACCCC

TTGCTCCCTTCAATGCTAGAAAATCGAGTTGGCAAAATGGGGTTTGGGCCCCTCAGA

GCCCTGCCCTGCACCCTTGTACAGTGTCTGTGCCATGGATTTCGTTTTTCTTGGGGTA

CTCTTGATGTGAAGATAATTTGCA

BRSA.8072C1n2_s_at
                                                           (SEQ ID NO: 191)
GAGTGTCTCAGAAGTGTGCTCCTCTGGCCTCAGTTCTCCTCTTTTGGAACAACATAA

AACAAATTTAATTTTCTACGCCTCTGGGGATATCTGCTCAGCCAATGGAAAATCTGG
```

```
GTTCAACCAGCCCCTGCCATTTCTTAAGACTTTCTGCTCCACTCACAGGATCCTGAG

CTGCACTTACCTGTGAGAGTCTTCAAACTTTTAAACCTTGCCAGTCAGGACTTTTGC

TATTGCA

Hs369056.20C1n2_at
                                                    (SEQ ID NO: 192)
GAGGGACGTCAGAAAATCAGTGCATTGTGGAGTCACTTTTCTGATAAAGGGCACAT

CAGACTGCAAATGGTCCAGACAGCCAGATTCAGGACACTGATGAGTTTCTGGGGTC

ACCATAGCATCCCTGGAGTCAGCTGCTCTGCAGCCTGAAGGAGGGCTGACAGTGTG

GAGTCACTGCTATTACTTAATGAAATTATATAGAAATTCTATAATGATTATGTAATT

GCATAATGAAAACTCTCCATATCAGAGTTCAGAATATCTCCCAATTTCCAGTACAGA

ATATTATCCATAAC

Hs488293.0CB1n69_at
                                                    (SEQ ID NO: 193)
GACAGCAATAACTTCGTTTTAGAAACATTCAAGCAATAGCTTTATAGCTTCAACATA

TGGTACGTTTTAACCTTGAAAGTTTTGCAATGATGAAAGCAGTATTTGTACAAATGA

AAAGCAGAATTCTCTTTTATATGGTTTATACTGTTGATCAGAAATGTTGATTGTGCA

TTGAGTATTAAAAAATTAGATGTATATTATTCATTGTTCTTTACTCATGAGTACCTTA

TAATAATAATAATGTATTCTTTGTTAACAATGCCATGTTGGTACTAGTTATTAATCAT

ATC

Hs494173.0CB4n15_at
                                                    (SEQ ID NO: 194)
GGCAGGATATTGTAAGCCTTGAAAAAGAATTAGGCAGGATATCGGAAGCCCTGATT

AGATTCTATCCTAAGAGCAACAGAAGATCACTGACAGTGTTTTAAATAGATAGACT

AGTTTATTAGATTTGCAGTTTAGAAGTTCCCTTTTTTTGTAATTATTGGACAGTGTAG

AGACCGGATGGTGAGAGATGAGTTAGGAAGTTGTGACAGCTCTCTATACCTACCGC

TAATGTAGAGGATTATTTATTTTCATTTCATTACCATTCGTGT

Hs513726.0C2n39_s_at
                                                    (SEQ ID NO: 195)
GTAATATGTTTATAATCCTTTAGATCTTATAAATATGTGGTATAAGGAATGCCATAT

AATGTGCCAAAAATCTGAGTGCATTTAATTTAATGCTTGCTTATAGTGCTAAAGTTA

AATGATCTTAATTCTTTGCAATTATATATGAAAAATGACTGATTTTTCTTAAAATAT

GTAACTTATATAAATATATCTGTTTGTACAGATTTTAACCATAA

Hs514006.0C1n8_at
                                                    (SEQ ID NO: 196)
GTATCCTTGAACTGGAAACCATCCACGATCGAGTATCGAGTCATTCAACACTATCAA

TTCCTGGGTGACTTTTTGAAAAAGTAGTATCTCTTGTTGCAAGAAATGCTCCATCTG

TGAGTCCATGTCTCTCACTGGAATTGGATGGAAGTGGTGAATTTCAGCCAAAGTGG

CCAAAGAAATCCTGTTCCTGTGATTCTGACGTCATCAGCCTCTGCACCTCTGTCTTCC

CTTCTGCCACATGTTGCCTGTTCTCCGTGACTTTGGTAAGA

Hs522202.0C1n6_at
                                                    (SEQ ID NO: 197)
GAGAGAGTGATCACGCTGCTGTGCCCACCTATGCGGTAGACCTTGTTCCTGGGTTGG

GAGATGTTTTATGATCAGGGTGCAGTAGAAAGAGCACACTAGTAGCAGTAAAGAGA

GGTGACCCTGGCTGCAGTTCTGCCTCTAACTTCCTGAGTGACCTCAGGCTAGTCACA

CAGTGACTGCTCCCCACATTTCTTTTTGTAAGCTGCAAGGATTGAATCAGACAATAG

CCTCTAAGTTTCTTCTGAACTCTCATACTCAGGGATGCCAA
```

-continued

Hs524348.0CB1n97_at
(SEQ ID NO: 198)
TTCCCTCCCACTAATTTGTTGGCCTTTAACAGCAATTTTGAAAACTGGGTCTTCTGGT

TATGTTTTTGTTTTAAAATCTTTAAATTAGAGGATGCTGTGCCATTGAGTACTTTAAG

TTAATATGAGGTTCTGGTTCAAGGAAAACTTACGTTGGATCTGAACCAATGAGCAG

ATATTTTGATATGTGCCACTCTTGCATATACATCTCAGTCCTAACTAAAGGTTCTAGT

GGCATCCAGGACCTTTAGGGAGGCATTT

Hs524348.2C1n5_s_at
(SEQ ID NO: 199)
CACTGCGTCTGGCAATAATGTAACTTTGAAGCTTAAAAATTAATCCCAGTTTGTAGC

AATAACAGAAGACTATCTACAACGGAAGAAAGAAGCAACTGCCTTACAGTTCTGTA

AAGAATTGGCAAGAAAATAAAGCCTATAGTTGCC

Hs528836.0C1n3_s_at
(SEQ ID NO: 200)
CCCTTACTTACATACTAGCTTCCAAGGACAGGTGGAGGTAGGGCCAGCCTGGCGGG

AGTGGAGAAGCCCAGTCTGTCCTATGTAAGGGACAAAGCCAGGTCTAATGGTACTG

GGTAGGGGGCACTGCCAAGACAATAAGCTAGGCTACTGGGTCCAGCTACTACTTTG

GTGGGATTCAGGTGAGTCTCCATGCACTTCACATGTTACCCAGTGTTCTTGTTACTTC

CAAGGAGAACCAAGAATGGCTCTGTCACACTCGAAGCCAGGTTTGATC

Hs591893.1C1n4_s_at
(SEQ ID NO: 201)
CCTCCTTTCTAAATGCAGCGACCTGTGTTCTTCAGCCCTATCCCTTTCTATTCCTCTG

ACCCCGCCTCCTTTCTAAATGCAGCGACCTCTGTTCTTCAGCCCTATCCCTTTCTATT

CCTCTGACCCCGCCTCCTTTCTAAATGCAGCGACCTCTG

Hs7155.0CB1n102_at
(SEQ ID NO: 202)
GGCGTCGGCGCCTAGGGCGAAGTGAGCCAGGGTGCAGTCGGGAAGCTCCAGGACG

AAGCGGCGCGGCGGAGCCATGGCCCCAGCGCAGACCCCGCGCCGCCCGAGCAGCG

GCCCCGACAGTGGCCCCGCGCAGGAGCCGGCGGGCGAAGGCCATGGGCGCCTCAGC

GACGCCGCCCTCGGCCCCGCCTCGGAAACGAAACCTGGCGGGAGCCAGGCGCCGGC

GGGAAACGAAACCCGGAGGGAGCCAGGCGCCAGCGGGAAACGAAAGCGAAGCGT

---

The invention claimed is:

1. A method of diagnosing and treating an individual as having a DNA damage response deficient (DDRD) cancer comprising;
   a. measuring expression levels of at least two genes in a test sample of tumour cells obtained from the individual to determine a test score, wherein the at least two genes are selected from the group consisting of CXCL10, IDO1, CD2, GBP5, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1; and
   b. treating the individual with a DNA-damage therapeutic agent, wherein the individual is diagnosed as having the DDRD cancer because a test score of the test sample exceeds a threshold score, and said exceeding occurs if the test score, based on the expression levels of the at least two genes, exceeds a threshold score based on the same genes.

2. The method of claim 1, wherein the at least two genes are selected from the group consisting of CXCL10, IDO1, CD2, GBP5, ITGAL, LRP4, and APOL3.

3. The method of claim 1, wherein the cancer is selected from melanoma, colon cancer, breast cancer, and ovarian cancer.

4. The method of claim 3, wherein the cancer is associated with one or more mutations in the Fanconi anemia/BRCA pathway.

5. The method of anyone of claims 1-4, wherein the DNA-damage therapeutic agent comprises one or more substances selected from: a DNA damaging agent, a DNA repair targeted therapy, an inhibitor of DNA damage signalling, an inhibitor of DNA damage induced cell cycle arrest, a histone deacetylase inhibitor, and a heat shock protein inhibitor.

6. The method of claim 5, wherein the DNA-damage therapeutic agent comprises doxorubicin, epirubicin, cyclophosphamide, ionising radiation, cisplatin, carboplatin, a PARP inhibitor, or a combination thereof.

7. The method of claim 6, wherein the cancer is breast cancer.

8. The method of claim 5, wherein the DNA-damage therapeutic agent comprises oxaliplatin, irinotecan, or a combination thereof.

9. The method of claim 8, wherein the cancer is colorectal cancer.

10. The method of claim 5, wherein the DNA-damage therapeutic agent comprises cisplatin, carboplatin, a PARP inhibitor, or a combination thereof.

11. The method of claim 10, wherein the cancer is ovarian cancer.

12. A method of treating cancer, comprising administering a DNA-damage therapeutic agent to an individual, wherein:
   a. the individual has been selected for the treatment because the combined expression level of at least two genes in a cancer sample from the individual is higher than an established threshold value, thereby diagnosing the individual as having a DDRD cancer; and
   b. the combined expression level of the at least two genes is based on the expression of at least two genes selected from the group consisting of CXCL10, IDO1, CD2, GBP5, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

13. The method of claim 12, wherein the at least two genes are selected from the group consisting of CXCL10, IDO1, CD2, GBP5, ITGAL, LRP4, and APOL3.

14. The method of claim 12, wherein the cancer is selected from melanoma, colon cancer, breast cancer, and ovarian cancer.

15. The method of claim 12, wherein the cancer is associated with one or more mutations in the Fanconi anemia/BRCA pathway.

16. The method of anyone of claims 12-15, wherein the DNA-damage therapeutic agent comprises one or more substances selected from: a DNA damaging agent, a DNA repair targeted therapy, an inhibitor of DNA damage signalling, an inhibitor of DNA damage induced cell cycle arrest, a histone deacetylase inhibitor, and a heat shock protein inhibitor.

17. The method of claim 12, wherein the DNA-damage therapeutic agent comprises doxorubicin, epirubicin, cyclophosphamide, ionising radiation, cisplatin, carboplatin, a PARP inhibitor, or a combination thereof.

18. The method of claim 17, wherein the cancer is breast cancer.

19. The method of claim 12, wherein the DNA-damage therapeutic agent comprises oxaliplatin, irinotecan, or a combination thereof.

20. The method of claim 19, wherein the cancer is colorectal cancer.

21. The method of claim 16, wherein the DNA-damage therapeutic agent comprises cisplatin, carboplatin, a PARP inhibitor, or a combination thereof.

22. The method of claim 21, wherein the cancer is ovarian cancer.

23. A method of treating cancer, comprising administering a modulator of DNA-damage-related immune signalling to an individual, wherein:
   a. the individual has been selected for the treatment because the combined expression level of at least two genes in a cancer sample from the individual is higher than an established threshold value, thereby diagnosing the individual as having a DDRD cancer; and
   b. the combined expression level of the at least two genes is based on the expression of at least two genes selected from the group consisting of CXCL10, IDO1, CD2, GBP5, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

24. The method of claim 23, wherein at least one of the at least two genes is selected from the group consisting of CXCL10, IDO1, CD2, GBP5, ITGAL, CDR1, CD274, CD109, FOSB, FAM19A5, NLRC5, ANXA1, RSAD2, and IKZF3.

25. The method of claim 23, wherein at least one of the at least two genes is selected from the group consisting of CXCL10, IDO1, CD2, GBP5, CDR1, CD109, FOSB, FAM19A5, NLRC5, RSAD2, and IKZF3.

26. The method of claim 23, wherein at least one of the at least two genes is selected from the group consisting of CXCL10, IDO1, GBP5, CD274, and IKZF3.

27. The method of any one of claims 23-26, wherein the cancer is selected from melanoma, colon cancer, breast cancer, and ovarian cancer.

28. The method of claim 23, wherein the cancer is associated with one or more mutations in the Fanconi anemia/BRCA pathway.

* * * * *

SEQUENCE LISTING

<160> NUMBER OF SEQ ID NOS: 202

<210> SEQ ID NO 1
<211> LENGTH: 541
<212> TYPE: DNA
<213> ORGANISM: Homo sapiens

<400> SEQUENCE: 1

```
gggaccaagg tggagatcaa acgtaagtgc actttcctaa tgcttttttct tataaggttt    60 taaatttgga gcctttttgt gtttgagata ttagctcagg tcaattccaa agagtaccag   120
attctttcaa aaagtcagat gagtaaggga tagaaaagta gttcatctta aggaacagcc   180
aagcgctagc cagttaagtg aggcatctca attgcaagat tttctctgca tcggtcaggt   240
tagtgatatt aacagcgaaa agagattttt gtttagggga aagtaattaa gttaacactg   300
tggatcacct tcggccaagg gacacgactg gagattaaac gtaagtaatt tttcactatt   360
gtcttctgaa atttgggtct gatggccagt attgactttt agaggcttaa ataggagttt   420
```

| | |
|---|---|
| ggtaaagatt ggtaaatgag ggcatttaag atttgccatg ggttgcaaaa gttaaactca | 480 |
| gcttcaaaaa tggatttgga gaaaaaaaga ttaaattgct ctaaactgaa tgacacaaag | 540 |
| t | 541 |

```
<210> SEQ ID NO 2
<211> LENGTH: 600
<212> TYPE: DNA
<213> ORGANISM: Homo sapiens

<400> SEQUENCE: 2
```

| | |
|---|---|
| tttattggtc ttcagatgtg gctgcaaaca cttgagactg aactaagctt aaaacacggt | 60 |
| acttagcaat cggggttgcca gcaaagcact ggatgcaagc cttgccttcc agaagcttac | 120 |
| cagtcgggtt gccagcaaag cagtggatgc aagacttgcc ctccaggagc ttaccatcac | 180 |
| aacgaagaag acaaataaat gcataatata tagacgacat aaatccatac tgtacacatt | 240 |
| taagaataaa cagtccagta gtaagaggca gtacatattc aatctgctga gaatgtaga | 300 |
| caataactac tataagaatc ctaatgctac agaagtcact ggctgctggg aaaccgggga | 360 |
| aaacttggct atggacgtgg gggcttgtgt cggactctga ataaagagca gaatgattgg | 420 |
| cgtcctactg agatacatag taagggggc gagggcaggg aggaagtggc aagaataaca | 480 |
| tttgtgaaga tgtccaggtg agaaatagag gttttaatgc tcaagatgtt tccttttccc | 540 |
| ttttaaatct gacctgtgat ttccagcatt gctatttcga atatcactga ttgttttttaa | 600 |

```
<210> SEQ ID NO 3
<211> LENGTH: 600
<212> TYPE: DNA
<213> ORGANISM: Homo sapiens

<400> SEQUENCE: 3
```

| | |
|---|---|
| tgtggcacat atacaccatg gaatactatg cagccataaa aaagaatggg atcatgtcct | 60 |
| gtgcagcaac gtggatggag ctggaagcca ttatcctaaa tgaactcact cagaaacaga | 120 |
| aaaccaaata ccacatgttc tcacttataa gtagaagcta acattgagt acacatggat | 180 |
| acaaagaagg gaaccgcaga cactgggggcc tacctgaggt cggagcatgg aaggagggtg | 240 |
| aggatcaaaa aactacctat ctggtactat gcttttatc tggatgatga ataatctgt | 300 |
| acaacaaacc ctggtgacat gcaatttacc tatatagcaa gcctacacat gtgcccctga | 360 |
| acctaaaaaa aaagttaaaa gaaaacgtt tggattattt tccctctttc gaacaaagac | 420 |
| attggtttgc ccaaggacta caaataaacc aacgggaaaa agaaaggtt ccagttttgt | 480 |
| ctgaaaattc tgattaagcc tctgggccct acagcctgga gaacctggag aatcctacac | 540 |
| ccacagaacc cggctttgtc cccaaagaat aaaaacacct ctctaaaaaa aaaaaaaaaa | 600 |

```
<210> SEQ ID NO 4
<211> LENGTH: 600
<212> TYPE: DNA
<213> ORGANISM: Homo sapiens

<400> SEQUENCE: 4
```

| | |
|---|---|
| tccttatggg gcccggtatg tgggctccat ggtggctgat gttcatcgca ctctggtcta | 60 |
| cggagggata tttctgtacc ccgctaacaa gaagagcccc aatggaaagc tgagactgct | 120 |
| gtacgaatgc aacccccatgg cctacgtcat ggagaaggct gggggaatgg ccaccactgg | 180 |
| gaaggaggcc gtgttagacg tcattcccac agacattcac cagagggcgc cggtgatctt | 240 |
| gggatccccc gacgacgtgc tcgagttcct gaaggtgtat gagaagcact ctgcccagtg | 300 |

```
agcacctgcc ctgcctgcat ccggagaatt gcctctacct ggaccttttg tctcacacag    360
cagtaccctg acctgctgtg caccttacat tcctagagag cagaaataaa aagcatgact    420
atttccacca tcaaatgctg tagaatgctt ggcactccct aaccaaatgc tgtctccata    480
atgccactgg tgttaagata tatttttgagt ggatggagga gaaataaaact tattcctcct    540 taaaaaaaaa aaaaaaaaaa aaaaaaaaaa aaaaaaaaaa aaaaaaaaaa aaaaaaaaaa    600

<210> SEQ ID NO 5
<211> LENGTH: 600
<212> TYPE: DNA
<213> ORGANISM: Homo sapiens

<400> SEQUENCE: 5
cgggcgtggt agcgggcgcc tgtagtccca gctactcggg aggctgaggc aggagaatgg     60
cgtgaacccg ggaggcggag cttgcagtga gccgagatcg cgccactgca ctccagcctg    120
ggcgacagag cgagactccg tctcaaaaaa aaaaaaaaaa aaaaaatac aaaaattagc    180 cgggcgtggt ggcccacgcc tgtaatccca gctactcggg aggctaaggc aggaaaattg    240
tttgaaccca ggaggtggag gctgcagtga gctgagattg tgccacttca ctccagcctg    300
ggtgacaaag tgagactccg tcacaacaac aacaacaaaa agcttcccca actaaagcct    360
agaagagctt ctgaggcgct gctttgtcaa aaggaagtct ctaggttctg agctctggct    420
ttgccttggc tttgccaggg ctctgtgacc aggaaggaag tcagcatgcc tctagaggca    480
aggaggggag gaacactgca ctcttaagct tccgccgtct caaccccctca caggagctta    540 ctggcaaaca tgaaaaatcg cttaccatt aaagttctca atgcaaccat aaaaaaaaaa    600

<210> SEQ ID NO 6
<211> LENGTH: 600
<212> TYPE: DNA
<213> ORGANISM: Homo sapiens

<400> SEQUENCE: 6
tacagatact cagaagccaa taacatgaca ggagctggga ctggtttgaa cacagggtgt     60
gcagatgggg agggggtact ggccttgggc ctcctatgat gcagacatgg tgaatttaat    120
tcaaggagga ggagaatgtt ttaggcaggt ggttatatgt gggaagataa ttttattcat    180
ggatccaaat gtttgttgag tccttcttt gtgctaaggt tcttgcggtg aaccagaatt    240
ataacagtga gctcatctga ctgttttagg atgtacagcc tagtgttaac attcttggta    300 tcttttgtg ccttatctaa aacatttctc gatcactggt ttcagatgtt catttattat    360 attctttttca aagattcaga gattggcttt tgtcatccac tattgtatgt tttgtttcat    420
tgacctctag tgatacccttg atctttccca ctttctgttt tcggattgga gaagatgtac    480
cttttttgtc aactcttact tttatcagat gatcaactca cgtatttgga tctttatttg    540
ttttctcaaa taaatattta aggttataca tttaaaaaaa aaaaaaaaaa aaaaaaaaaa    600

<210> SEQ ID NO 7
<211> LENGTH: 600
<212> TYPE: DNA
<213> ORGANISM: Homo sapiens

<400> SEQUENCE: 7
tgagaagtag ttactgtgca catgtgtaga tttgcagttc tgtggctcct gatggatctg     60
agaagatgga cgtggaggat gaaaatctgt ctgattattt tgaactgatg tttgttgcta    120
```

-continued

```
tggagatgct gcctatatgt tgatgttgca gacgttaagt cactagccca cagccttgta    180
ttccatactc agagaccctg ctacttactt gacatctcaa cttgaaagtc caattaatat    240
gcacttcaaa ctttaatagg cttcaaacag aatttctttc attatctctg caaaacagct    300
tctctcatca tcttgaaatt agtgaatggc attttactgt tttagttgga gtcatttctg    360
tggttttctt tcacatccta cataacaatc catcagtaag ttctatgagc tcttctttga    420
aaacaaacag aatccaactg tttcattccc acttctgctc tggtcaagcc actgccaaca    480 ctcacccttta ttattgtagc accctcattg cctagttctg tcccacagat ttccaataaa    540
aggtgaataa aatcaggtca ctcttctgct aaaaaaaaaa aaaaaaaaaa aaaaaaaaaa    600
```

<210> SEQ ID NO 8
<211> LENGTH: 600
<212> TYPE: DNA
<213> ORGANISM: Homo sapiens
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (356)..(364)
<223> OTHER INFORMATION: n is a, c, g, or t

<400> SEQUENCE: 8

```
nnnnntttgc tacagccagg gttagctcag caggtgaaaa ccccgagggt gggtgaaacc    60
cctctggggc tcagacatgc aaaccttggg catctctctg tcccagctgg ccccgccagc    120
cggtaggaag tttcccctga gttctcagtt ttttcttctg aaaatgaggg ggttgtatgc    180
aaggttctcc tcctggcctg tggtccccag agaagggcag gaaggaacct tagataattc    240
tcatatgcat ttaacagacg aggaaactga gacccgagc cgtcacatca atacctcatt    300
tgatcttcat aagagcacct ggaggagggg ggtggggtgt ttgtgtttgt ttaaannnnn    360
nnnngtgaaa aaaatgaaga taggcatttt gtagacaatc tggaagttct ggaccggaat    420
ccatgatgta gtcagggaag aaatgacccg tgtccagtaa ccccaggcct cgagtgtgtg    480
gtgtattttt ctacataatt gtaatcattc tatacataca aattcatgtc ttgaccatca    540
tattaatatt tggtaagttt ctctctcttt agagactcca caataaagtt ttcaacatgg    600
```

<210> SEQ ID NO 9
<211> LENGTH: 394
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (201)..(223)
<223> OTHER INFORMATION: n is a, c, g, or t
<220> FEATURE:
<221> NAME/KEY: misc_feature

```
<222> LOCATION: (226)..(227)
<223> OTHER INFORMATION: n is a, c, g, or t
<220> FEATURE:
<221> NAME/KEY: misc_feature
<222> LOCATION: (229)..(232)
<223> OTHER INFORMATION: n is a, c, g, or t

<400> SEQUENCE: 9
tnttntnttt tttttttttt tttttttttt tncatagttg ttatcttaag gtgatttcca      60 atttttttt  ccatttacat  ttttccacaa  gcattgtcca  ctttattctg  taacctttt c     120 aactaccatt ttgaaatttg cttttatcca tgtggttgtt tgtgatgaac tacaggttgc     180
tgactttctt cccttctgt  nnnnnnnnnn nnnnnnnnnn nnngtnntnn nnctcaagag     240
gatctcatca gtggaatcat tagatcaaag gatatgactg ttgctcagct ctctgtgtgt     300
atgtaaatta ataggctgtt tatttgagca gttgtaggct tacaaaaata ttgagtcaaa     360
agtatagaat tcccatatat tctcctcttc tccc                                 394

<210> SEQ ID NO 10
<211> LENGTH: 600
<212> TYPE: DNA
<213> ORGANISM: Homo sapiens

<400> SEQUENCE: 10
atcttcccac ctcgatgggg ggttgctgat aagaccttca ggcctcctta ttaccatagg      60
aactgcatga gtgagttcat gggactcatc cgaggtcact atgaggcaaa gcaaggtggg     120
ttcctgccag gggagggag  tctacacagc acaatgaccc cccatggacc tgatgctgac     180
tgctttgaga aggccagcaa ggtcaagctg gcacctgaga ggattgccga tggcaccatg     240
gcatttatgt ttgaatcatc tttaagtctg gcggtcacaa agtggggact caaggcctcc     300
aggtgtttgg atgagaacta ccacaagtgc tgggagccac tcaagagcca cttcactccc     360
aactccagga acccagcaga acctaattga gactggaaca ttgctaccat aattaagagt     420
agatttgtga agattcttct tcagaatctc atgctttctg gtagtattgg aggaggggt     480 tggttaaaat gaaaattcac ttttcatagt caagtaactc agaactttta tggaaacgca     540
tttgcaaagt tctatggctg tcaccttaat tactcaataa acttgctggt gttctgtgga     600

<210> SEQ ID NO 11
<211> LENGTH: 600
<212> TYPE: DNA
<213> ORGANISM: Homo sapiens

<400> SEQUENCE: 11
gggagctaag tatccagcct ctcccaaacc tctttgaaca aagcttctgt ccctcccaca      60
cctctcacct cacaggcaca tcaggctgca gaatgcgctt tagaaagcat tgttttagtc     120
caggcacagt ggctcacgcc tgtaatccca gcactttggg aggccgaggt gggtggatca     180
caaggttggg agattgagac catcctggct aacacagtga aaccctgtct ctactaaaaa     240
aatacaaaaa attagcttgg cgtggtggtg ggcgcctgta gtcccagcag cttgggaggc     300
tgaggctgga gaatggtgtg aacccaggag gcggagcttg cagtgagcca agatcgcgcc     360
actgcactcc agcccgggtg acagagcaag actccgtctc aaaaaaaga aagaaaaaa      420 gaaagcattg ttttaattga gaggggcagg gctggagaag gagcaagttg tgggagcca      480 ggcttccctc acgcagcctg tggtggatgt gggaaggaga tcaacttctc ctcactctgg     540
gacagacgat gtatggaaac taaaaagaac atgcggcacc ttaaaaaaaa aaaaaaaaaa     600
```

<210> SEQ ID NO 12
<211> LENGTH: 600
<212> TYPE: DNA
<213> ORGANISM: Homo sapiens

<400> SEQUENCE: 12

```
tttattggtc ttcagatgtg gctgcaaaca cttgagactg aactaagctt aaaacacggt      60
acttagcaat cgggttgcca gcaaagcact ggatgcaagc cttgccttcc agaagcttac     120
cagtcgggtt gccagcaaag cagtggatgc aagacttgcc ctccaggagc ttaccatcac     180
aacgaagaag acaaataaat gcataatata tagacgacat aaatccatac tgtacacatt     240
taagaataaa cagtccagta gtaagaggca gtacatattc aatctgctga gaaatgtaga     300
caataactac tataagaatc ctaatgctac agaagtcact ggctgctggg aaaccgggga     360
aaacttggct atggacgtgg gggcttgtgt cggactctga ataaagagca gaatgattgg     420
cgtcctactg agatacatag taaggggggc gagggcaggg aggaagtggc aagaataaca     480
tttgtgaaga tgtccaggtg agaaatagag gtttaatgc tcaagatgtt tccttttccc     540
ttttaaatct gacctgtgat tccagcatt gctatttcga atatcactga ttgttttaa      600
```

<210> SEQ ID NO 13
<211> LENGTH: 600
<212> TYPE: DNA
<213> ORGANISM: Homo sapiens

<400> SEQUENCE: 13

```
atcccaaagg cccttttttag ggccgaccac ttgctcatct gaggagttgg acacttgact      60
gcgtaaagtg caacagtaac gatgttggaa ggcttatgat tttactgtgt atgtatttgg     120
gagaagaaat tctgtcagct cccaaaggat aaaccagcag ttgctttatt ggtcttcaga     180
tgtggctgca aacacttgag actgaactaa gcttaaaaca cggtacttag caatcgggtt     240
gccagcaaag cactggatgc aagccttgcc ttccagaagc ttaccagtcg ggttgccagc     300
aaagcagtgg atgcaagact tgccctccag gagcttacca tcacaacgaa gaagacaaat     360
aaatgcataa tatatagacg acataaatcc atactgtaca catttaagaa taaacagtcc     420
agtagtaaga ggcagtacat attcaatctg ctgagaaatg tagacaataa ctactataag     480
aatcctaatg ctacagaagt cactggctgc tgggaaaccg gggaaaactt ggctatggac     540
gtggggcctt gtgtcggact ctgaataaag agcagaatga ttggcaaaaa aaaaaaaaaa     600
```

<210> SEQ ID NO 14
<211> LENGTH: 600
<212> TYPE: DNA
<213> ORGANISM: Homo sapiens

<400> SEQUENCE: 14

```
cgtcttctaa atttccccat cttctaaacc caatccaaat ggcgtctgga agtccaatgt      60
ggcaaggaaa aacaggtctt catcgaatct actaattcca cccttttat tgacacagaa     120
aatgttgaga atcccaaatt tgattgattt gaagaacatg tgagaggttt gactagatga     180
tggatgccaa tattaaatct gctggagttt catgtacaag atgaaggaga ggcaacatcc     240
aaaatagtta agacatgatt tccttgaatg tggcttgaga aatatggaca cttaatacta     300
ccttgaaaat aagaatagaa ataaggatg ggattgtgga atggagattc agttttcatt     360
tggttcatta attctataag ccataaaaca ggtaatataa aaagcttcca tgattctatt     420
tatatgtaca tgagaaggaa cttccaggtg ttactgtaat tcctcaacgt attgtttcga     480
```

```
cagcactaat ttaatgccga tatactctag atgaagtttt acattgttga gctattgctg    540
ttctcttggg aactgaactc actttcctcc tgaggctttg gatttgacat tgcatttgac    600

<210> SEQ ID NO 15
<211> LENGTH: 600
<212> TYPE: DNA
<213> ORGANISM: Homo sapiens

<400> SEQUENCE: 15
actcaaatgc tcagaccagc tcttccgaaa accaggcctt atctccaaga ccagagatag     60
tggggagact tcttggcttg gtgaggaaaa gcggacatca gctggtcaaa caaactctct    120 gaaccccctcc ctccatcgtt ttcttcactg tcctccaagc cagcgggaat ggcagctgcc   180
acgccgcccc aaaagcacac tcatcccctc acttgccgcg tcgccctccc aggctctcaa    240
caggggagag tgtggtgttt cctgcaggcc aggccagctg cctccgcgtg atcaaagcca    300
cactctgggc tccagagtgg ggatgacatg cactcagctc ttggctccac tgggatggga    360
ggagaggaca agggaaatgt caggggcggg gagggtgaca gtggccgccc aaggcccacg    420
agcttgttct tgttctttg tcacagggac tgaaaacctc tcctcatgtt ctgctttcga     480
ttcgttaaga gagcaacatt ttacccacac acagataaag ttttcccttg aggaaacaac    540
agctttaaaa gaaaagaaa aaaaagtct ttggtaaatg gcaaaaaaaa aaaaaaaaa      600

<210> SEQ ID NO 16
<211> LENGTH: 600
<212> TYPE: DNA
<213> ORGANISM: Homo sapiens

<400> SEQUENCE: 16
gggatttgtt aaaatggagg tctttggtga ccttaacaga aagggttttt gaggagtagt     60
ggagtgggga ggggcagcag gaaggggaga ttgtacacac cccaggagac aagtcttcta    120
gcagttctgc cagaatgggc aggagagaag tgccatagag ctggaaggct acattgaata    180
gagaaatttc tttaacttgt tttttaagaa gggtgataaa aaggcatgtt ctgatggtga    240
tagggatgtt tccataactg gaaagaaatt gatgtgcaag agaaagaata taattgcagg    300
aggacttgaa gaagttggag agaaaaagcc tttagggacc ctgaaccaat gaatctgaaa    360
ttccccaact gccagatgta tcttcatttt tcattttccg ggagatgtaa tatgtcctaa    420
aaatcacagt cgctagattg aaatcaacct taaaaatcat ctagtccaat gtctactccc    480
agtccactac ttgaatcccc tgtgtcccct cccagtagtc gtcttgacaa cctccactga    540
aaggcaattt ctacactcca tccaccccac caccaaccca tggttcatga tctcttcgga    600

<210> SEQ ID NO 17
<211> LENGTH: 600
<212> TYPE: DNA
<213> ORGANISM: Homo sapiens

<400> SEQUENCE: 17
ttactatatc aacaactgat aggagaaaca ataaactcat tttcaaagtg aatttgttag     60
aaatggatga taaatattg gttgacttcc ggctttctaa gggtgatgga ttggagttca    120
agagacactt cctgaagatt aaagggaagc tgattgatat tgtgagcagc cagaaggttt    180
ggcttcctgc cacatgatcg gaccatcggc tctggggaat cctgatggag tttcactctt    240
gtctcccagg ctggagtaca atggcatgat ctcagcttac tgcaacctcc gtctcctggg    300
```

-continued

| | |
|---|---|
| ttcaagcgat tctcctgcct cagccttcca agtagctggg attacaggtg cccaccacca | 360 |
| cacctggcta ggttttgtat ttttagtaga gatggggttt ttttcatgtt ggccaggctg | 420 |
| atctggaact cctgacctca agtgatccac ctgccttggc ctcccaaagt gctgggattt | 480 |
| taggtgtgag ccacctcgcc tggcaaggga ttctgttctt agtccttgaa aaataaagt | 540 |
| tctgaatctt caaaaaaaaa aaaaaaaaaa aaaaaaaaaa aaaaaaaaaa aaaaaaaaaa | 600 |

<210> SEQ ID NO 18
<211> LENGTH: 600
<212> TYPE: DNA
<213> ORGANISM: Homo sapiens

<400> SEQUENCE: 18

| | |
|---|---|
| gtgtatcatg agccaaccct caaaggaccc gtattacagt gccacgttgg aaaacgctac | 60 |
| aggaagcatg acctatccac atctttccaa gatagacact aacatgtcat gtcccaaaca | 120 |
| ttagcacgtg ggggttgagc tctgtgcagt aatcgagatt gggagaattt gggcagcgcg | 180 |
| tgagaagtgc taagctactt gttttctcac ttgagcccgg gtaggctgtg ttggccctca | 240 |
| cttgggattc tcagcagtta catgaaagtt gtgctgataa tctcttctct tgtaccaatt | 300 |
| ttagtcaggc agaaaatggt aaacatgagg gtgctcttgt gacttaattt ttgttcaagg | 360 |
| gactaaattg cttatgttta ttccctgtca gcggagtgga gaatgtcatt catcaataaa | 420 |
| ccaaagccaa tagctggaga attgagatct ggttgaaagt ggtttatggt ttacatgctg | 480 |
| tactatcctg aggaattgcg agatattgct gaggggaaaa aaaaatgacc ttttcttgaa | 540 |
| atgtaacttg aaaacaaaat aaaatgtgga acataaaaaa aaaaaaaaaa aaaaaaaaaa | 600 |

<210> SEQ ID NO 19
<211> LENGTH: 600
<212> TYPE: DNA
<213> ORGANISM: Homo sapiens

<400> SEQUENCE: 19

| | |
|---|---|
| ccagaggcag aaggattggg actaggccaa catagagatt ggcgatggtt gtgagattct | 60 |
| aagagtgtgt gtgcatcttg acaatattag aggaggctga gcccaagcag gcacattctc | 120 |
| ttcgacccct ccctcattca gtctgctttg gagtctactg aacatcaagc ttgctatgag | 180 |
| caggatctta gagctgagga attggcctcc caatccgaac aggtgttata atcctttctt | 240 |
| aataggttgt gctgtggacc caatgtgagg gctgtgctgg tgtaaatggt gacatattga | 300 |
| gctgggggga tgctttcggg gtgggggggac tggttccatt ccatcaaagg ccctcttgag | 360 |
| agtctatcca gggacccatt gttttacttt aacagaccag aaaagatgtt tgttttccat | 420 |
| gtcattaccc ccagggata ccgaatgtgt gggtagaaat ttctctgtag attaaaaatc | 480 |
| agatttttac atggattcaa caaggagcg tcacttggat ttttgttttc atccatgaat | 540 |
| gtagctgctt ctgtgtaaaa tgccattttg ctattaaaaa tcaattcacg ctggaaaaaa | 600 |

<210> SEQ ID NO 20
<211> LENGTH: 600
<212> TYPE: DNA
<213> ORGANISM: Homo sapiens

<400> SEQUENCE: 20

| | |
|---|---|
| gcacgtctac ggggctggac agagtgtggt taaccgggga actgggcaag ccggcgccga | 60 |
| gcctgcgtca gccgtgcaag ccgctccttc aggaacttcc gcttgtcgct ggtgtcgctc | 120 |
| cgctccttca ggagccagct gtaggtgtcc ttgtcctgca ggagctgcag catggccttc | 180 |

```
tgaagctgct ggccgtacgt ctggagcatg aagaactgga tgatcaaagg gatgtggctg      240
gagatgcgct tgctggcctc ctggtgatag gccatcaggt gctgaaagat ctcctccatg      300
gaagagtctg ttgccgagct ggactggaaa gccccaaaat cccaggattt cttcttcttt      360
tcttcttcca gctccttctc tctgaccttc tgcaatgcac ccctgtatac ctggtcctgg      420
cagtagacaa tctgttccat ctggaagtgg aggcggatca gcttctcacc ttctctctct      480
tgttctgctc taatgtcttc aattttggac ttggcggttc tgtggaggtt aaaaaactct      540
tcaaaatttt ttatcgccaa ctttttgta caaagttggc cttataaaga aagcattgct      600
```

<210> SEQ ID NO 21
<211> LENGTH: 600
<212> TYPE: DNA
<213> ORGANISM: Homo sapiens
<220> FEATURE:
<221> NAME/KEY: misc_feature
<222> LOCATION: (1)..(107)
<223> OTHER INFORMATION: n is a, c, g, or t

<400> SEQUENCE: 21

```
nnnnnnnnnn nnnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnnncca aatgagtgat      120
gcattgaccg ttcgtaattc ttggatgcaa aagtagaact caagctactt aataacaatc      180
atggtggcat gggcaccagc aagtcagggt ggacaacagc catagttctg gagcatggtc      240
ctcaagacta ccttttgtat gcagagtatt aacactttaa ctcttagatc cttggaacat      300
aaggaagaga ggctggaaca aaaagggggtt ggcatttgga ggtggagagg tagtgtaagg      360
cacaactgtt tatcaactgg tatctaagta tttcaggcca gacacgtggc tcacacctct      420
aatcccagca ctttgggagc tgagccagga ggattgcttg agtctaggag ttcaagaccg      480
gtctgggcaa catggtgaaa ccctgtctct acaaaaaaat acaaaaatta gccaggtgtg      540
gtggggcacg cctatggtcc cagctactgg ggaggctgag atgggaggat ccacctgagc      600
```

<210> SEQ ID NO 22
<211> LENGTH: 477
<212> TYPE: DNA
<213> ORGANISM: Homo sapiens

<400> SEQUENCE: 22

```
tttttttaa ttaacttgac tttattgata gttacagcac aatttattaa ttaacttgac       60
tttattgata gttacagcac aatctgtcca aaaccaccag aatatacatt cttttcaaga      120
gctcaaatgg aacatttacc acaaaagacc atattctggg cttcaaaata agcctaaata      180
aatacaaaag catttaggac ctatgaatca gaagactgaa tatgcacata tacaaaatga      240
gaatcattct ctcacataca aaacttatat aggtagtaaa gatacagttg attaggtaga      300
tttgaatgtt gaatcactga catttcctga aggtagagct acaaattact ttttttaaaac      360 cactaaccca cccccacctt acctcactta ctcttttgg ccttaccacc tactttagtc      420
ataccctata catgttactc agaccaaatg gctctcataa acaatctcag tatatgt       477
```

<210> SEQ ID NO 23
<211> LENGTH: 600
<212> TYPE: DNA
<213> ORGANISM: Homo sapiens
<220> FEATURE:
<221> NAME/KEY: misc_feature
<222> LOCATION: (229)..(316)

<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t

<400> SEQUENCE: 23

| | | | | | |
|---|---|---|---|---|---|
| ttaagaaggt | atggaaagag | tctgggagtg | actaaactat | ccaatgtcat | tgaaataaag | 60 |
| caatgaagaa | taagagtaat | ttttgttgct | ttattaaatt | ttttctcaca | gaattcttta | 120 |
| taaaaacacc | atgtccctaa | aatgtcattc | aacatatatg | cacaccttcg | atgtatagga | 180 |
| cactgatcaa | aaaagacaga | gaaatgtgtc | cctggtgttt | tgtttttgnn | nnnnnnnnnn | 240 |
| nnnnnnnnnn | nnnnnnnnnn | nnnnnnnnnn | nnnnnnnnnn | nnnnnnnnnn | nnnnnnnnnn | 300 |
| nnnnnnnnnn | nnnnnnggga | ctacaggcac | ataccaccac | acctggcttc | atgttcccgg | 360 |
| tattagtaca | atgccaaaat | atttaaaatt | cttaaaggtt | aactcaaata | tcttaagttt | 420 |
| tacttcactt | acaatttcaa | taatgctgaa | attttgattg | aatattgtgt | ttgtagtgct | 480 |
| acctcttttt | cgttcataag | aacaaaagcc | tatcattctc | ttagtttcta | aaaaatatat | 540 |
| gttcatatgg | tttagataca | tatataaata | tntacacaaa | acaatgtttt | ttgagttgta | 600 |

<210> SEQ ID NO 24
<211> LENGTH: 429
<212> TYPE: DNA
<213> ORGANISM: Homo sapiens

<400> SEQUENCE: 24

| | | | | | |
|---|---|---|---|---|---|
| gcccgtgccg | ccccagccgc | tgccgcctgc | accggacccg | gagccgccat | gcccaagtgt | 60 |
| cccaagtgca | acaaggaggt | gtacttcgcc | gagagggtga | cctctctggg | caaggactgg | 120 |
| catcggccct | gcctgaagtg | cgagaaatgt | gggaagacgc | tgacctctgg | gggccacgct | 180 |
| gagcacgaag | gcaaacccta | ctgcaaccac | ccctgctacg | cagccatgtt | tgggcctaaa | 240 |
| ggctttgggc | ggggcggagc | cgagagccac | actttcaagt | aaaccaggtg | gtggagaccc | 300 |
| catccttggc | tgcttgcagg | gccactgtcc | aggcaaatgc | caggccttgt | ccccagatgc | 360 |
| ccagggctcc | cttgttgccc | ctaatgctct | cagtaaacct | gaacacttgg | aaaaaaaaaa | 420 |
| aaaaaaaaa | | | | | | 429 |

<210> SEQ ID NO 25
<211> LENGTH: 600
<212> TYPE: DNA
<213> ORGANISM: Homo sapiens

<400> SEQUENCE: 25

| | | | | | |
|---|---|---|---|---|---|
| caaccaggaa | gaaccgtacc | agaaccactc | cggccgattc | gtctgcactg | tacccggcta | 60 |
| ctactactc | accttccagg | tgctgtccca | gtgggaaatc | tgcctgtcca | tcgtctcctc | 120 |
| ctcaaggggc | caggtccgac | gctccctggg | cttctgtgac | accaccaaca | aggggctctt | 180 |
| ccaggtggtg | tcagggggca | tggtgcttca | gctgcagcag | ggtgaccagg | tctgggttga | 240 |
| aaaagacccc | aaaaagggtc | acatttacca | gggctctgag | gccgacagcg | tcttcagcgg | 300 |
| cttcctcatc | ttcccatctg | cctgagccag | ggaaggaccc | cctcccccac | ccacctctct | 360 |
| ggcttccatg | ctccgcctgt | aaaatggggg | cgctattgct | tcagctgctg | aagggagggg | 420 |
| gctggctctg | agagcccag | gactggctgc | ccgtgacac | atgctctaag | aagctcgttt | 480 |
| cttagacctc | ttcctggaat | aaacatctgt | gtctgtgtct | gctgaacatg | agcttcagtt | 540 |
| gctactcgga | gcattgagag | ggaggcctaa | gaataataac | aatccagtgc | ttaagagtca | 600 |

```
<210> SEQ ID NO 26
<211> LENGTH: 600
<212> TYPE: DNA
<213> ORGANISM: Homo sapiens

<400> SEQUENCE: 26
gggtcgaccc ttgccactac acttcttaag gcgagcatca aaagccgggg aggttgatgt      60
tgaacagcac actttagcca agtatttgat ggagctgact ctcatcgact atgatatggt     120
gcattatcat ccttctaagg tagcagcagc tgcttcctgc ttgtctcaga aggttctagg     180
acaaggaaaa tggaacttaa agcagcagta ttacacagga tacacagaga atgaagtatt     240
ggaagtcatg cagcacatgg ccaagaatgt ggtgaaagta aatgaaaact taactaaatt     300
catcgccatc aagaataagt atgcaagcag caaactcctg aagatcagca tgatccctca     360
gctgaactca aaagccgtca aagaccttgc ctccccactg ataggaaggt cctaggctgc     420
cgtgggccct ggggatgtgt gcttcattgt gccctttttc ttattggttt agaactcttg     480
attttgtaca tagtcctctg gtctatctca tgaaacctct tctcagacca gttttctaaa     540
catatattga ggaaaaataa agcgattggt ttttcttaag gtaaaaaaaa aaaaaaaaa      600

<210> SEQ ID NO 27
<211> LENGTH: 600
<212> TYPE: DNA
<213> ORGANISM: Homo sapiens

<400> SEQUENCE: 27
cagaaaggcc cgcccctccc cagacctcga gttcagccaa aacctcccca tggggcagca      60
gaaaactcat tgtccccttc ctctaattaa aaaagataga aactgtcttt ttcaataaaa     120
agcactgtgg atttctgccc tcctgatgtg catatccgta cttccatgag gtgttttctg     180
tgtgcagaac attgtcacct cctgaggctg tgggccacag ccacctctgc atcttcgaac     240
tcagccatgt ggtcaacatc tggagttttt ggtctcctca gagagctcca tcacaccagt     300
aaggagaagc aatataagtg tgattgcaag aatggtagag gaccgagcac agaaatctta     360
gagatttctt gtcccctctc aggtcatgtg tagatgcgat aaatcaagtg attggtgtgc     420
ctgggtctca ctacaagcag cctatctgct taagagactc tggagtttct tatgtgccct     480
ggtggacact tgcccaccat cctgtgagta aaagtgaaat aaaagctttg actagaaaaa     540
aaaaaaaaaa aaaaaaaaa aaaaaaaaaa aaaaaaaaaa aaaaaaaaaa aaaaaaaaaa     600

<210> SEQ ID NO 28
<211> LENGTH: 600
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t

<400> SEQUENCE: 28
tcagcactga gtgttcaaag acagtaggac gtcggttgct gacctgcctc ttagaagcta      60
gtttaactca gcgggtaagg atctaggact tctacattag ttaccactgt aatgataaca     120
ccaccagaaa agtctgtagt ttaatatttc ccaccttatg cctgtttctt cattcacgca     180
```

| | |
|---|---|
| aagaaaataa aaatataata cctaagcctc tttgtattac ataaagcaaa atgcaaagca | 240 |
| ctgtatcttc caaatacttc ctcttgatat ggtggaatta tagagtagta tcatttgtaa | 300 |
| cntgaaatgt cttctagggt tgctatgcga aagcaagact gtggtttcat tccaatttcc | 360 |
| tgtatatcgg aatcatcacc atctgtatat gtgtgattga ggtgttgggg atgtcctttg | 420 |
| cactgaccct gaactgccag attgacaaaa ccagccagac catagggcta tgatctgcag | 480 |
| tagtcctgtg gtgaagagac ttgtttcatc tccgggaaat gcaaaaccat ttataggcat | 540 |
| gaagccctac atgatcactt gcagggtgan cctcctccca tccttttccc ttttagggtc | 600 |

<210> SEQ ID NO 29
<211> LENGTH: 600
<212> TYPE: DNA
<213> ORGANISM: Homo sapiens

<400> SEQUENCE: 29

| | |
|---|---|
| gcctgggacg ctgctgctgt tcaggaaacg atggcagaac gagaagctcg ggttggatgc | 60 |
| cggggatgaa tatgaagatg aaaacccttta tgaaggcctg aacctggacg actgctccat | 120 |
| gtatgaggac atctcccggg gcctccaggg cacctaccag gatgtgggca gcctcaacat | 180 |
| aggagatgtc cagctggaga agccgtgaca cccctactcc tgccaggctg cccccgcctg | 240 |
| ctgtgcaccc agctccagtg tctcagctca cttccctggg acattctcct ttcagccctt | 300 |
| ctggggcttc ccttagtcat attccccag tgggggggtgg gagggtaacc tcactcttct | 360 |
| ccaggccagg cctccttgga ctccctgggg gtgtcccac tcttcttccc tctaaactgc | 420 |
| cccacctcct aacctaatcc ccccgcccg ctgccttttcc caggctcccc tcaccccagc | 480 |
| gggtaatgag cccttaatcg ctgcctctag gggagctgat tgtagcagcc tcgttagtgt | 540 |
| cacccccctcc tccctgatct gtcagggcca cttagtgata ataaattctt cccaactgca | 600 |

<210> SEQ ID NO 30
<211> LENGTH: 600
<212> TYPE: DNA
<213> ORGANISM: Homo sapiens

<400> SEQUENCE: 30

| | |
|---|---|
| ggattcagcc agtgcggatt ttccatataa tccaggacaa ggccaagcta taagaaatgg | 60 |
| agtcaacaga aactcggcta tcattggagg cgtcattgct gtggtgattt tcaccatcct | 120 |
| gtgcaccctg gtcttcctga tccggtacat gttccgccac aagggcacct accataccaa | 180 |
| cgaagcaaag ggggcggagt cggcagagag cgcggacgcc gccatcatga acaacgaccc | 240 |
| caacttcaca gagaccattg atgaaagcaa aaaggaatgg ctcatttgag gggtggctac | 300 |
| ttggctatgg gatagggagg agggaattac taggaggag agaaagggac aaaagcaccc | 360 |
| tgcttcatac tcttgagcac atccttaaaa tatcagcaca gttggggga ggcaggcaat | 420 |
| ggaatataat ggaatattct tgagactgat cacaaaaaaa aaaaaccttt ttaatatttc | 480 |
| tttatagctg agttttccct tctgtatcaa aacaaaataa tacaaaaaat gcttttagag | 540 |
| tttaagcaat ggttgaaatt tgtaggtaat atctgtctta ttttgtgtgt gtttagaggt | 600 |

<210> SEQ ID NO 31
<211> LENGTH: 600
<212> TYPE: DNA
<213> ORGANISM: Homo sapiens

<400> SEQUENCE: 31

| | |
|---|---|
| atgtccaaaa agatacagaa gaactaaaga gctgtggtat acaagacata tttgttttct | 60 |

```
gcaccagagg ggaactgtca aaatatagag tcccaaacct tctggatctc taccagcaat    120
gtggaattat cacccatcat catccaatcg cagatggagg gactcctgac atagccagct    180
gctgtgaaat aatggaagag cttacaacct gccttaaaaa ttaccgaaaa accttaatac    240
actgctatgg aggacttggg agatcttgtc ttgtagctgc ttgtctccta ctatacctgt    300
ctgacacaat atcaccagag caagccatag acagcctgcg agacctaaga ggatccgggg    360
caatacagac catcaagcaa tacaattatc ttcatgagtt tcgggacaaa ttagctgcac    420
atctatcatc aagagattca caatcaagat ctgtatcaag ataaaggaat tcaaatagca    480
tatatatgac catgtctgaa atgtcagttc tctagcataa tttgtattga aatgaaacca    540
ccagtgttat caacttgaat gtaaatgtac atgtgcagat attcctaaag ttttattgac    600

<210> SEQ ID NO 32
<211> LENGTH: 600
<212> TYPE: DNA
<213> ORGANISM: Homo sapiens

<400> SEQUENCE: 32
ggtttccttc ccaggacagc tgcagggtag agatcatttt aagtgcttgt ggagttgaca     60
tccctattga ctctttccca gctgatatca gagacttaga cccagcactc cttggattag    120
ctctgcagag tgtcttggtt gagagaataa cctcatagta ccaacatgac atgtgacttg    180
gaaagagact agaggccaca cttgataaat catggggcac agatatgttc ccacccaaca    240
aatgtgataa gtgattgtgc agccagagcc agccttcctt caatcaaggt ttccaggcag    300
agcaaatacc ctagagattc tctgtgatat aggaaatttg gatcaaggaa gctaaaagaa    360
ttacagggat gttttttaatc ccactatgga ctcagtctcc tggaaatagg tctgtccact    420
cctggtcatt ggtggatgtt aaacccatat tcctttcaac tgctgcctgc tagggaaaac    480
tgctcctcat tatcatcact attattgctc accactgtat cccctctact tggcaagtgg    540
ttgtcaagtt ctagttgttc aataaatgtg ttaataatgc ttaaaaaaaa aaaaaaaaaa    600

<210> SEQ ID NO 33
<211> LENGTH: 600
<212> TYPE: DNA
<213> ORGANISM: Homo sapiens

<400> SEQUENCE: 33
attccaggaa gcatgggatt ttattttgct tgattttggg cacatgaaat aatagctcta     60
ggaaaatgcg catcttaatg actctttgta aagagaggca tttcttacaa ctgtgatgtt    120
tgcttacata aaagttacct cataagttaa ttctaacttt tattcttgaa ttttatttca    180
tttcaatagc ttgtttcatt tgcacgcctt tgtattttga ttgacctgta gaatggatgt    240
taggaaactc aaaattgaac acagtgaaac aaatggtatt tgaagaaatg taatatctttt    300 tatattctat ttatgatatc cataatcaaa tgagattatt ttaccacata atgttttaa    360 atatcagatt tttagtttgc agtttttagga aaatgcttta gatagaaaag gttcttatgc    420
attgaatttg gagtactacc aacaatgaat gaattttattt tttatattct tacacatttt    480
attggtcatt gtcacagata gtaaaatacta aaaatttcag gtcagtttgt tttgaaactg    540
aaattggaaa taaatctgga aatgttttgt tgcactaaaa taataaaatg aattgtactg    600

<210> SEQ ID NO 34
<211> LENGTH: 600
<212> TYPE: DNA
```

<213> ORGANISM: Homo sapiens

<400> SEQUENCE: 34

```
taggccagcc ctgtcaccac ctccactgcc atgaccaggc cgaaggcagg gaacgccctc    60
cccagtcccg ctgtccagca aggccccgag acttttcttc tgtgatttcc aaaagcaagg   120
cagccgtgct gttctagttc ctctccatcc gccacctccc ctcccgctgc cccagaagtt   180
tctatcattc catggagaaa gctgtgttcc aatgaatcct acctcttgcc cagtcccagg   240
cagagtaagc agggcccacc tagggaccaa gaaagagtag gaagaagggg acgagccggg   300
agcaaaacca cctcagacac ccgggccttc tcagccttct cccgcggcc agctgggtct    360
ccggggaccc tgggccctgg gccgcccatt cctggccctc ccgctgcatc tcagacctga   420
cacccaacgg ggggatgtgg tggcctgtgc ccaccttctc tccctcctcc cgacccgccc   480
cctcgccccc accctgtgt gtttcgccag ttaagcacct gtgactccag tacctactac    540
tggttttggg ttggttgttc tgtctttttt ttaattaaat aaaaacattt ttaaaatgtt   600
```

<210> SEQ ID NO 35
<211> LENGTH: 600
<212> TYPE: DNA
<213> ORGANISM: Homo sapiens

<400> SEQUENCE: 35

```
tgctcagacc agctcttccg aaaaccaggc cttatctcca agaccagaga tagtggggag    60
acttcttggc ttggtgagga aaagcggaca tcagctggtc aaacaaactc tctgaacccc   120
tccctccatc gttttcttca ctgtcctcca agccagcggg aatggcagct gccacgccgc   180
cctaaaagca cactcatccc ctcacttgcc gcgtcgccct ccaggctct caacagggga    240
gagtgtggtg tttcctgcag gccaggccag ctgcctccgc gtgatcaaag ccacactctg   300
ggctccagag tggggatgac atgcactcag ctcttggctc cactgggatg ggaggagagg   360
acaagggaaa tgtcagggc ggggagggtg acagtggccg cccaaggccc acgagcttgt    420
tctttgttct ttgtcacagg gactgaaaac ctctcctcat gttctgcttt cgattcgtta   480
agagagcaac attttacccca cacacagata aagttttccc ttgaggaaac aacagcttta   540
aaagaaaaag aaaaaaaaag tctttggtaa atggcaaaaa aaaaaaaaaa aaaaaaaaa    600
```

<210> SEQ ID NO 36
<211> LENGTH: 600
<212> TYPE: DNA
<213> ORGANISM: Homo sapiens

<400> SEQUENCE: 36

```
tccccagaca ccgccacatg gcttcctcct gcgtgcatgt gcgcacacac acacacacac    60
gcacacacac acacacacac tcactgcgga gaaccttgtg cctggctcag agccagtctt   120
tttggtgagg gtaaccccaa acctccaaaa ctcctgcccc tgttctcttc cactctcctt   180
gctacccaga aatcatctaa atacctgccc tgacatgcac acctcccctg ccccaccagc   240
ccactggcca tctccacccg gagctgctgt gtcctctgga tctgctcgtc atttccttc    300
ccttctccat ctctctggcc ctctaccct gatctgacat cccactcac gaatattatg    360
cccagtttct gcctctgagg gaaagcccag aaaaggacag aaacgaagta gaaaggggcc   420
cagtcctggc ctggcttctc ctttggaagt gaggcattgc acgggagac gtacgtatca    480
gcggcccctt gactctgggg actccggggtt tgagatggac acactggtgt ggattaacct   540
gccaggggaga cagagctcac aataaaaatg gctcagatgc cacttcaaag aaaaaaaaaa   600
```

<210> SEQ ID NO 37
<211> LENGTH: 420
<212> TYPE: DNA
<213> ORGANISM: Homo sapiens

<400> SEQUENCE: 37

```
gggcggttct ccaagcaccc agcatcctgc tagacgcgcc gcgcaccgac ggaggggaca    60
tgggcagagc aatggtggcc aggctcgggc tggggctgct gctgctggca ctgctcctac   120
ccacgcagat ttattccagt gaaacaacaa ctggaacttc aagtaactcc tcccagagta   180
cttccaactc tggttggcc ccaaatccaa ctaatgccac caccaaggtg gctggtggtg    240
ccctgcagtc aacagccagt ctcttcgtgg tctcactctc tcttctgcat ctctactctt   300
aagagactca ggccaagaaa cgtcttctaa atttccccat cttctaaacc caatccaaat   360
ggcgtctgga agtccaatgt ggcaaggaaa acaggtctt catcgaatct actaattcca    420
```

<210> SEQ ID NO 38
<211> LENGTH: 600
<212> TYPE: DNA
<213> ORGANISM: Homo sapiens
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (514)..(515)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (526)..(527)
<223> OTHER INFORMATION: n is a, c, g, or t
<220> FEATURE:
<221> NAME/KEY: misc_feature
<222> LOCATION: (583)..(585)
<223> OTHER INFORMATION: n is a, c, g, or t

<400> SEQUENCE: 38

```
accctgtgcc agaaaagcct cattcgttgt gcttgaaccc ttgaatgcca ccagctgtca    60
tcactacaca gccctcctaa gaggcttcct ggaggtttcg agattcagat gccctgggag   120
atcccagagt ttcctttccc tcttggccat attctggtgt caatgacaag gagtaccttg   180
gctttgncac atgtcaaggc tgaagaaaca gtgtctccaa cagagctcct tgtgttatct   240
gtttgtacat gtgcatttgt acagtaattg gtgtgacagt gttctttgtg tgaattacag   300
gcaagaattg tggctgagca aggcacatag tctactcagt ctattcctaa gtcctaactc   360
ctccttgtgg tgttggattt gtaaggcact ttatcccttt tgtctcatgt ttcatcgtaa   420
atggcatagg cagagatgat acctaattct gcatttgatt gtcactttt gtacctgcat    480
taatttaata aaatattctt attttatttg ttanntngta nannannatg tccatttct    540
tgtttatttt gtgtttaata aaatgttcag tttaacatcc cannngagaa agttaaaaaa   600
```

<210> SEQ ID NO 39
<211> LENGTH: 523
<212> TYPE: DNA
<213> ORGANISM: Homo sapiens

<400> SEQUENCE: 39

| | | | | | | |
|---|---|---|---|---|---|---|
| ctcctggttc | aaaagcagct | aaaccaaaag | aagcctccag | acagccctga | gatcacctaa | 60 |
| aaagctgcta | ccaagacagc | cacgaagatc | ctaccaaaat | gaagcgcttc | ctcttcctcc | 120 |
| tactcaccat | cagcctcctg | gttatggtac | agatacaaac | tggactctca | ggacaaaacg | 180 |
| acaccagcca | aaccagcagc | ccctcagcat | ccagcaacat | aagcggaggc | attttccttt | 240 |
| tcttcgtggc | caatgccata | tccacctct | tctgcttcag | ttgaggtgac | acgtctcagc | 300 |
| cttagccctg | tgcccctga | aacagctgcc | accatcactc | gcaagagaat | cccctccatc | 360 |
| tttgggaggg | gttgatgcca | gacatcacca | ggttgtagaa | gttgacaggc | agtgccatgg | 420 |
| gggcaacagc | caaaataggg | gggtaatgat | gtaggggcca | agcagtgccc | agctgggggt | 480 |
| caataaagtt | acccttgtac | ttgcaaaaaa | aaaaaaaaaa | aaa | | 523 |

<210> SEQ ID NO 40
<211> LENGTH: 600
<212> TYPE: DNA
<213> ORGANISM: Homo sapiens

<400> SEQUENCE: 40

| | | | | | | |
|---|---|---|---|---|---|---|
| gccatcaaga | atttactgaa | agcagttagc | aaggaaaggt | ctaaaagatc | tccttaaaac | 60 |
| cagaggggag | caaaatcgat | gcagtgcttc | caaggatgga | ccacacagag | gctgcctctc | 120 |
| ccatcacttc | cctacatgga | gtatatgtca | agccataatt | gttcttagtt | tgcagttaca | 180 |
| ctaaaaggtg | accaatcatg | gtcaccaaat | cagctgctac | tactcctgta | ggaaggttaa | 240 |
| tgttcatcat | cctaagctat | tcagtaataa | ctctaccctg | gcactataat | gtaagctcta | 300 |
| ctgaggtgct | atgttcttag | tggatgttct | gaccctgctt | caaatatttc | cctcacccttt | 360 |
| cccatcttcc | aagggtataa | ggaatctttc | tgctttgggg | tttatcagaa | ttctcagaat | 420 |
| ctcaaataac | taaaaggtat | gcaatcaaat | ctgctttta | aagaatgctc | tttacttcat | 480 |
| ggacttccac | tgccatcctc | ccaaggggcc | caaattcttt | cagtggctac | ctacatacaa | 540 |
| ttccaaacac | atacaggaag | gtagaaatat | ctgaaaatgt | atgtgtaagt | attcttattt | 600 |

<210> SEQ ID NO 41
<211> LENGTH: 513
<212> TYPE: DNA
<213> ORGANISM: Homo sapiens

<400> SEQUENCE: 41

| | | | | | | |
|---|---|---|---|---|---|---|
| gggaaatcag | tgaatgaagc | ctcctatgat | ggcaaataca | gctcctattg | ataggacata | 60 |
| gtggaagtgg | gctacaacgt | agtacgtgtc | gtgtagtacg | atgtctagtg | atgagtttgc | 120 |
| taatacaatg | ccagtcaggc | cacctacggt | gaaaagaaag | atgaatccta | gggctcagag | 180 |
| cactgcagca | gatcatttca | tattgcttcc | gtggagtgtg | gcgagtcagc | taaatggcag | 240 |
| gggcagcaag | atggtgttgc | agacccaggt | cttcatttct | ctgttgctct | ggatctctgg | 300 |
| tgcctacggg | gacatcgtga | tgacccagtc | tccagactcc | ctggctgtgt | ctctgggcga | 360 |
| gagggccacc | atcaagtgca | agtccagcca | gagtatttta | tataggtcca | acaacaagaa | 420 |
| ctacttagct | tggtaccagc | agaaagcagg | acagcctcct | aaattgttca | tttactgggc | 480 |
| atctacccgg | gaatccgggg | tccctgaccg | att | | | 513 |

<210> SEQ ID NO 42
<211> LENGTH: 600
<212> TYPE: DNA
<213> ORGANISM: Homo sapiens

<400> SEQUENCE: 42
aacgaaagtc tagcctttcg tacccgtata tataaagaca cccctgttct gattggacaa      60
ggcagccttt cccctgcagc tcgattggtg gagacgccca ctccctgaca gaacatctcc     120
tgcatgtaga ccaaatatta aaactttcct ccgtccatct ttaactgctg gtgttttcaa     180
ccctttcccc tctgtgccat gtttctagct tttatttaaa acgtactttg gttttccttg     240
gcaaaattgt gtctagctac taggatgacg tgtcttaatt ttttttttaaa tgttggcgct     300 gaaactggct tgatcaacg ttttaaaaag acgcgcgcta gttgtgattg gccaagtgat     360
ttcttcttac cctcttaagt ttagaaaggt taatttcata tcttgatttg tctatttaaa     420
cttggagata ttttcaataa tttgttccaa atgcaccatg actattaact cataagtaac     480
aatatgaaac ctgatgttaa gctacatgaa cacatttaat ttcaccacaa tatgacatcc     540
tcatatgaaa gcactctctt atcttttaca agttcaactg gtatttgtgt aatctgctgt     600

<210> SEQ ID NO 43
<211> LENGTH: 600
<212> TYPE: DNA
<213> ORGANISM: Homo sapiens
<220> FEATURE:
<221> NAME/KEY: misc_feature
<222> LOCATION: (102)..(104)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (389)..(390)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:

```
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t

<400> SEQUENCE: 43
tgctaccatg cctgactagt ttttgtattt ttagtagaga cagggtttga ccatattggc      60
caggttggtc ttggactcct gacaagtgat ccgccctcct cnnncncncg aagtgctagg     120
gttacnaggt gtgaaccacc atgcctaact atcgttgcta ctttctattg gaagagaagg     180
cagccctgat ttagtctgtt tacagtctgc attatgtgga gaatagagag ccatcatagt     240
ccctaaaact ttccttgcca gttaacccag caggacaacc tgtctttgtc tcttgacaac     300
tgttaactga gaacagggcc cttgctcctc taggtgtgca cattaaggac tttgcacagt     360
gtggatgtag tcatgctgc tctgccntnn agtacatgct gcttgaattt tcatcatnan     420
cctccacncc ttncacctnc nngnnaaaaa aaaagcgtgc aggaagtagc atttcagatc     480
cttctccacc acctctgctt cccttctccc ttcttttcct ccttgcagca ttccctttag     540
tacnagggag ggatggtggt tgaaaatggg gggaatgatg ttgctcagaa aaaaaaaaaa     600

<210> SEQ ID NO 44
<211> LENGTH: 600
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 44
ataatgctgg aaacagaagc accaaactga ttgtgcaatt actccttttg tagaagaggc      60
caaaatcctc ctcctccttc ctttctccta tattcactcc tccaggatca taaagcctcc     120
ctcttgttta tctgtgtctg tctgtctgat tggttagatt tggctncsct tccaagctaa     180
tggtgtcagg tggagaacag agcaaccttc cctcggaagg agacaattcg aggtgctggt     240
acatttccct tgttttctat gttcttcttt ctagtgggtc tcatgtagag atagagatat     300 tttttttgttt tagagattcc aaagtatata ttttttagtgt aagaaatgta ccctctccac     360
actccatgat gtaaatagaa ccaggaataa atgtgtcatt gtgataatcc catagcaatt     420
tatggtaaga acaagacccc tttccctcac caccgagtct cgtggtctgt gtctgtgaac     480
cagggcaggt aattgtgaca ctgcatctca tagaactctg cctgcccaga ttttgtgtg     540 ctcacctcaa tgggtgaaaa ataaagtctg tgtaaactgt taaaaaaaaa aaaaaaaaa     600

<210> SEQ ID NO 45
<211> LENGTH: 497
<212> TYPE: DNA
<213> ORGANISM: Homo sapiens
<220> FEATURE:
<221> NAME/KEY: misc_feature
<222> LOCATION: (383)..(384)
<223> OTHER INFORMATION: n is a, c, g, or t
<220> FEATURE:
<221> NAME/KEY: misc_feature
<222> LOCATION: (464)..(466)
<223> OTHER INFORMATION: n is a, c, g, or t
```

```
<220> FEATURE:
<221> NAME/KEY: misc_feature
<222> LOCATION: (469)..(469)
<223> OTHER INFORMATION: n is a, c, g, or t

<400> SEQUENCE: 45
tcctcagacc cagtaattcc acccctagga atccagctta cacacacaag aaagaaaaga      60
taaatgtaca aggttagtca ctgcacagtg agacagcaaa agattagaaa gaacccaagt     120
gattattgat ctgggtttta ttcctttata gcccaaccat atgatggaat actataatgt     180
tgtaaaaatg ggttaagagt tctttatgaa ttggtgtgga aacatcgcca agatatgaaa     240
gccaaatgca gaaaaatata tgtggtatgc tattatctat gtgaaaaaga cattactatt     300
ctctggaagg ataaacacaa atttgagaat ggtggatatc tggggtgaga ggtatccttt     360
tcactgttct ttaaaagttt tgnnattttg gtgtttgcct attcaaaaaa atggttaaaa     420
tcagttgcca ccaattaaaa attaggagaa tgcatataaa gaannnaant tcctgttaaa     480
aaaaaaaaaa aaaaaaa                                                    497

<210> SEQ ID NO 46
<211> LENGTH: 600
<212> TYPE: DNA
<213> ORGANISM: Homo sapiens

<400> SEQUENCE: 46
gcccatagtc ccatcttttt acaggcattt tttacacctg gagcagccag aggacgcatg      60
catggctctt cggaaggtaa tttagggatc acccatgtaa gtttcctaag gatttcttta     120
acatggttct tctgattcag tccggccaat taaatctaaa tccacccctg aaagccatct     180
ggtgtggata acaagcccac aaatgagcag tcagcttttt gtgcccttta gggcctggga     240
caaccacggg atctaaaagg ggctggaact agaggtcttg agctcctgtt cctaaaatca     300
tcttcatcct atatctgcag ccttctcctg ccacggcatg cacccacaca tgcgagcctc     360
ccgggtactg tcatcctgaa ttctgagacc atccagcact tcctttagtt ttgccctggt     420
gctgttgact tttgtttact gaagagtgtg ctggaggcag acaagggac atggaaggct      480 gcaatttaag agtctaaaag gttttagaat cctgaaggag gtttaacaag ctgaattgaa     540
gaataatacc tttctcaact ggagagaatt tacatgattg cattattgtt aaaattaaca     600

<210> SEQ ID NO 47
<211> LENGTH: 600
<212> TYPE: DNA
<213> ORGANISM: Homo sapiens

<400> SEQUENCE: 47
atcatttagt tgaatcatta taagtctagg actgtctgta gatgtaaatt tgttaagaat      60
taggactcaa gagtagaatt cctttaatcc acatagactt acaatggtgc tgtgcacatg     120
gagcccctaa atcattgctg actgagtaga tttcccaggg taagcccaag aagttactcc     180 tagaagggc tggtaggga aagagccaac atcccacatg cctgcccact ttgggtctgg      240
tcccaagaaa caaactccag tggcctcgaa aatttaatat tgctgtcaga agggcctccc     300
cttcaaagga acaggtcctg atagctcttg ttatatgcaa agtggaaagg taacgtgact     360
gttctctgca tttcctgcct ttcaattgag tgaagacaga cagatgattt attgggcatt     420
tcctagcctc cccttcacca taggaaacca gactgaaaaa aaggtgcaaa ttttaaaaag     480
atgtgtgagt atcttgaggg ggctggggga gaattcctgt gtaccactaa agcaaaaaaa     540
```

```
gaaaactctc taacagcagg acctctgatc tggaggcata ttgaccataa atttacgcca    600
```

<210> SEQ ID NO 48
<211> LENGTH: 491
<212> TYPE: DNA
<213> ORGANISM: Homo sapiens

<400> SEQUENCE: 48

```
tttttctgag caacatcatt cccccattt tcaaccacca tccctccctg gtactaaagg      60
gaatgctgca aggaggaaaa gaagggagaa gggaagcaga ggtggtggag aaggatctga    120
aatgctactt cctgcacgct ttttttcttc ttggaggtgg aaggagtgga ggatgatgat    180
gaaaattcaa gcagcatgta ctagacggca gagcagcatg agctacatcc acactgtgca    240
aagtccttaa tgtgcacacc tagaggagca agggccctgt tctcagttaa cagttgtcaa    300
gagacaaaga caggttgtcc tgctgggtta actggcaagg aaagttttag ggactatgat    360
ggctctctat tctccacata atgcagactg taaacagact aaatcagggc tgccttctct    420
tccaatagaa agtagcaacg atagttaggc atggtggttc acaccttgta accctagcac    480
ttcgtgggca g                                                         491
```

<210> SEQ ID NO 49
<211> LENGTH: 600
<212> TYPE: DNA
<213> ORGANISM: Homo sapiens

<400> SEQUENCE: 49

```
atcagaacaa tttcatgtta tacaaataac atcagaaaaa tatcttaaat tatatggcat     60
attctattga ttcatccaca aatttataag tccttaccac ctttcattat attggtacta   120
ggcattatag tagtgctagg cactatagta atgctggggt ataaacaaga ataaaacaaa   180
ataagttcct tatttcaggt aacttacagt ataggtcagt ggttcttagc ttgcttttta   240
attatgaatt cctttgaaag tctagtaaaa taatccaaca ccattattcc ccattgcaca   300
taccccccaga tgttttagac atattttcaa ttgctccatg gaccttaaga aaacttggtt   360
ggtgtgcagt ttggtgtatt atgggtaaga ctggacctgg tgttagaaaa tctgcatttg   420
aggctttgtt ctgacagtgt ctagtgtaaa catgggcaga ccacttaaac ctctctttag   480
tcttctctgt agaatgatga taataccatc taattagcag gattgttgtt ttattcagtg   540
agacagcata tgtaaataac ttagtaaaat aaaaagcaac gtgtttataa tggtaaaaaa   600
```

<210> SEQ ID NO 50
<211> LENGTH: 600
<212> TYPE: DNA
<213> ORGANISM: Homo sapiens

<400> SEQUENCE: 50

```
tgggaatcat gaactccttc gtcaacgaca tcttcgaacg catcgcgggt gaggcttccc     60
gcctggcgca ttacaacaag cgctcgacca tcacctccag ggagatccag acggccgtgc   120
gcctgctgct gcccggggag ttggccaagc acgccgtgtc cgagggcacc aaggccgtca   180
ccaagtacac cagcgctaag taaacttgcc aaggagggac tttctctgga atttcctgat   240
atgaccaaga aagcttctta tcaaaagaag cacaattgcc ttcggttacc tcattatcta   300
ctgcagaaaa gaagacgaga atgcaaccat acctagatgg acttttccac aagctaaagc   360
tggcctcttg atctcattca gattccaaag agaatcattt acaagttaat ttctgtctcc   420
ttggtccatt ccttctctct aataatcatt tactgttcct caaagaattg tctacattac   480
```
ccatctcctc ttttgcctct gagaaagagt atataagctt ctgtacccca ctgggggtt     540 ggggtaatat tctgtggtcc tcagccctgt accttaataa atttgtatgc cttttctctt    600

```
<210> SEQ ID NO 51
<211> LENGTH: 600
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
```

<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 51

```
gaaagtgata atacagaaag gtggggctgg tgtagggntn aagncaggat gctttggnan    60
agcatgnaag gtcnccgant ccagtgntna ggaactaatg angggttttnt naagancgtn   120
atgagatcaa tgcngatgag ncacttagaa gnagcaatta gttaggcaaa gggaagtgaa   180
tgtgnaggag gaacaagcat tccaggcaag aagaacaccc tatcgaaaag cctggaagca   240
aaacattagt gaggctacct ttcataaatt gctttctgta agtcatgcca ttgtgtagtc   300
ttaattgctt tctctcacca gggaaggtgt gggaaggact tgtgaaatac atattcgagg   360
aaaaactatg cacaaggccg tgcatttaaa aataaactcc ctaaggctgg ggtgaaacct   420
gctacggtct gcgcaagttg actgttaatg aatttgattc tcaggtgtga gtgattaaaa   480
gaacactgat catgtcattt tcttttggt cactaattcc ctccctccct tctctttctt   540
ttctttttc ttttctttc tttttcttc tttcttccg acagagaaag actccatctc        600
```

<210> SEQ ID NO 52
<211> LENGTH: 600
<212> TYPE: DNA
<213> ORGANISM: Homo sapiens

<400> SEQUENCE: 52

```
taagatgttt aagtatatcc aaccgtccca gaccacattg gcctatttcc tcctcttggc    60
aacactgctc gggttttccc ctcgcatcat ccttatgcta tgacactgga ctaaattgta   120
ataatacatt ttcttgttaa tctcctcatt atactatgag ctccttgagg acaggtactt   180
tgtcttgctc acatctgtag attcaatgcc tggcacagcg attgatattg caagggcact   240
taataaatgg ttttttgaata aaagaattgc ttaaagtaaa atatagctgt aaattgtatt   300
ataaaaggac agtgggtggc agtctgaggt ctgctattta ctggtttggg caagttactt   360
aatctgtttg cttcctcagc tgtacgatgg gtaaaataat agtggttatc acaacagggt   420
ggttacagcg atgaaatgag attatgtgtg taggctacca cataattgta aagctgatat   480
ttaaatggaa cagatactgc acagacactt gaggtctgag aataagatta ggtcaaccag   540
agtattaatg ggttaaataa aggtgacatc ctatgcaacc aacggtttga tctttatgct   600
```

<210> SEQ ID NO 53
<211> LENGTH: 600
<212> TYPE: DNA
<213> ORGANISM: Homo sapiens

<400> SEQUENCE: 53

```
gtcttccagt cagtcagtgt cttccagaaa aatctacgtc ttccaccaaa tccaggtctt    60
ccagtcaatc cacatcttcc ggaaaaaatc caggtcttcc agccaatata tgtcttcctg   120
aagatccacg tcttccagaa aatccatgtc ttccagaaaa tccatgtctt ccagtaacct   180
cccagtcttc cagaaaatcc acgtcttccc aacaatccaa gtcttccgga taatttgggt   240
cttcctgaaa atctacgtct tccaaaaaag ccatgtcttc cagaaaatcc acatcttcca   300
atggcctcca ggtcttccag actatccatg tcttccagaa aatccttgtc ttcccttaaa   360
tctatagctt ccaaaaaatc cgggtcttcc aggaaatccg tgtcttccag caagtccacg   420
```

```
tcttccaaca aagccatgtc ttccagacta tccatgtctt ccagaaaatc cttgtcttcc      480
ctcaaatcca tagcttccga aaaatccagg tcttccagga atccgtgtc ttccagcaaa       540 tccacgtctt ccaacaaagc catgtcttcc atcaaattaa tgtcttccag cctacttgtg      600
```

<210> SEQ ID NO 54
<211> LENGTH: 600
<212> TYPE: DNA
<213> ORGANISM: Homo sapiens

<400> SEQUENCE: 54

```
agcatcgttt atgaaaacaa ctaaatattc actaatggtg ccagtggaat aaatcagaga      60
acatcccctg ctacgtaact ctctgcatac atcaaagaga atggtgtggc tttgcttttt      120
caacaatcta ctgagtggcc atgggcatgt ggatatggcc atgaatgagc aagatcctct      180
ctgatcctgt agaagttaag ttctaccaga taacttgctg cttcaacaaa aagatttacc      240 ttttaaata aatgttgtag aatacttaaa aaaacaaac tagaatttgc ctgtgtgcag        300
ccagtaacat gtctatttaa cctggacacc ttttgaggaa tattctcaga ttgcccccat      360
gctgtttata agacattgtt ccttatacac ctgtttatga atgaaaagaa acataaggag      420
tgggtacaaa gacttctatc tatgaatgat taaaaaggct agagtacgaa tacttcttga     480
acctttggta ctaaatgctt ttcatgttct atataaatgt agaaaacatt ttacaaatcc      540
tgtaaataaa ctgtttattt tttatagaaa gccaaaaaaa aaaaaaaaa aaaaaaaaa       600
```

<210> SEQ ID NO 55
<211> LENGTH: 600
<212> TYPE: DNA
<213> ORGANISM: Homo sapiens

<400> SEQUENCE: 55

```
tctttcaaca tttagatagt ctttcttaat atttccagga gagtacctca ttttttatttt     60 gaaaaccatt cagcacattt atcttatgta acatgcagag catatatcta tctgtatttt      120
taaaattttc ctgttactca ttgatacata gtacttaatt acatgttatt ccatgtacac      180
tgaaaacaat ataggaaata tatacatcta agacttctac tttgtacagt cttcattaa      240 ataagaatac ttacacatac attttcagat atttctacct tcctgtatgt gtttggaatt     300
gtatgtaggt agccactgaa agaatttggg cccttgggga ggatggcagt ggaagtccat     360
gaagtaaaga gcattcttta aaaagcagat ttgattgcat accttttagt tatttgagat     420
tctgagaatt ctgataaacc ccaaagcaga aagattcctt agtacccttg aagatggga      480 aaggtgaggg aaatatttga agcagggtca gaacatccac taagaacata gcacctcagt    540
agagcttaca ttatagtgcc agggtagagt tattactgaa ccaactttt tgtacaaagt     600
```

<210> SEQ ID NO 56
<211> LENGTH: 600
<212> TYPE: DNA
<213> ORGANISM: Homo sapiens

<400> SEQUENCE: 56

```
tccatcaggg cacggtagaa gttggagtct gtaggacttg gcaaatgcat tctttcatcc     60
ccctgaatga caaggtagcg ctgggggtct cgggccattt tggagaattc gatgatcaac     120
tcacggaact ttgggcgact atctgcgtct atcatccagc acttgaccat gatcatgtag     180
acatcgatgg tacatatggg tggctgaggg aggcgttctc ctttctccag gatggaggag    240
```

```
atctcgctgg cagggattcc gtcatatggc ttggatccaa aggtcatcaa ctcccaaacg    300
gtcaccccgt agctccagac atcactctgg tgggtataga ttctgtgtaa aattgattcc    360
aatgccatcc acttgatagg cactttgcct ccttctgcat ggtattcttt ctcttccgca    420
cccagcagtt tggccagccc aaaatctgtg atcttgacat gctgcggtgt tttcaccagt    480
acgttcctgg ctgccaggtc gcggtgcacc aagcgacggt cctccaagta gttcatgccc    540
tttgcgatct gcacacacca gttgagcagg tactgggagc caatattgtc tttgtgccaa    600
```

<210> SEQ ID NO 57
<211> LENGTH: 340
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 57

```
ctgtccagaa tgtagaggac agacccatgg gaacttcaaa attccctct caatncccat     60 tttatgttag aaaatcaagt accgagaatg ttaangttaa attatgtgac caaacaagg    120 aaagaggctg gtaaaactgc attttgcaca aaagtgttga ttcaacatga agtcaaataa    180
tatgttctaa tgaaaccaca cctctcacac acatatcctt tctctcaaac ctcggtgtta    240
ctctggccaa aagtcttagg tttcttgaag tgtttgtgga agagtagatg gagttttatt    300
taacattatc aagaaatcca agctgcagac cccacacata                          340
```

<210> SEQ ID NO 58
<211> LENGTH: 520
<212> TYPE: DNA
<213> ORGANISM: Homo sapiens
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (418)..(419)
<223> OTHER INFORMATION: n is a, c, g, or t

<400> SEQUENCE: 58

```
agactttta gtagcttcca actacaaaaa aagagaaata atcaattatg tactaatcag     60
acacttttaa aaattacaac agtttattca gagaaacaag ctttgtgtga cattctaagc    120
ggattttatt ctgcaggtcc ttttaacata atgagtaata tttgtgttgg aatgactga    180 gaagaaattt cataatgatg tgaagatcta cctgtaaata gttcctctgt cgtatgctgg    240
tatttatatt ctagcatctc aacagtgctg atggtcactc atcttggagt tccctgaatt    300 ttttttttt tttcaaaact cctgtaatgt tacattaccc atacttttgt tgttgctgct    360
gttgttgttg ttttgagacg gagtgtcgct ctgtcgccca ggctggagtg cangtngnnc    420
cgcgcccggc acatgactgc atactttcaa ggagaggact cagagctttt atttatttaa    480
agaaacttga aaggaggaaa gtggattaag aaaaaaaaaa                          520
```

-continued

<210> SEQ ID NO 59
<211> LENGTH: 600
<212> TYPE: DNA
<213> ORGANISM: Homo sapiens

<400> SEQUENCE: 59

```
ttttttttttt ttttacataa aggcatgaat atacaaggta atgtcagcag ctgtactcca      60
ctctttattc gttgcaaatc tacctatttg tttccaaagg atgtctgcaa ataaataggt     120
aacattgtac agctttcaac agtggatcag aacatagatg tctcttctaa ttcacaagta     180
ccaatggctc aattaattta agggacattt tctgagttgt gtgatttcac atgtatttat     240
cgtgtctaga agtgtgcaaa cttttgtttc atttctctct tagatttctg taggaagagt     300
taaaggatgt gaagtagtca ttttacttat tcataacaca ttttagggaa aattgtgctg     360
ttgctgttgg ggagaaagtt aaagctatca actataacct ggactccagt ccaatttttc     420
acatctggtt gctacttttta aaaaggatca ttttaatttt taaatgcaga atgtgttgca     480
ctttaccttt gacattccag gtttcctcat ggtcatttag aaaaataaag caggaaattc     540
taatgcctta gcatctactt taataagatg tttgcattta taaaaataac aagaaactga     600
```

<210> SEQ ID NO 60
<211> LENGTH: 463
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 60

```
tttaatttttt tggaaggata tacaccacat atcccatggg caataaagcg cattcaatgt      60
gtttataagc caaacagtca ctttgtttaa gcaaacacaa gtacaaagta aaatagaacc     120
acaaaataat gaactgcatg ttcataacat acaaaaatcg ccgcctactc agtaggtaac     180
tacaacattc caactcctga atatatttat aaatttacat tttcagttaa aaaaatagac     240
ttttgagagt tcagattttg ttttagattt tgttttctta cattctggag aacccgaagc     300
tncagctcag cccctcttcc cttatttttgc tccccaaagc cttcccccca aatcatcact     360
cnnctgcccc ccttaagggc tagagggtga ggcatgtccc tcacaattgg cacatggtnc     420
aaggccatca ggcaagggng cattcacaca aaagggcacc agg                       463
```

<210> SEQ ID NO 61
<211> LENGTH: 600
<212> TYPE: DNA
<213> ORGANISM: Homo sapiens

<400> SEQUENCE: 61

```
gaaacaactg gtaaacacag taagcccatt tctgggcttt tagaaaaaca ttgctctctt      60
ttctttcccc acccagtgta ttcccaagga cttaatgctg cactctgacc tagccctcaa     120
```

```
tgatggttaa aactgattct gaaccaaagg taaacagggt tcctcccat gccttggaga    180 gctccagtct gcagaaagct aatgaagccc ttgaagcagt atcttgtctt ccatccacac   240
tttattgaaa tgcttttgaa tcttattgtg ttgtaattac atactataga aaactccgcc   300
aacctctatt tcaaggtttg ggcccatgac tctcgctaaa acatttcagt tccatttcc    360 agaacatacc atttctaaat gcatctgtga gggccctcca caagtatttt cagtccacat   420
ttcagaaaac ttgaaagtga cgcaggttcc tgacttagtt gatggtgggt aaagggaatg   480
ccattatgag tggtggaggt tgttttcttt tttcttgcca tattctcagc ataatatttg   540
aaacctacaa agaagtttg ataatataac tgtatatttt atgcctgcac tagtggagga    600
```

<210> SEQ ID NO 62
<211> LENGTH: 600
<212> TYPE: DNA
<213> ORGANISM: Homo sapiens

<400> SEQUENCE: 62

```
gaggtaggaa ctgatattcc cattgtacag atgagaagac agatgctcag agagcttatt   60
tgtctgttga agccaaaacc tgtgcccttg accacaatgg acactatatc ttctgagctc   120
cacttaatta gagaatttgg atcaagtgac taaataaatc acacaccaca cacattaaga   180
tacgccagag tgacagggac attaaataaa tcaagtatcc atgaagtttg ctgccttcca   240
aatcagcccc ctattctttt gccctaagat atcccatcat agtctgtttc cttcccttct   300
ctctttgccc tcaaccttc cttccctctt atccatggga atgactctag gaatcctgtt    360
gagtgtatgt gtgtgcgtgt tcttttcttt ttctctcatg aatattacac ttttattagc   420
cagctatact tgtgttgatg aaaaagacaa aatggaattt tgttttcctt taacaatcaa   480
gtatgaatgg tctgcttaca ggatgtccct tcttggggtc cttggaggta acaaaagctc   540
atcattaaac aggtagctat catttctaca tgcttagtat cacttccgat tatcttattc   600
```

<210> SEQ ID NO 63
<211> LENGTH: 600
<212> TYPE: DNA
<213> ORGANISM: Homo sapiens

<400> SEQUENCE: 63

```
gggctgaggg tcctgaggag agagagagag gccacgtgga tggaggactg tcacccctt    60 ctcggttctg tcacccccctt gagtctaact cactgttgag gggaggaaga aggggggatgg  120 acggaaggga gaccgaggaa aggctttcgg gagtggggac attatccccc cagaggtgtg    180
ctgccccacc cagctgcacc ccacaatctg gccaactcat ttcacagtat aaatcactcc   240
agcaggacgg catcacagca gcccctgctg cctgaaatca gagcggccca acgaggaagg   300
ccaggagggt cggctggcag ggggcagggt cttgggataa cactgtcatc agaaacaagg   360 ctggggggctg atttcggggt ggggagcctt aggaggccag aaattccaat cagagccagt   420 tttctggga gggagtggct agacagtcaa ggaaggacgt tcacatttca aaagaagtcg    480
ggtgggggga tgagattatt ctagggggc atcgaattcc ctttaagggg ggggctcact    540
tctgcccaga gtaaagagga tctcacacca tggaaatgtg ccaacttttt tgtacaaagt   600
```

<210> SEQ ID NO 64
<211> LENGTH: 600
<212> TYPE: DNA
<213> ORGANISM: Homo sapiens

<400> SEQUENCE: 64

```
cttccattcc tcatgatttt agggttatcc tcattcagat ctactctagt tataatagta      60 cttaaacag agcacagaat taaaccatta gtatgtgaat ctgcaaaaag agaacttgtt       120
ttagactctt ctacagttta gacttcaatg tgcatactaa atgcataaca ttcgtatcaa     180
ataattaaca tttatataca attaacaaat aaggacaaat tttatacaaa acttctacta    240
ctgctataat ttttgaaaac atttaaccca ctagcaagag gtaagacagc actgccttt      300 taaaagacag gtcacttgaa tagagaatat aagatataac cataagtagg agtataaaca    360 ataattttc ttcttgtgga atgtttttaa atttccttc ttatattatt attcttcctt      420
aggttttttt agacaggtca tttcttcctg aatgattttc ctttttcttt tattttatt     480 ttttgaagga ggattattta ctggtggtct aaaagaagta ccttcaactt cttcataatt    540
gtagccaaag cggaaatgga atatttaata attcttacat ctcactaatg tagtcttctg    600

<210> SEQ ID NO 65
<211> LENGTH: 427
<212> TYPE: DNA
<213> ORGANISM: Homo sapiens

<400> SEQUENCE: 65
aataattata aagtttattt aaatgttgat tgtcccaagg tctacagttt cttttctgtt    60
gtgtcatcag tgacaaagag taaaaaaaag gaaactccca tatttagcac tttagagtaa    120
aacacatgga tcatcgttat taacagtcct ctgggcgtgc tggagctcac tgagaaggct    180 tctatttga gcttggaatg ttgtgctgag ctgtgcagcc tgttcctgca tctgttgttc     240 ctgcatttc tgttgctctg ccagccaatt tgtttggct atctccattt aactcacttg      300
ttcctgatgg agtctctccc tctcctgcat catttgctcg ttctgccttt gaatcgccgc    360
caacctttgc gcttcagcct tttcagcttc tgctttcact tgtgcctctg aggagaaaaa    420
gataatc                                                              427

<210> SEQ ID NO 66
<211> LENGTH: 600
<212> TYPE: DNA
<213> ORGANISM: Homo sapiens

<400> SEQUENCE: 66
gtgtcaacat ttatgctcct aaaggatgtt gggtcaaatg aaatgttcct cattgtttct    60
ctctcttgat ctctccttca ctccttctct tccttgcagg atctccaact ccttcataag    120
ggcactctgt gttacccctt taaacaaaat aaagaagtcc tacattctgc ccagattttt    180
ttcaggctcc accaaagggt tgggtgaatt atggcccaaa agttggtgag gatgatggtg    240
aaccttcaat caccttcagt ctcccaacca acaatggtca tggcttgttt tctccctgga    300
ttacatggag aaaatcatgc cctacttttt ggacctgttg cttctacatt tgtatggtaa    360
ctgtgaaacc atcctaatga acagcaaaca ttaaccacta cataaaatgt agactttgaa    420
taaaaacaca gctaagtact aaccagcttg ccctttaagc caattccctg tagctactta    480
cagcacgact gttagctcct ttccttatag tttcttactg ccttaaagtc acatagatgt    540
ggtcacaagg cactaacttc ccttagttat ttctataaga taatatatgt aacgttggca    600

<210> SEQ ID NO 67
<211> LENGTH: 600
<212> TYPE: DNA
<213> ORGANISM: Homo sapiens
```

<400> SEQUENCE: 67

```
agtgcagaga ggatgagaat atccttcatg gggtccagtt ccaaatctga agcataattt      60
ccaaccatca aaatattgga aataggaatg cctagcattt tatggacatt catgacccgg     120
ctttgagaag tcatagatct actcatgttt aaaaagttgt cttgaagaac ctcactgcaa     180
tcatccactt tagtaagcaa ggccacatat gctataccac agtttaatac ttctttgtga     240
acttgcttca cttttgccaa catttttagag tagagattgt caatagagtt gatgtctaag     300
acataagcca cacagtgaat cctgtccttc agagatggag aggtgataaa agtagaatgc     360
tcaggtgtaa ttggtttacg ggaattaaac tgttataaaa acataaggta acattcagaa     420
atcagagagc ctctgtttaa cccttaaaga cacaattaat gcttctaata ctgtaactac     480
tgatctccct ctttctcctc agctactctt tccccaaaca gtagcacctc ctctttactt     540
cctttctcac tgggggggcat aatgccacca acttttttgt acaaagttcc cttttttaatg    600
```

<210> SEQ ID NO 68
<211> LENGTH: 577
<212> TYPE: DNA
<213> ORGANISM: Homo sapiens

<400> SEQUENCE: 68

```
ttatcttata ctaaattcca acatgtatct gagtttgctt ctagattttc tgttctgtcc      60
cagtggttgg atatttcttc atacacgtct atcatactgt tttgactata gaggcttttc     120
agtgtcattt aatatctgtg atggcaatcc ctactcaaag ctctttgttt tcagtgttcc     180
tgtattgctc ttttgttaat ccctaatat aaaagtaaat aataacccag ttggcatatt       240
attttgatga cattaaattg gggagaatag atactgtgat ttttgaagct tcctacaaat     300
atgatatgct tttcatttgt gcaagtactt tagtataatg ttaactggtg gtggtaatgg     360
aggaaattct gtcatgttcc ttactttag tttcctctag cgctttctat ttttttattt       420
tttttcagat gggagtcttgc tctgtcttct atccaggctg aggcaggagg atcacttgaa     480
cccagtagtt caaggctgca gtgagctatg gttacaccac tgcactccag cctgggtgac     540
agagcaagat gccatctctt aaaaaaaaaa aaaaaaa                               577
```

<210> SEQ ID NO 69
<211> LENGTH: 600
<212> TYPE: DNA
<213> ORGANISM: Homo sapiens

<400> SEQUENCE: 69

```
gttaatatct ttttcgttta ttgtctgtct ctgaaggtag ggactttgcc tcatttactg      60
cttttcagtt cttggaacaa tgctcggcac ataggcaatc aacgaatgtt tgttgaataa     120
atgatttttt tctctggaaa ttgtcaaaat ctgcatgagg tgtatcaggc cagccattgt     180
cagcctcagt ttagaggcaa ggaaataggt tcagaaaggt tcaaggacgt gctgaagtca     240
cagggcgagg cagcagcaga gagcctgctt gttgagagcc aagtcttatg ggacttgcct     300
ccttctctcc cactgaggct ggggacacca ggtgcccag aggcatgtgg atacctccag       360
tgggaggtta ggagagtgct acacagaaac tctgagttct aacactcttg gaccataaa       420
aaatggaaca agtctgggca tggtaactca cgcctgtaat cacagtattt tgagaggctg     480
aggtgggagg atcacttgtg gccaggagtt cgaggctgca gtgagctatg atcctgccac     540
tgtactccag cctgggcaac acagagagac ctcacttctt taaaaaaaaa aaaaaaaaaa    600
```

<210> SEQ ID NO 70
<211> LENGTH: 600
<212> TYPE: DNA
<213> ORGANISM: Homo sapiens

<400> SEQUENCE: 70

```
aggagaaagg gaagtcaaat gtctcgtcca agtctacaca gctaaaaagg ggcagaacta      60
gggtgacgct caggcctcat ttagagatcg ggggttggcg agaagtgggg tgggcttctg     120
gaggggctgg gagagcccca caaggctgca gagggtggtg agcccggagt gggcctggcc     180
tggtgtgggc tgggggtatg ggcaggagct gcagacagca gggctgcacc agcggaccag     240
tttcagaggc aagggttcta ggcccttgag aatccacagt gccaaacaga cccagatagc     300
tacggggttg gtacctgggg aggccttagg acaggcagaa agtcccagag gcgagggcgt     360
tgcctgggga cgttttttgct ccctgtcctg ctgacagagc ataggaagtg tgaatgtttt    420
ctaccccctc ctctctcggc tcagcagagc tccagcgagc caagtccttg tctgtggaga     480
cgcatcagtc cctggctcta gggaataggg agtcccacag acaggggggt gtcagcaagc     540
tgagagggtc tgtaagtagg tacggaattg agtcaggaaa cagtctgggt gtggagtgag     600
```

<210> SEQ ID NO 71
<211> LENGTH: 600
<212> TYPE: DNA
<213> ORGANISM: Homo sapiens
<220> FEATURE:
<221> NAME/KEY: misc_feature
<222> LOCATION: (65)..(83)
<223> OTHER INFORMATION: n is a, c, g, or t
<220> FEATURE:
<221> NAME/KEY: misc_feature
<222> LOCATION: (132)..(144)
<223> OTHER INFORMATION: n is a, c, g, or t

<400> SEQUENCE: 71

```
tgcaaaaagc caaaaaaagc agcttttaac attatatcat tatatcacaa ttttgaaaca      60
tgggnnnnnn nnnnnnnnnn nnnccattgt gtggataaaa tggtctccgt gacattgagc     120
agagtgttat cnnnnnnnnn nnnnacatta ttgcacagag atttctcatc aatgttcttc     180
agtttttatg tctttcccta aatgtgaata agtgctatgg ataaaataca aatgtagaaa     240
ataacagcag catgatttgt caaagttaat ccctataatt tagtaagaaa aaatggatat     300
aaacaaaata agtgctcttt ctaaactgta ctaaattttc aaaatattg ttttaatgca      360 gtgaaggtcc tgaaaagcct attgaaagcg atgctgagtc ctgttttcaa aagtgtcctg    420
tttgggtttt cttggtgaag agcagaattt caagtgaagt aatcgacgga ctaatttaaa    480
acaaaacagc cctcggcttc cctattggcc tgtgagggca ccggctccgg gaccctgacc    540
tgggaggcag cgagtggtgg gggtgcctgg cccccatcta cacgtacaca ggctggccaa    600
```

<210> SEQ ID NO 72
<211> LENGTH: 600
<212> TYPE: DNA
<213> ORGANISM: Homo sapiens

<400> SEQUENCE: 72

```
gcacgtctac ggggctggac agagtgtggt taaccgggga actgggcaag ccggcgccga      60
gcctgcgtca gccgtgcaag ccgctccttc aggaacttcc gcttgtcgct ggtgtcgctc     120
cgctccttca ggagccagct gtaggtgtcc ttgtcctgca ggagctgcag catggccttc     180
tgaagctgct ggccgtacgt ctggagcatg aagaactgga tgatcaaagg gatgtggctg     240
```

| | |
|---|---|
| gagatgcgct tgctggcctc ctggtgatag gccatcaggt gctgaaagat ctcctccatg | 300 |
| gaagagtctg ttgccgagct ggactggaaa gccccaaaat cccaggattt cttcttcttt | 360 |
| tcttcttcca gctccttctc tctgaccttc tgcaatgcac ccctgtatac ctggtcctgg | 420 |
| cagtagacaa tctgttccat ctggaagtgg aggcggatca gcttctcacc ttctctctct | 480 |
| tgttctgctc taatgtcttc aattttggac ttggcggttc tgtggaggtt aaaaaactct | 540 |
| tcaaaatttt ttatcgccaa cttttttgta caaagttggc cttataaaga aagcattgct | 600 |

<210> SEQ ID NO 73
<211> LENGTH: 600
<212> TYPE: DNA
<213> ORGANISM: Homo sapiens
<220> FEATURE:
<221> NAME/KEY: misc_feature
<222> LOCATION: (1)..(261)
<223> OTHER INFORMATION: n is a, c, g, or t
<220> FEATURE:
<221> NAME/KEY: misc_feature
<222> LOCATION: (522)..(549)
<223> OTHER INFORMATION: n is a, c, g, or t

<400> SEQUENCE: 73

| | |
|---|---|
| nnnnnnnnnn nnnnnnnnnn nnnnnnnnnn nnnnnnnnnn nnnnnnnnnn nnnnnnnnnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nctaaaaaaa tatgtactgc ttattttgtt agcatacttt | 300 |
| taattatatt cttattcttt ctacccctct caaaatgtat ttttccagct tgccatttaa | 360 |
| ttggtaaaca gctgtaaagt tcaaacgtga aattcttaaa gctccctaga gacatacaca | 420 |
| ataacttctg tggcatggac ttttctcggc attaaaaaaa tctagtacct ctcttggcca | 480 |
| gaacccctaa ttttacactt tatggtgttg cgtcgttttt cnnnnnnnnn nnnnnnnnnn | 540 |
| nnnnnnnnnt tactggcaag tttttcctcc aaacagtttt ctaatcaagt ctaataagtt | 600 |

<210> SEQ ID NO 74
<211> LENGTH: 600
<212> TYPE: DNA
<213> ORGANISM: Homo sapiens
<220> FEATURE:
<221> NAME/KEY: misc_feature
<222> LOCATION: (1)..(44)
<223> OTHER INFORMATION: n is a, c, g, or t
<220> FEATURE:
<221> NAME/KEY: misc_feature
<222> LOCATION: (95)..(121)
<223> OTHER INFORMATION: n is a, c, g, or t
<220> FEATURE:
<221> NAME/KEY: misc_feature
<222> LOCATION: (144)..(172)
<223> OTHER INFORMATION: n is a, c, g, or t

<400> SEQUENCE: 74

| | |
|---|---|
| nnnnnnnnnn nnnnnnnnnn nnnnnnnnnn nnnnnnnnnn nnnngatgag ccaggcatgg | 60 |
| tggtatgtgc ctttagtccc agctatctgg gaatnnnnnn nnnnnnnnnn nnnnnnnnnn | 120 |
| ntgacggcaa gagcctgtct ctgnnnnnnn nnnnnnnnnn nnnnnnnnnn nntctgatca | 180 |
| gttaaatgaa tatggaaact taatcttgta ccccttacct cccaagcata cagccacagt | 240 |
| ttaccgttgg agggatcttt ccacggaggt aaacagtgct gttttctcca agtgccagaa | 300 |
| caaaaacaca acagcacaca cacaatgaga tggtttggct ctgtgtcccc aaccaaatct | 360 |

```
catctcaaat tgtgtttggc tctgtgtccc aaccaaatc tcatctcaaa ttgtgtttgg    420
ctctgtgtcc ccatccaaat ctcatctcaa attgtaatcc ccatgtgtca agagagcaac   480
ctggtgggag gtgactaggt catggggtg gttttctca tgctgctctc atgatggtaa    540
gtgagttctc acaggatctg atagtttaaa agtgtttagg ggctgggagc agtggctcat  600
```

<210> SEQ ID NO 75
<211> LENGTH: 600
<212> TYPE: DNA
<213> ORGANISM: Homo sapiens

<400> SEQUENCE: 75

```
gggtgaggac ccacagctct gatgtgggcg cttcaggcca tggtggagct gagattcagg    60
ttggcttttc ccctcagctc ccagctggct ggtgaaccca tcatcatagc caaaagtact   120
cagcagcagc acctccaggt ccagaggcac ctccagctgc atgcacacac aatgaatgaa   180
agactgccag gtgtccgaac cctggacatg cagcttgttg agttgcagga tgactctctg   240
ttcagggtcc aaggtctcgt tcctggaatc caggtccgtg ttggggagga agaacttcat   300
cttggcgttc agccattctg ggtctttggt gagcagcctc acaagacagc tccacaggtt   360
cttgttgccg agctggaggc caacggggtc catgaggagc cagccttggt ctcctcgttc   420
atgataggtg ctctagggtc cccacggaga gggtctcatg ggtgtctggg ctatgtgtgc   480
cttgagctgg attgacaggt tgtttccata gtgcagactc cctcagcgct cgcggctcct   540
ccgcgctctg cacgaaactg aaagtagaag ccgccgccta gagctgctcc gccagtgcat   600
```

<210> SEQ ID NO 76
<211> LENGTH: 600
<212> TYPE: DNA
<213> ORGANISM: Homo sapiens

<400> SEQUENCE: 76

```
tggcaaggac attgtttttg tctagtgtct caagcttctc taccaagaga gtcatatttc    60
ttatctccac ctccagctgg tcaacaattt ctgagcttcc accaaaactc tccttcagct   120
gtatgaccag tttttccatc tccttcactt ctaccttgat cagctcgaag tccagttcag   180
tgtaagaaat ggtatccttc tccatgatgt caattcggac agttaggttt aacagtttct   240
tttcatacac actaattaat tggacatatt ccctcacttt agaaagttct ttctcaaact   300
tctgagaaag aacatgagct gtgaattcca agcgttccac tctgtccacg ggaaaggtgg   360
tgtctggcag ggaaacagag cactggcagg tcccacggtc atccacggag ccggtgaaat   420
tggaaaacaa ctgggacaca gaacctccgc tgcctaagct gcggctggag ctggagcccg   480
acctggagct ggagctgaag ctggagctgg agtcaacacc tggaaagag ctgaagccgg    540 ggctgggaat tggaggtccc acatccccca atcccctgc agcttggcca aggaagccaa   600
```

<210> SEQ ID NO 77
<211> LENGTH: 600
<212> TYPE: DNA
<213> ORGANISM: Homo sapiens

<400> SEQUENCE: 77

```
tcttttattg aaagaaaaaa caatacaatg gactttaaaa agctacattt gttatggttc    60
ataaggacag aggtttacac aggttttata tatgtacaca ctgacaatac tatatcacaa   120
catcagaggc accatttttg ccacagaatt aggtaatgaa taaaacttct ccaaattaat   180
```

```
ctgtttaaaa aatatctaaa atggtacagt atatttgagg attatataaa tatgtgagac    240
atatttagat attttttaaa aatagtgttt atatatatgc atcacaatct tctctaattc    300
tcaaaatatt atggcaccaa aattctgttt gtcaaataaa acacaagatg ctgtaatatg    360
tatccaagca ccagcttagc acagtattta attctccccc aaactgaaag actgctaaca    420
ggtacaaact gaactgaata tttcacacaa ccattgaaat aatttaggcc ctcaaatttt    480 tttttttatta gctgattgtt tttagagaaa aagagggag ctaaaccatt tacattaatg    540
ttgctctgtg tgatagaatc aatcctaggg ctcagagaag atattcctag gcactggaga    600
```

<210> SEQ ID NO 78
<211> LENGTH: 475
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t

<400> SEQUENCE: 78

```
tcaaacttga atcntttaaa tttattttct gcttaagcag gtttgagttg ggttttctat    60
ttgcaatagc aaaagtcctg actggcaagg tttaaaagtt tgaagactct cacaggtaag    120
tgcagctcag gatcctgtga gtgcagcaga aagtcttaag aaatggcagg ggctggttga    180
acccagattt tccattggct gagcagatat ccccagaggc gtagaaaatt aaatttgttt    240
tatgttgttc caaaagagga gaactgaggc cagaggagca cacttctgag acactcattt    300
ttgctgggta gaggaactct ctgggcaagc aggaccatcg atattagagc agctggcctc    360
aggaggggag taagagcccc atccctgaag gtacacaagt tgtggcagca accatctggc    420
ctgcagtttc cagaggggag tcaggcgtgg ggtgggactg gagtgaacgg gtacc         475
```

<210> SEQ ID NO 79
<211> LENGTH: 600
<212> TYPE: DNA
<213> ORGANISM: Homo sapiens

<400> SEQUENCE: 79

```
tttttttcttc ttttcctctt gggttttccc aaagtagagt tgtttgcaat atccacagta    60
tccattttgc cacatgcttg gtcactttcc ttccttgctt ccgggctttc tggcacttct    120
ccttgtttaa gacttagttt gatgtcaggc ctctcttccc tttcttttcg atcactttct    180
tggaaagaca atttgtcttg gattgcattt ttgaagcttt tataaatgtg aattaaatcg    240
gggtattcct gcatgttgac ctcgctgaac agtgcttcca aaactgacag gttaaatgtc    300
ttctccagtt cactgagaac attgtacacc actctttgta cagggaccag gtttctacaa    360
gaatcttcag aatcttcaaa cattttattt gtgatgagtt cccgatcgcg gaggccctca    420
aggaatggaa atgtcttttt tattgcattt gatatctcca gcttatgtct ttgaagtgc     480 ttgaatacag tgtcatagac aagtccctca tctacatcct ggtcttccgt gaacagcctg    540
gctcggaagg tcctacgccc acggactctc actgattgct agcacagcag tctgagccaa    600
```

<210> SEQ ID NO 80
<211> LENGTH: 600
<212> TYPE: DNA
<213> ORGANISM: Homo sapiens

<400> SEQUENCE: 80

```
ccttccccat ttctcacttt ccacaggtgg gatgtggcag tcctcatgga agactcttga    60
```

```
acaagtgtcg caacagaaca gctccctcc gtcccggcac acctcacact catccaagtt    120
tctcatctag aaggtaaaac agtgtccacg tcactgggaa tcacaagatt caggaaggcc    180
acccctctgg gcatctagaa cacactgctt atgtgtgagc ctgtatagac aggcatatgc    240 ttctcccctgg gatatgaagg aaaaatatgg catggagatt tcagaacaaa tcctggtctg    300
cagtgaagtt caggaggaag gggtatatgt cagaataaaa acgttttcct tataaaacca    360
gagattatga cacagaaagc ctagcaacaa agcaagagga tgatcttata ggaatctgaa    420
taattgtatt atgctgcaga taaaaccagg ttttgaagta aaagtgttaa atccatttgt    480
ctatactaca aatcaactca tgaaagggag acccagagaa ttacatatga tggaataacc    540
ttctaagata tcatcacatc ccatattctt ggccataagt tccccatgag ttgaagacag    600

<210> SEQ ID NO 81
<211> LENGTH: 600
<212> TYPE: DNA
<213> ORGANISM: Homo sapiens
<220> FEATURE:
<221> NAME/KEY: misc_feature
<222> LOCATION: (445)..(456)
<223> OTHER INFORMATION: n is a, c, g, or t

<400> SEQUENCE: 81
gtggctgttg ctggccccac ctccgcttat gtccttaaca tgcctcaggt ggttcatccc     60
ttttggcact catggtgccc cctgtgggct gatacaggag tgagtctact gtgaaggcac    120
tcagtatagt ggaaaaaaca aatatcaacc tcctgctttt tttcagtgta aaaactataa    180
gctctatggg agtttctgca gatggtacca taatggcctg agggaggagt atcacagtca    240
cagagtattg gttctctcac tgcataagcc atggttttac ccaccttcac aggctaaagg    300
tgcttcataa ccttgttcat gtattgaggt tctgttggct cttgtaatgg taatttcaca    360
tgtgggcagt tgttcatatt gatgtttcta taggggtatg atagctggag aggtctgcgc    420
cactgtcttg ctctgccttg atcannnnnn nnnnnnaaca agaatttgtc tcctcctagt    480 ttttctttt ctcttaaccg acctaggttt agccttttaa tccttctccc tcctctgctt    540
ctaatgtcat tgtttctttg tatgcctatc atatctacat gctacatgac cttcagctgg    600

<210> SEQ ID NO 82
<211> LENGTH: 600
<212> TYPE: DNA
<213> ORGANISM: Homo sapiens

<400> SEQUENCE: 82
agttttaagg aaaaattgta tgatttaaaa gattataaaa ctttattact gggctattta     60
cacattttaa ttgtttctca taaaatatat aacattacaa tatttatgga agtaggatat    120
ttttgtatca tatgtacgat gataatttat agggtatttt aaatgatgtt tttagcctc    180 cttaagtttt aagtggatct tgcaaatgaa aacaagtatt attgagtttg acatactcaa    240
attgcccaaa tatcagctgt ttaaacaacc aagtcatcat tgatacttta gtaaaggtta    300
gtaaatgtca tcaaaggctt atttgcagtt tacagttttt attacttagg agacttaagg    360
agtacctgcc aggtttgtcc atgctaatgc tacgattttg ttttttgtagt tcaaccatat    420 tttgtatgga gatactttga ggctctgtaa atttctggtt actcctcaga acccactaga    480
tttagcattt catggatgac ttgtgtttga acaattatta ctataatggt tgccagatga    540
ttattttctt attctcttct tgttctaca tggagaaata aaaccaataa ataagggaga    600
```

<210> SEQ ID NO 83
<211> LENGTH: 276
<212> TYPE: DNA
<213> ORGANISM: Homo sapiens

<400> SEQUENCE: 83
gtgccaatgt gaagtctgga ttttaattgg catgttattg ggtatcaaga aaattaatgc    60
acaaaaccac ttattatcat ttgttatgaa atcccaatta tctttacaaa gtgtttaaag   120
tttgaacata gaaaataatc tctctgctta attgttatct cagaagacta cattagtgag   180
atgtaagaat tattaaatat tccatttccg ctttggctac aattatgaag aagttgaagg   240
tacttctttt agaccaccag taaataatcc tccttc                              276

<210> SEQ ID NO 84
<211> LENGTH: 184
<212> TYPE: DNA
<213> ORGANISM: Homo sapiens

<400> SEQUENCE: 84
aatgcttatg tctaaaagag ctcgctggca agctgcctct tgagtttgtt ataaaagcga    60
actgttcaca aaatgatccc atcaaggccc tcccataatt aacactcaaa actatttta   120 aaatatgcat ttgaagcatc tgttgattgt atggatgtaa gtgttcttac atagttagtt   180
atat                                                                184

<210> SEQ ID NO 85
<211> LENGTH: 206
<212> TYPE: DNA
<213> ORGANISM: Homo sapiens

<400> SEQUENCE: 85
ctgggcacct ctgggacagc aaaaaaaact gcagaatgca tccctaaaac tcacgagaga    60
ggcagtaagg aacccagcac aaaagaaccc tcaacccata taccaccact ggattccaag   120
ggagccaact cggtctgaga gaggaggagg tatcttggga tcaagactgc agtttgggaa   180
tgcatggaca ccggatttgt ttctta                                        206

<210> SEQ ID NO 86
<211> LENGTH: 268
<212> TYPE: DNA
<213> ORGANISM: Homo sapiens

<400> SEQUENCE: 86
accatgttca tcttgtcctc caagttatgg gggatcttgt actgacaatc tgtgttttcc    60
aggagttacg tcaaactacc tgtactggtt taaataagtt tacctttcc tccaggaaat   120 ataatgattt ctgggaacat gggcatgtat atatatatat ggagagagaa ttttgcacat   180
attatacata ttttgtgcta atcttgtttt cctcttagta ttcctttgta taaattagtg   240
tttgtctagc atgtttgttt aatcctt                                       268

<210> SEQ ID NO 87
<211> LENGTH: 234
<212> TYPE: DNA
<213> ORGANISM: Homo sapiens

<400> SEQUENCE: 87
gatggctggt ctgcccccta ggagactccg tcgctccaat tacttccgac ttcctccctg    60
tgaaaatgtg gatttgcaga gacccaatgg tctgtgatca ttgaaaaaga ggaaagaaga   120

```
aaaaatgtat gggtgagagg aaggaggatc tccttcttct ccaaccattg acagctaacc    180
cttagacagt atttcttaaa ccaatccttt tgcaatgtcc agcttttacc ccta          234

<210> SEQ ID NO 88
<211> LENGTH: 231
<212> TYPE: DNA
<213> ORGANISM: Homo sapiens

<400> SEQUENCE: 88
ggcatggagc atctgtacag catgaagtgc aagaacgtgg tgcccctcta tgacctgctg    60
ctggagatgc tggacgccca ccgcctacat gcgcccacta gccgtggagg ggcatccgtg    120
gaggagacgg accaaagcca cttggccact gcgggctcta cttcatcgca ttccttgcaa    180
aagtattaca tcacggggga ggcagagggt ttccctgcca cagtctgaga g             231

<210> SEQ ID NO 89
<211> LENGTH: 241
<212> TYPE: DNA
<213> ORGANISM: Homo sapiens

<400> SEQUENCE: 89
gaaattagag tcctatattc aactaaagtt acaacttcca taacttctaa aaagtgggga    60
accagagatc tacaggtaaa acctggtgaa tctctagaag ttatacaaac cacagatgac    120
acaaaagttc tctgcagaaa tgaagaaggg aaatatggtt atgtccttcg gagttaccta    180
gcggacaatg atggagagat ctatgatgat attgctgatg gctgcatcta tgacaatgac    240
t                                                                   241

<210> SEQ ID NO 90
<211> LENGTH: 199
<212> TYPE: DNA
<213> ORGANISM: Homo sapiens

<400> SEQUENCE: 90
ttagatttcc agcttgtcac cttcaaggtt accttgtgaa taggactttt ttgagctatt    60
tctatccagt tgactatgga ttttgcctgt tgctttgttt ccaccaactc tccctgaaga    120
tgaggcgcac agacagacaa ctcacaggca agaacagcct ggtccatctt gaaagattct    180
caagactatt ctccacaag                                                 199

<210> SEQ ID NO 91
<211> LENGTH: 210
<212> TYPE: DNA
<213> ORGANISM: Homo sapiens
<220> FEATURE:
<221> NAME/KEY: misc_feature
<222> LOCATION: (70)..(70)
<223> OTHER INFORMATION: n is a, c, g, or t

<400> SEQUENCE: 91
tgtttaaaaa tgttgtgggt acatagtatg tgttgtgggt acatcgtatg tgttgtgggt    60
acatagtatn gtggggtcca tgagatgttt tgatacaggc atgcaatgtg aaataagcac    120
atcatgggga atgggtatc cctcccctca agcgtttatc cttcaagtta taaaaaattc    180
aattacagtc ttagttatgt caaaatgtac                                     210

<210> SEQ ID NO 92
<211> LENGTH: 148
<212> TYPE: DNA
```

<213> ORGANISM: Homo sapiens

<400> SEQUENCE: 92

| accagaattt atggatgaac tgattgctta tattttagtc agggtttata aatgtagatg | 60 |
| gtcaaattta cattgcctag tgatggaaaa ttcaactttt tttgattttt ttttccaata | 120 |
| ttaaaaaagg ctctgtatgc atggtggg | 148 |

<210> SEQ ID NO 93
<211> LENGTH: 227
<212> TYPE: DNA
<213> ORGANISM: Homo sapiens

<400> SEQUENCE: 93

| aagattcctg tgtactggtt tacatttgtg tgagtggcat actcaagtct gctgtgcctg | 60 |
| tcgtcgtgac tgtcagtatt ctcgctattt tatagtcgtg ccatgttgtt actcacagcg | 120 |
| ctctgacata ctttcatgtg gtaggttctt tctcaggaac tcagtttaac tattatttat | 180 |
| tgatatatca ttacctttga aaagcttcta ctggcacaat ttattat | 227 |

<210> SEQ ID NO 94
<211> LENGTH: 245
<212> TYPE: DNA
<213> ORGANISM: Homo sapiens

<400> SEQUENCE: 94

| tctcctctca tctgcatttc tcagaaatgc cctccctgcc cagtggtgac tttccctcgt | 60 |
| cactcctatg gagttctacc tggagcccag ccatgtgtgg aactgtgaag tttactcctc | 120 |
| tgtaaagatg gtttaaagaa agtcagcttc tgaaatgtaa caatgctaac ccttgctgga | 180 |
| accctgtaag aaatagccct gctgatagtt ttctaggttt atcatgtttg attttacac | 240 |
| tgaaa | 245 |

<210> SEQ ID NO 95
<211> LENGTH: 221
<212> TYPE: DNA
<213> ORGANISM: Homo sapiens

<400> SEQUENCE: 95

| gaattttct ctatttccag cacgctgatt tgatttaaaa atgtaataag accaagagtt | 60 |
| ggagtaaagg gatattcatt ccatgttaaa agtggcttca tagctactga caaatgtctg | 120 |
| aactattgtc gtgcccttca aaactggagt tttctaaaat aatcttattt ttatacttgt | 180 |
| atgttccagc aatttaagat atataccatt gaaagggaaa t | 221 |

<210> SEQ ID NO 96
<211> LENGTH: 176
<212> TYPE: DNA
<213> ORGANISM: Homo sapiens

<400> SEQUENCE: 96

| ggctgagcaa ggcacatagt ctactcagtc tattcctaag tcctaactcc tccttgtggt | 60 |
| gttggatttg taaggcactt tatcccttt gtctcatgtt tcatcgtaaa tggcataggc | 120 |
| agagatgata cctaattctg catttgattg tcacttttg tacctgcatt aattta | 176 |

<210> SEQ ID NO 97
<211> LENGTH: 219
<212> TYPE: DNA
<213> ORGANISM: Homo sapiens

<400> SEQUENCE: 97
aacgcaggcc gctttattcc tctgtactta gatcaacttg accgtactaa aatcccttc    60 tgttttaacc agttaaacat gcctcttcta cagctccatt tttgatagtt ggataatcca   120
gtatctgcca agagcatgtt gggtctcccg tgactgctgc ctcatcgata ccccatttag   180
ctccagaaag caaagaaaac tcgagtaaca cttgtttga                          219

<210> SEQ ID NO 98
<211> LENGTH: 171
<212> TYPE: DNA
<213> ORGANISM: Homo sapiens

<400> SEQUENCE: 98
tcatctccgt attcttcagc ttcatccaaa actgacttag aagcctccct tgaccctcac    60
ctgactattc acaggttata gcactttatg ttttcagtt ctgttatttt aattggtgcc   120
tctgtttgtg atctttaaga acataaaatt ctggcaagta actatttgct a           171

<210> SEQ ID NO 99
<211> LENGTH: 262
<212> TYPE: DNA
<213> ORGANISM: Homo sapiens

<400> SEQUENCE: 99
cactttgcag ccttgagagg tgcagaagag acaccgaggg gttcaccacc agagccacca    60
ttgtcagaga ggcgtccagc tgtgtccacc tgggactctg ccttcagggc ttcttgcctg   120
gctgggagct gcacaggcag actcctggga cggtgtgccg acagctctgg gcaccccctt   180
ctaggatctg attcctgagg aatcacaatg tggatttcac aatcacttcc agtgtctttt   240
gccaacctct gtgaacagat gt                                           262

<210> SEQ ID NO 100
<211> LENGTH: 248
<212> TYPE: DNA
<213> ORGANISM: Homo sapiens

<400> SEQUENCE: 100
aagtttgcac agttctagac acgataaata catgtgaaat cacacaactc agaaaatgtc    60
ccttaaatta attgagccat tggtacttgt gaattagaag agacatctat gttctgatcc   120
actgttgaaa gctgtacaat gttacctatt tatttgcaga catcctttgg aaacaaatag   180
gtagatttgc aacaaataaa gagtggagta cagctgctga cattaccttg tatattcatg   240
cctttatg                                                           248

<210> SEQ ID NO 101
<211> LENGTH: 252
<212> TYPE: DNA
<213> ORGANISM: Homo sapiens
<220> FEATURE:
<221> NAME/KEY: misc_feature
<222> LOCATION: (123)..(124)
<223> OTHER INFORMATION: n is a, c, g, or t

<400> SEQUENCE: 101
gactgcacag cagcaagaca gattgccatg gagcatgttg tgcccaacta gggacagcgc    60
agatagattc tgtaatttgc ctaacaatgt ctataggatg atcccatttg tcaaaaaaaa   120
aanngaactg ggcttattg atgtcaccta aatgcaccta aacttctttt ttgccccatg   180

-continued

```
ctcttctgta ctcttgatct ttccccaaat ttttaaaaac atgacactca ttcccttatt      240
tttcctactt ag                                                          252

<210> SEQ ID NO 102
<211> LENGTH: 224
<212> TYPE: DNA
<213> ORGANISM: Homo sapiens

<400> SEQUENCE: 102
ttaattgctt tctctcacca gggaaggtgt gggaaggact tgtgaaatac atattcgagg       60
aaaaactatg cacaaggccg tgcatttaaa aataaactcc ctaaggctgg ggtgaaacct     120
gctacggtct gcgcaagttg actgttaatg aatttgattc tcaggtgtga gtgattaaaa     180
gaacactgat catgtcattt tcttttggt cactaattcc ctcc                       224

<210> SEQ ID NO 103
<211> LENGTH: 266
<212> TYPE: DNA
<213> ORGANISM: Homo sapiens

<400> SEQUENCE: 103
gtcatccaga gttataatgg cccattatct aatggtcaga gtttacttag gctttcacta      60
cttccactgc ccacttgaaa cagggaaaaa tattttcccc ccgcgctgtg agtgtgctat     120
ttagagctga ccacaagcgg ggggaagaga ggatggctcg gatgctgcat ttccactgag     180
aacacaaggc tggcaaagct tgtctgctgc ccagcaagca cttcaggctc acaccatttt     240
aggttcactt taagtagttt ctcaat                                          266

<210> SEQ ID NO 104
<211> LENGTH: 251
<212> TYPE: DNA
<213> ORGANISM: Homo sapiens

<400> SEQUENCE: 104
tggacagtgg acgtctgtca cccaagagag ttgtgggaga caagatcaca gctatgagca      60
cctcgcacgg tgtccaggat gcacagcaca atccatgatg cgtttctcc ccttacgcac     120 tttgaaaccc atgctagaaa agtgaataca tctgactgtg ctccactcca acctccagcc     180
tggatgtccc tgtctgggcc cttttctgt tttttattct atgttcagca ccactggcac     240
caaatacatt t                                                          251

<210> SEQ ID NO 105
<211> LENGTH: 247
<212> TYPE: DNA
<213> ORGANISM: Homo sapiens
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
```

```
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (139)..(141)
<223> OTHER INFORMATION: n is a, c, g, or t

<400> SEQUENCE: 105
tccatggcaa cagtcccaac atgtttgaga cttcagctaa aggaatggat gtatnnnggn     60
gtgtagtctt cagtatatca ctgtatttcc gtaatactag actcnaagnt atgcnagatn    120
gnttattccc ttngtgaann nggagttgct cattacgttc ttgaaatatc gcacatcctg    180
ttggttcttc aaaggaagcc tttccaccag attagtgttc aagtctttgc agaggagacc    240
aactttt                                                               247

<210> SEQ ID NO 106
<211> LENGTH: 211
<212> TYPE: DNA
<213> ORGANISM: Homo sapiens

<400> SEQUENCE: 106
aaggctatgc tttcaatctc ctacacaaat tttacatctg gaatgatctg aaggttcttc     60
aaagacattc aaaattaggc ttttttatgt cctgttttaa gtgaaaatat ttattcttct    120
aagggtccat tttatttgta ttcattcttt tgtaaacctc tttacatttc tctttacatt    180
ttattctttg cccaaatcaa aagtgattcc t                                   211

<210> SEQ ID NO 107
<211> LENGTH: 187
<212> TYPE: DNA
<213> ORGANISM: Homo sapiens
<220> FEATURE:
<221> NAME/KEY: misc_feature
<222> LOCATION: (146)..(146)
<223> OTHER INFORMATION: n is a, c, g, or t

<400> SEQUENCE: 107
cttagcatta gaacactcag taatcatatg aattgtgcat ttgtttgttt tgcttaactc     60
tttctgtttg tttatgtttg gggttttatt gttgttgttt cacttttctc ccatctcttc    120
ctgacttggt caaatccaaa ggaatnttcc aaattgtggg gagcaaggca tctgaaatgg    180
ctaaaac                                                               187

<210> SEQ ID NO 108
<211> LENGTH: 234
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (148)..(148)
```

```
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 108
atgctatatg ctgtatccca cctttctctg aatgttacat tttctcccct atcccaggct      60
gcatctaaga aaactcaaag ggaatatgct atctatcttt tccgagcaat gaaagctctn     120
gggttttttc cttgcttttc agggcacnat acttctcttt cttcctggtt agacaggata     180
agttctgagt cccntggtat catcagctta cttcttctct gttaaatatt caca           234

<210> SEQ ID NO 109
<211> LENGTH: 248
<212> TYPE: DNA
<213> ORGANISM: Homo sapiens

<400> SEQUENCE: 109
gtggtcttcc tctgaatatt agcagaagtt tcttattcaa aggcctcctc ccagaagaag      60
tcagtgggaa gagatggcca ggggaggaag tgggtttatt ttctgttgct attgatagtc     120
attgtattac tagaaatgaa ctgttgatga atagaatata ttcaggacaa tttggtcaat     180
tccaatgcaa gtacggaaac tgagttgtcc caaattgatg tgacagtcag gctgtttcat     240
cttttttg                                                             248

<210> SEQ ID NO 110
<211> LENGTH: 277
<212> TYPE: DNA
<213> ORGANISM: Homo sapiens

<400> SEQUENCE: 110
tatcctatta ctgtacttag ttggctatgc tggcatgtca ttatgggtaa aagtttgatg      60
gatttatttg tgagttattt ggttatgaaa atctagagat tgaagttttt cattagaaaa     120
taacacacat aacaagtcta tgatcatttt gcatttctgt aatcacagaa tagttctgca     180
atatttcatg tatattggaa ttgaagttca attgaatttt atctgtattt agtaaaaatt     240
aactttagct ttgatactaa tgaataaagc tgggttt                              277

<210> SEQ ID NO 111
<211> LENGTH: 245
<212> TYPE: DNA
<213> ORGANISM: Homo sapiens

<400> SEQUENCE: 111
gggattttga gctatcatct ctgcacatgc ttagtgagaa gactacacaa catttctaag      60
aatctgagat tttatattgt cagttaacca ctttcattat tcattcacct caggacatgc     120
agaaatattt cagtcagaac tgggaaacag aaggacctac attctgctgt cacttatgtg     180
tcaagaagca gatgatcgat gaggcaggtc agttgtaagt gagtcacatt gtagcattaa     240
attct                                                                245

<210> SEQ ID NO 112
<211> LENGTH: 284
<212> TYPE: DNA
<213> ORGANISM: Homo sapiens

<400> SEQUENCE: 112
ttgaatagat catcagtggc cactgatgta attaatcatg tctatgtaat gaagctgcca      60
```

```
taaaaaaccc aggaggacag tgttgagaga gcttctaggt tggtgaacac ttggggtgt      120 ctggaagaca gcccacctgg agaggacacg gaggctcttc gcaccttccc ccatacctgg    180
ctctctccat ctcttcattt gtccatctgt atcttttca ttatattatc cttgataata      240
aactggtaaa tataagtgtt tccctaagtt ctatgagcca ccat                      284

<210> SEQ ID NO 113
<211> LENGTH: 290
<212> TYPE: DNA
<213> ORGANISM: Homo sapiens

<400> SEQUENCE: 113
aggcctctga ttgcacttgt gtaggatgaa gctggtgggt gatgggaact cagcacctcc    60
cctcaggcag aaaagaatca tctgtggagc ttcaaaagaa ggggcctgga gtctctgcag    120
accaattcaa cccaaatctc gggggctctt tcatgattct aatgggcaac cagggttgaa    180
acccttattt ctagggtctt cagttgtaca agactgtggg tctgtaccag agcccccgtc    240
agagtagaat aaaaggctgg gtagggtaga gattcccatg tgcagtggag                290

<210> SEQ ID NO 114
<211> LENGTH: 270
<212> TYPE: DNA
<213> ORGANISM: Homo sapiens

<400> SEQUENCE: 114
atacgttttt cactttctga ccaggaccat gcctgtggag tagatgttga caagaaacac    60
tgaccagatc aaaatgtgtc tcaaggagaa tggcacaatt ttgtgcaaat gaatcaagga    120
agtcttattg cacaagagta tcctggaacc cagtgcaatt gatttttag aaaaatatat     180 cacataggggg aaaaaaactg gaatatgttg aaggagacgt atataatatt tagcatccag   240
attgatgact tctgccctaa ctatgcaatg                                     270

<210> SEQ ID NO 115
<211> LENGTH: 230
<212> TYPE: DNA
<213> ORGANISM: Homo sapiens

<400> SEQUENCE: 115
cgcttgaacc tggaaagtgg acattgcagt gagctgagat tgtgccactg cactccagcc    60
tgggcaacac agcgagactc tgtctcaaaa aaaaaaaaa agaaagaaa aaaagagaa       120 aactcagaga ttcgtggaga ctggaaccac gggtgtggag agaggggtta gtagagacca    180
gattctgcag gtactataat gacattccca ggctaaggag tttagatctt                230

<210> SEQ ID NO 116
<211> LENGTH: 283
<212> TYPE: DNA
<213> ORGANISM: Homo sapiens

<400> SEQUENCE: 116
atctacaccc tcaggaataa gaaagtgaag ggggcagcga ggaggctgct gcggagtctg    60
gggagaggcc aggctgggca gtgagtagtt ggggagggga gaaagtatta agccagaacc    120
caaggatgga aataccccctt agtgagtcag tttagacttc aggctgttca ttttttgtatg  180 ataatctgca agatttgtcc taaggagtcc aatgggggat atgttttcct cccgtgagga    240
aatgtttagt tcttgaggga aaaatcccta aatcctctat ata                      283
```

<210> SEQ ID NO 117
<211> LENGTH: 111
<212> TYPE: DNA
<213> ORGANISM: Homo sapiens

<400> SEQUENCE: 117
gggtagcaag ttcaccacag tgttaatggg ggtcccaagg tattcttccc ccaggcctag    60
gtatagggct attactcctc tctgctccag gtgtagacat acatttacat t            111

<210> SEQ ID NO 118
<211> LENGTH: 238
<212> TYPE: DNA
<213> ORGANISM: Homo sapiens

<400> SEQUENCE: 118
tggagggtga aattctgata gacttgaggc tttgagatgt ggtcctgggg tggagcaaga    60
caagaaaagt actggagatt ggggtttgag gagtctatgc aattattttt attttttaaaa  120 atctttgtgg ctacatagca ggtgtatata tttatgtgg aagtgagata tttcgataca    180
gacatacaat gtataatcac aggcatacaa tgtagacagg cataaagtgt atagtcac     238

<210> SEQ ID NO 119
<211> LENGTH: 299
<212> TYPE: DNA
<213> ORGANISM: Homo sapiens

<400> SEQUENCE: 119
aatgtgaaac tgctccatga accccaaaga attatgcaca tagatgcgat cattaagatg    60
cgaagccatc gagttaccac ctggcatgct taaactgtaa agagtgggtc aaagtaaact   120
gaattggaaa atccaaagtt atgcagaaaa acaataaagg atagtaaa aagggttaac     180 gagccagtcc aggggaagcg aagaagacaa aaagagtcct tttctgggcc aagtttgata  240
aattaggcct cccgacccctt tgctctgttg ctttatcaac tctactcggc ataacaat    299

<210> SEQ ID NO 120
<211> LENGTH: 294
<212> TYPE: DNA
<213> ORGANISM: Homo sapiens

<400> SEQUENCE: 120
gattaagaac agtttttttca acaaatagtg ttgggacaat gggtgtccac atgcaaaaga   60
ataaagttgt ccccttacct tacaccatct ccaaaaatta actcaaaata tgtcaaagac  120
ataaacgtaa gagctaaaac tgtaaaactc ctagaataaa acataggagt aaatcttcat  180
gaccttggat taggccattg tgtcttaaat ataacaccaa aagaataagt aataaaaaaa  240
tagataaatt gaactccatc aaaattaaaa gcctttgtgc ttcataggac acca         294

<210> SEQ ID NO 121
<211> LENGTH: 269
<212> TYPE: DNA
<213> ORGANISM: Homo sapiens

<400> SEQUENCE: 121
tctcaagcta tgatcagaag actttaatta tatattttca tcctataagc ttaaatagga   60
aagtttcttc aacaggatta cagtgtagct acctacatgc tgaaaaatat agcctttaaa  120
tcatttttat attataactc tgtataatag agataagtcc attttttaaa aatgttttcc  180
ccaaaccata aaaccctata caagttgttc tagtaacaat acatgagaaa gatgtctatg  240
tagctgaaaa taaaatgacg tcacaagac        269

<210> SEQ ID NO 122
<211> LENGTH: 287
<212> TYPE: DNA
<213> ORGANISM: Homo sapiens

<400> SEQUENCE: 122
tctttctttt ccagacaact ttgaatggag aggagcaaat tagtcttttg gtttaattct        60
gtctcagttt gcttatctaa agaaaggaaa acagagtggc tacacttgtt tagaaccata       120
tgcatactcc agagaaagat gctctattaa tccaaaaaaa tacagccact tgaaaccagc       180
caaagcgaaa gtgtaaggga cttcatggaa aggaggcagt tcaccaaagt attgaggggt       240
tttatatttt aaactccgcc agtgaattga cgtgttatgt cacttac                    287

<210> SEQ ID NO 123
<211> LENGTH: 275
<212> TYPE: DNA
<213> ORGANISM: Homo sapiens

<400> SEQUENCE: 123
gaatttattg gagcatgacc acggaggata gtatgagccc taaaaatcca gactctttcg        60
atacccagga ccaagccaca gcaggtcctc catcccaaca gccatgcccg cattagctct       120
tagacccaca gactggtttt gcaacgttta caccgactag ccaggaagta cttccacctc       180
gggcacattt tgggaagttg cattcctttg tcttcaaact gtgaagcatt tacagaaacg       240
catccagcaa gaatattgtc cctttgagca gaaat                                 275

<210> SEQ ID NO 124
<211> LENGTH: 276
<212> TYPE: DNA
<213> ORGANISM: Homo sapiens

<400> SEQUENCE: 124
tccccggtta ctacctctta tccatccccg gccaccacct catacccatc ccctgtgccc        60
acctccttct cctctcccgg ctcctcgacc tacccatccc ctgtgcacag tggcttcccc       120
tccccgtcgg tggccaccac gtactcctct gttccccctg ctttcccggc ccaggtcagc       180
agcttcccct tcctcagctgt caccaactcc ttcagcgcct ccacagggct ttcggacatg       240
acagcaacct tttctcccag gacaattgaa atttgc                                 276

<210> SEQ ID NO 125
<211> LENGTH: 292
<212> TYPE: DNA
<213> ORGANISM: Homo sapiens

<400> SEQUENCE: 125
atgaagactt ggctgattca gatgccaggg ccttgtatga agcaggagaa aggagaaagg        60
ggacagacgt aaacgtgttc aataccatcc ttaccaccag aagctatcca caacttcgca       120
gagtgtttca gaaatacacc aagtacagta agcatgacat gaacaaagtt ctggacctgg       180
agttgaaagg tgacattgag aaatgcctca gagctatcgt gaagtgcgcc acaagcaaac       240
cagcttttctt tgcagagaag cttcatcaag ccatgaaagt atgtaccatt ct              292

<210> SEQ ID NO 126
<211> LENGTH: 237
<212> TYPE: DNA

<213> ORGANISM: Homo sapiens

<400> SEQUENCE: 126

| tgccttgtgt cttccgtttg acggaagaga atggattctg gtatctagac caaatcagaa | 60 |
| gggaacagta cattccaaat gaagaatttc ttcattctga tctcctagaa gacagcaaat | 120 |
| accgaaaaat ctactccttt actcttaagc ctcgaacaat tgaagatttt gagtctatga | 180 |
| atacatacct gcagacatct ccatcatctg tgtttactag taatcatttt gttcctt | 237 |

<210> SEQ ID NO 127
<211> LENGTH: 285
<212> TYPE: DNA
<213> ORGANISM: Homo sapiens

<400> SEQUENCE: 127

| ggtatagcat atgtggcctt gcttactaaa gtggatgatt gcagtgaggt tcttcaagac | 60 |
| aacttttta acatgagtag atctatgact tctcaaagcc gggtcatgaa tgtccataaa | 120 |
| atgctaggca ttcctatttc caatattttg atggttggaa attatgcttc agatttggaa | 180 |
| ctggacccca tgaaggatat tctcatcctc tctgcactga gcagatgct gcgggctgca | 240 |
| gatgattttt tagaagattt gcctcttgag gaaactggtg cattt | 285 |

<210> SEQ ID NO 128
<211> LENGTH: 233
<212> TYPE: DNA
<213> ORGANISM: Homo sapiens

<400> SEQUENCE: 128

| tgcttatccg ttagccgtgg tgatttagca ggaagctgtg agagcagttt ggtttctagc | 60 |
| atgaagacag agccccaccc tcagatgcac atgagctggc gggattgaaa gatgctgtct | 120 |
| tcgtactggg aaagggattt tcagccctca gaatcgctcc accttgcagc tctccccttc | 180 |
| tctgtattcc tagaaaactga cacatgctga acatcacagc ttatttcctc att | 233 |

<210> SEQ ID NO 129
<211> LENGTH: 270
<212> TYPE: DNA
<213> ORGANISM: Homo sapiens

<400> SEQUENCE: 129

| taggcaccac atgggatcct tgttcttcct ccttgtaagc agtaattgaa atcagtttgg | 60 |
| cagcctggtt tacagtgacc atggtggctt gtctcccgtg ctcttacctc actctgttga | 120 |
| tgttgtaaaa cctccagcta acttcatggg gtggctgacc cacgttgctc atttattcat | 180 |
| tcaacacata ttcattgacc atctactcta tgccaggtat tgttatcagc actgggaata | 240 |
| gatcagtgaa ctattgatct atttgtctaa | 270 |

<210> SEQ ID NO 130
<211> LENGTH: 79
<212> TYPE: DNA
<213> ORGANISM: Homo sapiens

<400> SEQUENCE: 130

| ctcagttctg gtccttcaag cctgtatggt ttggattttc agtaggggac agttgatgtg | 60 |
| gagtcaatct ctttggtac | 79 |

<210> SEQ ID NO 131
<211> LENGTH: 256

```
<212> TYPE: DNA
<213> ORGANISM: Homo sapiens

<400> SEQUENCE: 131
ctgaggtgct atgttcttag tggatgttct gaccctgctt caaatatttc cctcaccttt        60
cccatcttcc aagggtataa ggaatctttc tgctttgggg tttatcagaa ttctcagaat       120
ctcaaataac taaaaggtat gcaatcaaat ctgctttta aagaatgctc tttacttcat        180
ggacttccac tgccatcctc ccaagggggcc caaattcttt cagtggctac ctacatacaa      240
ttccaaacac atacag                                                      256

<210> SEQ ID NO 132
<211> LENGTH: 94
<212> TYPE: DNA
<213> ORGANISM: Homo sapiens

<400> SEQUENCE: 132
taacaaatca tcaacttcca ctggtcaata tatagatttt gggtgtctga ggccccaaga        60
ttagatgcca ctaatctcca aagattccct ccaa                                   94

<210> SEQ ID NO 133
<211> LENGTH: 254
<212> TYPE: DNA
<213> ORGANISM: Homo sapiens

<400> SEQUENCE: 133
gcagggtctt gggataacac tgtcatcaga acaaggctg ggggctgatt tcggggtggg         60
gagccttagg aggccagaaa ttccaatcag agccagtttt tctgggaggg agtggctaga      120
cagtcaagga aggacgttca catttcaaaa gaagtcgggt ggggggatga gattattcta      180 gggggggcatc gaattcccctt taagggggggg gctcacttct gcccagagta aagaggatct   240
cacaccatgg aaat                                                        254

<210> SEQ ID NO 134
<211> LENGTH: 298
<212> TYPE: DNA
<213> ORGANISM: Homo sapiens

<400> SEQUENCE: 134
tagttatact tacacactcc tctcatgttg tctatggagt ggtggatgct gcagggaggg        60
tgacatccta gttagtccta agagccagac tgcctgaagc tcactataac aagtcctgcc      120
ttggggaaga aggaagtgtg tctctgtgaa cctcccacct gggccgaaag ggaggccact      180
ctctctgctg cctctccca accttggcct tctgtgctcc tagtgaacct ctcaccccct       240
gcctacagcc tcgaatctca gaccatgatg acctctggtc accctgaatc agagcttt        298

<210> SEQ ID NO 135
<211> LENGTH: 292
<212> TYPE: DNA
<213> ORGANISM: Homo sapiens

<400> SEQUENCE: 135
gtaaaattcc tatgtcagca ccctaatgag acaaatgaca tcctaattct tccccttggc        60
ttgccagttt gtaggtacta gttttttcaga agttactcta aaatatttct gattgcagct      120
ccttcctaaa gagcagtatg agcagcatgt ggttatttat gtattcactc ttttctccta       180
cttctgtggt gacctggaac aaattctctt atgtatgtaa agattggaca gcccacctga      240
```

```
ttccgatgtc acttagatac actgttttg tatcagcctc ttctcttaga aa          292
```

```
<210> SEQ ID NO 136
<211> LENGTH: 180
<212> TYPE: DNA
<213> ORGANISM: Homo sapiens

<400> SEQUENCE: 136
gattgttggc caatagacct tccactccag tagagaggga ggacttggct ctgagaacct   60
ccatctgacc taagaggaaa cctcctctcc tatggccatc tcctcctcct gtcctttaag  120
tcctctgtgg ttactatatc tccttttccc tttcttaccc tttcgcttag caatttcaat  180

<210> SEQ ID NO 137
<211> LENGTH: 141
<212> TYPE: DNA
<213> ORGANISM: Homo sapiens

<400> SEQUENCE: 137
aagttctttg ggatagaggg tgaagaactt gggacatggg ctgtttcagg gcagctgaag   60
ttcaaagggg aataggtaat tgggggggaag gggggaagtt ggggcagaaa gggattgttg  120
ggccaatagg acctttccac t                                            141

<210> SEQ ID NO 138
<211> LENGTH: 248
<212> TYPE: DNA
<213> ORGANISM: Homo sapiens
<220> FEATURE:
<221> NAME/KEY: misc_feature
<222> LOCATION: (161)..(200)
<223> OTHER INFORMATION: n is a, c, g, or t

<400> SEQUENCE: 138
aggattatac ttcagtccct gctttacatt tatttcttaa agaagcttct ggtaaattag   60
agcaatagca tcggcttagt ttagtgttgt tctgttggac taaggatatc agttctatcc  120
gtatggtcgg gcctaaagcc tgggaaatat ttaatgaagg nnnnnnnnnn nnnnnnnnnn  180
nnnnnnnnnn nnnnnnnnnn ataacaaata acaaaacaaa aaccaagcca tttcccttta  240
tagtaaga                                                           248

<210> SEQ ID NO 139
<211> LENGTH: 259
<212> TYPE: DNA
<213> ORGANISM: Homo sapiens

<400> SEQUENCE: 139
acagaagcca ttgcctccct tgtttaccttt gggtccacct ccaccaaaac ccaacagacc   60
accaaatgtt gacctgacga aattccacaa aacctcttct ggaaacagta ctagcaaagg  120
ccagacgtct tactcaacaa cttccctgcc accacctcca ccatcccatc cggccagcca  180
accaccattg ccagcatctc acccatcaca accaccagtc ccaagcctac ctcccagaaa  240
cattaaacct ccgtttgac                                               259

<210> SEQ ID NO 140
<211> LENGTH: 199
<212> TYPE: DNA
<213> ORGANISM: Homo sapiens

<400> SEQUENCE: 140
gcacagctca gcacaacatt ccaagctcaa aatagaagcc ttctcagtga gctccagcac   60
```

```
gcccagagga ctgttaataa cgatgatcca tgtgttttac tctaaagtgc taaatatggg    120
agtttccttt tttttactct tgtcactga tgacacaaca gaaaagaaac tgtagacctt    180
gggacaatca acatttaaa                                                 199
```

<210> SEQ ID NO 141
<211> LENGTH: 279
<212> TYPE: DNA
<213> ORGANISM: Homo sapiens

<400> SEQUENCE: 141

```
cctgccctgg aagtaatctt gctgtcctgg aatctcctcg gggatgaggc agctgccgag    60
ctggcccagg tgctgccgaa gatgggccgg ctgaagagag tggacctgga gaagaatcag    120
atcacagctt tgggggcctg gctcctggct gaaggactgg cccaggggtc tagcatccaa    180
gtcatccgcc tctggaataa ccccattccc tgcgacatgg cccagcacct gaagagccag    240
gagcccaggc tggactttgc cttctttgac aaccagccc                            279
```

<210> SEQ ID NO 142
<211> LENGTH: 198
<212> TYPE: DNA
<213> ORGANISM: Homo sapiens

<400> SEQUENCE: 142

```
gcacagctca gcacaacatt ccaagctcaa aatagaagcc ttctcagtga gctccagcac    60
gcccagagga ctgttaataa cgatgatcca tgtgttttac tctaaagtgc taaatatggg    120
agtttccttt ttttactctt tgtcactgat gacacaacag aaaagaaact gtagaccttg    180
ggacaatcaa catttaaa                                                  198
```

<210> SEQ ID NO 143
<211> LENGTH: 183
<212> TYPE: DNA
<213> ORGANISM: Homo sapiens

<400> SEQUENCE: 143

```
gagagttcaa ctaagaaagg tcacatatgt gaaagcccaa ggacactgtt tgatatacag    60
caggtattca atcagtgtta tttgaaacca atctgaatt tgaagtttga atcttctgag    120
ttggaatgaa ttttttttcta gctgagggaa actgtatttt tctttccca aagaggaatg    180 taa                                                                   183
```

<210> SEQ ID NO 144
<211> LENGTH: 294
<212> TYPE: DNA
<213> ORGANISM: Homo sapiens

<400> SEQUENCE: 144

```
ctcgattatt ccctgtacaa tatttaaaat ttattgcttg atactttga caacaaatta     60 ggttttgtac aattgaactt aaataaatgt cattaaaata aataaatgca atatgtatta    120
atattcattg tataaaaata gaagaataca aacatatttg ttaaatattt acatatgaaa    180
tttaatatag ctatttttat ggaattttc attgatatga aaaatatgat attgcatatg    240
catagttccc atgttaaatc ccattcataa ctttcattaa agcatttact ttga           294
```

<210> SEQ ID NO 145
<211> LENGTH: 231
<212> TYPE: DNA

<213> ORGANISM: Homo sapiens

<400> SEQUENCE: 145

| | |
|---|---|
| gcaaataaat tcatacatag tacatacaaa ataagagaaa aaattaaatt gcagatggtt | 60 |
| aaatatcaca tcacttaact gatgttactg aaaatgtatt ttcctgcata atcatatggt | 120 |
| tgacagtatg cattaagaag gtaagtaaaa caatgaagac aatttttgatt taatatggta | 180 |
| atgcacaatt ccaactaacg tacattcaac agatcatgaa attgggttat t | 231 |

<210> SEQ ID NO 146
<211> LENGTH: 175
<212> TYPE: DNA
<213> ORGANISM: Homo sapiens

<400> SEQUENCE: 146

| | |
|---|---|
| ttgccttcta aatatactga aatgatttag atatgtgtca acaattaatg atctttttatt | 60 |
| caatctaaga aatggtttag tttttctctt tagctctatg gcatttcact caagtggaca | 120 |
| ggggaaaaag taattgccat gggctccaaa gaatttgctt tatgttttta gctat | 175 |

<210> SEQ ID NO 147
<211> LENGTH: 192
<212> TYPE: DNA
<213> ORGANISM: Homo sapiens

<400> SEQUENCE: 147

| | |
|---|---|
| cctggccact cgcaagacct tttatctgaa aaccagccaa gctttattca cgacacactt | 60 |
| cttcccttca ctctcccact tctgtggtca actccctgca gaactcccaa actgccgttc | 120 |
| ttttcgatag ctcacgatgg tgtatgagtg tcaatcatct gacccttctt ggagtctcat | 180 |
| atttcgtgga ac | 192 |

<210> SEQ ID NO 148
<211> LENGTH: 187
<212> TYPE: DNA
<213> ORGANISM: Homo sapiens

<400> SEQUENCE: 148

| | |
|---|---|
| ctgaggaccg gctgcagacc tcactctgag tggcaggcag agaaccaaag ctgcttcgct | 60 |
| gctctccagg gagaccctcc tgggatgggc ctgagaggcc ggggctcagg gaaggggctg | 120 |
| ggatcggaac ttcctgctct tgtttctgga caactttccc cttctgcttt aaaggttgtc | 180 |
| gattatt | 187 |

<210> SEQ ID NO 149
<211> LENGTH: 254
<212> TYPE: DNA
<213> ORGANISM: Homo sapiens

<400> SEQUENCE: 149

| | |
|---|---|
| agtgtgatgg atccccttta ggttatttag gggtatatgt cccctgcttg aaccctgaag | 60 |
| gccaggtaat gagccatggc cattgtcccc agctgaggac caggtgtctc taaaaaccca | 120 |
| aacatcctgg agagtatgcg agaacctacc aagaaaaaca gtctcattac tcatatacag | 180 |
| caggcaaaga gacagaaaat taactgaaaa gcagtttaga gactggggga ggccggatct | 240 |
| ctagagccat cctg | 254 |

<210> SEQ ID NO 150
<211> LENGTH: 192

<212> TYPE: DNA
<213> ORGANISM: Homo sapiens

<400> SEQUENCE: 150

```
gcgttacaga tggacgtagc tgccttggtt ttccagtcct caagggaata ctgaagatgc      60
tgactgaagg ggattggatg ttgattttag aagatgagag actccagcca cctttgtaaa     120
gcactagtgt ttgtcattta tgtaagtcag gtcggctcag gtcttgatag tccgtcttgg     180
tgtgaggcat gc                                                         192
```

<210> SEQ ID NO 151
<211> LENGTH: 157
<212> TYPE: DNA
<213> ORGANISM: Homo sapiens

<400> SEQUENCE: 151

```
cacagtaatg tcgaaactag gcctttgaac caaggcagtc tagggtaaaa tatagtttca      60
aagtatgaat aagaattggt atttgtgtta tctttgagta agaaactgtc cgatatgaat     120
cacaacgtgg gtgaatgtag tattttcctg aagtgtg                              157
```

<210> SEQ ID NO 152
<211> LENGTH: 187
<212> TYPE: DNA
<213> ORGANISM: Homo sapiens

<400> SEQUENCE: 152

```
ggccatgaac atcacctgca caggacgggg accagacaac tgtatccagt gtgcccacta      60
cattgacggc ccccactgcg tcaagacctg cccggcagga gtcatgggag aaaacaacac     120
cctggtctgg aagtacgcag acgccggcca tgtgtgccac ctgtgccatc caaactgcac     180
ctacggg                                                               187
```

<210> SEQ ID NO 153
<211> LENGTH: 102
<212> TYPE: DNA
<213> ORGANISM: Homo sapiens

<400> SEQUENCE: 153

```
atcacaggtt tgagctgaat tatcacatga atataaatgg gaaatcagtg ttttagagag      60
agaactttc gacatatttc ctgttcccct ggaataaaaa ca                         102
```

<210> SEQ ID NO 154
<211> LENGTH: 203
<212> TYPE: DNA
<213> ORGANISM: Homo sapiens

<400> SEQUENCE: 154

```
agtttcagac aaatgttcag tgtgagtgag gaaaacatgt tcagtgagga aaaaacattc      60
agacaaatgt tcagtgagga aaaaagggg aagttgggga taggcagatg ttgacttgag     120
gagttaatgt gatctttggg gagatacatc ttatagagtt agaaatagaa tctgaatttc     180
taaagggaga ttctggcttg gga                                             203
```

<210> SEQ ID NO 155
<211> LENGTH: 273
<212> TYPE: DNA
<213> ORGANISM: Homo sapiens

<400> SEQUENCE: 155

| | |
|---|---|
| aacttaagct gaatgtgtaa tggatttgtc tatagttta catattggga agcatttaa | 60 |
| aataggtttt aatcttacat aaaattactt ttatacttgt gttaacattt cttctgtgc | 120 |
| cttttgggta attaatttc tgttatgaat ttctggtgcc tatgagctag ctatcaccta | 180 |
| cctgaaaggt gcttagaggt gaaggtactg tttctaaaaa cacatcactg tgacaccttt | 240 |
| ctatcctcac attttcaagc ttgcctcttt tct | 273 |

<210> SEQ ID NO 156
<211> LENGTH: 135
<212> TYPE: DNA
<213> ORGANISM: Homo sapiens

<400> SEQUENCE: 156

| | |
|---|---|
| gtgactgctt atgaagggtt attgctcagc taagtatttc tgaatgagtc ttaggtctgt | 60 |
| tggccttcaa tctctaccga aaccctgaga acttgatgat gcttttgttt tctgagaatc | 120 |
| gtttcagtgt gctgg | 135 |

<210> SEQ ID NO 157
<211> LENGTH: 218
<212> TYPE: DNA
<213> ORGANISM: Homo sapiens

<400> SEQUENCE: 157

| | |
|---|---|
| catttgctgc aactctcagt ggtaagaatg attaagtgca gctataggag aatacttcca | 60 |
| ttggcatgcc acctgcgtaa acacacaat tttgttaaga tatacaataa aattattatg | 120 |
| ctaatagcaa atattttatg tagctcacta tgttccatgt agtcttctaa gtgcttcatg | 180 |
| ttagtcccca gttaaacacc tggttttgga aggctgag | 218 |

<210> SEQ ID NO 158
<211> LENGTH: 132
<212> TYPE: DNA
<213> ORGANISM: Homo sapiens

<400> SEQUENCE: 158

| | |
|---|---|
| gtgagcctgc cagcgtttgc gacgtccccg cacgacaggc tcatactttc tgaggatcgt | 60 |
| gcatagcata ggacgtctga acctttgtac aaatgtgtag atgacatctt gctacagctt | 120 |
| ttatttgtga at | 132 |

<210> SEQ ID NO 159
<211> LENGTH: 129
<212> TYPE: DNA
<213> ORGANISM: Homo sapiens

<400> SEQUENCE: 159

| | |
|---|---|
| gtaaattcaa tacaatgtca gttttaaaa gtcaaagtta gatcaagaga atatttcaga | 60 |
| gttttggttt acacatcaag aaacagacac acatacctag gaaagattta cacaatagat | 120 |
| aatcatctt | 129 |

<210> SEQ ID NO 160
<211> LENGTH: 229
<212> TYPE: DNA
<213> ORGANISM: Homo sapiens

<400> SEQUENCE: 160

| | |
|---|---|
| actgtacaaa gtataagtct tagatgtata tatttcctat attgttttca gtgtacatgg | 60 |
| aataacatgt aattaagtac tatgtatcaa tgagtaacag gaaaattta aaaatacaga | 120 |

```
tagatatatg ctctgcatgt tacataagat aaatgtgctg aatggttttc aaataaaaat    180
gaggtactct cctggaaata ttaagaaaga ctatctaaat gttgaaaga               229

<210> SEQ ID NO 161
<211> LENGTH: 181
<212> TYPE: DNA
<213> ORGANISM: Homo sapiens

<400> SEQUENCE: 161
gaggaccgag cacagaaatc ttagagattt cttgtcccct ctcaggtcat gtgtagatgc    60
gataaatcaa gtgattggtg tgcctgggtc tcactacaag cagcctatct gcttaagaga   120
ctctggagtt tcttatgtgc cctggtggac acttgcccac catcctgtga gtaaaagtga   180
a                                                                    181

<210> SEQ ID NO 162
<211> LENGTH: 280
<212> TYPE: DNA
<213> ORGANISM: Homo sapiens

<400> SEQUENCE: 162
tctgaactct caaaagtcta tttttttaac tgaaaatgta aatttataaa tatattcagg    60
agttggaatg ttgtagttac ctactgagta ggcggcgatt tttgtatgtt atgaacatgc   120
agttcattat tttgtggttc tattttactt tgtacttgtg tttgcttaaa caaagtgact   180
gtttggctta taaacacatt gaatgcgctt tattgcccat gggatatgtg gtgtatatcc   240
ttccaaaaaa ttaaaacgaa aataaagtag ctgcgattgg                        280

<210> SEQ ID NO 163
<211> LENGTH: 166
<212> TYPE: DNA
<213> ORGANISM: Homo sapiens

<400> SEQUENCE: 163
attcctgtca ttacccattg taacagagcc acaaactaat actatgcaat gtttaccaa     60 taatgcaata caaaagacct caaaatacct gtgcatttct tgtaggaaaa caacaaaagg   120
taattatgtg taattatact agaagttttg taatctgtat cttatc                  166

<210> SEQ ID NO 164
<211> LENGTH: 136
<212> TYPE: DNA
<213> ORGANISM: Homo sapiens

<400> SEQUENCE: 164
caggacccat cacgcctgtg cagtggcccc cacagaaaga ctgagctcaa ggtgggaacc    60
acgtctgcta acttggagcc ccagtgccaa gcacagtgcc tgcatgtatt tatccaataa   120
atgtgaaatt ctgtcc                                                   136

<210> SEQ ID NO 165
<211> LENGTH: 237
<212> TYPE: DNA
<213> ORGANISM: Homo sapiens

<400> SEQUENCE: 165
aaagtggcat ttcttgtgatt ggaaagggggg aaggatctta ttgcacttgg gctgttcaga   60
atgtagaaag gacatatttg aggaagtatc tatttgagca ctgatttact ctgtaaaaag   120
```

-continued

```
caaaatctct ctgtcctaaa ctaatggaag cgattctccc atgctcatgt gtaatggttt    180
taacgttact cactggagag attggacttt ctggagttat ttaaccacta tgttcag       237
```

<210> SEQ ID NO 166
<211> LENGTH: 86
<212> TYPE: DNA
<213> ORGANISM: Homo sapiens

<400> SEQUENCE: 166

```
tttataatgt cccttcacaa acccagtgtt ttaggagcat gagtgccgtg tgtgtgcgtc    60
ctgtcggagc cctgtctcct ctctct                                         86
```

<210> SEQ ID NO 167
<211> LENGTH: 159
<212> TYPE: DNA
<213> ORGANISM: Homo sapiens

<400> SEQUENCE: 167

```
caccctcaga tgcacatgag ctggcgggat tgaaggatgc tgtcttcgta ctgggaaagg    60
gattttcagc cctcagaatc gctccacctt gcagctctcc ccttctctgt attcctagaa   120
actgacacat gctgaacatc acagcttatt tcctcattt                          159
```

<210> SEQ ID NO 168
<211> LENGTH: 175
<212> TYPE: DNA
<213> ORGANISM: Homo sapiens

<400> SEQUENCE: 168

```
aaatttaatt ttctacgcct ctggggatat ctgctcagcc aatggaaaat ctgggttcaa    60 ccagccctg ccatttctta agactttctg ctgcactcac aggatcctga gctgcactta   120
cctgtgagag tcttcaaact tttaaacctt gccagtcagg acttttgcta ttgca        175
```

<210> SEQ ID NO 169
<211> LENGTH: 191
<212> TYPE: DNA
<213> ORGANISM: Homo sapiens

<400> SEQUENCE: 169

```
ctactcctta cagtctctag aattaaatgt actcatttag acaacatatt aaatgcatat    60
tttagccact ttagagaaac ctcataggca cagagtttcc aagattaatt ttaagaatat   120
cttcacgaac ttgaccctcc tactccacat tgcaacattt ccatcagaca gcatttcaat   180
tccagtatta t                                                        191
```

<210> SEQ ID NO 170
<211> LENGTH: 172
<212> TYPE: DNA
<213> ORGANISM: Homo sapiens

<400> SEQUENCE: 170

```
gtcatcatat ataattaaac agcttttaa agaaacataa ccacaaacct tttcaaataa    60
taataataat aataataaaa aatgtatttt aaagatggcc tgtggttatc ttggaaattg   120
gtgatttatg ctagaaagct tttaatgttg gtttattgtt gaattcctag aa            172
```

<210> SEQ ID NO 171
<211> LENGTH: 239
<212> TYPE: DNA
<213> ORGANISM: Homo sapiens

<400> SEQUENCE: 171

```
catggattag ctggaagatc tgtatttgat ggaagacctt gaaattattg gaagacatgg      60
atttcctgga agacgtggat tttcctggaa gatctggatt tggtggaaga ccagtaattg     120
ctggaagact ggatttgctg gaagacttga tttactggaa gacttggagc ttcttggaag     180
acatggattg tccggaagac atggattgtc tggaagatgt ggattttctg gaagctcag     239
```

<210> SEQ ID NO 172
<211> LENGTH: 255
<212> TYPE: DNA
<213> ORGANISM: Homo sapiens

<400> SEQUENCE: 172

```
gtggaggaaa ctaaacattc ccttgatggt ctcaagctat gatcagaaga ctttaattat      60
atattttcat cctataagct aaataggaaa gtttcttca acaggattac agtgtagcta     120
cctacatgct gaaaaatata gcctttaaat catttttata ttataactct gtataataga     180
gataagtcca ttttttaaaa atgttttccc caaaccataa aaccctatac aagttgttct     240
agtaacaata catga                                                     255
```

<210> SEQ ID NO 173
<211> LENGTH: 238
<212> TYPE: DNA
<213> ORGANISM: Homo sapiens

<400> SEQUENCE: 173

```
tcaataaggg cgttcttcct tgcaagttga acattattg tgctaggatt gctctctaga      60
caagccagaa gtgacttatt aaactattga aggaaaagga ctcaagaaaa ataataaaag     120
accataaata agggcgaaaa cattaccatg tgaaaagaat gtatttcacc tgcaagttac     180
aaaaaaatag tttgtgcatt gcaaataagc aaagacttgg attgacttta cattcatc      238
```

<210> SEQ ID NO 174
<211> LENGTH: 230
<212> TYPE: DNA
<213> ORGANISM: Homo sapiens

<400> SEQUENCE: 174

```
aagctgtgtt gttgcttctt gtgaaggcca tgatattttg ttttccccca attaattgct      60
attgtgttat tttactactt ctctctgtat tttttcttgc attgacatta tagacattga     120
ggacctcatc caaacaattt aaaaatgagt gtgaaggggg aacaagtcaa atatttta     180 aaagatcttc aaaaataatg cctctgtcta gcatgccaac aagaatgcat                230
```

<210> SEQ ID NO 175
<211> LENGTH: 166
<212> TYPE: DNA
<213> ORGANISM: Homo sapiens

<400> SEQUENCE: 175

```
tgcctgttgt agaccacagt cacacactgc tgtagtcttc cccagtcctc attcccagct      60
gcctcttcct actgcttccg tctatcaaaa agccccttg gccaggttc cctgagctgt     120 gggattctgc actggtgctt tggattccct gatatgttcc ttcaaa                  166
```

<210> SEQ ID NO 176
<211> LENGTH: 137
<212> TYPE: DNA

<213> ORGANISM: Homo sapiens

<400> SEQUENCE: 176

| gtcagacaga tgtggttgca tcctaactcc atgtctctga gcattagatt tctcatttgc | 60 |
| caataataat acctccctta gaagtttgtt gtgaggatta ataatgtaa ataaagaact | 120 |
| agcataacac tcaaaaa | 137 |

<210> SEQ ID NO 177
<211> LENGTH: 227
<212> TYPE: DNA
<213> ORGANISM: Homo sapiens

<400> SEQUENCE: 177

| tctgtgtgtg ccctgtaacc tgactggtta acagcagtcc tttgtaaaca gtgttttaaa | 60 |
| ctctcctagt caatatccac cccatccaat ttatcaagga agaaatggtt cagaaaatat | 120 |
| tttcagccta cagttatgtt cagtcacaca cacatacaaa atgttccttt tgcttttaaa | 180 |
| gtaattttg actcccagat cagtcagagc ccctacagca ttgttaa | 227 |

<210> SEQ ID NO 178
<211> LENGTH: 218
<212> TYPE: DNA
<213> ORGANISM: Homo sapiens

<400> SEQUENCE: 178

| gtttaagcct ggaacttgta agaaaatgaa aatttaattt ttttttctag gacgagctat | 60 |
| agaaaagcta ttgagagtat ctagttaatc agtgcagtag ttggaaacct tgctggtgta | 120 |
| tgtgatgtgc ttctgtgctt ttgaatgact ttatcatcta gtctttgtct attttttcctt | 180 |
| tgatgttcaa gtcctagtct ataggattgg cagtttaa | 218 |

<210> SEQ ID NO 179
<211> LENGTH: 243
<212> TYPE: DNA
<213> ORGANISM: Homo sapiens

<400> SEQUENCE: 179

| gactgaggga tcgtagattt ttacaatctg tatctttgac aattctgggt gcgagtgtga | 60 |
| gagtgtgagc agggcttgct cctgccaacc acaattcaat gaatccccga cccccctacc | 120 |
| ccatgctgta cttgtggttc tctttttgta ttttgcatct gaccccgggg ggctgggaca | 180 |
| gattggcaat gggccgtccc ctctcccctt ggttctgcac tgttgccaat aaaaagctct | 240 |
| taa | 243 |

<210> SEQ ID NO 180
<211> LENGTH: 267
<212> TYPE: DNA
<213> ORGANISM: Homo sapiens

<400> SEQUENCE: 180

| ggagggaagg caagattctt tccccctccc tgctgaagca tgtggtacag aggcaagagc | 60 |
| agagcctgag aagcgtcagg tcccacttct gccatgcagc tactatgagc cctcggggcc | 120 |
| tcctcctggg cctcagcttg cccagataca tacctaaata tatatatata tatatgaggg | 180 |
| agaacgcctc acccagattt tatcatgctg gaaagagtgt atgtatgtga agatgcttgg | 240 |
| tcaacttgta cccagtgaac acacaaa | 267 |

<210> SEQ ID NO 181
<211> LENGTH: 267
<212> TYPE: DNA
<213> ORGANISM: Homo sapiens

<400> SEQUENCE: 181

```
ggagggaagg caagattctt tcccctccc tgctgaagca tgtggtacag aggcaagagc      60
agagcctgag aagcgtcagg tcccacttct gccatgcagc tactatgagc cctcggggcc    120
tcctcctggg cctcagcttg cccagataca tacctaaata tatatatata tatatgaggg    180
agaacgcctc acccagattt tatcatgctg gaaagagtgt atgtatgtga agatgcttgg    240
tcaacttgta cccagtgaac acacaaa                                         267
```

<210> SEQ ID NO 182
<211> LENGTH: 206
<212> TYPE: DNA
<213> ORGANISM: Homo sapiens

<400> SEQUENCE: 182

```
tattcttcta taacactcta tatagagcta tgtgagtact aatcacattg aataatagtt     60
ataaaattat tgtatagaca tctgcttctt aaacagattg tgagttcttt gagaaacagc    120
gtggatttta cttatctgtg tattcacaga gcttagcaca gtgcctggta atgagcaagc    180
atacttgcca ttactttttcc ttccca                                         206
```

<210> SEQ ID NO 183
<211> LENGTH: 264
<212> TYPE: DNA
<213> ORGANISM: Homo sapiens

<400> SEQUENCE: 183

```
cctaatttga gggtcagttc ctgcagaagt gcccttttgcc tccactcaat gcctcaattt     60
gttttctgca tgactgagag tctcagtgtt ggaacgggac agtatttatg tatgagtttt    120
tcctatttat tttgagtctg tgaggtcttc ttgtcatgtg agtgtggttg tgaatgattt    180
cttttgaaga tatattgtag tagatgttac aattttgtcg ccaaactaaa cttgctgctt    240
aatgatttgc tcacatctag taaa                                            264
```

<210> SEQ ID NO 184
<211> LENGTH: 226
<212> TYPE: DNA
<213> ORGANISM: Homo sapiens

<400> SEQUENCE: 184

```
ggacactttt gaaaacagga ctcagcatcg ctttcaatag gcttttcagg accttcactg      60
cattaaaaca atattttta aaatttagta cagtttagaa agagcactta ttttgtttat    120
atccattttt tcttactaaa ttataggat taactttgac aaatcatgct gctgttattt     180
tctacatttg tatttatcc atagcactta ttcacattta ggaaaa                    226
```

<210> SEQ ID NO 185
<211> LENGTH: 275
<212> TYPE: DNA
<213> ORGANISM: Homo sapiens

<400> SEQUENCE: 185

```
cagtttctgt tctctcacag gtgataaaca atgcttttg tgcactacat actcttcagt      60
gtagagctct tgtttatgg gaaaaggctc aaatgccaaa ttgtgtttga tggattaata    120
```

```
tgcccttttg ccgatgcata ctattactga tgtgactcgg ttttgtcgca gctttgcttt    180
gtttaatgaa acacacttgt aaacctcttt tgcactttga aaaagaatcc agcgggatgc    240
tcgagcacct gtaaacaatt ttctcaacct atttg                              275

<210> SEQ ID NO 186
<211> LENGTH: 275
<212> TYPE: DNA
<213> ORGANISM: Homo sapiens

<400> SEQUENCE: 186
cagtttctgt tctctcacag gtgataaaca atgcttttttg tgcactacat actcttcagt    60
gtagagctct tgttttatgg gaaaaggctc aaatgccaaa ttgtgtttga tggattaata   120
tgcccttttg ccgatgcata ctattactga tgtgactcgg ttttgtcgca gctttgcttt   180
gtttaatgaa acacacttgt aaacctcttt tgcactttga aaaagaatcc agcgggatgc   240
tcgagcacct gtaaacaatt ttctcaacct atttg                              275

<210> SEQ ID NO 187
<211> LENGTH: 114
<212> TYPE: DNA
<213> ORGANISM: Homo sapiens

<400> SEQUENCE: 187
agcaagtgta gacaccttcg agggcagaga tcgggagatt taagatgtta cagcatatttt    60 tttttcttg ttttacagta ttcaattttg tgttgattca gctaaattat gaaa           114

<210> SEQ ID NO 188
<211> LENGTH: 205
<212> TYPE: DNA
<213> ORGANISM: Homo sapiens

<400> SEQUENCE: 188
gtctcacata tttatataat cctcaaatat actgtaccat tttagatatt ttttaaacag    60
attaatttgg agaagttttta ttcattacct aattctgtgg caaaaatggt gcctctgatg   120
ttgtgatata gtattgtcag tgtgtacata tataaaacct gtgtaaacct ctgtccttat   180
gaaccataac aaatgtagct tttta                                          205

<210> SEQ ID NO 189
<211> LENGTH: 158
<212> TYPE: DNA
<213> ORGANISM: Homo sapiens

<400> SEQUENCE: 189 cagcccccacc cctgtaaatg gaatttacca gatgaaggga atgaagtccc tcactgagcc    60
tcagatttcc tcacctgtga aatgggctga ggcaggaaat gggaaaaagt gttagtgctt   120
ccaggcggca ctgacagcct cagtaacaat aaaaacaa                            158

<210> SEQ ID NO 190
<211> LENGTH: 254
<212> TYPE: DNA
<213> ORGANISM: Homo sapiens

<400> SEQUENCE: 190
tcagctgccc tgaaacagcc catgtcccaa gttcttcacc tctatccaaa gaacttgatt    60
tgcatggatt ttggataaat catttcagta tcatctccat catatgcctg acccccttgct   120 cccttcaatg ctagaaaatc gagttggcaa aatgggggttt gggcccctca gagccctgcc   180
```
ctgcacccct gtacagtgtc tgtgccatgg atttcgtttt tcttggggta ctcttgatgt    240
gaagataatt tgca                                                      254

<210> SEQ ID NO 191
<211> LENGTH: 235
<212> TYPE: DNA
<213> ORGANISM: Homo sapiens

<400> SEQUENCE: 191
gagtgtctca gaagtgtgct cctctggcct cagttctcct cttttggaac aacataaaac    60
aaatttaatt ttctacgcct ctggggatat ctgctcagcc aatggaaaat ctgggttcaa   120
ccagcccctg ccatttctta agactttctg ctccactcac aggatcctga gctgcactta   180
cctgtgagag tcttcaaact tttaaacctt gccagtcagg acttttgcta ttgca         235

<210> SEQ ID NO 192
<211> LENGTH: 296
<212> TYPE: DNA
<213> ORGANISM: Homo sapiens

<400> SEQUENCE: 192
gagggacgtc agaaaatcag tgcattgtgg agtcactttt ctgataaagg gcacatcaga    60
ctgcaaatgg tccagacagc cagattcagg acactgatga gtttctgggg tcaccatagc   120
atccctggag tcagctgctc tgcagcctga aggagggctg acagtgtgga gtcactgcta   180
ttacttaatg aaattatata gaattctat aatgattatg taattgcata atgaaaactc   240
tccatatcag agttcagaat atctcccaat ttccagtaca gaatattatc cataac        296

<210> SEQ ID NO 193
<211> LENGTH: 290
<212> TYPE: DNA
<213> ORGANISM: Homo sapiens

<400> SEQUENCE: 193
gacagcaata acttcgtttt agaaacattc aagcaatagc tttatagctt caacatatgg    60
tacgttttaa ccttgaaagt tttgcaatga tgaaagcagt atttgtacaa atgaaaagca   120
gaattctctt ttatatggtt tatactgttg atcagaaatg ttgattgtgc attgagtatt   180
aaaaaattag atgtatatta ttcattgttc tttactcatg agtaccttat aataataata   240
atgtattctt tgttaacaat gccatgttgg tactagttat taatcatatc                290

<210> SEQ ID NO 194
<211> LENGTH: 269
<212> TYPE: DNA
<213> ORGANISM: Homo sapiens

<400> SEQUENCE: 194
ggcaggatat tgtaagcctt gaaaagaat taggcaggat atcggaagcc ctgattagat     60
tctatcctaa gagcaacaga agatcactga cagtgtttta aatagataga ctagtttatt   120
agatttgcag tttagaagtt cccttttttt gtaattattg gacagtgtag agaccggatg   180
gtgagagatg agttaggaag ttgtgacagc tctctatacc taccgctaat gtagaggatt   240 atttatttc atttcattac cattcgtgt                                       269

<210> SEQ ID NO 195
<211> LENGTH: 215
<212> TYPE: DNA

<213> ORGANISM: Homo sapiens

<400> SEQUENCE: 195

| | |
|---|---|
| gtaatatgtt tataatcctt tagatcttat aaatatgtgg tataaggaat gccatataat | 60 |
| gtgccaaaaa tctgagtgca tttaatttaa tgcttgctta tagtgctaaa gttaaatgat | 120 |
| cttaattctt tgcaattata tatgaaaaat gactgatttt tcttaaaata tgtaacttat | 180 |
| ataaatatat ctgtttgtac agattttaac cataa | 215 |

<210> SEQ ID NO 196
<211> LENGTH: 269
<212> TYPE: DNA
<213> ORGANISM: Homo sapiens

<400> SEQUENCE: 196

| | |
|---|---|
| gtatccttga actggaaacc atccacgatc gagtatcgag tcattcaaca ctatcaattc | 60 |
| ctgggtgact ttttgaaaaa gtagtatctc ttgttgcaag aaatgctcca tctgtgagtc | 120 |
| catgtctctc actggaattg gatggaagtg gtgaatttca gccaaagtgg ccaaagaaat | 180 |
| cctgttcctg tgattctgac gtcatcagcc tctgcacctc tgtcttccct tctgccacat | 240 |
| gttgcctgtt ctccgtgact ttggtaaga | 269 |

<210> SEQ ID NO 197
<211> LENGTH: 268
<212> TYPE: DNA
<213> ORGANISM: Homo sapiens

<400> SEQUENCE: 197

| | |
|---|---|
| gagagagtga tcacgctgct gtgcccacct atgcggtaga ccttgttcct gggttgggag | 60 |
| atgttttatg atcagggtgc agtagaaaga gcacactagt agcagtaaag agaggtgacc | 120 |
| ctggctgcag ttctgcctct aacttcctga gtgacctcag gctagtcaca cagtgactgc | 180 |
| tccccacatt tcttttgta agctgcaagg attgaatcag acaatagcct ctaagttcct | 240 |
| tctgaactct catactcagg gatgccaa | 268 |

<210> SEQ ID NO 198
<211> LENGTH: 258
<212> TYPE: DNA
<213> ORGANISM: Homo sapiens

<400> SEQUENCE: 198

| | |
|---|---|
| ttccctccca ctaatttgtt ggcctttaac agcaattttg aaaactgggt cttctggtta | 60 |
| tgttttgtt ttaaaatctt taaattagag gatgctgtgc cattgagtac tttaagttaa | 120 |
| tatgaggttc tggttcaagg aaaacttacg ttggatctga accaatgagc agatattttg | 180 |
| atatgtgcca ctcttgcata tacatctcag tcctaactaa aggttctagt ggcatccagg | 240 |
| acctttaggg aggcattt | 258 |

<210> SEQ ID NO 199
<211> LENGTH: 147
<212> TYPE: DNA
<213> ORGANISM: Homo sapiens

<400> SEQUENCE: 199

| | |
|---|---|
| cactgcgtct ggcaataatg taactttgaa gcttaaaaat taatcccagt ttgtagcaat | 60 |
| aacagaagac tatctacaac ggaagaaaga agcaactgcc ttacagttct gtaaagaatt | 120 |
| ggcaagaaaa taaagcctat agttgcc | 147 |

<210> SEQ ID NO 200
<211> LENGTH: 274
<212> TYPE: DNA
<213> ORGANISM: Homo sapiens

<400> SEQUENCE: 200

```
cccttactta catactagct tccaaggaca ggtggaggta gggccagcct ggcgggagtg      60
gagaagccca gtctgtccta tgtaaggac aaagccaggt ctaatggtac tgggtagggg     120
gcactgccaa gacaataagc taggctactg ggtccagcta ctactttggt gggattcagg    180
tgagtctcca tgcacttcac atgttaccca gtgttcttgt tacttccaag gagaaccaag    240
aatggctctg tcacactcga agccaggttt gatc                                 274
```

<210> SEQ ID NO 201
<211> LENGTH: 155
<212> TYPE: DNA
<213> ORGANISM: Homo sapiens

<400> SEQUENCE: 201

```
cctcctttct aaatgcagcg acctgtgttc ttcagcccta tcccttttcta ttcctctgac    60 cccgcctcct ttctaaatgc agcgacctct gttcttcagc cctatcccttt tctattcctc   120 tgacccccgcc tcctttctaa atgcagcgac ctctg                              155
```

<210> SEQ ID NO 202
<211> LENGTH: 275
<212> TYPE: DNA
<213> ORGANISM: Homo sapiens

<400> SEQUENCE: 202

```
ggcgtcggcg cctagggcga agtgagccag ggtgcagtcg ggaagctcca ggacgaagcg     60
gcgcggcgga gccatggccc cagcgcagac cccgcgccgc ccgagcagcg gccccgacag    120
tggcccgcgc aggagccggc gggcgaaggc catgggcgcc tcagcgacgc cgccctcggc    180
cccgcctcgg aaacgaaacc tggcgggagc caggcgccgg cgggaaacga aacccggagg    240
gagccaggcg ccagcgggaa acgaaagcga agcgt                               275
```